United States Patent
Naito et al.

(10) Patent No.: US 11,795,236 B2
(45) Date of Patent: Oct. 24, 2023

(54) METHOD FOR TREATING CANCER COMPRISING ADMINISTRATION OF ANTI-HER2 ANTIBODY-DRUG CONJUGATE

(71) Applicant: Daiichi Sankyo Company, Limited, Tokyo (JP)

(72) Inventors: Hiroyuki Naito, Tokyo (JP); Yusuke Ogitani, Tokyo (JP); Takeshi Masuda, Tokyo (JP); Takashi Nakada, Tokyo (JP); Masao Yoshida, Tokyo (JP); Shinji Ashida, Tokyo (JP); Koji Morita, Tokyo (JP); Hideki Miyazaki, Tokyo (JP); Yuji Kasuya, Tokyo (JP); Ichiro Hayakawa, Tokyo (JP); Yuki Abe, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 325 days.

(21) Appl. No.: 16/130,615

(22) Filed: Sep. 13, 2018

(65) Prior Publication Data
US 2019/0077880 A1   Mar. 14, 2019

Related U.S. Application Data

(60) Division of application No. 15/221,851, filed on Jul. 28, 2016, now Pat. No. 10,155,821, which is a (Continued)

(30) Foreign Application Priority Data

Jan. 31, 2014 (JP) .................. 2014-017777
Aug. 22, 2014 (JP) .................. 2014-168944
Nov. 10, 2014 (JP) .................. 2014-227886

(51) Int. Cl.
*A61K 47/68* (2017.01)
*A61K 39/395* (2006.01)
(Continued)

(52) U.S. Cl.
CPC .......... *C07K 16/32* (2013.01); *A61K 31/4745* (2013.01); *A61K 39/395* (2013.01); *A61K 47/6803* (2017.08); *A61K 47/6849* (2017.08); *A61K 47/6851* (2017.08); *A61K 47/6855* (2017.08); *A61K 47/6857* (2017.08);
(Continued)

(58) Field of Classification Search
CPC ........ C07K 16/32; C07K 16/28; C07K 16/30; C07K 16/3015; C07K 16/3023; C07K 16/303; C07K 16/3046; C07K 16/3069; C07K 2317/24; C07K 2317/73; A61K 31/4745; A61K 39/395; A61K 47/6803; A61K 47/6849; A61K 47/6851; A61K 47/6855; A61K 47/6857; A61K 47/6859; A61K 47/6869; A61K 2039/505; A61K 2039/545; A61K 47/6889; C07D 491/22; C07D 491/052; A61P 35/00; A61P 35/02
See application file for complete search history.

(56) References Cited

U.S. PATENT DOCUMENTS 5,677,171 A   10/1997   Hudziak et al.
5,821,337 A   10/1998   Carter et al.
(Continued)

FOREIGN PATENT DOCUMENTS

CA   2 927 832 A1   11/2011
CA   2 859 255 A1    6/2013
(Continued)

OTHER PUBLICATIONS

Moghaddas et al (J. Res. Parm Pract, 5(4):227-233, 2016).*
(Continued)

*Primary Examiner* — Julie Wu
*Assistant Examiner* — John L Van Druff
(74) *Attorney, Agent, or Firm* — Foley & Lardner LLP

(57) ABSTRACT

As an antitumor drug which is excellent in terms of antitumor effect and safety and has an excellent therapeutic effect, there is provided an antibody-drug conjugate in which an antitumor compound represented by the following formula is conjugated to an anti-HER2 antibody via a linker having a structure represented by the following formula: $-L^1-L^2-L^P-NH-(CH_2)n^1-L^a-(CH_2)n^2-C(=O)-$ wherein the anti-HER2 antibody is connected to the terminal $L^1$, and the antitumor compound is connected to the carbonyl group of the $-(CH_2)n^2-C(=O)-$ moiety with the nitrogen atom of the amino group at position 1 as the connecting position

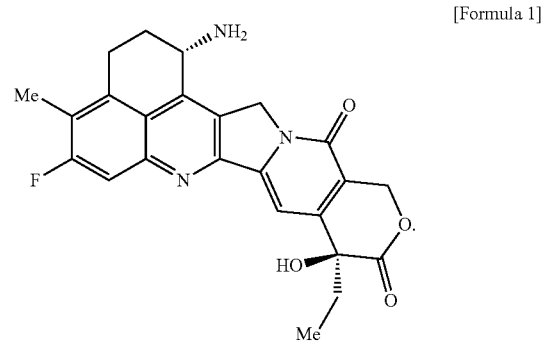

[Formula 1]

12 Claims, 14 Drawing Sheets
Specification includes a Sequence Listing.

Related U.S. Application Data continuation of application No. PCT/JP2015/000355, filed on Jan. 28, 2015.

(51) Int. Cl.
| | |
|---|---|
| *A61K 31/4745* | (2006.01) |
| *A61K 39/00* | (2006.01) |
| *C07K 16/32* | (2006.01) |
| *C07D 491/22* | (2006.01) |
| *C07K 16/28* | (2006.01) |
| *C07K 16/30* | (2006.01) |
| *C07D 491/052* | (2006.01) |

(52) U.S. Cl.
CPC ...... *A61K 47/6859* (2017.08); *A61K 47/6869* (2017.08); *C07D 491/22* (2013.01); *C07K 16/28* (2013.01); *C07K 16/30* (2013.01); *C07K 16/303* (2013.01); *C07K 16/3015* (2013.01); *C07K 16/3023* (2013.01); *C07K 16/3046* (2013.01); *C07K 16/3069* (2013.01); *A61K 2039/505* (2013.01); *A61K 2039/545* (2013.01); *C07D 491/052* (2013.01); *C07K 2317/24* (2013.01); *C07K 2317/73* (2013.01)

(56) References Cited

U.S. PATENT DOCUMENTS

| | | |
|---|---|---|
| 5,834,476 A | 11/1998 | Terasawa et al. |
| 5,837,673 A | 11/1998 | Tsujihara et al. |
| 5,892,043 A | 4/1999 | Tsujihara et al. |
| 6,214,345 B1 | 4/2001 | Firestone et al. |
| 6,291,671 B1 | 9/2001 | Inoue et al. |
| 6,835,807 B1 | 12/2004 | Susaki et al. |
| 7,041,818 B2 | 5/2006 | Susaki et al. |
| 7,449,184 B2 | 11/2008 | Allison et al. |
| 7,585,491 B2 | 9/2009 | Govindan |
| 7,837,980 B2 | 11/2010 | Alley et al. |
| 7,999,083 B2 | 8/2011 | Govindan et al. |
| 8,802,820 B2 | 8/2014 | Chamberlain et al. |
| 9,808,537 B2 | 11/2017 | Masuda et al. |
| 9,850,312 B2 | 12/2017 | Agatsuma et al. |
| 9,872,924 B2 | 1/2018 | Naito et al. |
| 10,195,288 B2 | 2/2019 | Masuda et al. |
| 10,227,417 B2 | 3/2019 | Agatsuma et al. |
| 10,383,878 B2 | 8/2019 | Hettmann et al. |
| 2003/0148931 A1 | 8/2003 | Takahashi et al. |
| 2003/0166513 A1 | 9/2003 | Imura et al. |
| 2004/0185053 A1 | 9/2004 | Govindan |
| 2005/0123536 A1 | 6/2005 | Law et al. |
| 2005/0271671 A1 | 12/2005 | Griffiths |
| 2005/0276812 A1 | 12/2005 | Ebens et al. |
| 2006/0018899 A1 | 1/2006 | Kao et al. |
| 2006/0193865 A1 | 8/2006 | Govindan |
| 2007/0071764 A1 | 3/2007 | Sullivan et al. |
| 2008/0050310 A1 | 2/2008 | Ebens, Jr. et al. |
| 2008/0131363 A1 | 6/2008 | Govindan et al. |
| 2008/0161245 A1 | 7/2008 | Kratz et al. |
| 2008/0305044 A1 | 12/2008 | McDonagh et al. |
| 2009/0274713 A1 | 11/2009 | Chari et al. |
| 2009/0286258 A1 | 11/2009 | Kaur et al. |
| 2010/0120816 A1 | 5/2010 | Fontana et al. |
| 2011/0059076 A1 | 3/2011 | McDonagh et al. |
| 2011/0070248 A1 | 3/2011 | Ichikawa et al. |
| 2011/0293513 A1 | 12/2011 | Govindan et al. |
| 2012/0121615 A1 | 5/2012 | Flygare et al. |
| 2012/0171201 A1 | 7/2012 | Sapra |
| 2012/0201809 A1 | 8/2012 | Bhat et al. |
| 2013/0089872 A1 | 4/2013 | Nakamura et al. |
| 2013/0123178 A1 | 5/2013 | Dimarchi et al. |
| 2015/0297748 A1 | 10/2015 | Masuda et al. |
| 2015/0352224 A1 | 12/2015 | Naito et al. |
| 2016/0279259 A1 | 9/2016 | Masuda et al. |
| 2016/0287722 A1 | 10/2016 | Govindan |
| 2016/0297890 A1 | 10/2016 | Agatsuma et al. |

FOREIGN PATENT DOCUMENTS

| | | |
|---|---|---|
| CN | 1764478 A | 4/2006 |
| CN | 101023100 A | 8/2007 |
| CN | 101490087 A | 7/2009 |
| CN | 102481364 A | 5/2012 |
| EP | 0 495 432 A1 | 7/1992 |
| EP | 0 737 686 A1 | 10/1996 |
| EP | 0 916 348 A1 | 5/1999 |
| EP | 1 155 702 A1 | 11/2001 |
| EP | 2 594 589 A1 | 5/2013 |
| EP | 2 799 452 A1 | 11/2014 |
| EP | 2 907 824 A1 | 8/2015 |
| EP | 2 910 573 A1 | 8/2015 |
| JP | H05-059061 A | 3/1993 |
| JP | H06-087746 A | 3/1994 |
| JP | H08-337584 A | 12/1996 |
| JP | H10-095802 A | 4/1998 |
| JP | H1171280 A | 3/1999 |
| JP | H11-092405 A | 4/1999 |
| JP | 2002-060351 A | 2/2002 |
| JP | 2005-511627 A | 4/2005 |
| JP | 2006-511526 A | 4/2006 |
| JP | 2008-521828 A | 6/2008 |
| JP | 2009-538629 A | 11/2009 |
| JP | 2011-519864 A | 7/2011 |
| JP | 2011-524001 A | 8/2011 |
| JP | 2012-509259 A | 4/2012 |
| JP | 2012-100671 A | 5/2012 |
| JP | 2013-500253 A | 1/2013 |
| JP | 2013-534535 A | 9/2013 |
| JP | 2013-534906 A | 9/2013 |
| KR | 10-2001-0052385 A | 6/2001 |
| KR | 10-2011-0044808 A | 4/2011 |
| RU | 2404810 C2 | 7/2008 |
| TW | 1232930 | 5/2005 |
| TW | 200817434 A | 4/2008 |
| WO | WO-97/46260 A1 | 12/1997 |
| WO | WO-00/25825 A1 | 5/2000 |
| WO | WO-01/00244 A2 | 1/2001 |
| WO | WO-02/00734 A1 | 1/2002 |
| WO | WO-03/015826 A1 | 2/2003 |
| WO | WO-03/043583 A2 | 5/2003 |
| WO | WO-2005/112919 A2 | 12/2005 |
| WO | WO-2006/065533 A2 | 6/2006 |
| WO | WO-2006/092230 A2 | 9/2006 |
| WO | WO-2007/100385 A2 | 9/2007 |
| WO | WO-2008/144891 A1 | 12/2008 |
| WO | WO-2010/136569 A1 | 12/2010 |
| WO | WO-2011/011474 A1 | 1/2011 |
| WO | WO-2011/068845 A1 | 6/2011 |
| WO | WO-2011/145744 A1 | 11/2011 |
| WO | WO-2011/155579 A1 | 12/2011 |
| WO | WO-2012/019024 A2 | 2/2012 |
| WO | WO-2012/064733 A2 | 5/2012 |
| WO | WO-2013/068946 A2 | 5/2013 |
| WO | WO-2013/077458 A1 | 5/2013 |
| WO | WO-2013/163229 A1 | 10/2013 |
| WO | WO-2013/188740 A1 | 12/2013 |
| WO | WO-2014/057687 A1 | 4/2014 |
| WO | WO-2014061277 A1 | 4/2014 |
| WO | WO-2014/107024 A1 | 7/2014 |

OTHER PUBLICATIONS

Blok et al (Clinical Medicine Insights: Oncology 2013 7:41-51).*
Hurvitz et al (Cancer Treatment Reviews, 39:219-229, 2013).*
Russian Office Action dated Mar. 5, 2019 in corresponding application No. 2016143351.
Sievers et al, Antibody-Drug Conjugates in Cancer Therapy, Annual Review of Medicine, 2013, vol. 64, No. 1, pp. 15-29.
United States Office Action dated Apr. 5, 2019 in U.S. Appl. No. 15/821,697.
Acchione et al, Impact of linker and conjugation chemistry on antigen binding, Fc receptor binding and thermal stability of model antibody-drug conjugates, mAbs, 2012, pp. 362-372.
Colombian Reconsideration Petition dated Mar. 15, 2018 in corresponding application No. NC2016/0000187.

(56) References Cited

OTHER PUBLICATIONS

Rowinsky, Preclinical and Clinical Development of Exatecan(DX-8951f), Camptothecins in Cancer Therapy, 2005, pp. 317-318.
Adams et al., "Humanization of a recombinant monoclonal antibody to produce a therapeutic HER dimerization inhibitor, pertuzumab," Cancer Immunol. Immunother. 55:717-727 (2006).
Alley et al., "Antibody-drug conjugates: targeted drug delivery for cancer," Current Opinion in Chemical Biology 14:529-537 (2010).
Barginear et al., "Trastuzumab-DM1: A Review of the Novel Immuno-Conjugate for HER2-Overexpressing Breast Cancer," The Open Breast Cancer Journal 1:25-30 (2009).
Baselga et al., "Phase II Study of Weekly Intravenous Recombinant Humanized Anti-p185$^{HER2}$ Monoclonal Antibody in Patients with HER2/neu-Overexpressing Metastatic Breast Cancer," J. Clin. Oncol. 14(3):737-744 (Mar. 1996).
Beck, Alain, "The Next Generation of Antibody-drug Conjugates Comes of Age," Discov. Med. 10(53):329-339 (Oct. 16, 2010).
Burke, P.J. et al., "Design, Synthesis, and Biological Evaluation of Antibody—Drug Conjugates Comprised of Potent Camptothecin Analogues", Bioconjugate Chemistry, Jun. 17, 2009, 20(6):1242-1250.
Burris, III et al., "Phase II Study of the Antibody Drug Conjugate Trastuzumab-DM1 for the Treatment of Human Epidermal Growth Factor Receptor 2 (HER2)—Positive Breast Cancer After Prior HER2-Directed Therapy," J. Clin. Oncol. 29(4):398-405 (Feb. 2011).
Thomas M. Cardillo, "Humanized Anti-Trop-2 IgG-SN-38 Conjugate for Effective Treatment of Diverse Epithelial Cancers: Preclinical Studies in Human Cancer Xenograft Models and Monkeys," Clinical Cancer Research vol. 17, No. 10, Mar. 3, 2011, pp. 3157-3169.
Coussens et al., "Tyrosine Kinase Receptor with Extensive Homology to EGF Receptor Shares Chromosomal Location with neu Oncogene," Science 230(4730):1132-1139 (Dec. 1985).
Damle, Nitin K., "Tumour-targeted chemotherapy with immunoconjugates of calicheamicin," Expert Opin. Biol. Ther. 4(9):1445-1452 (2004).
De Jager et al., "DX-8951f: Summary of Phase I Clinical Trials," Ann. N.Y. Acad. Sci. 922:260-273 (2000).
Di Fiore et al., "erbB-2 Is a Potent Oncogene When Overexpressed in NIH/3T3 Cells," Science 237:178-182 (Jul. 1987).
Ducry et al., "Antibody—Drug Conjugates: Linking Cytotoxic Payloads to Monoclonal Antibodies," Bioconjugate Chem. 21:5-13 (2010).
Esteva et al., "A Phase II Study of Intravenous Exatecan Mesylate (DX-8951f) Administered Daily for 5 Days Every 3 Weeks to Patients with Metastatic Breast Carcinoma", American Cancer Society, 2003, 900-907.
Fendly et al., "Characterization of Murine Monoclonal Antibodies Reactive to Either the Human Epidermal Growth Factor Receptor or HER2/neu Gene Product," Cancer Research 50:1550-1558 (1990).
Fukushige et al., "Localization of a Novel v-erbB-Related Gene, c-erbB-2, on Human Chromosome 17 and Its Amplification in a Gastric Cancer Cell Line," Mol. Cell. Biol. 6(3):955-958 (1986).
Graus-Porta et al., "ERbB-2, the preferred heterodimerization partner of all ErbB receptors, is a mediator of lateral signaling," EMBO J. 16(7):1647-1655 (1997).
Gravalos et al., "HER2 in gastric cancer: a new prognostic factor and a novel therapeutic target," Ann. Oncol. 19:1523-1529 (2008).
Hardwick et al., "Immunohistochemical detection of p53 and c-erbB-2 in oesophageal carcinoma; no correlation with prognosis," Eur. J. Surg. Oncol. 23:30-35 (1997).
Hudis, M.D., Clifford A., "Trastuzumab—Mechanism of Action and Use in Clinical Practice," N. Engl. J. Med. 357(1):39-51 (2007).
Hudziak et al., "Increased expression of the putative growth factor receptor p185$^{HER2}$ causes transformation and tumorigenesis of NIH 3T3 cells," Proc. Natl. Acad. Sci. USA 84:7159-7163 (1987).
Inoue et al., "CM-Dextran-Polyalcohol-Camptothecin Conjugate: DE-310 with a Novel Carrier System and Its Preclinical Data," Polymer Drugs in the Clinical Stage, 145-153 (2003).
Joto et al., "DX-8951F, a Water-Soluble Camptothecin Analog, Exhibits Potent Antitumor Activity Against a Human Lung Cancer Cell Line and its SN-38-Resistant Variant," Int. J. Cancer 72:680-686 (1997).
Kaptain et al., "Her-2/neu and Breast Cancer," Diagn. Mol. Pathol. 10(3):139-152 (2001).
Karunagaran et al., "ErbB-2 is a common auxiliary subunit of NDF and EGF receptors: implications for breast cancer," EMBO J. 15(2):254-264 (1996).
Korkaya et al., "HER2 regulates the mammary stem/progenitor cell population driving tumorigenesis and invasion," Oncogene 27:6120-6130 (2008).
Kumazawa et al., "Antitumor activity of DX-8951f: a new camptothecin derivative," Exp. Opin. Invest. Drugs 7(4):625-632 (1998).
Kumazawa et al., "Potent and broad antitumor effects of DX-8951f, a water-soluble camptothecin derivative, against various human tumors xenografted in nude mice," Cancer Chemother. Pharmacol. 42:210-220 (1998).
Kumazawa et al., "DE-310, a novel macromolecular carrier system for the camptothecin analog DX-8951f: Potent antitumor activities in various murine tumor models," Cancer Sci. 95(2):168-175 (Feb. 2004).
Masucuchi, "Pharmacokinetics of DE-310, a novel macromolecular carrier system for the camptothecin analog DX-8951f, in tumor-bearing mice," Pharmazie 59: 374-377 (2004).
Mitsui et al., "A New Water-soluble Camptothecin Derivative, DX-8951f, Exhibits Potent Antitumor Activity against Human Tumors in vitro and in vivo," Jpn. J. Cancer Res. 86:776-782 (Aug. 1995).
Nakada et al., "Novel antibody drug conjugates containing exatecan derivative-based cytotoxic payloads," Bioorganic & Medical Chemistry Letters 26(6):1542-1545 (2016).
Ochi, "A possible mechanism for the long-lasting antitumor effect of the macromolecular conjugate DE-310: mediation by cellular uptake and drug release of its active camptothecin analog DX-8951," Cancer Chemother Pharmacol (2005) 55: 323-332.
Senter et al., "The discovery and development of brentuximab vedotin for use in relapsed Hodgkin lymphoma and systemic anaplastic large cell lymphoma," Nature Biotechnology 30(7):631-637 (Jul. 2012).
Shiose, "Systematic Research of Peptide Spacers Controlling Drug Release from Macromolecular Prodrug System, Carboxymethyldextran Polyalcohol-Peptide-Drug Conjugates," Bioconjugate Chem. 20, 60-70 (2009).
Slamon et al., "Human Breast Cancer: Correlation of Relapse and Survival with Amplification of the HER-2/neu Oncogene," Science 235:177-182 (1987).
Slamon et al., "Studies of the HER-2/neu Proto-oncogene in Human Breast and Ovarian Cancer," Science 244:707-712 (1989).
Sliwkowski et al., "Coexpression of erbB2 and erbB3 Proteins Reconstitutes a High Affinity Receptor for Heregulin." J. Biol. Chem. 269(20):14661-14665 (1994).
Sliwkowski et al., "Nonclinical Studies Addressing the Mechanism of Action of Trastuzumab (Herceptin)," Semin. Oncol. 26(4) Suppl. 12: 60-70 (Aug. 1999).
Soepenberg, "Liquid chromatographic assays for DE-310, a novel camptothecin analog, and two major enzymatic products in human matrices," Journal of Chromatography B, 799, 15-22 (2004).
Soepenberg et al., "Phase I and Pharmacokinetic Study of DE-310 in Patients with Advanced Solid Tumors," Clin. Cancer Res. 11:703-711 (Jan. 15, 2005).
Takiguchi et al., "Antitumor Effect of DX-8951, a Novel Camptothecin Analog, on Human Pancreatic Tumor Cells and Their CPT-11-resistant Variants Cultured in vitro and Xeografted in Nude Mice," Jpn. J. Cancer Res. 88:760-769 (Aug. 1997).
Vogel et al., "Efficacy and Safety of Trastuzumab as a Single Agent in First-Line Treatment of HER2-Overexpressing Metastatic Breast Cancer," J. Clin. Oncol. 20(3):719-726 (Feb. 2002).
Wente et al., "DE-310, a macromolecular prodrug of the topoisomerase-I-inhibitor exatecan (DX-8951), in patients with operable solid tumors," Investigational New Drugs 23:339-347 (2005).

(56) References Cited

OTHER PUBLICATIONS

Yano et al., "Comparison of HER2 gene amplification assessed by fluorescence in situ hybridization and HER2 protein expression assessed by immunohistochemistry in gastric cancer," Oncol. Rep. 15:65-71 (2006).
International Search Report issued in International Patent Application No. PCT/JP2015/000355 dated Apr. 21, 2015.
Non-Final Office Action issued in U.S. Appl. No. 14/436,458 dated Jul. 19, 2016.
Non-Final Office Action issued in U.S. Appl. No. 14/435,114 dated Jul. 21, 2016.
Non-Final Office Action issued in U.S. Appl. No. 15/180,203 dated Jul. 25, 2016.
Non-Final Office Action issued in U.S. Appl. No. 15/187,179 dated Oct. 21, 2016.
Decision to Grant issued in Japanese Patent Application No. 2016-166850 dated Oct. 18, 2016.
Office Action issued in Chinese Patent Application No. 201380053256.2 dated Nov. 1, 2016.
Office Action issued in Japanese Patent Application No. 2016-540705 dated Dec. 6, 2016.
Office Action issued in Canada Application No. 2885800 dated Mar. 28, 2017.
Office Action issued in Colombia Application No. NC2016/0000187 dated May 9, 2017.
European Search Report issued in corresponding U.S. Appl. No. 14/874,745 dated May 10, 2017.
Office Action issued in Taiwanese Patent Application No. 102136742 dated May 15, 2017.
Non-Final Office Action issued in U.S. Appl. No. 15/221,851 dated Jul. 7, 2017.
European Search Report issued in corresponding application No. 15743738.5 dated Aug. 9, 2017.
European Search Report issued in corresponding application No. 15776810.2 dated Aug. 11, 2017.
Final Office Action issued in U.S. Appl. No. 15/221,851 dated Nov. 13, 2017.
Office Action in corresponding application No. PCT/JP2017/036215 dated Nov. 21, 2017.
Allowance issued in connection with Taiwanese Patent Application No. 104103127, dated Apr. 11, 2018.
Office Action issued in connection with Canadian Patent Application No. 2,939,802, dated Apr. 13, 2018.
Notice of Grounds for Rejection issued in connection with Korean Patent Application No. 10-2016-7015961, dated May 1, 2018.
Notice of Allowance issued in U.S. Appl. No. 15/221,851 dated Jun. 13, 2018.
Behrens et al, Methods for site-specific drug conjugation to antibodies, mAbs, 2014, vol. 6, No. 1. pp. 46-53.
Shen et al, Conjugation site modulates the in vivo stability and therapeutic activity of antibody-drug conjugates, Nature Biotechnology, 2012, vol. 30, pp. 184-189.
Taiwanese Office Action dated Jul. 30, 2018 in corresponding application No. 104111534.
Australian Intellectual Property Office, "Examination Report No. 2 for Standard Patent Application," Australian Patent Application No. 2014371934, dated Sep. 13, 2019.
Basu et al., "The Epithelial/Carcinoma Antigen EGP-1 Recognized by Monoclonal Antibody RS7-3G11, is Phosphorylated on Serine 303," Int. J. Cancer 62(4):472-479 (1995).
Calabrese et al., "Assignment of TACSTD1 (alias TROP1, M4S1)to human chromosome 2p21 and refinement of mapping of TACSTD2 (alias TROP2, M1S1) to human chromosome 1p32 by in situ hybridization," Cytogenet Cell Genet. 92(1-2):164-165 (2001).
Chinese Office Action issued to corresponding App. No. 201480071134.0—dated Aug. 20, 2019 (5 pages).
El Sewedy et al., "Cloning of the Murine Trop2 Gene: Conservation of a PIP2-Binding Sequence in the Cytoplasmic Domain of Trop-2," Int. J. Cancer 75(2):324-330 (1998).

Faulk et al., "Antigens of human trophoblasts: A working hypothesis for their role in normal and abnormal pregnancies," Proc. Natl. Acad. Sci. USA 75(4):1947-1951 (1978).
Fong et al., "High expression of TROP2 correlates with poor prognosis in pancreatic cancer," Br. J. Cancer 99(8):1290-1295 (2008).
Fong et al., "TROP2: a novel prognostic marker in squamous cell carcinoma of the oral cavity," Mod. Pathol. 21(2):186-191 (2008).
Fornaro et al., "Cloning of the Gene Encoding Trop-2, a Cell-Surface Glycoprotein Expressed by Human Carcinomas," Int. J. Cancer 62(5):610-618 (1995).
International Search Report for corresponding Application No. PCT/JP2014/006421 dated Mar. 17, 2015.
Linnenbach et al., "Sequence investigation of the major gastrointestinal tumor-associated antigen gene family, GA733," Proc. Natl. Acad. Sci. 86(1):27-31 (Jan. 1989).
Lipinski et al., "Human trophoblast cell-surface antigens defined by monoclonal antibodies," Proc. Natl. Acad. Sci. 78(8):5147-5150 (Aug. 1981).
Mühlmann et al., "TROP2 expression as prognostic marker for gastric carcinoma," J. Clin. Pathol. 62(2):152-158 (2009).
Ning et al., "TROP2 expression and its correlation with tumor proliferation and angiogenesis in human gliomas," Neurol. Sci. 34(10):1745-1750 (2013).
Ohmachi et al., "Clinical Significance of TROP2 Expression in Colorectal Cancer," Clin. Cancer Res. 12(10):3057-3063 (May 15, 2006).
Ripani et al., "Human Trop-2 is a Tumor-Associated Calcium Signal Transducer," Int. J. Cancer 76(5):671-676 (1998).
Stepan et al., "Expression of Trop2 Cell Surface Glycoprotein in Normal and Tumor Tissues: Potential Implications as a Cancer Therapeutic Target," Journal of Histochemistry & Cytochemistry vol. 59, No. 7, pp. 701-710.
Wang et al., "Identification of Trop-2 as an oncogene and an attractive therapeutic target in colon cancers," Mol. Cancer Ther. 7(2):280-285 (Feb. 2008).
IN Office Action issued in the corresponding Indian Patent Application Ser. No. 201647013640, dated Jul. 19, 2019.
Russian Office Action dated Oct. 11, 2018 in corresponding application No. 2016123597.
Barok et al, Trastuzumab-DM1 is highly effective in preclinical models of HER2-positive gastric cancer, Cancer Letters, 2011, vol. 306, No. 2, pp. 172-179.
Oguma et al, Validation study of a method for assaying DE-310, a macromolecular carrier conjugate containing an anti-tumor camptothecin derivative, and the free drug in tumor tissue by high performance liquid chromatography/atmospheric pressure chemical ionization tandem mass spectrometry, Biomedical Chromatography, 2005, vol. 19, No. 1, pp. 19-26.
Chinese Search Report dated Jun. 24, 2020 for corresponding Application No. 108114649.
Shiose et al., "Relationship between Drug Release of DE-310, Macromolecular Prodrug of DX-8951f, and Cathepsins Activity in Several Tumors," Biol. Pharm. Bull., vol. 30, Issue 12, 2007, pp. 2365-2370.
English language Translation of the "Written Opinion," issued in connection with Brazilian Patent Application No. 112016013482-6, dated Apr. 8, 2021.
English language Translation of the "Written Opinion," issued in connection with Brazilian Patent Application No. 122020020973-9, dated Apr. 8, 2021.
English language Translation of the "Written Opinion," issued in connection with Brazilian Patent Application No. 112015006521-0, dated Apr. 16, 2021.
Baselga, J., et al., "Recombinant Humanized Anti-HER2 Antibody (Herceptin TM) Enhances the Antitumor Activity of Paclitacel and Doxorubicin against HER2/neu Overexpressing Human Breast Cancer Xenografts," Cancer Research, 58:2825-2831 (1998).
Hotaling, T.E., et al., "The humanized anti-HER2 antibody rhuMAb HER2 mediates antibody dependent cell-mediated cytotoxicity via FcyR III," [Abstract], Proc. Annual Meeting Am Assoc Cancer Res, 37:471 (1996).

(56) References Cited

OTHER PUBLICATIONS

Hudziak, R.M., et al., "p185HER2 Monoclonal Antibody Has Antiproliferative Effects In Vitro and Sensitizes Human Breast Tumor Cells to Tumor Necrosis Factor," Molecular and Cellular Biology, 9(3):1165-1172 (1989).
Lewis, G.D., et al., "Differential responses of human tumor cell lines to anti-p185HER2 monoclonal antibodies," Cancer Immunology Immunotherapy, 37:255-263 (1993).
Office Action issued in corresponding Egyptian Patent Application No. PCT1073/2016 dated Jan. 3, 2022 (English summary included).
Pegram, M.D., et al., "Antibody dependent cell-mediated cytotoxicity in breast cancer patients in Phase III clinical trials of a humanized anti-HER2 antibody," [Abstract], Proc Am Assoc Cancer Res, 38:602 (1997).
Sliwkowski, M.X., et al., "Nonclinical Studies Addressing the Mechanism of Action of Trastuzumab (Herceptin)," Seminars in Oncology, 26(4):60-70, Suppl. 12 (1999).
Yarden, Y., et al., "Untangling the ErbB Signalling Network," Nature Reviews, Molecular Cell Biology, Macmillan Magazines Ltd., 2:127-137 (2001).
Abstract of Davoli, et al., "Progression and treatment of HER2-positive breast cancer", Cancer Chemother Pharmacol. 65(4): 611-23 (2010).
Callahan and Hurvitz, "HER2-Positive Breast Cancer: Current Management of Early, Advanced, and Recurrent Disease", Curr Opin Obstet Gynecol. 23(1): 37-43 (2011).
Dosio et al., "Antibody-targeted leucinostatin A", Journal of Controlled Release, No. 32, (1994), pp. 37-44.
Giridhar, "HER2-positive breast cancer: What is it?", Mayo Clinic, Mayo Foundation for Medical Education and Research (2020).
Indian Intellectual Property Office, "Office Action," issued in connection with Indian Patent Application No. 202018030127, dated Nov. 29, 2021.
McDonagh et al., "Engineered antibody-drug conjugates with defined sites and stoichiometries of drug attachment," Protein Engineering, Design & Selection, 2006, 19(7):299-307.
Office Action dated Sep. 16, 2021 issued in a corresponding Australian Patent Application No. 2020200548, (15 pages).
Russian Patent Office, "Office Action," issued in connection with Russian Patent Application No. 2018128384/04(045536), dated Dec. 20, 2021.
Tian et al., "A general approach to site-specific antibody drug conjugates," PNAS, vol. 111, No. 5, Feb. 4, 2014, pp. 1766-1771.

\* cited by examiner

FIG.1

SEQ ID NO: 1 - Amino acid sequence of heavy chain of humanized anti-HER2 monoclonal antibody EVQLVESGGGLVQPGGSLRLSCAASGFNIKDTYIHWVRQAPGKGLEWVARIYPTNGYTRYADSV
KGRFTISADTSKNTAYLQMNSLRAEDTAVYYCSRWGGDGFYAMDYWGQGTLVTVSSASTKGPSV
FPLAPSSKSTSGGTAALGCLVKDYFPEPVTVSWNSGALTSGVHTFPAVLQSSGLYSLSSVVTVP
SSSLGTQTYICNVNHKPSNTKVDKKVEPKSCDKTHTCPPCPAPELLGGPSVFLFPPKPKDTLMI
SRTPEVTCVVVDVSHEDPEVKFNWYVDGVEVHNAKTKPREEQYNSTYRVVSVLTVLHQDWLNGK
EYKCKVSNKALPAPIEKTISKAKGQPREPQVYTLPPSREEMTKNQVSLTCLVKGFYPSDIAVEW
ESNGQPENNYKTTPPVLDSDGSFFLYSKLTVDKSRWQQGNVFSCSVMHEALHNHYTQKSLSLSP
GK

FIG.2

SEQ ID NO: 2 - Amino acid sequence of light chain of humanized anti-HER2 monoclonal antibody DIQMTQSPSSLSASVGDRVTITCRASQDVNTAVAWYQQKPGKAPKLLIYSASFLYSGVPSRFSG
SRSGTDFTLTISSLQPEDFATYYCQQHYTTPPTFGQGTKVEIKRTVAAPSVFIFPPSDEQLKSG
TASVVCLLNNFYPREAKVQWKVDNALQSGNSQESVTEQDSKDSTYSLSSTLTLSKADYEKHKVY
ACEVTHQGLSSPVTKSFNRGEC

SEQUENCE LISTING

```
<160> NUMBER OF SEQ ID NOS: 13

<210> SEQ ID NO 1
<211> LENGTH: 450
<212> TYPE: PRT
<213> ORGANISM: Artificial Sequence
<220> FEATURE:
<223> OTHER INFORMATION: Description of Artificial Sequence: Synthetic
      heavy chain of Trastuzumab polypeptide
```

<400> SEQUENCE: 1

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415
```

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
            435                 440                 445

Gly Lys
    450

<210> SEQ ID NO 2
<211> LENGTH: 214
<212> TYPE: PRT
<213> ORGANISM: Artificial Sequence
<220> FEATURE:
<223> OTHER INFORMATION: Description of Artificial Sequence: Synthetic
      light chain of Trastuzumab polypeptide

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Gly Gly Phe Gly
1

<210> SEQ ID NO 4

```
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Glu Gly Gly Phe
1

<210> SEQ ID NO 5
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Ser Gly Gly Phe
1

<210> SEQ ID NO 6
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Lys Gly Gly Phe
1

<210> SEQ ID NO 7
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Gly Gly Phe Gly Gly
1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Gly Gly Phe Gly Gly Gly Phe
1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 9
```

```
His His His His His His
1               5

<210> SEQ ID NO 10
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Asp Gly Gly Phe
1

<210> SEQ ID NO 11
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Asp Gly Gly Phe Gly
1               5

<210> SEQ ID NO 12
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 12

Asp Asp Gly Gly Phe Gly
1               5

<210> SEQ ID NO 13
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 13

Lys Asp Gly Gly Phe Gly
1               5
```

METHOD FOR TREATING CANCER COMPRISING ADMINISTRATION OF ANTI-HER2 ANTIBODY-DRUG CONJUGATE

CROSS-REFERENCE TO RELATED APPLICATIONS

This application is a divisional of U.S. patent application Ser. No. 15/221,851 filed on Jul. 28, 2016, which is a continuation application filed under 35 U.S.C. § 111(a) claiming the benefit under 35 U.S.C. §§ 120 and 365(c) of International Application No. PCT/JP2015/000355 filed on Jan. 28, 2015, which is based upon and claims the benefit of priority of Japanese Patent Application No. 2014-017777, filed on Jan. 31, 2014, Japanese Patent Application No. 2014-168944, filed on Aug. 22, 2014, and Japanese Patent Application No. 2014-227886, filed on Nov. 10, 2014, the contents of which are hereby incorporated by reference in their entireties.

SEQUENCE LISTING

The instant application contains a Sequence Listing which has been submitted electronically in ASCII format and is hereby incorporated by reference in its entirety. Said ASCII copy, created on Feb. 28, 2017, is named 111119-0105_SL.txt and is 8,545 bytes in size.

TECHNICAL FIELD

The present invention relates to an antibody-drug conjugate having an antitumor drug conjugated to an anti-HER2 antibody via a linker structure moiety, the conjugate being useful as an antitumor drug.

BACKGROUND ART

An antibody-drug conjugate (ADC) having a drug with cytotoxicity conjugated to an antibody, whose antigen is expressed on the surface of cancer cells and which also binds to an antigen capable of cellular internalization, and therefore can deliver the drug selectively to cancer cells, is thus expected to cause accumulation of the drug within cancer cells and to kill the cancer cells (see, Non-patent Literatures 1 to 3). As an ADC, Mylotarg (registered trademark; Gemtuzumab ozogamicin) in which calicheamicin is conjugated to an anti-CD33 antibody is approved as a therapeutic agent for acute myeloid leukemia. Further, Adcetris (registered trademark; Brentuximab vedotin), in which auristatin E is conjugated to an anti-CD30 antibody, has recently been approved as a therapeutic agent for Hodgkin's lymphoma and anaplastic large cell lymphoma (see, Non-patent Literature 4). The drugs contained in ADCs which have been approved until now target DNA or tubulin.

With regard to an antitumor agent, camptothecin derivatives, low-molecular-weight compounds that inhibit topoisomerase I to exhibit an antitumor effect, are known. Among these, an antitumor compound represented by the formula below

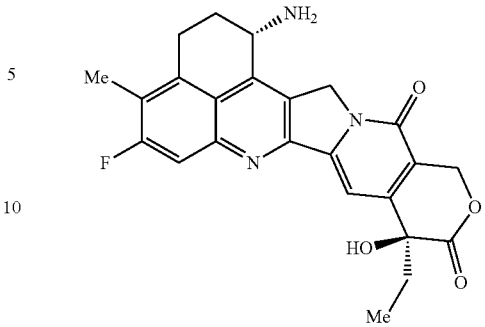

[Formula 1]

(exatecan, chemical name: (1S,9S)-1-amino-9-ethyl-5-fluoro-2,3-dihydro-9-hydroxy-4-methyl-1H,12H-benzo[de]pyrano[3',4':6,7]indolizino[1,2-b]quinolin-10,13(9H,15H)-dione) is a water soluble derivative of camptothecin (Patent Literatures 1 and 2). Unlike irinotecan currently used in clinical settings, this compound does not require activation by an enzyme for exhibiting its antitumor effect. Further, its inhibitory activity on topoisomerase I was observed to be higher than SN-38 which is the main pharmaceutically active substance of irinotecan and topotecan also used in clinical settings, and higher in vitro cytocidal activity was confirmed against various cancer cells. In particular, it was confirmed to have the effect against cancer cells that have resistance to SN-38 or the like due to expression of P-glycoprotein. Further, in a human tumor subcutaneously transplanted mouse model, it was confirmed to have a potent antitumor effect, and thus has undergone clinical studies, but has not been placed on the market yet (see, Non-patent Literatures 5 to 10). It remains unclear whether or not exatecan acts effectively as an ADC.

DE-310 is a complex in which exatecan is conjugated to a biodegradable carboxymethyldextran polyalcohol polymer via a GGFG peptide spacer (SEQ ID NO: 3) (Patent Literature 3). By converting exatecan into the form of a polymer prodrug, a high blood retention property can be maintained and also a high targeting property to tumor areas is passively increased by utilizing the increased permeability of newly formed blood vessels within tumors and retention property in tumor tissues. With DE-310, through cleavage of the peptide spacer by enzyme, exatecan and exatecan with glycine connected to an amino group are continuously released as main active substance, and as a result, the pharmacokinetics are improved. DE-310 was found to have higher effectiveness than exatecan administered alone even though the total dosage of exatecan contained in D310 is lower than in the case of administration of exatecan alone according to various tumor evaluation models in non-clinical studies. A clinical study was conducted for DE-310, and effective cases were also confirmed, including a report suggesting that the main active substance accumulates in tumors more than in normal tissues. However, there is also a report indicating that accumulation of DE-310 and the main active substance in tumors is not much different from accumulation in normal tissues in humans, and thus no passive targeting is observed in humans (see, Non-patent Literatures 11 to 14). As a result, DE-310 was not also commercialized, and it remains unclear whether or not exatecan effectively acts as a drug directed to such targeting.

As a compound relating to DE-310, a complex in which a structure moiety represented by —NH—$(CH_2)_4$—C(=O)— is inserted between the -GGFG- spacer (SEQ ID NO: 3) and exatecan to form -GGFG (SEQ ID NO: 3)-NH—$(CH_2)_4$—C(=O)— used as a spacer structure is also known (Patent Literature 4). However, the antitumor effect of said complex is not known at all.

HER2 is one of the products of a typical growth factor receptor type oncogene identified as human epidermal cell growth factor receptor 2-related oncogene, and is a transmembrane receptor protein having a molecular weight of 185 kDa and having a tyrosine kinase domain (Non-patent Literature 15). The DNA sequence and amino acid sequence of HER2 are disclosed on a public database, and can be referred to, for example, under Accession No. M11730 (GenBank), NP_004439.2 (NCBI), or the like.

HER2 (neu, ErbB-2) is one of the members of the EGFR (epidermal growth factor receptor) family and is activated by autophosphorylation at intracellular tyrosine residues by its homodimer formation or heterodimer formation with another EGFR receptor HER1 (EGFR, ErbB-1), HER3 (ErbB-3), or HER4 (ErbB-4) (Non-patent Literatures 16 to 18), thereby playing an important role in cell growth, differentiation, and survival in normal cells and cancer cells (Non-patent Literatures 19 and 20). HER2 is overexpressed in various cancer types such as breast cancer, gastric cancer, and ovarian cancer (Non-patent Literatures 21 to 26) and has been reported to be a negative prognosis factor for breast cancer (Non-patent Literatures 27 and 28).

Trastuzumab is a humanized antibody of a mouse anti-HER2 antibody 4D5 (Non-patent Literature 29 and Patent Literature 5), named as recombinant humanized anti-HER2 monoclonal antibody (huMAb4D5-8, rhuMAb HER2, Herceptin®) (Patent Literature 6). Trastuzumab specifically binds to the extracellular domain IV of HER2 and induces antibody-dependent cellular cytotoxicity (ADCC) or exerts an anticancer effect via the inhibition of signal transduction from HER2 (Non-patent Literatures 30 and 31). Trastuzumab is highly effective for tumors overexpressing HER2 (Non-patent Literature 32) and as such, was launched in 1999 in the USA and in 2001 in Japan as a therapeutic agent for patients with metastatic breast cancer overexpressing HER2.

Although the therapeutic effect of trastuzumab on breast cancer has been adequately proven (Non-patent Literature 33), allegedly about 15% of patients with breast cancer overexpressing HER2 who have received a wide range of conventional anticancer therapies are responders to trastuzumab. About 85% of patients of this population have no or merely weak response to trastuzumab treatment.

Thus, the need for a therapeutic agent targeting HER2 expression-related diseases has been recognized for patients affected by tumors overexpressing HER2 with no or weak response to trastuzumab or HER2-related disorders. T-DM1 (trastuzumab emtansine, Kadcyla®; Non-patent Literature 34) having an antitumor drug conjugated to trastuzumab via a linker structure, and pertuzumab (Perjeta®; Non-patent Literature 35 and Patent Literature 7) designed to target the extracellular domain II of HER2 and inhibit heterodimer formation have been developed. However, their responsiveness, activity strength, and accepted indications are still insufficient, and there are unsatisfied needs for targeting HER2.

CITATION LIST

Patent Literatures

[Patent Literature 1] Japanese Patent Laid-Open No. 5-59061
[Patent Literature 2] Japanese Patent Laid-Open No. 8-337584
[Patent Literature 3] International Publication No. WO 1997/46260
[Patent Literature 4] International Publication No. WO 2000/25825
[Patent Literature 5] U.S. Pat. No. 5,677,171
[Patent Literature 6] U.S. Pat. No. 5,821,337
[Patent Literature 7] International Publication No. WO 01/00244

Non-Patent Literatures

[Non-patent Literature 1] Ducry, L., et al., Bioconjugate Chem. (2010) 21, 5-13.
[Non-patent Literature 2] Alley, S. C., et al., Current Opinion in Chemical Biology (2010) 14, 529-537.
[Non-patent Literature 3] Damle N. K. Expert Opin. Biol. Ther. (2004) 4, 1445-1452.
[Non-patent Literature 4] Senter P. D., et al., Nature Biotechnology (2012) 30, 631-637.
[Non-patent Literature 5] Kumazawa, E., Tohgo, A., Exp. Opin. Invest. Drugs (1998) 7, 625-632.
[Non-patent Literature 6] Mitsui, I., et al., Jpn J. Cancer Res. (1995) 86, 776-782.
[Non-patent Literature 7] Takiguchi, S., et al., Jpn J. Cancer Res. (1997) 88, 760-769.
[Non-patent Literature 8] Joto, N. et al. Int J Cancer (1997) 72, 680-686.
[Non-patent Literature 9] Kumazawa, E. et al., Cancer Chemother. Pharmacol. (1998) 42, 210-220.
[Non-patent Literature 10] De Jager, R., et al., Ann N Y Acad Sci (2000) 922, 260-273.
[Non-patent Literature 11] Inoue, K. et al., Polymer Drugs in the Clinical Stage, Edited by Maeda et al. (2003) 145-153.
[Non-patent Literature 12] Kumazawa, E. et al., Cancer Sci (2004) 95, 168-175.
[Non-patent Literature 13] Soepenberg, O. et al., Clinical Cancer Research, (2005) 11, 703-711.
[Non-patent Literature 14] Wente M. N. et al., Investigational New Drugs (2005) 23, 339-347.
[Non-patent Literature 15] Coussens L, et al., Science. 1985; 230(4730):1132-1139.
[Non-patent Literature 16] Graus-Porta G, et al., EMBO J. 1997; 16; 1647-1655.
[Non-patent Literature 17] Karunagaran D, et al., EMBO J. 1996; 15:254-264.
[Non-patent Literature 18] Sliwkowski M X, et al., J. Biol. Chem. 1994; 269:14661-14665.
[Non-patent Literature 19] Di Fore P P, et al., Science. 1987; 237:178-182.
[Non-patent Literature 20] Hudziak R M, et al., Proc Natl Acad Sci USA. 1987; 84:7159-7163.
[Non-patent Literature 21] Hardwick R, et al., Eur. J Surg Oncol. 1997 (23):30-35.
[Non-patent Literature 22] Korkaya H, et al., Oncogene. 2008; 27 (47):6120-6130.
[Non-patent Literature 23] Yano T, et al., Oncol Rep. 2006; 15(1):65-71.
[Non-patent Literature 24] Slamon D J, et al., Science. 1987; 235:177-182.
[Non-patent Literature 25] Gravalos C, et al., Ann Oncol 19: 1523-1529, 2008.
[Non-patent Literature 26] Fukushige S et al., Mol Cell Biol 6: 955-958, 1986.

[Non-patent Literature 27] Slamon D J, et al. Science. 1989; 244:707-712.
[Non-patent Literature 28] Kaptain S et al., Diagn Mol Pathol 10:139-152, 2001.
[Non-patent Literature 29] Fendly. et al., Cancer Research 1990(50):1550-1558.
[Non-patent Literature 30] Sliwkowski M X, et al., Semin Oncol. 1999; 26(4, Suppl 12):60-70.
[Non-patent Literature 31] Hudis C A, et al., N Engl J Med. 357: 39-51, 2007.
[Non-patent Literature 32] Vogel C L, et al., J Clin Oncol. 2002; 20(3):719-726.
[Non-patent Literature 33] Baselga et al., J. Clin. Oncol. 14:737-744 (1996).
[Non-patent Literature 34] Burris III et al., J Clin Oncol 2011; 29:398-405.
[Non-patent Literature 35] Adams C W, et al., Cancer Immunol Immunother. 2006; 6:717-727.

SUMMARY OF INVENTION

Technical Problem

With regard to the treatment of tumors by antibodies, an insufficient antitumor effect may be observed even when the antibody recognizes an antigen to bind to tumor cells, and there are cases in which a more effective antitumor antibody is needed. Further, many antitumor low-molecular-weight compounds have problems in safety like side effects and toxicity even if the compounds have an excellent antitumor effect. It has remained an objective to achieve a superior therapeutic effect by further enhancing safety. Thus, an object of the present invention is to provide an antitumor drug having an excellent therapeutic effect, which is excellent in terms of antitumor effect and safety.

Solution to Problem

The inventors considered that an anti-HER2 antibody is an antibody which is capable of targeting tumor cells, that is, having a property of recognizing tumor cells, a property of binding to tumor cells, a property of internalizing within tumor cells, a cytotoxic activity against tumor cells, a cytocidal activity against tumor cells, or the like; thus, when the antitumor compound exatecan is converted into an antibody-drug conjugate, via a linker structure moiety, by conjugation to this antibody, the antitumor compound can be more surely delivered to tumor cells to specifically exhibit the antitumor effect of the compound in tumor cells, and thus the antitumor effect can be surely exhibited and also an enhanced cytocidal effect of the anti-HER2 antibody can be expected, and the dose of the antitumor compound can be reduced compared to the case of administering the compound alone, and thus influences of the antitumor compound on normal cells can be alleviated so that a higher safety can be achieved.

In this connection, the inventors created a linker with a specific structure and succeeded in obtaining an antibody-drug conjugate in which the anti-HER2 antibody and exatecan are conjugated to each other via the linker, and confirmed an excellent antitumor effect exhibited by the conjugate to thereby complete the present invention.

Specifically, the present invention relates to the following.
[1] An antibody-drug conjugate wherein an antitumor compound represented by the following formula:

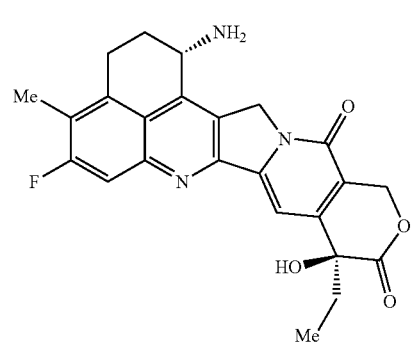

[Formula 2]

is conjugated to an anti-HER2 antibody via a linker having a structure represented by the following formula:

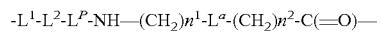

-L$^1$-L$^2$-L$^P$-NH—(CH$_2$)$n^1$-L$^a$-(CH$_2$)$n^2$-C(=O)— via a thioether bond which is formed at a disulfide bond moiety present in the hinge part of the anti-HER2 antibody.

Here, the anti-HER2 antibody is connected to the terminal L$^1$,
the antitumor compound is connected to the carbonyl group of the —(CH$_2$)n$^2$-C(=O)— moiety with the nitrogen atom of the amino group at position 1 as the connecting position, wherein
n$^1$ represents an integer of 0 to 6,
n$^2$ represents an integer of 0 to 5,
L$^1$ represents -(Succinimid-3-yl-N)—(CH$_2$)n$^3$-C(=O)—, wherein n$^3$ represents an integer of 2 to 8,
L$^2$ represents —NH—(CH$_2$CH$_2$—O)n$^4$-CH$_2$CH$_2$—C(=O)— or a single bond,
wherein n$^4$ represents an integer of 1 to 6,
L$^P$ represents a peptide residue consisting of 2 to 7 amino acids,
L$^a$ represents —O— or a single bond, and
-(Succinimid-3-yl-N)— has a structure represented by the following formula:

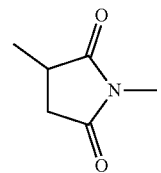

[Formula 3]

which is connected to the anti-HER2 antibody at position 3 thereof and is connected to the methylene group in the linker structure containing this structure on the nitrogen atom at position 1.

The present invention further relates to each of the following.
[2] The antibody-drug conjugate according to [1], wherein the peptide residue L$^P$ is a peptide residue comprising an amino acid selected from phenylalanine, glycine, valine, lysine, citrulline, serine, glutamic acid, and aspartic acid.
[3] The antibody-drug conjugate according to [1] or [2], wherein L$^P$ is a peptide residue selected from the following group:

-GGF-, (SEQ ID NO: 10)

```
    -DGGF-,

-(D-)D-GGF-,       (SEQ ID NO: 4)
    -EGGF-,

-GGFG-,            (SEQ ID NO: 3)

-SGGF-,            (SEQ ID NO: 5)

-KGGF-,            (SEQ ID NO: 6)

-DGGFG-,           (SEQ ID NO: 11)

-GGFGG-,           (SEQ ID NO: 7)

-DDGGFG-,          (SEQ ID NO: 12)

-KDGGFG-,          (SEQ ID NO: 13)
    and

-GGFGGGF-;         (SEQ ID NO: 8)
``` wherein "(D-)D" represents D-aspartic acid.

[4] The antibody-drug conjugate according to [1] or [2], wherein $L^P$ is a peptide residue consisting of 4 amino acids.

[5] The antibody-drug conjugate according to any one of [1] to [4], wherein $L^P$ is the tetrapeptide residue -GGFG (SEQ ID NO: 3)-.

[6] The antibody-drug conjugate according to any one of [1] to [5], wherein $n^3$ is an integer of 2 to 5, and $L^2$ is a single bond.

[7] The antibody-drug conjugate according to any one of [1] to [5], wherein $n^3$ is an integer of 2 to 5, $L^2$ is —NH—$(CH_2CH_2$—O$)n^4$-$CH_2CH_2$—C(=O)—, and $n^4$ is 2 or 4.

[8] The antibody-drug conjugate according to any one of [1] to [7], wherein —NH—$(CH_2)n^1$-$L^a$-$(CH_2)n^2$-C(=O)— is a partial structure having a chain length of 4 to 7 atoms.

[9] The antibody-drug conjugate according to any one of [1] to [7], wherein —NH—$(CH_2)n^1$-$L^a$-$(CH_2)n^2$-C(=O)— is a partial structure having a chain length of 5 or 6 atoms.

[10] The antibody-drug conjugate according to any one of [1] to [9], wherein —NH—$(CH_2)n^1$-$L^a$-$(CH_2)n^2$-C(=O)— is
—NH—$CH_2CH_2$—C(=O)—,
—NH—$CH_2CH_2CH_2$—C(=O)—,
—NH—$CH_2CH_2CH_2CH_2$—C(=O)—,
—NH—$CH_2CH_2CH_2CH_2CH_2$—C(=O)—,
—NH—$CH_2$—O—$CH_2$—C(=O)—,
—NH—$CH_2CH_2$—O—$CH_2$—C(=O)—, or
—NH—$CH_2CH_2$—O—C(=O)—.

[11] The antibody-drug conjugate according to any one of [1] to [9], wherein —NH—$(CH_2)n^1$-$L^a$-$(CH_2)n^2$-C(=O)— is
—NH—$CH_2CH_2CH_2$—C(=O)—,
—NH—$CH_2$—O—$CH_2$—C(=O)—, or
—NH—$CH_2CH_2$—O—$CH_2$—C(=O)—.

[12] The antibody-drug conjugate according to any one of [1] to [9], wherein the drug-linker structure moiety having the drug connected to -$L^1$-$L^2$-$L^P$-NH—$(CH_2)n^1$-$L^a$-$(CH_2)n^2$-C(=O)— is one drug-linker structure selected from the following group:
-(Succinimid-3-yl-N)—$CH_2CH_2$—C(=O)-GGFG (SEQ ID NO: 3)-NH—$CH_2CH_2$—C(=O)—(NH-DX),
-(Succinimid-3-yl-N)—$CH_2CH_2$—C(=O)-GGFG (SEQ ID NO: 3)-NH—$CH_2CH_2CH_2$—C(=O)—(NH-DX),
-(Succinimid-3-yl-N)—$CH_2CH_2CH_2CH_2CH_2$—C(=O)-GGFG (SEQ ID NO: 3)-NH—$CH_2CH_2$—C(=O)—(NH-DX),
-(Succinimid-3-yl-N)—$CH_2CH_2CH_2CH_2CH_2$—C(=O)-GGFG (SEQ ID NO: 3)-NH—$CH_2CH_2CH_2$—C(=O)—(NH-DX),
-(Succinimid-3-yl-N)—$CH_2CH_2CH_2CH_2CH_2$—C(=O)-GGFG (SEQ ID NO: 3)-NH—$CH_2CH_2CH_2CH_2CH_2$—C(=O)—(NH-DX),
-(Succinimid-3-yl-N)—$CH_2CH_2CH_2CH_2CH_2$—C(=O)-GGFG (SEQ ID NO: 3)-NH—$CH_2$—O—$CH_2$—C(=O)—(NH-DX),
-(Succinimid-3-yl-N)—$CH_2CH_2CH_2CH_2CH_2$—C(=O)-GGFG (SEQ ID NO: 3)-NH—$CH_2CH_2$—O—$CH_2$—C(=O)—(NH-DX),
-(Succinimid-3-yl-N)—$CH_2CH_2CH_2CH_2CH_2$—C(=O)-GGFG (SEQ ID NO: 3)-NH—$CH_2CH_2$—O—C(=O)—(NH-DX),
-(Succinimid-3-yl-N)—$CH_2CH_2$—C(=O)—NH—$CH_2CH_2$—O—$CH_2CH_2$—O—$CH_2CH_2$—C(=O)-GGFG (SEQ ID NO: 3)-NH—$CH_2CH_2$—C(=O)— (NH-DX),
-(Succinimid-3-yl-N)—$CH_2CH_2$—C(=O)—NH—$CH_2CH_2$—O—$CH_2CH_2$—O—$CH_2CH_2$—C(=O)-GGFG (SEQ ID NO: 3)-NH—$CH_2CH_2CH_2$—C(=O)—(NH-DX),
-(Succinimid-3-yl-N)—$CH_2CH_2$—C(=O)—NH—$CH_2CH_2$—O—$CH_2CH_2$—O—$CH_2CH_2$—O—$CH_2CH_2$—O—$CH_2CH_2$—C(=O)-GGFG (SEQ ID NO: 3)-NH—$CH_2CH_2$—C(=O)—(NH-DX),
-(Succinimid-3-yl-N)—$CH_2CH_2$—C(=O)—NH—$CH_2CH_2$—O—$CH_2CH_2$—O—$CH_2CH_2$—O—$CH_2CH_2$—O—$CH_2CH_2$—C(=O)-GGFG (SEQ ID NO: 3)-NH—$CH_2CH_2CH_2$—C(=O)—(NH-DX),
wherein -(Succinimid-3-yl-N)— has a structure represented by the following formula:

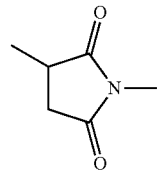

[Formula 4]

which is connected to the anti-HER2 antibody at position 3 thereof and is connected to the methylene group in the linker structure containing this structure on the nitrogen atom at position 1,
—(NH-DX) represents a group represented by the following formula:

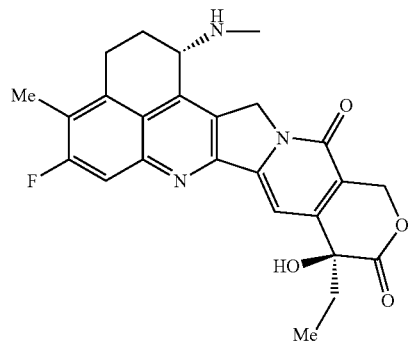

[Formula 5]

wherein the nitrogen atom of the amino group at position 1 is the connecting position, and -GGFG (SEQ ID NO: 3)- represents the tetrapeptide residue -Gly-Gly-Phe-Gly- (SEQ ID NO: 3).

[13] The antibody-drug conjugate according to any one of [1] to [9], wherein the drug-linker structure moiety having the drug connected to -L$^1$-L$^2$-L$^P$-NH—(CH$_2$)n$^1$-L$^a$-(CH$_2$)n$^2$-C(=O)— is one drug-linker structure selected from the following group:

-(Succinimid-3-yl-N)—CH$_2$CH$_2$CH$_2$CH$_2$CH$_2$—C(=O)-GGFG (SEQ ID NO: 3)-NH—CH$_2$—O—CH$_2$—C(=O)—(NH-DX), -(Succinimid-3-yl-N)—CH$_2$CH$_2$CH$_2$CH$_2$CH$_2$—C(=O)-GGFG (SEQ ID NO: 3)-NH—CH$_2$CH$_2$—O—CH$_2$—C(=O)—(NH-DX), -(Succinimid-3-yl-N)—CH$_2$CH$_2$—C(=O)—NH—CH$_2$CH$_2$—O—CH$_2$CH$_2$—O—CH$_2$CH$_2$—C(=O)-GGFG (SEQ ID NO: 3)-NH—CH$_2$CH$_2$CH$_2$—C(=O)—(NH-DX).

Here, -(Succinimid-3-yl-N)—, —(NH-DX), and -GGFG (SEQ ID NO: 3)- are as defined above.

[14] An antibody-drug conjugate wherein an antitumor compound represented by the following formula:

[Formula 6]

is conjugated to an anti-HER2 antibody via a linker having a structure represented by the following formula:

-L$^1$-L$^2$-L$^P$-NH—(CH$_2$)$n^1$-L$^a$-(CH$_2$)$n^2$-C(=O)— via a thioether bond which is formed at a disulfide bond moiety present in the hinge part of the anti-HER2 antibody, wherein the anti-HER2 antibody is connected to the terminal L$^1$, the antitumor compound is connected to the carbonyl group of the —(CH$_2$)n$^2$-C(=O)— moiety, wherein n$^1$ represents an integer of 0 to 6, n$^2$ represents an integer of 0 to 5, L$^1$ represents -(Succinimid-3-yl-N)—(CH$_2$)n$^3$-C(=O)—, wherein n$^3$ represents an integer of 2 to 8, L$^2$ represents —NH—(CH$_2$CH$_2$—O)n$^4$-CH$_2$CH$_2$—C(=O)— or a single bond, wherein n$^4$ represents an integer of 1 to 6, L$^P$ represents the tetrapeptide residue -GGFG (SEQ ID NO: 3)-, L$^a$ represents —O— or a single bond, and -(Succinimid-3-yl-N)— has a structure represented by the following formula:

[Formula 7]

which is connected to the anti-HER2 antibody at position 3 thereof and is connected to the methylene group in the linker structure containing this structure on the nitrogen atom at position 1.

[15] The antibody-drug conjugate according to [14], wherein n$^1$ is 3, n$^2$ is 0, n$^3$ is 2, L$^2$ is —NH—(CH$_2$CH$_2$—O)n$^4$-CH$_2$CH$_2$—C(=O)—, n$^4$ is 2, and L$^a$ is a single bond, n$^1$ is 1, n$^2$ is 1, n$^3$ is 5, L$^2$ is a single bond, and L$^a$ is —O—, or n$^1$ is 2, n$^2$ is 1, n$^3$ is 5, L$^2$ is a single bond, and L$^a$ is —O—.

[16] The antibody-drug conjugate according to [14] or [15], wherein n$^3$ is 2 or 5, and L$^2$ is a single bond.

[17] The antibody-drug conjugate according to [14] or [15], wherein n$^3$ is 2 or 5, L$^2$ is —NH—(CH$_2$CH$_2$—O)n$^4$-CH$_2$CH$_2$—C(=O)—, and n$^4$ is 2 or 4.

[18] The antibody-drug conjugate according to any one of [14] to [17], wherein —NH—(CH$_2$)n$^1$-L$^a$-(CH$_2$)n$^2$-C(=O)— is

—NH—CH$_2$CH$_2$CH$_2$—C(=O)—,

—NH—CH$_2$—O—CH$_2$—C(=O)—, or

—NH—CH$_2$CH$_2$—O—CH$_2$—C(=O)—.

[19] The antibody-drug conjugate according to any one of [14] to [18], wherein the drug-linker structure moiety having the drug connected to -L$^1$-L$^2$-L$^P$-NH—(CH$_2$)n$^1$-L$^a$-(CH$_2$)n$^2$-C(=O)— is one drug-linker structure selected from the group consisting of the following:

-(Succinimid-3-yl-N)—CH$_2$CH$_2$—C(=O)-GGFG (SEQ ID NO: 3)-NH—CH$_2$CH$_2$—C(=O)—(NH-DX), -(Succinimid-3-yl-N)—CH$_2$CH$_2$—C(=O)-GGFG (SEQ ID NO: 3)-NH—CH$_2$CH$_2$CH$_2$—C(=O)—(NH-DX), -(Succinimid-3-yl-N)—CH$_2$CH$_2$CH$_2$CH$_2$CH$_2$—C(=O)-GGFG (SEQ ID NO: 3)-NH—CH$_2$CH$_2$—C(=O)—(NH-DX), -(Succinimid-3-yl-N)—CH$_2$CH$_2$CH$_2$CH$_2$CH$_2$—C(=O)-GGFG (SEQ ID NO: 3)-NH—CH$_2$CH$_2$CH$_2$—C(=O)—(NH-DX), -(Succinimid-3-yl-N)—CH$_2$CH$_2$CH$_2$CH$_2$CH$_2$—C(=O)-GGFG (SEQ ID NO: 3)-NH—CH$_2$CH$_2$CH$_2$CH$_2$CH$_2$—C(=O)—(NH-DX), -(Succinimid-3-yl-N)—CH$_2$CH$_2$CH$_2$CH$_2$CH$_2$—C(=O)-GGFG (SEQ ID NO: 3)-NH—CH$_2$—O—CH$_2$—C(=O)—(NH-DX), -(Succinimid-3-yl-N)—CH$_2$CH$_2$CH$_2$CH$_2$CH$_2$—C(=O)-GGFG (SEQ ID NO: 3)-NH—CH$_2$CH$_2$—O—CH$_2$—C(=O)—(NH-DX), -(Succinimid-3-yl-N)—CH$_2$CH$_2$CH$_2$CH$_2$CH$_2$—C(=O)-GGFG (SEQ ID NO: 3)-NH—CH$_2$CH$_2$—O—C(=O)—(NH-DX), -(Succinimid-3-yl-N)—CH$_2$CH$_2$—C(=O)—NH—CH$_2$CH$_2$—O—CH$_2$CH$_2$—O—CH$_2$CH$_2$—C(=O)-GGFG (SEQ ID NO: 3)-NH—CH$_2$CH$_2$—C(=O)— (NH-DX), -(Succinimid-3-yl-N)—CH$_2$CH$_2$—C(=O)—NH—CH$_2$CH$_2$—O—CH$_2$CH$_2$—O—CH$_2$CH$_2$—C(=O)-GGFG (SEQ ID NO: 3)-NH—CH$_2$CH$_2$CH$_2$—C(=O)—(NH-DX), -(Succinimid-3-yl-N)—CH$_2$CH$_2$—C(=O)—NH—CH$_2$CH$_2$—O—CH$_2$CH$_2$—O—CH$_2$CH$_2$—O—CH$_2$CH$_2$—

O—CH$_2$CH$_2$—C(=O)-GGFG (SEQ ID NO: 3)-NH—CH$_2$CH$_2$—C(=O)—(NH-DX),
-(Succinimid-3-yl-N)—CH$_2$CH$_2$—C(=O)—NH—CH$_2$CH$_2$—O—CH$_2$CH$_2$—O—CH$_2$CH$_2$—O—CH$_2$CH$_2$—O—CH$_2$CH$_2$—C(=O)-GGFG (SEQ ID NO: 3)-NH—CH$_2$CH$_2$CH$_2$—C(=O)—(NH-DX), wherein, -(Succinimid-3-yl-N)— has a structure represented by the following formula:

[Formula 8]

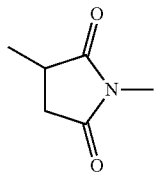

which is connected to the anti-HER2 antibody at position 3 thereof and is connected to the methylene group in the linker structure containing this structure on the nitrogen atom at position 1,
—(NH-DX) represents a group represented by the following formula:

[Formula 9]

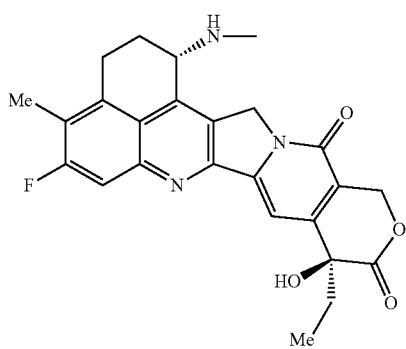

wherein the nitrogen atom of the amino group at position 1 is the connecting position, and
-GGFG (SEQ ID NO: 3)- represents the tetrapeptide residue -Gly-Gly-Phe-Gly- (SEQ ID NO: 3).

[20] The antibody-drug conjugate according to any one of [14] to [18], wherein the drug-linker structure moiety having the drug connected to -L$^1$-L$^2$-L$^P$-NH—(CH$_2$)n$^1$-L$^a$-(CH$_2$)n$^2$-C(=O)— is one drug-linker structure selected from the following group:
-(Succinimid-3-yl-N)—CH$_2$CH$_2$CH$_2$CH$_2$CH$_2$—C(=O)-GGFG (SEQ ID NO: 3)-NH—CH$_2$—O—CH$_2$—C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$—O—CH$_2$—C(=O)—(NH-DX), and
-(Succinimid-3-yl-N)—CH$_2$CH$_2$—C(=O)—NH—CH$_2$CH$_2$—O—CH$_2$CH$_2$—O—CH$_2$CH$_2$—C(=O)-GGFG (SEQ ID NO: 3)-NH—CH$_2$CH$_2$CH$_2$—C(=O)—(NH-DX).

Here, -(Succinimid-3-yl-N)—, —(NH-DX), and -GGFG (SEQ ID NO: 3)- are as defined above.

[21] The antibody-drug conjugate according to any one of [1] to [20], wherein the average number of units of the selected one drug-linker structure conjugated per antibody molecule is in the range of from 1 to 10.

[22] The antibody-drug conjugate according to any one of [1] to [20], wherein the average number of units of the selected one drug-linker structure conjugated per antibody molecule is in the range of from 2 to 8.

[23] The antibody-drug conjugate according to any one of [1] to [20], wherein the average number of units of the selected one drug-linker structure conjugated per antibody molecule is in the range of from 3 to 8.

[24] A drug containing the antibody-drug conjugate according to any one of [1] to [23], a salt thereof or a hydrate thereof.

[25] An antitumor drug and/or anticancer drug containing the antibody-drug conjugate according to any one of [1] to [23], a salt thereof or a hydrate thereof.

[26] The antitumor drug and/or anticancer drug according to [25], which is for use against lung cancer, urothelial cancer, colorectal cancer, prostate cancer, ovarian cancer, pancreatic cancer, breast cancer, bladder cancer, gastric cancer, gastrointestinal stromal tumor, uterine cervix cancer, esophageal cancer, squamous cell carcinoma, peritoneal cancer, liver cancer, hepatocellular cancer, colon cancer, rectal cancer, colorectal cancer, endometrial cancer, uterine cancer, salivary gland cancer, kidney cancer, vulval cancer, thyroid cancer, penis cancer, leukemia, malignant lymphoma, plasmacytoma, myeloma, or sarcoma.

[27] A pharmaceutical composition containing the antibody-drug conjugate according to any one of [1] to [23], a salt thereof or a hydrate thereof as an active component, and a pharmaceutically acceptable formulation component.

[28] The pharmaceutical composition according to [27], which is for use against lung cancer, urothelial cancer, colorectal cancer, prostate cancer, ovarian cancer, pancreatic cancer, breast cancer, bladder cancer, gastric cancer, gastrointestinal stromal tumor, uterine cervix cancer, esophageal cancer, squamous cell carcinoma, peritoneal cancer, liver cancer, hepatocellular cancer, colon cancer, rectal cancer, colorectal cancer, endometrial cancer, uterine cancer, salivary gland cancer, kidney cancer, vulval cancer, thyroid cancer, penis cancer, leukemia, malignant lymphoma, plasmacytoma, myeloma, or sarcoma.

[29] A method for treating tumor and/or cancer comprising administering the antibody-drug conjugate according to any one of [1] to [23], a salt thereof or a hydrate thereof.

[30] A method for producing an antibody-drug conjugate comprising reacting a compound represented by the following formula:

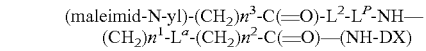

(maleimid-N-yl)-(CH$_2$)n$^3$-C(=O)-L$^2$-L$^P$-NH—(CH$_2$)n$^1$-L$^a$-(CH$_2$)n$^2$-C(=O)—(NH-DX)

with an anti-HER2 antibody or a reactive derivative thereof and conjugating a drug-linker moiety to the antibody by a method for forming a thioether bond at a disulfide bond site present in the hinge part of the antibody.

In the formula, n$^3$ represents an integer of 2 to 8,
L$^2$ represents —NH—(CH$_2$CH$_2$—O)n$^4$-CH$_2$CH$_2$—C(=O)— or a single bond,
wherein n$^4$ represents an integer of 1 to 6,
L$^P$ represents a peptide residue consisting of 2 to 7 amino acids selected from phenylalanine, glycine, valine, lysine, citrulline, serine, glutamic acid, and aspartic acid,
n$^1$ represents an integer of 0 to 6,
n$^2$ represents an integer of 0 to 5,
L$^a$ represents —O— or a single bond,
(maleimid-N-yl)- is a group represented by the following formula:

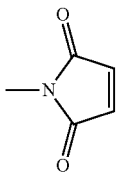

wherein the nitrogen atom is the connecting position, and —(NH-DX) is a group represented by the following formula:

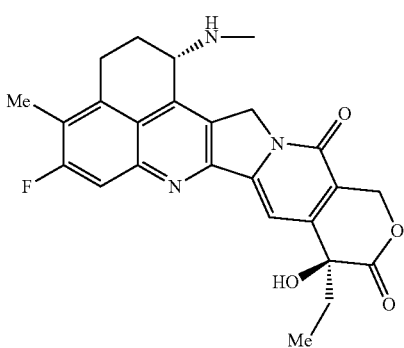

wherein the nitrogen atom of the amino group at position 1 is the connecting position.

[31] The production method according to [30], wherein the method for conjugating a drug-linker moiety to an anti-HER2 antibody is a method of reducing the antibody to convert the antibody to a reactive derivative.

[32] The production method according to [30] or [31], wherein the average number of units of the selected one drug-linker structure conjugated per antibody molecule is in the range of from 1 to 10.

[33] The production method according to [30] or [31], wherein the average number of units of the selected one drug-linker structure conjugated per antibody molecule is in the range of from 2 to 8.

[34] The production method according to [30] or [31], wherein the average number of units of the selected one drug-linker structure conjugated per antibody molecule is in the range of from 3 to 8.

[35] An antibody-drug conjugate obtained by the production method according to any of [30] to [34].

[36] An antibody-drug conjugate obtained by forming a thioether bond at a sulfide bond site in the hinge part of the antibody, wherein the anti-HER2 antibody is treated in a reducing condition and thereafter reacted with a compound selected from the group shown below:

(maleimid-N-yl)-$CH_2CH_2$—C(=O)-GGFG (SEQ ID NO: 3)-NH—$CH_2CH_2$—C(=O)—(NH-DX),
(maleimid-N-yl)-$CH_2CH_2CH_2$—C(=O)-GGFG (SEQ ID NO: 3)-NH—$CH_2CH_2$—C(=O)—(NH-DX),
(maleimid-N-yl)-$CH_2CH_2CH_2CH_2$—C(=O)-GGFG (SEQ ID NO: 3)-NH—$CH_2CH_2$—C(=O)—(NH-DX),
(maleimid-N-yl)-$CH_2CH_2CH_2CH_2CH_2$—C(=O)-GGFG (SEQ ID NO: 3)-NH—$CH_2CH_2$—C(=O)—(NH-DX),
(maleimid-N-yl)-$CH_2CH_2$—C(=O)-GGFG (SEQ ID NO: 3)-NH—$CH_2CH_2CH_2$—C(=O)—(NH-DX),
(maleimid-N-yl)-$CH_2CH_2CH_2$—C(=O)-GGFG (SEQ ID NO: 3)-NH—$CH_2CH_2CH_2$—C(=O)—(NH-DX),
(maleimid-N-yl)-$CH_2CH_2CH_2CH_2$—C(=O)-GGFG (SEQ ID NO: 3)-NH—$CH_2CH_2CH_2$—C(=O)—(NH-DX),
(maleimid-N-yl)-$CH_2CH_2CH_2CH_2CH_2$—C(=O)-GGFG (SEQ ID NO: 3)-NH—$CH_2CH_2CH_2$—C(=O)—(NH-DX),
(maleimid-N-yl)-$CH_2CH_2$—C(=O)-GGFG (SEQ ID NO: 3)-NH—$CH_2CH_2CH_2CH_2$—C(=O)—(NH-DX),
(maleimid-N-yl)-$CH_2CH_2CH_2$—C(=O)-GGFG (SEQ ID NO: 3)-NH—$CH_2CH_2CH_2CH_2$—C(=O)—(NH-DX),
(maleimid-N-yl)-$CH_2CH_2CH_2CH_2$—C(=O)-GGFG (SEQ ID NO: 3)-NH—$CH_2CH_2CH_2CH_2$—C(=O)—(NH-DX),
(maleimid-N-yl)-$CH_2CH_2CH_2CH_2CH_2$—C(=O)-GGFG (SEQ ID NO: 3)-NH—$CH_2CH_2CH_2CH_2$—C(=O)—(NH-DX),
(maleimid-N-yl)-$CH_2CH_2$—C(=O)-GGFG (SEQ ID NO: 3)-NH—$CH_2CH_2CH_2CH_2CH_2$—C(=O)—(NH-DX),
(maleimid-N-yl)-$CH_2CH_2CH_2$—C(=O)-GGFG (SEQ ID NO: 3)-NH—$CH_2CH_2CH_2CH_2CH_2$—C(=O)—(NH-DX),
(maleimid-N-yl)-$CH_2CH_2CH_2CH_2$—C(=O)-GGFG (SEQ ID NO: 3)-NH—$CH_2CH_2CH_2CH_2CH_2$—C(=O)—(NH-DX),
(maleimid-N-yl)-$CH_2CH_2CH_2CH_2CH_2$—C(=O)-GGFG (SEQ ID NO: 3)-NH—$CH_2CH_2CH_2CH_2CH_2$—C(=O)—(NH-DX),
(maleimid-N-yl)-$CH_2CH_2$—C(=O)-GGFG (SEQ ID NO: 3)-NH—$CH_2$—O—$CH_2$—C(=O)—(NH-DX),
(maleimid-N-yl)-$CH_2CH_2CH_2$—C(=O)-GGFG (SEQ ID NO: 3)-NH—$CH_2$—O—$CH_2$—C(=O)—(NH-DX),
(maleimid-N-yl)-$CH_2CH_2CH_2CH_2$—C(=O)-GGFG (SEQ ID NO: 3)-NH—$CH_2$—O—$CH_2$—C(=O)—(NH-DX),
(maleimid-N-yl)-$CH_2CH_2CH_2CH_2CH_2$—C(=O)-GGFG (SEQ ID NO: 3)-NH—$CH_2$—O—$CH_2$—C(=O)—(NH-DX),
(maleimid-N-yl)-$CH_2CH_2$—C(=O)-GGFG (SEQ ID NO: 3)-NH—$CH_2CH_2$—O—$CH_2$—C(=O)—(NH-DX),
(maleimid-N-yl)-$CH_2CH_2CH_2$—C(=O)-GGFG (SEQ ID NO: 3)-NH—$CH_2CH_2$—O—$CH_2$—C(=O)—(NH-DX),
(maleimid-N-yl)-$CH_2CH_2CH_2CH_2$—C(=O)-GGFG (SEQ ID NO: 3)-NH—$CH_2CH_2$—O—$CH_2$—C(=O)—(NH-DX),
(maleimid-N-yl)-$CH_2CH_2CH_2CH_2CH_2$—C(=O)-GGFG (SEQ ID NO: 3)-NH—$CH_2CH_2$—O—$CH_2$—C(=O)—(NH-DX),
(maleimid-N-yl)-$CH_2CH_2CH_2CH_2CH_2$—C(=O)-GGFG (SEQ ID NO: 3)-NH—$CH_2CH_2$—O—C(=O)—(NH-DX),
(maleimid-N-yl)-$CH_2CH_2$—C(=O)—NH—$CH_2CH_2$—O—$CH_2CH_2$—O—$CH_2CH_2$—C(=O)-GGFG (SEQ ID NO: 3)-NH—$CH_2CH_2$—C(=O)— (NH-DX),
(maleimid-N-yl)-$CH_2CH_2$—C(=O)—NH—$CH_2CH_2$—O—$CH_2CH_2$—O—$CH_2CH_2$—O—$CH_2CH_2$—C(=O)-GGFG (SEQ ID NO: 3)-NH—$CH_2CH_2$—C(=O)— (NH-DX),
(maleimid-N-yl)-$CH_2CH_2$—C(=O)—NH—$CH_2CH_2$—O—$CH_2CH_2$—O—$CH_2CH_2$—O—$CH_2CH_2$—C(=O)-GGFG (SEQ ID NO: 3)-NH—$CH_2CH_2$—C(=O)— (NH-DX),
(maleimid-N-yl)-$CH_2CH_2$—C(=O)—NH—$CH_2CH_2$—O—$CH_2CH_2$—O—$CH_2CH_2$—C(=O)-GGFG (SEQ ID NO: 3)-NH—$CH_2CH_2CH_2$—C(=O)—(NH-DX),
(maleimid-N-yl)-$CH_2CH_2$—C(=O)—NH—$CH_2CH_2$—O—$CH_2CH_2$—O—$CH_2CH_2$—C(=O)-GGFG (SEQ ID NO: 3)-NH—$CH_2CH_2CH_2$—C(=O)— (NH-DX),
(maleimid-N-yl)-$CH_2CH_2$—C(=O)—NH—$CH_2CH_2$—O—$CH_2CH_2$—O—$CH_2CH_2$—O—$CH_2CH_2$—C(=O)-GGFG (SEQ ID NO: 3)—$CH_2CH_2CH_2$—C(=O)— (NH-DX),
(maleimid-N-yl)-$CH_2CH_2$—C(=O)—NH—$CH_2CH_2$—O—$CH_2CH_2$—O—$CH_2CH_2$—C(=O)-GGFG (SEQ ID NO: 3)-NH—$CH_2$—O—$CH_2$—C(=O)—(NH-DX),
(maleimid-N-yl)-$CH_2CH_2$—C(=O)—NH—$CH_2CH_2$—O—$CH_2CH_2$—O—$CH_2CH_2$—C(=O)-GGFG (SEQ ID NO: 3)-NH—$CH_2$—O—$CH_2$—C(=O)—(NH-DX),
(maleimid-N-yl)-$CH_2CH_2$—C(=O)—NH—$CH_2CH_2$—O—$CH_2CH_2$—O—$CH_2CH_2$—O—

CH₂CH₂—C(=O)-GGFG (SEQ ID NO: 3)-NH—CH₂—O—CH₂—C(=O)—(NH-DX),
(maleimid-N-yl)-CH₂CH₂—C(=O)—NH—CH₂CH₂—O—CH₂CH₂—O—CH₂CH₂—C(=O)-GGFG (SEQ ID NO: 3)-NH—CH₂CH₂—O—CH₂—C(=O)—(NH-DX),
(maleimid-N-yl)-CH₂CH₂—C(=O)—NH—CH₂CH₂—O—CH₂CH₂—O—CH₂CH₂—O—CH₂CH₂—C(=O)-GGFG (SEQ ID NO: 3)-NH—CH₂CH₂—O—CH₂—C(=O)—(NH-DX), and
(maleimid-N-yl)-CH₂CH₂—C(=O)—NH—CH₂CH₂—O—CH₂CH₂—O—CH₂CH₂—O—CH₂CH₂—O—CH₂CH₂—C(=O)-GGFG (SEQ ID NO: 3)-NH—CH₂CH₂—O—CH₂—C(=O)—(NH-DX).

In the above, (maleimid-N-yl)- is a group represented by the following formula:

[Formula 12]

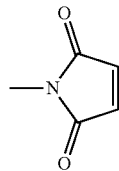

wherein the nitrogen atom is the connecting position, and —(NH-DX) is a group represented by the following formula:

[Formula 13]

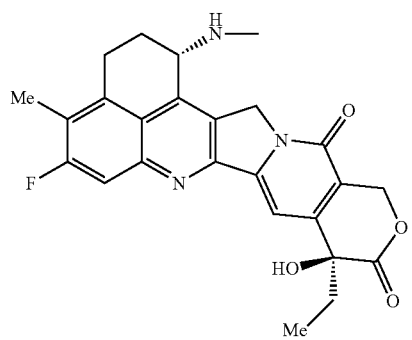

wherein the nitrogen atom of the amino group at position 1 is the connecting position, and
-GGFG (SEQ ID NO: 3)- represents the tetrapeptide residue -Gly-Gly-Phe-Gly- (SEQ ID NO: 3)

[37] An antibody-drug conjugate obtained by forming a thioether bond at a sulfide bond site present in the hinge part of the antibody, wherein the anti-HER2 antibody is treated in a reducing condition and thereafter reacted with a compound selected from the group shown below:
(maleimid-N-yl)-CH₂CH₂—C(=O)—NH—CH₂CH₂—O—CH₂CH₂—O—CH₂CH₂—C(=O)-GGFG (SEQ ID NO: 3)-NH—CH₂CH₂CH₂—C(=O)—(NH-DX),
(maleimid-N-yl)-CH₂CH₂CH₂CH₂CH₂—C(=O)-GGFG (SEQ ID NO: 3)-NH—CH₂—O—CH₂—C(=O)—(NH-DX), and
(maleimid-N-yl)-CH₂CH₂CH₂CH₂—C(=O)-GGFG (SEQ ID NO: 3)-NH—CH₂CH₂—O—CH₂—C(=O)—(NH-DX).

Here, (maleimid-N-yl)-, —(NH-DX), and -GGFG (SEQ ID NO: 3)- are as defined above.

[38] The antibody-drug conjugate according to [36] or [37], wherein the average number of units of the selected one drug-linker structure conjugated per antibody molecule is in the range of from 1 to 10.
[39] The antibody-drug conjugate according to [36] or [37], wherein the average number of units of the selected one drug-linker structure conjugated per antibody molecule is in the range of from 2 to 8.
[40] The antibody-drug conjugate according to [36] or [37], wherein the average number of units of the selected one drug-linker structure conjugated per antibody molecule is in the range of from 3 to 8.

Advantageous Effects of Invention

With an anti-HER2 antibody-drug conjugate having the antitumor compound exatecan conjugated via a linker with a specific structure, an excellent antitumor effect and safety can be achieved.

BRIEF DESCRIPTION OF DRAWINGS

FIG. 1 shows an amino acid sequence of a heavy chain of a humanized anti-HER2 monoclonal antibody (SEQ ID NO: 1).
FIG. 2 shows an amino acid sequence of a light chain of a humanized anti-HER2 monoclonal antibody (SEQ ID NO: 2).

DESCRIPTION OF EMBODIMENTS

Figure 3:
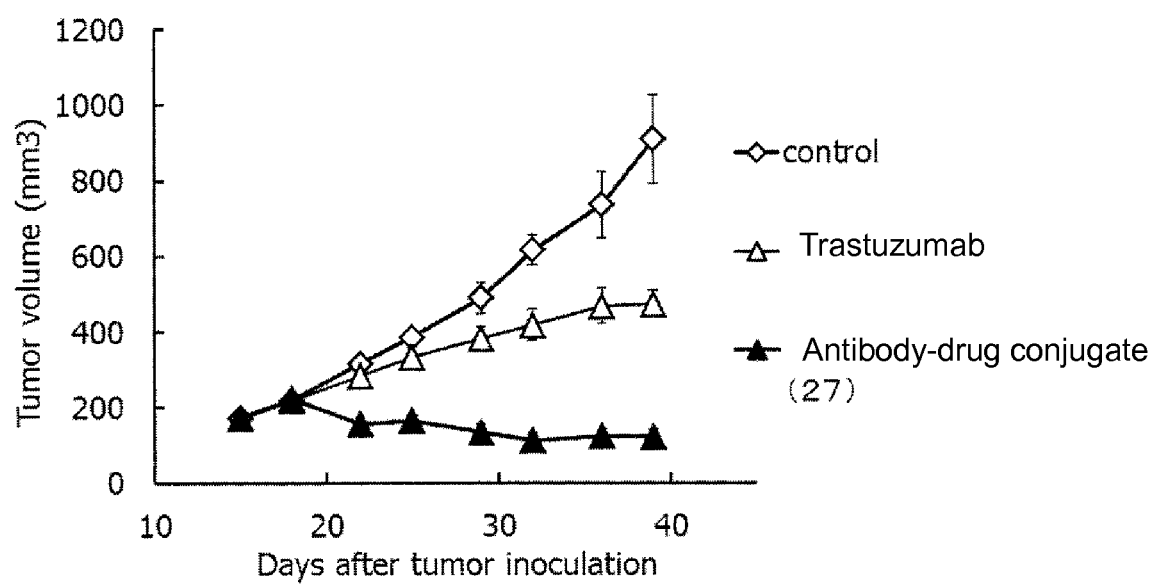
FIG. 3 is a diagram showing the antitumor effect of an antibody-drug conjugate (27) or trastuzumab on a nude mouse with subcutaneously transplanted human breast cancer line KPL-4 cells. In the drawing, the abscissa depicts days after tumor inoculation, and the ordinate depicts tumor volume.

Hereinafter, preferred modes for carrying out the present invention are described with reference to the drawings. The embodiments described below are given merely for illustrating one example of a typical embodiment of the present invention and are not intended to limit the scope of the present invention.

The anti-HER2 antibody-drug conjugate of the present invention is an antitumor drug in which an anti-HER2 antibody is conjugated to an antitumor compound via a linker structure moiety and is explained in detail hereinbelow.

[Antibody]

The anti-HER2 antibody used in the anti-HER2 antibody-drug conjugate of the present invention may be derived from any species, and preferred examples of the species can include humans, rats, mice, and rabbits. In case when the antibody is derived from other than human species, it is preferably chimerized or humanized using a well known technique. The antibody of the present invention may be a polyclonal antibody or a monoclonal antibody and is preferably a monoclonal antibody.

The anti-HER2 antibody is the antibody, which is capable of targeting tumor cells, that is, possesses a property of recognizing a tumor cell, a property of binding to a tumor cell, a property of internalizing in a tumor cell, cytocidal activity against tumor cells, or the like, and can be conjugated with a drug having antitumor activity via a linker to form an antibody-drug conjugate.

The binding activity of the antibody against tumor cells can be confirmed using flow cytometry. The internalization of the antibody into tumor cells can be confirmed using (1) an assay of visualizing an antibody incorporated in cells under a fluorescence microscope using a secondary antibody (fluorescently labeled) binding to the therapeutic antibody (Cell Death and Differentiation (2008) 15, 751-761), (2) an assay of measuring a fluorescence intensity incorporated in cells using a secondary antibody (fluorescently labeled) binding to the therapeutic antibody (Molecular Biology of the Cell, Vol. 15, 5268-5282, December 2004), or (3) a Mab-ZAP assay using an immunotoxin binding to the therapeutic antibody wherein the toxin is released upon incorporation into cells to inhibit cell growth (Bio Techniques 28: 162-165, January 2000) As the immunotoxin, a recombinant complex protein of a diphtheria toxin catalytic domain and protein G may be used.

The antitumor activity of the antibody can be confirmed in vitro by determining inhibitory activity against cell growth. For example, a cancer cell line overexpressing a target protein for the antibody is cultured, and the antibody is added at varying concentrations into the culture system to determine an inhibitory activity against focus formation, colony formation, and spheroid growth. The antitumor activity can be confirmed in vivo, for example, by administering the antibody to a nude mouse with a transplanted tumor cell line highly expressing the target protein, and determining change in the cancer cell.

Since the compound conjugated in the antibody-drug conjugate exerts an antitumor effect, it is preferred but not essential that the antibody itself should have an antitumor effect. For the purpose of specifically and selectively exerting the cytotoxic activity of the antitumor compound against tumor cells, it is important and also preferred that the antibody should have the property of internalizing to migrate into tumor cells.

The anti-HER2 antibody can be obtained by a procedure known in the art. For example, the antibody of the present invention can be obtained using a method usually carried out in the art, which involves immunizing animals with an antigenic polypeptide and collecting and purifying antibodies produced in vivo. The origin of the antigen is not limited to humans, and the animals may be immunized with an antigen derived from a non-human animal such as a mouse, a rat and the like. In this case, the cross-reactivity of antibodies binding to the obtained heterologous antigen with human antigens can be tested to screen for an antibody applicable to a human disease.

Alternatively, antibody-producing cells which produce antibodies against the antigen are fused with myeloma cells according to a method known in the art (e.g., Kohler and Milstein, Nature (1975) 256, p. 495-497; and Kennet, R. ed., Monoclonal Antibodies, p. 365-367, Plenum Press, N.Y. (1980)) to establish hybridomas, from which monoclonal antibodies can in turn be obtained.

The antigen can be obtained by genetically engineering host cells to produce a gene encoding the antigenic protein. Specifically, vectors that permit expression of the antigen gene are prepared and transferred to host cells so that the gene is expressed. The antigen thus expressed can be purified. The antibody can also be obtained by a method of immunizing animals with the above-described genetically engineered antigen-expressing cells or a cell line expressing the antigen.

The anti-HER2 antibodies that can be used in the present invention are not particularly limited and are preferably, for example, those having properties as described below.
(1) An anti-HER2 antibody having the following properties:
    (a) specifically binding to HER2, and
    (b) having an activity of internalizing in HER2-expressing cells by binding to HER2.

(2) The antibody according to (1) above, wherein the antibody binds to the extracellular domain of HER2.
(3) The antibody according to (1) or (2) above, wherein the antibody is a monoclonal antibody.
(4) The antibody according to any of (1) to (3) above, wherein the antibody has an antibody-dependent cellular cytotoxicity (ADCC) activity and/or a complement-dependent cytotoxicity (CDC) activity
(5) The antibody according to any of (1) to (4) above, wherein the antibody is a mouse monoclonal antibody, a chimeric monoclonal antibody, or a humanized monoclonal antibody.
(6) The antibody according to any of (1) to (5) above, wherein the antibody is a humanized monoclonal antibody comprising a heavy chain consisting of the amino acid sequence represented by SEQ ID NO: 1 and a light chain consisting of the amino acid sequence represented by SEQ ID NO: 2.
(7) The antibody according to any of (1) to (6) above, wherein the antibody lacks a lysine residue at the carboxyl terminus of the heavy chain.
(8) The antibody according to (7) above, wherein the antibody comprises a heavy chain consisting of an amino acid sequence consisting of amino acid residues 1 to 449 of SEQ ID NO: 1 and a light chain consisting of an amino acid sequence consisting of amino acid residues 1 to 214 of SEQ ID NO: 2.
(9) An antibody obtained by a method for producing the antibody according to any of (1) to (8) above, the method comprising the steps of: culturing a host cell transformed with an expression vector containing a polynucleotide encoding the antibody; and collecting the antibody of interest from the cultures obtained in the preceding step.

Hereinafter, the anti-HER2 antibody used in the invention is described.

The terms "cancer" and "tumor" as used herein are used with the same meaning.

The term "gene" as used herein includes not only DNA, but also mRNA thereof, cDNA thereof and cRNA thereof.

The term "polynucleotide" as used herein is used with the same meaning as a nucleic acid and also includes DNA, RNA, probes, oligonucleotides, and primers.

The terms "polypeptide", "protein" and "protein" as used herein are used without distinction.

The term "cell" as used herein also includes cells in an animal individual and cultured cells.

The term "HER2" as used herein is used with the same meaning as HER2 protein.

Examples of the anti-HER2 antibody as used herein can include, but not particularly limited to, pertuzumab (International Patent Publication No. WO 01/00245) and trastuzumab (U.S. Pat. No. 5,821,337). Trastuzumab is preferred. However, the anti-HER2 antibody of the present invention is not limited thereto as long as it is an anti-HER2 antibody specifically binding to HER2, and more preferably having an activity of internalizing in HER2-expressing cells by binding to HER2.

The term "trastuzumab" as used herein is also called HERCEPTIN®, huMAb4D5-8, or rhuMAb4D5-8 and is a humanized antibody comprising a heavy chain consisting of an amino acid sequence consisting of amino acid residues 1 to 449 of SEQ ID NO: 1 (FIG. 1) and a light chain consisting of an amino acid sequence consisting of amino acid residues 1 to 214 of SEQ ID NO: 2 (FIG. 2).

The term "specifically binding" as used herein means binding that is not nonspecific adsorption. Examples of the criterion for determining whether the binding is specific or not can include dissociation constant (hereinafter referred to as "KD"). The KD value of the antibody for the HER2 protein is preferably $1 \times 10^{-5}$ M or smaller, $5 \times 10^{-6}$ M or smaller, $2 \times 10^{-6}$ M or smaller, or $1 \times 10^{-6}$ M or smaller, more preferably $5 \times 10^{-7}$ M or smaller, $2 \times 10^{-7}$ M or smaller, or $1 \times 10^{-7}$ M or smaller, further preferably $5 \times 10^{-8}$ M or smaller, $2 \times 10^{-8}$ M or smaller, or $1 \times 10^{-8}$ M or smaller, and most preferably $5 \times 10^{-9}$ M or smaller, $2 \times 10^{-9}$ M or smaller, or $1 \times 10^{-9}$ M or smaller. The binding between the HER2 protein and the antibody can be measured using a method known in the art, such as surface plasmon resonance, ELISA, or RIA.

The term "CDR" as used herein refers to a complementarity determining region (CDR). It is known that each heavy and light chain of an antibody molecule has three complementarity determining regions (CDRs). The CDR is also called the hypervariable domain, and is present in a variable region of each heavy and light chain of an antibody. It is a site which has unusually high variability in its primary structure, and there are three separate CDRs in the primary structure of each heavy and light polypeptide chain. In this specification, as for the CDRs of an antibody, the CDRs of the heavy chain are represented by CDRH1, CDRH2, and CDRH3 from the amino-terminal side of the amino acid sequence of the heavy chain, and the CDRs of the light chain are represented by CDRL1, CDRL2, and CDRL3 from the amino-terminal side of the amino acid sequence of the light chain. These sites are proximate to one another in the tertiary structure and determine the specificity for an antigen to which the antibody binds.

The phrase "hybridization is performed under stringent conditions" as used herein refers to a process in which hybridization is performed under conditions under which identification can be achieved by performing hybridization at 68° C. in a commercially available hybridization solution ExpressHyb Hybridization Solution (manufactured by Clontech, Inc.) or by performing hybridization at 68° C. in the presence of 0.7 to 1.0 M NaCl using a filter having DNA immobilized thereon, followed by performing washing at 68° C. using 0.1 to 2×SSC solution (1×SSC solution is composed of 150 mM NaCl and 15 mM sodium citrate) or under conditions equivalent thereto.

1. HER2

HER2 is one of the oncogene products of a typical growth factor receptor oncogene identified as human epidermal cell growth factor receptor 2-related oncogene, and is a transmembrane receptor protein having a molecular weight of 185 kDa and having a tyrosine kinase domain. HER2 is a member of the EGFR family consisting of HER1 (EGFR, ErbB-1), HER2 (neu, ErbB-2), HER3 (ErbB-3), and HER4 (ErbB-4) and is known to be autophosphorylated at intracellular tyrosine residues by its homodimer formation or heterodimer formation with another EGFR receptor HER1, HER3, or HER4 and is itself activated in that manner, thereby playing an important role in cell growth, differentiation, and survival in normal cells and tumor cells.

As for the HER2 protein to be used in the present invention, the HER2 protein can be directly purified from HER2-expressing cells of a human or a non-human mammal (such as a rat or a mouse) and used, or a cell membrane fraction of the above-described cells can be prepared and used. Further, HER2 can be obtained by in vitro synthesis thereof or production thereof in a host cell through genetic engineering. In the genetic engineering, specifically, after HER2 cDNA is integrated into a vector capable of expressing HER2 cDNA, the HER2 protein can be obtained by synthesizing it in a solution containing an enzyme, a substrate and an energy substance required for transcription and translation, or by expressing HER2 in another prokaryotic or eucaryotic transformed host cell. Alternatively, the above-described genetically engineered HER2-expressing cells, or a cell line expressing HER2 may be used as the HER2 protein.

The DNA sequence and amino acid sequence of HER2 are disclosed on a public database, and can be referred to, for example, under Accession No. M11730 (GenBank), NP_004439.2 (NCBI), or the like.

Further, a protein which consists of an amino acid sequence wherein one or several amino acids are substituted, deleted and/or added in any of the above-described amino acid sequences of HER2 and also has a biological activity equivalent to that of the protein is also included in HER2.

Human HER2 protein is composed of a signal sequence consisting of N-terminal 22 amino acid residues, an extracellular domain consisting of 630 amino acid residues, a transmembrane domain consisting of 23 amino acid residues, and an intracellular domain consisting of 580 amino acid residues.

2. Production of Anti-HER2 Antibody

The antibody against HER2 of the present invention can be obtained according to, for example, a method usually carried out in the art, which involves immunizing animals with HER2 or an arbitrary polypeptide selected from the amino acid sequence of HER2 and collecting and purifying antibodies produced in vivo. The biological species of HER2 to be used as an antigen is not limited to being human, and an animal can be immunized with HER2 derived from an animal other than humans such as a mouse or a rat or with rat p185neu. In this case, by examining the cross-reactivity between an antibody binding to the obtained heterologous HER2 and human HER2, an antibody applicable to a human disease can be selected.

Further, a monoclonal antibody can be obtained from a hybridoma established by fusing antibody-producing cells which produce an antibody against HER2 with myeloma cells according to a known method (for example, Kohler and Milstein, Nature, (1975) 256, pp. 495-497; Kennet, R. ed., Monoclonal Antibodies, pp. 365-367, Plenum Press, N.Y. (1980)).

HER2 to be used as an antigen can be obtained by expressing HER2 gene in a host cell using genetic engineering.

Specifically, a vector capable of expressing HER2 gene is produced, and the resulting vector is transfected into a host cell to express the gene, and then, the expressed HER2 is purified.

Alternatively, the above-described genetically engineered HER2-expressing cells, or a cell line expressing HER2 may be used as the HER2 protein. The anti-HER2 antibody can be obtained by a preocedure known in the art. Hereinafter, a method of obtaining an antibody against HER2 is specifically described.

(1) Preparation of Antigen

Examples of the antigen to be used for producing the anti-HER2 antibody include HER2, or a polypeptide consisting of a partial amino acid sequence comprising at least 6 consecutive amino acids of HER2, or a derivative obtained by adding a given amino acid sequence or carrier thereto.

HER2 can be purified directly from human tumor tissues or tumor cells and used. Further, HER2 can be obtained by synthesizing it in vitro or by producing it in a host cell by genetic engineering.

With respect to the genetic engineering, specifically, after HER2 cDNA is integrated into a vector capable of expressing HER2 cDNA, HER2 can be obtained by synthesizing it in a solution containing an enzyme, a substrate and an energy substance required for transcription and translation, or by expressing HER2 in another prokaryotic or eucaryotic transformed host cell.

Further, the antigen can also be obtained as a secretory protein by expressing a fusion protein obtained by ligating the extracellular domain of HER2, which is a membrane protein, to the constant region of an antibody in an appropriate host-vector system.

HER2 cDNA can be obtained by, for example, a so-called PCR method in which a polymerase chain reaction is performed using a cDNA library expressing HER2 cDNA as a template and primers which specifically amplify HER2 cDNA (PCR; Saiki, R. K., et al., Science, (1988) 239, pp. 487-489).

As the in vitro synthesis of the polypeptide, for example, Rapid Translation System (RTS) manufactured by Roche Diagnostics, Inc. can be exemplified, but it is not limited thereto.

Examples of the prokaryotic host cells include *Escherichia coli* and *Bacillus subtilis*. In order to transform the host cells with a target gene, the host cells are transformed by a plasmid vector comprising a replicon, i.e., a replication origin derived from a species compatible with the host, and a regulatory sequence. Further, the vector preferably has a sequence capable of imposing phenotypic selectivity on the transformed cell.

Examples of the eucaryotic host cells include vertebrate cells, insect cells, and yeast cells. As the vertebrate cells, for example, simian COS cells (Gluzman, Y., Cell, (1981) 23, pp. 175-182, ATCC CRL-1650; ATCC: American Type Culture Collection), murine fibroblasts NIH3T3 (ATCC No. CRL-1658), and dihydrofolate reductase-deficient strains (Urlaub, G. and Chasin, L. A., Proc. Natl. Acad. Sci. USA (1980) 77, pp. 4126-4220) of Chinese hamster ovarian cells (CHO cells; ATCC: CCL-61); and the like are often used, however, the cells are not limited thereto.

The thus obtained transformant can be cultured according to a method usually carried out in the art, and by the culturing of the transformant, a target polypeptide is produced intracellularly or extracellularly.

A suitable medium to be used for the culturing can be selected from various commonly used culture media depending on the employed host cells. If *Escherichia coli* is employed, for example, an LB medium supplemented with an antibiotic such as ampicillin or IPMG as needed can be used.

A recombinant protein produced intracellularly or extracellularly by the transformant through such culturing can be separated and purified by any of various known separation methods utilizing the physical or chemical property of the protein.

Specific examples of the methods include treatment with a common protein precipitant, ultrafiltration, various types of liquid chromatography such as molecular sieve chromatography (gel filtration), adsorption chromatography, ion exchange chromatography, and affinity chromatography, dialysis, and a combination thereof.

Further, by attaching a tag of six histidine residues (SEQ ID NO: 9) to a recombinant protein to be expressed, the protein can be efficiently purified with a nickel affinity column. Alternatively, by attaching the IgG Fc region to a recombinant protein to be expressed, the protein can be efficiently purified with a protein A column.

By combining the above-described methods, a large amount of a target polypeptide can be easily produced in high yield and high purity.

The above-described transformant itself may be used as the antigen. A cell line expressing HER2 may also be used as the antigen. Examples of such a cell line can include human breast cancer lines SK-BR-3, BT-474, KPL-4, and JIMT-1, a human gastric cancer line NCI-N87, and a human ovarian cancer line SK-OV-3. The cell line of the present invention is not limited to these cell lines as long as it expresses HER2.

(2) Production of Anti-HER2 Monoclonal Antibody

Examples of the antibody specifically bind to HER2 include a monoclonal antibody specifically bind to HER2, and a method of obtaining such antibody is as described below.

The production of a monoclonal antibody generally requires the following operational steps of:

(a) purifying a biopolymer to be used as an antigen, or preparing antigen-expressing cells;

(b) preparing antibody-producing cells by immunizing an animal by injection of the antigen, collecting the blood, assaying its antibody titer to determine when the spleen is excised;

(c) preparing myeloma cells (hereinafter referred to as "myeloma");

(d) fusing the antibody-producing cells with the myeloma;

(e) screening a group of hybridomas producing a desired antibody;

(f) dividing the hybridomas into single cell clones (cloning);

(g) optionally, culturing the hybridoma or rearing an animal implanted with the hybridoma for producing a large amount of monoclonal antibody;

(h) examining the thus produced monoclonal antibody for biological activity and binding specificity, or assaying the same for properties as a labeled reagent; and the like.

Hereinafter, the method of producing a monoclonal antibody will be described in detail following the above steps, however, the method is not limited thereto, and, for example, antibody-producing cells other than spleen cells and myeloma can be used.

(a) Purification of Antigen

As the antigen, HER2 prepared by the method as described above or a partial peptide thereof can be used.

Further, a membrane fraction prepared from recombinant cells expressing HER2 or the recombinant cells expressing HER2 themselves, and also a partial peptide of the protein of the invention chemically synthesized by a method known to those skilled in the art can also be used as the antigen.

Furthermore, a HER2-expressing cell line can also be used as the antigen.

(b) Preparation of Antibody-Producing Cells

The antigen obtained in the step (a) is mixed with an adjuvant such as Freund's complete or incomplete adjuvant or auxiliary agent such as aluminum potassium sulfate and the resulting mixture is used as an immunogen to immunize an experimental animal. Another method involves immunizing an experimental animal with antigen-expressing cells as an immunogen. As the experimental animal, any animal used in a known hybridoma production method can be used without hindrance. Specifically, for example, a mouse, a rat, a goat, sheep, cattle, a horse, or the like can be used. However, from the viewpoint of ease of availability of myeloma cells to be fused with the extracted antibody-producing cells, a mouse or a rat is preferably used as the animal to be immunized.

Further, the strain of a mouse or a rat to be used is not particularly limited, and in the case of a mouse, for example, various strains such as A, AKR, BALB/c, BDP, BA, CE, C3H, 57BL, C57BL, C57L, DBA, FL, HTH, HT1, LP, NZB, NZW, RF, R III, SJL, SWR, WB, and 129 and the like can be used, and in the case of a rat, for example, Wistar, Low, Lewis, Sprague, Dawley, ACI, BN, Fischer and the like can be used.

These mice and rats are commercially available from breeders/distributors of experimental animals, for example, CLEA Japan, Inc. and Charles River Laboratories Japan, Inc.

As the animal to be immunized, in consideration of compatibility of fusing with myeloma cells described below, in the case of a mouse, BALB/c strain, and in the case of a rat, Wistar and Low strains are particularly preferred.

Further, in consideration of antigenic homology between humans and mice, it is also preferred to use a mouse having decreased biological function to remove auto-antibodies, that is, a mouse with an autoimmune disease.

The age of such mouse or rat at the time of immunization is preferably 5 to 12 weeks of age, more preferably 6 to 8 weeks of age.

In order to immunize an animal with HER2 or a recombinant thereof, for example, a known method described in detail in, for example, Weir, D. M., Handbook of Experimental Immunology Vol. I. II. III., Blackwell Scientific Publications, Oxford (1987); Kabat, E. A. and Mayer, M. M., Experimental Immunochemistry, Charles C Thomas Publisher Springfield, Ill. (1964) or the like can be used.

Among these immunization methods, a preferred specific method in the present invention is, for example, as follows.

That is, first, a membrane protein fraction serving as the antigen or cells caused to express the antigen is/are intradermally or intraperitoneally administered to an animal. However, the combination of both routes of administration is preferred for increasing the immunization efficiency, and when intradermal administration is performed in the first half and intraperitoneal administration is performed in the latter half or only at the last dosing, the immunization efficiency can be particularly increased.

The administration schedule of the antigen varies depending on the type of animal to be immunized, individual difference or the like. However, in general, an administration schedule in which the frequency of administration of the antigen is 3 to 6 times and the dosing interval is 2 to 6 weeks is preferred, and an administration schedule in which the frequency of administration of the antigen is 3 to 4 times and the dosing interval is 2 to 4 weeks is more preferred.

Further, the dose of the antigen varies depending on the type of animal, individual differences or the like, however, the dose is generally set to 0.05 to 5 mg, preferably about 0.1 to 0.5 mg.

A booster immunization is performed 1 to 6 weeks, preferably 1 to 4 weeks, more preferably 1 to 3 weeks after the administration of the antigen as described above. When the immunogen is cells, $1 \times 10^6$ to $1 \times 10^7$ cells are used.

The dose of the antigen at the time of performing the booster immunization varies depending on the type or size of animal or the like, however, in the case of, for example, a mouse, the dose is generally set to 0.05 to 5 mg, preferably 0.1 to 0.5 mg, more preferably about 0.1 to 0.2 mg. When the immunogen is cells, $1 \times 10^6$ to $1 \times 10^7$ cells are used.

Spleen cells or lymphocytes including antibody-producing cells are aseptically removed from the immunized animal after 1 to 10 days, preferably 2 to 5 days, more preferably 2 to 3 days from the booster immunization. At this time, the antibody titer is measured, and if an animal having a sufficiently increased antibody titer is used as a supply source of the antibody-producing cells, the subsequent procedure can be carried out more efficiently.

Examples of the method of measuring the antibody titer to be used here include an RIA method and an ELISA method, but the method is not limited thereto. For example, if an ELISA method is employed, the measurement of the antibody titer in the invention can be carried out according to the procedures as described below.

First, a purified or partially purified antigen is adsorbed to the surface of a solid phase such as a 96-well plate for ELISA, and the surface of the solid phase having no antigen adsorbed thereto is covered with a protein unrelated to the antigen such as bovine serum albumin (BSA). After washing the surface, the surface is brought into contact with a serially-diluted sample (for example, mouse serum) as a primary antibody to allow the antibody in the sample to bind to the antigen.

Further, as a secondary antibody, an antibody labeled with an enzyme against a mouse antibody is added and is allowed to bind to the mouse antibody. After washing, a substrate for the enzyme is added and a change in absorbance which occurs due to color development induced by degradation of the substrate or the like is measured and the antibody titer is calculated based on the measurement.

The separation of the antibody-producing cells from the spleen cells or lymphocytes of the immunized animal can be carried out according to a known method (for example, Kohler et al., Nature (1975), 256, p. 495; Kohler et al., Eur. J. Immunol. (1977), 6, p. 511; Milstein et al., Nature (1977), 266, p. 550; Walsh, Nature (1977), 266, p. 495). For example, in the case of spleen cells, a general method in which the antibody-producing cells are separated by homogenizing the spleen to obtain the cells through filtration with a stainless steel mesh and suspending the cells in Eagle's Minimum Essential Medium (MEM) can be employed.

(c) Preparation of Myeloma Cells (Hereinafter Referred to as "Myeloma")

The myeloma cells to be used for cell fusion are not particularly limited and suitable cells can be selected from known cell lines. However, in consideration of convenience when a hybridoma is selected from fused cells, it is preferred to use an HGPRT (hypoxanthine-guanine phosphoribosyl transferase) deficient strain whose selection procedure has been established.

More specifically, examples of the HGPRT-deficient strain include X63-Ag8(X63), NS1-ANS/1(NS1), P3X63-Ag8.U1(P3U1), X63-Ag8.653(X63.653), SP2/0-Ag14(SP2/0), MPC11-45.6TG1.7(45.6TG), FO, S149/5XXO, and BU.1 derived from mice; 210.RSY3.Ag.1.2.3(Y3) derived from rats; and U266AR(SKO-007), GM1500.GTG-A12 (GM1500), UC729-6, LICR-LOW-HMy2(HMy2) and 8226AR/NIP4-1(NP41) derived from humans. These HGPRT-deficient strains are available from, for example, ATCC or the like.

These cell strains are subcultured in an appropriate medium such as an 8-azaguanine medium [a medium obtained by adding 8-azaguanine to an RPMI 1640 medium supplemented with glutamine, 2-mercaptoethanol, gentamicin, and fetal calf serum (hereinafter referred to as "FCS")], Iscove's Modified Dulbecco's Medium (hereinafter referred to as "IMDM"), or Dulbecco's Modified Eagle Medium (hereinafter referred to as "DMEM"). In this case, 3 to 4 days before performing cell fusion, the cells are subcultured in a normal medium (for example, an ASF104 medium (manufactured by Ajinomoto Co., Ltd.) containing 10% FCS) to ensure not less than $2\times10^7$ cells on the day of cell fusion.

(d) Cell Fusion

Fusion between the antibody-producing cells and the myeloma cells can be appropriately performed according to a known method (Weir, D. M. Handbook of Experimental Immunology Vol. I. II. III., Blackwell Scientific Publications, Oxford (1987); Kabat, E. A. and Mayer, M. M., Experimental Immunochemistry, Charles C Thomas Publisher, Springfield, Ill. (1964), etc.), under conditions such that the survival rate of cells is not excessively reduced.

As such a method, for example, a chemical method in which the antibody-producing cells and the myeloma cells are mixed in a solution containing a polymer such as polyethylene glycol at a high concentration, a physical method using electric stimulation, or the like can be used. Among these methods, a specific example of the chemical method is as described below.

That is, in the case where polyethylene glycol is used in the solution containing a polymer at a high concentration, the antibody-producing cells and the myeloma cells are mixed in a solution of polyethylene glycol having a molecular weight of 1500 to 6000, more preferably 2000 to 4000 at a temperature of from 30 to 40° C., preferably from 35 to 38° C. for 1 to 10 minutes, preferably 5 to 8 minutes.

(e) Selection of a Group of Hybridomas

The method of selecting hybridomas obtained by the above-described cell fusion is not particularly limited. Usually, an HAT (hypoxanthine, aminopterin, thymidine) selection method (Kohler et al., Nature (1975), 256, p. 495; Milstein et al., Nature (1977), 266, p. 550) is used.

This method is effective when hybridomas are obtained using the myeloma cells of an HGPRT-deficient strain which cannot survive in the presence of aminopterin. That is, by culturing unfused cells and hybridomas in an HAT medium, only hybridomas resistant to aminopterin are selectively allowed to survive and proliferate.

(f) Division into Single Cell Clone (Cloning)

As a cloning method for hybridomas, a known method such as a methylcellulose method, a soft agarose method, or a limiting dilution method can be used (see, for example, Barbara, B. M. and Stanley, M. S.: Selected Methods in Cellular Immunology, W. H. Freeman and Company, San Francisco (1980)). Among these methods, particularly, a three-dimensional culture method such as a methylcellulose method is preferred. For example, the group of hybridomas produced by cell fusion are suspended in a methylcellulose medium such as ClonaCell-HY Selection Medium D (manufactured by StemCell Technologies, Inc., #03804) and cultured. Then, the formed hybridoma colonies are collected, whereby monoclonal hybridomas can be obtained. The collected respective hybridoma colonies are cultured, and a hybridoma which has been confirmed to have a stable antibody titer in an obtained hybridoma culture supernatant is selected as a HER2 monoclonal antibody-producing hybridoma strain.

(g) Preparation of Monoclonal Antibody by Culturing Hybridoma

By culturing the thus selected hybridoma, a monoclonal antibody can be efficiently obtained. However, prior to culturing, it is preferred to perform screening of a hybridoma which produces a target monoclonal antibody.

In such screening, a known method can be employed.

The measurement of the antibody titer in the invention can be carried out by, for example, an ELISA method explained in item (b) described above.

The hybridoma obtained by the method described above can be stored in a frozen state in liquid nitrogen or in a freezer at −80° C. or below.

After completion of cloning, the medium is changed from an HT medium to a normal medium, and the hybridoma is cultured.

Large-scale culture is performed by rotation culture using a large culture bottle or by spinner culture. From the supernatant obtained by the large-scale culture, a monoclonal antibody which specifically binds to the protein of the invention can be obtained by purification using a method known to those skilled in the art such as gel filtration.

Further, the hybridoma is injected into the abdominal cavity of a mouse of the same strain as the hybridoma (for example, the above-described BALB/c) or a Nu/Nu mouse to proliferate the hybridoma, whereby the ascites containing a large amount of the monoclonal antibody of the invention can be obtained.

In the case where the hybridoma is administered in the abdominal cavity, if a mineral oil such as 2,6,10,14-tetramethyl pentadecane (pristane) is administrated 3 to 7 days prior thereto, a larger amount of the ascites can be obtained.

For example, an immunosuppressant is previously injected into the abdominal cavity of a mouse of the same strain as the hybridoma to inactivate T cells. 20 days thereafter, $10^6$ to $10^7$ hybridoma clone cells are suspended in a serum-free medium (0.5 ml), and the suspension is administrated in the abdominal cavity of the mouse. In general, when the abdomen is expanded and filled with the ascites, the ascites is collected from the mouse. By this method, the monoclonal antibody can be obtained at a concentration which is about 100 times or much higher than that in the culture solution.

The monoclonal antibody obtained by the above-described method can be purified by a method described in, for example, Weir, D. M.: Handbook of Experimental Immunology Vol. I, II, III, Blackwell Scientific Publications, Oxford (1978).

The thus obtained monoclonal antibody has high antigen specificity for HER2. Examples of the monoclonal antibody of the present invention can include, but are not particularly limited to, a mouse monoclonal antibody 4D5 (ATCC CRL 10463).

(h) Assay of Monoclonal Antibody

The isotype and subclass of the thus obtained monoclonal antibody can be determined as follows.

First, examples of the identification method include an Ouchterlony method, an ELISA method, and an RIA method.

An Ouchterlony method is simple, but when the concentration of the monoclonal antibody is low, a condensation operation is required.

On the other hand, when an ELISA method or an RIA method is used, by directly reacting the culture supernatant with an antigen-adsorbed solid phase and using antibodies corresponding to various types of immunoglobulin isotypes and subclasses as secondary antibodies, the isotype and subclass of the monoclonal antibody can be identified.

In addition, as a simpler method, a commercially available identification kit (for example, Mouse Typer Kit manufactured by Bio-Rad Laboratories, Inc.) or the like can also be used.

Further, the quantitative determination of a protein can be performed by the Folin Lowry method and a method of calculation based on the absorbance at 280 nm (1.4 (OD 280)=Immunoglobulin 1 mg/ml).

Further, even when the monoclonal antibody is separately and independently obtained by performing again the steps of (a) to (h) in (2), it is possible to obtain an antibody having a cytotoxic activity equivalent to that of the HER2 antibody obtained in the step of (g). As one example of such an antibody, an antibody which binds to the same epitope as the HER2 antibody obtained in the step of (g) can be exemplified. If a newly produced monoclonal antibody binds to a partial peptide or a partial tertiary structure to which the anti-HER2 antibody binds, it can be determined that the monoclonal antibody binds to the same epitope as the anti-HER2 antibody. Further, by confirming that the monoclonal antibody competes with the anti-HER2 antibody for the binding to HER2 (that is, the monoclonal antibody inhibits the binding between the anti-HER2 antibody and HER2), it can be determined that the monoclonal antibody binds to the same epitope as the anti-HER2 antibody even if the specific epitope sequence or structure has not been determined. When it is confirmed that the monoclonal antibody binds to the same epitope as the anti-HER2 antibody, the monoclonal antibody is strongly expected to have an antigen-binding affinity or biological activity equivalent to that of the anti-HER2 antibody.

(3) Other Antibodies

The antibody of the invention includes not only the above-described monoclonal antibody against HER2 but also a recombinant antibody obtained by artificial modification for the purpose of decreasing heterologous antigenicity to humans such as a chimeric antibody, a humanized antibody and a human antibody. These antibodies can be produced using a known method.

As the chimeric antibody, an antibody in which antibody variable and constant regions are derived from different species, for example, a chimeric antibody in which a mouse- or rat-derived antibody variable region is connected to a human-derived antibody constant region can be exemplified (see Proc. Natl. Acad. Sci. USA, 81, 6851-6855, (1984)). Examples of the chimeric antibody of the present invention can include, but are not particularly limited to, a chimeric antibody 4D5 comprising a heavy chain constant region of human IgG1 or IgG2.

As the humanized antibody, an antibody obtained by integrating only a complementarity determining region (CDR) into a human-derived antibody (see Nature (1986) 321, pp. 522-525), and an antibody obtained by grafting a part of the amino acid residues of the framework as well as the CDR sequence to a human antibody by a CDR-grafting method (WO 90/07861), and an antibody humanized using gene conversion mutagenesis strategy (U.S. Pat. No. 5,821, 337) can be exemplified.

The term "several" as used herein refers to 1 to 10, 1 to 9, 1 to 8, 1 to 7, 1 to 6, 1 to 5, 1 to 4, 1 to 3, or 1 or 2.

As the amino acid substitution in this specification, a conservative amino acid substitution is preferred. The conservative amino acid substitution refers to a substitution occurring within a group of amino acids related to amino acid side chains. Preferred amino acid groups are as follows: an acidic group (aspartic acid and glutamic acid); a basic group (lysine, arginine, and histidine); a non-polar group (alanine, valine, leucine, isoleucine, proline, phenylalanine, methionine, and tryptophan); and an uncharged polar family (glycine, asparagine, glutamine, cysteine, serine, threonine, and tyrosine). More preferred amino acid groups are as follows: an aliphatic hydroxy group (serine and threonine); an amide-containing group (asparagine and glutamine); an aliphatic group (alanine, valine, leucine, and isoleucine); and an aromatic group (phenylalanine, tryptophan, and tyrosine). Such an amino acid substitution is preferably performed within a range which does not impair the properties of a substance having the original amino acid sequence.

By combining a sequence having a high homology with the above-described heavy chain amino acid sequence with a sequence having a high homology with the above-described light chain amino acid sequence, it is possible to select an antibody having a biological activity equivalent to that of each of the above-described antibodies. Such a homology is generally a homology of 80% or more, preferably a homology of 90% or more, more preferably a homology of 95% or more, most preferably a homology of 99% or more. Further, by combining an amino acid sequence wherein one to several amino acid residues are substituted, deleted or added in the heavy chain or light chain amino acid sequence, it is also possible to select an antibody having a biological activity equivalent to that of each of the above-described antibodies. The term "homology" as used herein is used with the same meaning as "identity".

The homology between two amino acid sequences can be determined using default parameters of Blast algorithm version 2.2.2 (Altschul, Stephen F., Thomas L. Madden, Alejandro A. Schaeffer, Jinghui Zhang, Zheng Zhang, Webb Miller, and David J. Lipman (1997), "Gapped BLAST and PSI-BLAST: a new generation of protein database search programs", Nucleic Acids Res. 25: 3389-3402). The Blast algorithm can be used also through the Internet by accessing the site www.ncbi.nlm.nih.gov/blast.

Further, the antibody of the invention includes a human antibody which binds to HER2. An anti-HER2 human antibody refers to a human antibody having only a sequence of an antibody derived from a human chromosome. The anti-HER2 human antibody can be obtained by a method using a human antibody-producing mouse having a human chromosome fragment comprising heavy and light chain genes of a human antibody (see Tomizuka, K. et al., Nature Genetics (1997) 16, pp. 133-143; Kuroiwa, Y. et al., Nucl. Acids Res. (1998) 26, pp. 3447-3448; Yoshida, H. et al., Animal Cell Technology: Basic and Applied Aspects vol. 10, pp. 69-73 (Kitagawa, Y., Matuda, T. and Iijima, S. eds.), Kluwer Academic Publishers, 1999; Tomizuka, K. et al., Proc. Natl. Acad. Sci. USA (2000) 97, pp. 722-727, etc.).

Such a human antibody-producing mouse can be created specifically as follows. A genetically modified animal in which endogenous immunoglobulin heavy and light chain gene loci have been disrupted, and instead, human immunoglobulin heavy and light chain gene loci have been introduced via a yeast artificial chromosome (YAC) vector or the like is created by producing a knockout animal and a transgenic animal and mating these animals.

Further, according to a recombinant DNA technique, by using cDNAs encoding each of such a heavy chain and a light chain of a human antibody, and preferably a vector comprising such cDNAs, eukaryotic cells are transformed, and a transformant cell which produces a recombinant human monoclonal antibody is cultured, whereby the antibody can also be obtained from the culture supernatant.

Here, as the host, for example, eukaryotic cells, preferably mammalian cells such as CHO cells, lymphocytes, or myeloma cells can be used.

Further, a method of obtaining a phage display-derived human antibody selected from a human antibody library (see Wormstone, I. M. et al., Investigative Ophthalmology & Visual Science. (2002) 43 (7), pp. 2301-2308; Carmen, S. et al., Briefings in Functional Genomics and Proteomics (2002), 1 (2), pp. 189-203; Siriwardena, D. et al., Ophthalmology (2002) 109 (3), pp. 427-431, etc.) is also known.

For example, a phage display method in which a variable region of a human antibody is expressed on the surface of a phage as a single-chain antibody (scFv), and a phage which binds to an antigen is selected (Nature Biotechnology (2005), 23, (9), pp. 1105-1116) can be used.

By analyzing the gene of the phage selected based on the binding to an antigen, a DNA sequence encoding the variable region of a human antibody which binds to an antigen can be determined.

If the DNA sequence of scFv which binds to an antigen is determined, a human antibody can be obtained by preparing an expression vector comprising the sequence and introducing the vector into an appropriate host to express it (WO 92/01047, WO 92/20791, WO 93/06213, WO 93/11236, WO 93/19172, WO 95/01438, WO 95/15388; Annu. Rev. Immunol. (1994) 12, pp. 433-455, Nature Biotechnology (2005) 23 (9), pp. 1105-1116).

As one example of another index for use in the comparison of the properties of antibodies, the stability of antibodies can be exemplified. The differential scanning calorimetry (DSC) is a device capable of quickly and accurately measuring a thermal denaturation midpoint temperature (Tm) to be used as a favorable index of the relative conformational stability of proteins. By measuring the Tm values using DSC and comparing the values, a difference in thermal stability can be compared. It is known that the storage stability of antibodies shows some correlation with the thermal stability of antibodies (Lori Burton, et. al., Pharmaceutical Development and Technology (2007) 12, pp. 265-273), and a preferred antibody can be selected by using thermal stability as an index. Examples of other indices for selecting antibodies include the following features: the yield in an appropriate host cell is high; and the aggregability in an aqueous solution is low. For example, an antibody which shows the highest yield does not always show the highest thermal stability, and therefore, it is necessary to select an antibody most suitable for the administration to humans by making comprehensive evaluation based on the above-described indices.

In the present invention, a modified variant of the antibody is also included. The modified variant refers to a variant obtained by subjecting the antibody of the present invention to chemical or biological modification. Examples of the chemically modified variant include variants chemically modified by linking a chemical moiety to an amino acid skeleton, variants chemically modified with an N-linked or O-linked carbohydrate chain, etc. Examples of the biologically modified variant include variants obtained by post-translational modification (such as N-linked or O-linked glycosylation, N- or C-terminal processing, deamidation, isomerization of aspartic acid, or oxidation of methionine), and variants in which a methionine residue has been added to the N terminus by being expressed in a prokaryotic host cell. Further, an antibody labeled so as to enable the detection or isolation of the antibody or an antigen of the invention, for example, an enzyme-labeled antibody, a fluorescence-labeled antibody, and an affinity-labeled antibody are also included in the meaning of the modified variant. Such a modified variant of the antibody of the invention is useful for improving the stability and blood retention of the antibody, reducing the antigenicity thereof, detecting or isolating an antibody or an antigen, and so on.

Further, by regulating the modification of a glycan which is linked to the antibody of the invention (glycosylation, defucosylation, etc.), it is possible to enhance an antibody-dependent cellular cytotoxic activity. As the technique for regulating the modification of a glycan of antibodies, WO 99/54342, WO 00/61739, WO 02/31140, etc. are known. However, the technique is not limited thereto. In the antibody of the present invention, an antibody in which the modification of a glycan is regulated is also included.

In the case where an antibody is produced by first isolating an antibody gene and then introducing the gene into an appropriate host, a combination of an appropriate host and an appropriate expression vector can be used. Specific examples of the antibody gene include a combination of a gene encoding a heavy chain sequence of an antibody described in this specification and a gene encoding a light chain sequence thereof. When a host cell is transformed, it is possible to insert the heavy chain sequence gene and the light chain sequence gene into the same expression vector, and also into different expression vectors separately.

In the case where eukaryotic cells are used as the host, animal cells, plant cells, and eukaryotic microorganisms can be used. As the animal cells, mammalian cells, for example, simian COS cells (Gluzman, Y., Cell, (1981) 23, pp. 175-182, ATCC CRL-1650), murine fibroblasts NIH3T3 (ATCC No. CRL-1658), and dihydrofolate reductase-deficient strains (Urlaub, G. and Chasin, L. A., Proc. Natl. Acad. Sci. USA (1980) 77, pp. 4126-4220) of Chinese hamster ovarian cells (CHO cells; ATCC: CCL-61) can be exemplified.

In the case where prokaryotic cells are used, for example, *Escherichia coli* and *Bacillus subtilis* can be exemplified.

By introducing a desired antibody gene into these cells through transformation, and culturing the thus transformed cells in vitro, the antibody can be obtained. In the above-described culture method, the yield may sometimes vary depending on the sequence of the antibody, and therefore, it is possible to select an antibody which is easily produced as a pharmaceutical by using the yield as an index among the antibodies having an equivalent binding activity. Therefore, in the antibody of the present invention, an antibody obtained by a method of producing an antibody, characterized by including a step of culturing the transformed host cell and a step of collecting a desired antibody from a cultured product obtained in the culturing step is also included.

It is known that a lysine residue at the carboxyl terminus of the heavy chain of an antibody produced in a cultured mammalian cell is deleted (Journal of Chromatography A, 705: 129-134 (1995)), and it is also known that two amino acid residues (glycine and lysine) at the carboxyl terminus of the heavy chain of an antibody produced in a cultured mammalian cell are deleted and a proline residue newly located at the carboxyl terminus is amidated (Analytical Biochemistry, 360: 75-83 (2007)). However, such deletion and modification of the heavy chain sequence do not affect the antigen-binding affinity and the effector function (the activation of a complement, the antibody-dependent cellular cytotoxicity, etc.) of the antibody. Therefore, in the antibody according to the present invention, an antibody subjected to such modification and a functional fragment of the antibody is also included, and a deletion variant in which one or two amino acids have been deleted at the carboxyl terminus of the heavy chain, a variant obtained by amidation of the deletion variant (for example, a heavy chain in which the carboxyl terminal proline residue has been amidated), and the like are also included. The type of deletion variant having a deletion at the carboxyl terminus of the heavy chain of the antibody according to the invention is not limited to the above variants as long as the antigen-binding affinity and the effector function are conserved. The two heavy chains constituting the antibody according to the invention may be of one type selected from the group consisting of a full-length heavy chain and the above-described deletion variant, or may be of two types in combination selected therefrom. The ratio of the amount of each deletion variant can be affected by the type of cultured mammalian cells which produce the antibody according to the invention and the culture conditions, however, a case where one amino acid residue at the carboxyl terminus has been deleted in both of the two heavy chains contained as main components in the antibody according to the invention can be exemplified.

As isotype of the antibody of the invention, for example, IgG (IgG1, IgG2, IgG3, IgG4) can be exemplified, and IgG1 or IgG2 can be exemplified preferably.

As the biological activity of the antibody, generally an antigen-binding activity, an activity of internalizing in cells expressing an antigen by binding to the antigen, an activity of neutralizing the activity of an antigen, an activity of enhancing the activity of an antigen, an antibody-dependent cellular cytotoxicity (ADCC) activity, a complement-dependent cytotoxicity (CDC) activity, and an antibody-dependent cell-mediated phagocytosis (ADCP) can be exemplified. The biological activity of the antibody of the present invention is a binding activity to HER2, and preferably an activity of internalizing in HER2-expressing cells by binding to HER2. Further, the antibody of the present invention may have an ADCC activity, a CDC activity, and/or an ADCP activity in addition to an activity of internalizing in cells.

The obtained antibody can be purified to homogeneity. The separation and purification of the antibody may be performed employing a conventional protein separation and purification method. For example, the antibody can be separated and purified by appropriately selecting and combining column chromatography, filter filtration, ultrafiltration, salt precipitation, dialysis, preparative polyacrylamide gel electrophoresis, isoelectric focusing electrophoresis, and the like (Strategies for Protein Purification and Characterization: A Laboratory Course Manual, Daniel R. Marshak et al. eds., Cold Spring Harbor Laboratory Press (1996); Antibodies: A Laboratory Manual. Ed Harlow and David Lane, Cold Spring Harbor Laboratory (1988)), but the method is not limited thereto.

Examples of such chromatography include affinity chromatography, ion exchange chromatography, hydrophobic chromatography, gel filtration chromatography, reverse phase chromatography, and adsorption chromatography.

Such chromatography can be performed employing liquid chromatography such as HPLC or FPLC.

As a column to be used in affinity chromatography, a Protein A column and a Protein G column can be exemplified. For example, as a column using a Protein A column, Hyper D, POROS, Sepharose FF (Pharmacia Corporation) and the like can be exemplified.

Further, by using a carrier having an antigen immobilized thereon, the antibody can also be purified utilizing the binding property of the antibody to the antigen.

[Antitumor Compound]

The antitumor compound to be conjugated to the anti-HER2 antibody-drug conjugate of the present invention is explained. The antitumor compound used in the present invention is not particularly limited provided it is a compound having an antitumor effect and a substituent group or a partial structure allowing connection to a linker structure. When a part or whole linker is cleaved in tumor cells, the antitumor compound moiety is released to exhibit the antitumor effect of the antitumor compound. As the linker is cleaved at a connecting position to the drug, the antitumor compound is released in an unmodified structure to exhibit its intrinsic antitumor effect.

As the antitumor compound used in the present invention, exatecan (((1S,9S)-1-amino-9-ethyl-5-fluoro-2,3-dihydro-9-hydroxy-4-methyl-1H,12H-benzo[de]pyrano[3',4':6,7]indolizino[1,2-b]quinoline-10,13(9H,15H)-dione; shown in the following formula), one of the camptothecin derivatives, can be preferably used.

[Formula 14]

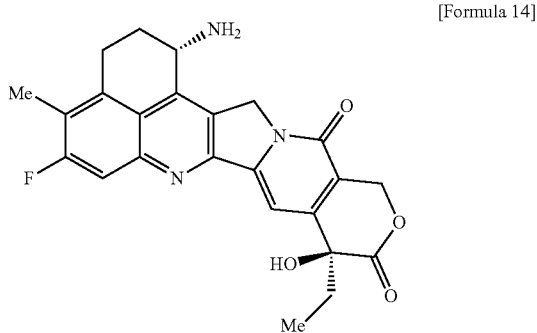 [SMILES: CC[C@@]1(O)C(=O)OCc2c1cc1n(c2=O)Cc2c-1nc1cc(F)c(C)c3c1c2[C@@H](N)CC3]

Although having an excellent antitumor effect, exatecan has not been commercialized as an antitumor drug. The compound can be easily obtained by a known method and the amino group at position 1 can be preferably used as the connecting position to the linker structure. Further, although exatecan can be also released in tumor cells while part of the linker is still attached thereto, it is an excellent compound exhibiting an excellent antitumor effect even in such a structure.

Because exatecan has a camptothecin structure, it is known that the equilibrium shifts to a structure with a closed lactone ring (closed ring) in an aqueous acidic medium (for example, pH 3 or so) but it shifts to a structure with an open lactone ring (open ring) in an aqueous basic medium (for example, pH 10 or so). A drug conjugate being introduced with an exatecan residue corresponding to the closed ring structure and the open ring structure is also expected to have the same antitumor effect and it is needless to say that any of these structures is within the scope of the present invention.

Further examples of the antitumor compound can include doxorubicin, daunorubicin, mitomycin C, bleomycin, cyclocytidine, vincristine, vinblastine, methotrexate, platinum-based antitumor agent (cisplatin or derivatives thereof), taxol or derivatives thereof, and other camptothecins or derivatives thereof (antitumor agent described in Japanese Patent Laid-Open No. 6-87746).

With regard to the antibody-drug conjugate, the number of conjugated drug molecules per antibody molecule is a key factor having an influence on efficacy and safety. Production of the antibody-drug conjugate is performed by defining the reaction conditions including the amounts of raw materials and reagents used for the reaction so as to have a constant number of conjugated drug molecules. A mixture containing different numbers of conjugated drug molecules is generally obtained unlike the chemical reaction of a low-molecular-weight compound. The number of drugs conjugated in an antibody molecule is expressed or specified by the average value, that is, the average number of conjugated drug molecules. Unless specifically described otherwise as a principle, the number of conjugated drug molecules means the average value except in the case in which it represents an antibody-drug conjugate having a specific number of conjugated drug molecules that is included in an antibody-drug conjugate mixture having different numbers of conjugated drug molecules.

The number of exatecan molecules conjugated to an antibody molecule is controllable, and as the average number of conjugated drug molecules per antibody molecule, about 1 to 10 exatecans can be connected. Preferably, it is 2 to 8, and more preferably 3 to 8. Meanwhile, a person skilled in the art can design a reaction for conjugating a required number of drug molecules to an antibody molecule based on the description of the Examples of the present application and can obtain an antibody-drug conjugate conjugated with a controlled number of exatecan molecules.

[Linker Structure]

With regard to the anti-HER2 antibody-drug conjugate of the present invention, the linker structure for conjugating an antitumor compound to the anti-HER2 antibody is explained. The linker has a structure of the following formula:

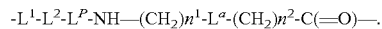

The antibody is connected to the terminal $L^1$ (terminal opposite to the connection to $L^2$), and the antitumor compound is connected to the carbonyl group of the $-L^a-(CH_2)n^2-C(=O)-$ moiety.

$n^1$ represents an integer of 0 to 6 and is preferably an integer of 1 to 5, and more preferably 1 to 3.

1. $L^1$ $L^1$ is represented by the following structure:

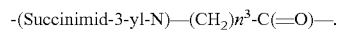

In the above, $n^3$ is an integer of 2 to 8, "-(Succinimid-3-yl-N)—" has a structure represented by the following formula:

[Formula 15]

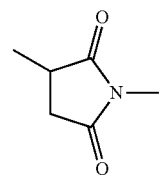

Position 3 of the above partial structure is the connecting position to the anti-HER2 antibody. The bond to the antibody at position 3 is characterized by bonding with thioether formation. The nitrogen atom at position 1 of the structure moiety is connected to the carbon atom of the methylene which is present within the linker including the structure. Specifically, -(Succinimid-3-yl-N)—$(CH_2)n^3$-C(=O)-$L^2$- is a structure represented by the following formula (herein, "antibody-S—" originates from an antibody).

[Formula 16]

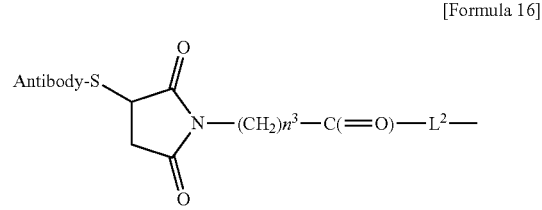

In the formula, $n^3$ is an integer of 2 to 8, and preferably 2 to 5.

Specific examples of $L^1$ can include
-(Succinimid-3-yl-N)—CH$_2$CH$_2$—C(=O)—,
-(Succinimid-3-yl-N)—CH$_2$CH$_2$CH$_2$—C(=O)—,
-(Succinimid-3-yl-N)—CH$_2$CH$_2$CH$_2$CH$_2$—C(=O)—, and
-(Succinimid-3-yl-N)—CH$_2$CH$_2$CH$_2$CH$_2$CH$_2$—C(=O)—.

2. $L^2$ $L^2$ is represented by the following structure:

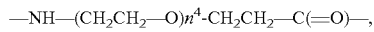

—NH—(CH$_2$CH$_2$—O)$n^4$-CH$_2$CH$_2$—C(=O)—, $L^2$ may not be present, and in such a case, $L^2$ is a single bond. $n^4$ is an integer of 1 to 6, and preferably 2 to 4. $L^2$ is connected to $L^1$ at its terminal amino group and is connected to $L^P$ at its carbonyl group at the other terminal.

Specific examples of $L^2$ can include
—NH—CH$_2$CH$_2$—O—CH$_2$CH$_2$—C(=O)—,
—NH—CH$_2$CH$_2$—O—CH$_2$CH$_2$—O—CH$_2$CH$_2$—C(=O)—,
—NH—CH$_2$CH$_2$—O—CH$_2$CH$_2$—O—CH$_2$CH$_2$—O—CH$_2$CH$_2$—C(=O)—,
—NH—CH$_2$CH$_2$—O—CH$_2$CH$_2$—O—CH$_2$CH$_2$—O—CH$_2$CH$_2$—O—CH$_2$CH$_2$—C(=O)—,
—NH—CH$_2$CH$_2$—O—CH$_2$CH$_2$—O—CH$_2$CH$_2$—O—CH$_2$CH$_2$—O—CH$_2$CH$_2$—O—CH$_2$CH$_2$—C(=O)—,
—NH—CH$_2$CH$_2$—O—CH$_2$CH$_2$—O—CH$_2$CH$_2$—O—CH$_2$CH$_2$—O—CH$_2$CH$_2$—O—CH$_2$CH$_2$—O—CH$_2$CH$_2$—C(=O)—.

3. $L^P$ $L^P$ is a peptide residue consisting of 2 to 7 amino acids. Specifically, it consists of an oligopeptide residue in which 2 to 7 amino acids are linked by peptide bonding. $L^P$ is connected to $L^2$ at its N terminus and is connected to the amino group of the —NH—(CH$_2$)n$^1$-L$^a$-(CH$_2$)n$^2$-C(=O)— moiety of the linker at its C terminus. Here, the term "peptide residue" or "oligopeptide residue" is a group derived from a peptide consisting of two or more amino acid residues and refers to a divalent group whose N terminus and C terminus are connecting positions.

The amino acid constituting $L^P$ in the linker is not particularly limited, however, examples thereof include an L- or a D-amino acid, preferably an L-amino acid. And, it can be an amino acid having a structure such as β-alanine, ε-aminocaproic acid, or γ-aminobutyric acid in addition to an α-amino acid, further, it can be a non-natural type amino acid such as N-methylated amino acid.

The amino acid sequence of $L^P$ is not particularly limited, but examples of the constituting amino acids include phenylalanine (Phe; F), tyrosine (Tyr; Y), leucine (Leu; L), glycine (Gly; G), alanine (Ala; A), valine (Val; V), lysine (Lys; K), citrulline (Cit), serine (Ser; S), glutamic acid (Glu; E), and aspartic acid (Asp; D). Among them, preferred examples include phenylalanine, glycine, valine, lysine, citrulline, serine, glutamic acid, and aspartic acid. From these amino acids, $L^P$ having a sequence of amino acids optionally selected with or without overlaps may be constructed. Depending on the type of the amino acids, the drug release pattern can be controlled. The number of amino acids can be between 2 to 7.

Specific examples of $L^P$ can include

| | |
|---|---|
| -GGF-, | (SEQ ID NO: 10) |
| -DGGF-, | |
| -(D-)D-GGF-, | (SEQ ID NO: 4) |
| -EGGF-, | |
| -GGFG-, | (SEQ ID NO: 3) |
| -SGGF-, | (SEQ ID NO: 5) |
| -KGGF-, | (SEQ ID NO: 6) |
| -DGGFG-, | (SEQ ID NO: 11) |
| -GGFGG-, | (SEQ ID NO: 7) |
| -DDGGFG-, | (SEQ ID NO: 12) |
| -KDGGFG-, and | (SEQ ID NO: 13) |
| -GGFGGGF-. | (SEQ ID NO: 8) |

In the above, "(D-)D" represents a D-aspartic acid. Particularly preferred examples of $L^P$ for the antibody-drug conjugate of the present invention can include the tetrapeptide residue -GGFG (SEQ ID NO: 3)-.

4. $L^a$-(CH$_2$)n$^2$-C(=O)—

$L^a$ in $L^a$-(CH$_2$)n$^2$-C(=O)— is a structure of —O— or a single bond. $n^2$ is an integer of 0 to 5, preferably 0 to 3, and more preferably 0 or 1.

Examples of $L^a$-(CH$_2$)n$^2$-C(=O)— can include the following structures:
—O—CH$_2$—C(=O)—,
—O—CH$_2$CH$_2$—C(=O)—,
—O—CH$_2$CH$_2$CH$_2$—C(=O)—,
—O—CH$_2$CH$_2$CH$_2$CH$_2$—C(=O)—,
—O—CH$_2$CH$_2$CH$_2$CH$_2$CH$_2$—C(=O)—,
—CH$_2$—C(=O)—,
—CH$_2$CH$_2$—C(=O)—,
—CH$_2$CH$_2$CH$_2$—C(=O)—,
—CH$_2$CH$_2$CH$_2$CH$_2$—C(=O)—,
—CH$_2$CH$_2$CH$_2$CH$_2$CH$_2$—C(=O)—,
—O—C(=O)—.

Among these,
—O—CH$_2$—C(=O)—,
—O—CH$_2$CH$_2$—C(=O)—,
—O—C(=O)—,
or a case in which $L^a$ is a single bond, and $n^2$ is 0 is preferred.

Specific examples of the structure represented by —NH—(CH$_2$)n$^1$-L$^a$ (CH$_2$)n$^2$-C(=O)— of the linker can include
—NH—CH$_2$—C(=O)—,
—NH—CH$_2$CH$_2$—C(=O)—,
—NH—CH$_2$—O—CH$_2$—C(=O)—,
—NH—CH$_2$CH$_2$—O—CH$_2$—C(=O)—,
—NH—CH$_2$CH$_2$CH$_2$—C(=O)—,
—NH—CH$_2$CH$_2$CH$_2$CH$_2$—C(=O)—,
—NH—CH$_2$CH$_2$CH$_2$CH$_2$CH$_2$—C(=O)—,
—NH—CH$_2$—O—C(=O)—,
—NH—CH$_2$CH$_2$—O—C(=O)—,
—NH—CH$_2$CH$_2$CH$_2$—O—C(=O)—,
—NH—CH$_2$CH$_2$CH$_2$CH$_2$—O—C(=O)—.

Among these,
—NH—CH$_2$CH$_2$CH$_2$—C(=O)—,
—NH—CH$_2$—O—CH$_2$—C(=O)—,
—NH—CH$_2$CH$_2$—O—CH$_2$—C(=O)—
are more preferred.

In the linker, the chain length of —NH—(CH$_2$)n$^1$-L$^a$-(CH$_2$)n$^2$-C(=O)— is preferably a chain length of 4 to 7 atoms, and more preferably a chain length of 5 or 6 atoms.

With regard to the anti-HER2 antibody-drug conjugate of the present invention, when it is transferred to the inside of tumor cells, it has been suggested that the linker moiety is cleaved and the drug derivative having a structure represented by NH$_2$—(CH$_2$)n$^1$-L$^a$-(CH$_2$)n$^2$-C(=O)—(NH-DX) is released to express an antitumor action. Examples of the antitumor derivative exhibiting an antitumor effect by releasing from the antibody-drug conjugate of the present invention include an antitumor derivative having a structure moiety in which a terminal of the structure represented by —NH—(CH$_2$)n$^1$-L$^a$-(CH$_2$)n$^2$-C(=O)— of the linker has an amino group, and those particularly preferred include the following.

NH$_2$—CH$_2$CH$_2$—C(=O)—(NH-DX),
NH$_2$—CH$_2$CH$_2$CH$_2$—C(=O)—(NH-DX),
NH$_2$—CH$_2$—O—CH$_2$—C(=O)—(NH-DX),
NH$_2$—CHCH$_2$—O—CH$_2$—C(=O)—(NH-DX)

Meanwhile, in case of NH$_2$—CH$_2$—O—CH$_2$—C(=O)— (NH-DX), it was confirmed that, as the aminal structure in the molecule is unstable, it again undergoes a self-degradation to release the following
HO—CH$_2$—C(=O)— (NH-DX). Those compounds can be also preferably used as a production intermediate of the antibody-drug conjugate of the present invention.

For the antibody-drug conjugate of the present invention in which exatecan is used as the drug, it is preferable that the drug-linker structure moiety [-L$^1$-L$^2$-L$^P$-NH—(CH$_2$)n$^1$-L$^a$-(CH$_2$)n$^2$-C(=O)—(NH-DX)] having the following structure is connected to an antibody. The average conjugated number of said drug-linker structure moieties per antibody molecule can be 1 to 10. Preferably, it is 2 to 8, and more preferably 3 to 8.

-(Succinimid-3-yl-N)—CH$_2$CH$_2$—C(=O)-GGFG (SEQ ID NO: 3)-NH—CH$_2$CH$_2$—C(=O)—(NH-DX),
-(Succinimid-3-yl-N)—CH$_2$CH$_2$—C(=O)-GGFG (SEQ ID NO: 3)-NH—CH$_2$CH$_2$CH$_2$—C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$—C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$CH$_2$—C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$CH$_2$CH$_2$CH$_2$—C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$—O—CH$_2$—C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$—O—CH$_2$—C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$—O—C(=O)—(NH-DX),
-(Succinimid-3-yl-N)—CH$_2$CH$_2$—C(=O)—NH—CH$_2$CH$_2$—O—CH$_2$CH$_2$—O—CH$_2$CH$_2$—C(=O)-GGFG (SEQ ID NO: 3)-NH—CH$_2$CH$_2$—C(=O)— (NH-DX),
-(Succinimid-3-yl-N)—CH$_2$CH$_2$—C(=O)—NH—CH$_2$CH$_2$—O—CH$_2$CH$_2$—O—CH$_2$CH$_2$—C(=O)-GGFG (SEQ ID NO: 3)-NH—CH$_2$CH$_2$CH$_2$—C(=O)— (NH-DX),
-(Succinimid-3-yl-N)—CH$_2$CH$_2$—C(=O)—NH—CH$_2$CH$_2$—O—CH$_2$CH$_2$—O—CH$_2$CH$_2$—O—CH$_2$CH$_2$—O—CH$_2$CH$_2$—C(=O)-GGFG (SEQ ID NO: 3)-NH—CH$_2$CH$_2$—C(=O)—(NH-DX),
-(Succinimid-3-yl-N)—CH$_2$CH$_2$—C(=O)—NH—CH$_2$CH$_2$—O—CH$_2$CH$_2$—O—CH$_2$CH$_2$—O—CH$_2$CH$_2$—O—CH$_2$CH$_2$—C(=O)-GGFG (SEQ ID NO: 3)-NH—CH$_2$CH$_2$CH$_2$—C(=O)—(NH-DX).

Among these, more preferred are the following.
-(Succinimid-3-yl-N)—CH$_2$CH$_2$—C(=O)-GGFG (SEQ ID NO: 3)-NH—CH$_2$CH$_2$CH$_2$—C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$CH$_2$—C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$—O—CH$_2$—C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$—O—CH$_2$—C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$—O—C(=O)—(NH-DX),
-(Succinimid-3-yl-N)—CH$_2$CH$_2$—C(=O)—NH—CH$_2$CH$_2$—O—CH$_2$CH$_2$—O—CH$_2$CH$_2$—C(=O)-GGFG (SEQ ID NO: 3)-NH—CH$_2$CH$_2$CH$_2$—C(=O)— (NH-DX),
-(Succinimid-3-yl-N)—CH$_2$CH$_2$—C(=O)—NH—CH$_2$CH$_2$—O—CH$_2$CH$_2$—O—CH$_2$CH$_2$—O—CH$_2$CH$_2$—O—CH$_2$CH$_2$—C(=O)-GGFG (SEQ ID NO: 3)-NH—CH$_2$CH$_2$CH$_2$—C(=O)—(NH-DX).

Particularly preferred are the following.
-(Succinimid-3-yl-N)—CH$_2$CH$_2$CH$_2$CH$_2$CH$_2$—C(=O)-GGFG (SEQ ID NO: 3)-NH—CH$_2$—O—CH$_2$—C(=O)—(NH-DX),
-(Succinimid-3-yl-N)—CH$_2$CH$_2$CH$_2$CH$_2$CH$_2$—C(=O)-GGFG (SEQ ID NO: 3)-NH—CH$_2$CH$_2$—O—CH$_2$—C(=O)—(NH-DX),
-(Succinimid-3-yl-N)—CH$_2$CH$_2$—C(=O)—NH—CH$_2$CH$_2$—O—CH$_2$CH$_2$—O—CH$_2$CH$_2$—C(=O)-GGFG (SEQ ID NO: 3)-NH—CH$_2$CH$_2$CH$_2$—C(=O)—(NH-DX).

With regard to the linker structure for conjugating the anti-HER2 antibody and the drug in the antibody-drug conjugate of the present invention, the preferred linker can be constructed by connecting preferred structures shown for each part of the linker explained above. As for the linker structure, those with the following structure can be preferably used. Meanwhile, the left terminal of these structures is the connecting position with the antibody and the right terminal is the connecting position with the drug.

-(Succinimid-3-yl-N)—CH$_2$CH$_2$—C(=O)-GGFG (SEQ ID NO: 3)-NH—CH$_2$CH$_2$—C(=O)—,
-(Succinimid-3-yl-N)—CH$_2$CH$_2$—C(=O)-GGFG (SEQ ID NO: 3)-NH—CH$_2$CH$_2$CH$_2$—C(=O)—,
-(Succinimid-3-yl-N)—CH$_2$CH$_2$CH$_2$CH$_2$CH$_2$—C(=O)-GGFG (SEQ ID NO: 3)-NH—CH$_2$CH$_2$—C(=O)—,
-(Succinimid-3-yl-N)—CH$_2$CH$_2$CH$_2$CH$_2$CH$_2$—C(=O)-GGFG (SEQ ID NO: 3)-NH—CH$_2$CH$_2$CH$_2$—C(=O)—,
-(Succinimid-3-yl-N)—CH$_2$CH$_2$CH$_2$CH$_2$CH$_2$—C(=O)-GGFG (SEQ ID NO: 3)-NH—CH$_2$CH$_2$CH$_2$CH$_2$CH$_2$—C(=O)—,
-(Succinimid-3-yl-N)—CH$_2$CH$_2$CH$_2$CH$_2$CH$_2$—C(=O)-GGFG (SEQ ID NO: 3)-NH—CH$_2$—O—CH$_2$—C(=O)—,
-(Succinimid-3-yl-N)—CH$_2$CH$_2$CH$_2$CH$_2$CH$_2$—C(=O)-GGFG (SEQ ID NO: 3)-NH—CH$_2$CH$_2$—O—CH$_2$—C(=O)—,
-(Succinimid-3-yl-N)—CH$_2$CH$_2$CH$_2$CH$_2$CH$_2$—C(=O)-GGFG (SEQ ID NO: 3)-NH—CH$_2$CH$_2$—O—C(=O)—,
-(Succinimid-3-yl-N)—CH$_2$CH$_2$—C(=O)—NH—CH$_2$CH$_2$—O—CH$_2$CH$_2$—O—CH$_2$CH$_2$—C(=O)-GGFG (SEQ ID NO: 3)-NH—CH$_2$CH$_2$—C(=O)—,
-(Succinimid-3-yl-N)—CH$_2$CH$_2$—C(=O)—NH—CH$_2$CH$_2$—O—CH$_2$CH$_2$—O—CH$_2$CH$_2$—C(=O)-GGFG (SEQ ID NO: 3)-NH—CH$_2$CH$_2$CH$_2$—C(=O)—,
-(Succinimid-3-yl-N)—CH$_2$CH$_2$—C(=O)—NH—CH$_2$CH$_2$—O—CH$_2$CH$_2$—O—CH$_2$CH$_2$—O—CH$_2$CH$_2$—C(=O)-GGFG (SEQ ID NO: 3)-NH—CH$_2$CH$_2$—C(=O)—, -(Succinimid-3-yl-N)—CH$_2$CH$_2$—C(=O)—NH—CH$_2$CH$_2$—O—CH$_2$CH$_2$—O—CH$_2$CH$_2$—O—CH$_2$CH$_2$—O—CH$_2$CH$_2$—C(=O)-GGFG (SEQ ID NO: 3)-NH—CH$_2$CH$_2$CH$_2$—C(=O)—.

Among these, more preferred are the following.

-(Succinimid-3-yl-N)—CH$_2$CH$_2$—C(=O)-GGFG (SEQ ID NO: 3)-NH—CH$_2$CH$_2$CH$_2$—C(=O)—, -(Succinimid-3-yl-N)—CH$_2$CH$_2$CH$_2$CH$_2$CH$_2$—C(=O)-GGFG (SEQ ID NO: 3)-NH—CH$_2$CH$_2$CH$_2$—C(=O)—, -(Succinimid-3-yl-N)—CH$_2$CH$_2$CH$_2$CH$_2$CH$_2$—C(=O)-GGFG (SEQ ID NO: 3)-NH—CH$_2$—O—CH$_2$—C(=O)—, -(Succinimid-3-yl-N)—CH$_2$CH$_2$CH$_2$CH$_2$CH$_2$—C(=O)-GGFG (SEQ ID NO: 3)-NH—CH$_2$CH$_2$—O—CH$_2$—C(=O)—, -(Succinimid-3-yl-N)—CH$_2$CH$_2$CH$_2$CH$_2$CH$_2$—C(=O)-GGFG (SEQ ID NO: 3)-NH—CH$_2$CH$_2$—O—C(=O)—, -(Succinimid-3-yl-N)—CH$_2$CH$_2$—C(=O)—NH—CH$_2$CH$_2$—O—CH$_2$CH$_2$—O—CH$_2$CH$_2$—C(=O)-GGFG (SEQ ID NO: 3)-NH—CH$_2$CH$_2$CH$_2$—C(=O)—, -(Succinimid-3-yl-N)—CH$_2$CH$_2$—C(=O)—NH—CH$_2$CH$_2$—O—CH$_2$CH$_2$—O—CH$_2$CH$_2$—O—CH$_2$CH$_2$—O—CH$_2$CH$_2$—C(=O)-GGFG (SEQ ID NO: 3)-NH—CH$_2$CH$_2$CH$_2$—C(=O)—.

Particularly preferred include the following.

-(Succinimid-3-yl-N)—CH$_2$CH$_2$CH$_2$CH$_2$CH$_2$—C(=O)-GGFG (SEQ ID NO: 3)-NH—CH$_2$—O—CH$_2$—C(=O)—, -(Succinimid-3-yl-N)—CH$_2$CH$_2$CH$_2$CH$_2$CH$_2$—C(=O)-GGFG (SEQ ID NO: 3)-NH—CH$_2$CH$_2$—O—CH$_2$—C(=O)—, -(Succinimid-3-yl-N)—CH$_2$CH$_2$—C(=O)—NH—CH$_2$CH$_2$—O—CH$_2$CH$_2$—O—CH$_2$CH$_2$—C(=O)-GGFG (SEQ ID NO: 3)-NH—CH$_2$CH$_2$CH$_2$—C(=O)—.

[Production Method]

Next, explanations are given for the representative method for producing the antibody-drug conjugate of the present invention or a production intermediate thereof. Meanwhile, the compounds are hereinbelow described with the compound number shown in each reaction formula. Specifically, they are referred to as a "compound of the formula (1)", a "compound (1)", or the like. The compounds with numbers other than those are also described similarly.

1. Production Method 1

The antibody-drug conjugate represented by the formula (1) in which the antibody is connected to the drug-linker structure via thioether can be produced by the following method, for example.

[Formula 17]

AB $L^{1'}-L^2-L^p-NH-(CH_2)n^1-L^a-(CH_2)n^2-C(=O)-(NH-DX) \xrightarrow{3a}$

2

$AB-L^1-L^2-L^p-NH-(CH_2)n^1-L^a-(CH_2)n^2-C(=O)-(NH-DX)$

1

[In the formula, AB represents an antibody having a sulfhydryl group, and $L^{1'}$ represents $L^1$ linker structure in which the linker terminal is a maleimidyl group (formula shown below)

[Formula 18]

(in the formula, the nitrogen atom is the connecting position), and specifically represents a group in which the -(Succinimid-3-yl-N)— moiety in -(Succinimid-3-yl-N)—(CH$_2$)n$^3$-C(=O)— of $L^1$ is a maleimidyl group. Further, the —(NH-DX) represents a structure represented by the following formula:

[Formula 19]

and it represents a group that is derived by removing one hydrogen atom of the amino group at position 1 of exatecan.]

Further, the compound of the formula (1) in the above reaction formula may be interpreted as a structure in which one structure moiety corresponding from the drug to the linker terminal connects to one antibody. However, it is only a description given for the sake of convenience, and there are actually many cases in which a plurality of the structure moieties are connected to one antibody molecule. The same applies to the explanation of the production method described below.

The antibody-drug conjugate (1) can be produced by reacting the compound (2), which is obtainable by the method described below, with the antibody (3a) having a sulfhydryl group.

The antibody (3a) having a sulfhydryl group can be obtained by a method well known in the art (Hermanson, G. T, Bioconjugate Techniques, pp. 56-136, pp. 456-493, Academic Press (1996)). Examples include: Traut's reagent is reacted with the amino group of the antibody; N-succinimidyl S-acetylthioalkanoates are reacted with the amino group of the antibody followed by reaction with hydroxylamine; after reacting with N-succinimidyl 3-(pyridyldithio)propionate, the antibody is reacted with a reducing agent; the antibody is reacted with a reducing agent such as dithiothreitol, 2-mercaptoethanol, and tris(2-carboxyethyl)phosphine hydrochloride (TCEP) to reduce the disulfide bond in the hinge part in the antibody to form a sulfhydryl group, but it is not limited thereto.

Specifically, using 0.3 to 3 molar equivalents of TCEP as a reducing agent per disulfide at the hinge part in the antibody and reacting with the antibody in a buffer solution containing a chelating agent, the antibody with partially or completely reduced disulfide at the hinge part in the antibody can be obtained. Examples of the chelating agent include ethylenediamine tetraacetic acid (EDTA) and diethylenetriamine pentaacetic acid (DTPA). It can be used at the concentration of 1 mM to 20 mM. Examples of the buffer solution which may be used include a solution of sodium phosphate, sodium borate, or sodium acetate. Specifically, by reacting the antibody with TCEP at 4° C. to 37° C. for 1 to 4 hours, the antibody (3a) having a partially or completely reduced sulfhydryl group can be obtained.

Meanwhile, by conducting the reaction for adding a sulfhydryl group to a drug-linker moiety, the drug-linker moiety can be conjugated by a thioether bond.

Using 2 to 20 molar equivalents of the compound (2) per the antibody (3a) having a sulfhydryl group, the antibody-drug conjugate (1) in which 2 to 8 drug molecules are conjugated per antibody molecule can be produced. Specifically, it is sufficient that the solution containing the compound (2) dissolved therein is added to a buffer solution containing the antibody (3a) having a sulfhydryl group for the reaction. Herein, examples of the buffer solution which may be used include sodium acetate solution, sodium phosphate, and sodium borate. The pH for the reaction is 5 to 9, and more preferably the reaction is performed near pH 7. Examples of the solvent for dissolving the compound (2) include an organic solvent such as dimethyl sulfoxide (DMSO), dimethylformamide (DMF), dimethyl acetamide (DMA), and N-methyl-2-pyridone (NMP).

It is sufficient that the organic solvent solution containing the compound (2) dissolved therein is added at 1 to 20% v/v to a buffer solution containing the antibody (3a) having a sulfhydryl group for the reaction. The reaction temperature is 0 to 37° C., more preferably 10 to 25° C., and the reaction time is 0.5 to 2 hours. The reaction can be terminated by deactivating the reactivity of unreacted compound (2) with a thiol-containing reagent. Examples of the thiol-containing reagent include cysteine and N-acetyl-L-cysteine (NAC). More specifically, 1 to 2 molar equivalents of NAC are added to the compound (2) used and, by incubating at room temperature for 10 to 30 minutes, the reaction can be terminated.

The produced antibody-drug conjugate (1) can, after concentration, buffer exchange, purification, and measurement of antibody concentration and average number of conjugated drug molecules per antibody molecule according to common procedures described below, be subjected to identification of the antibody-drug conjugate (1).

Common Procedure A: Concentration of Aqueous Solution of Antibody or Antibody-Drug Conjugate To a Amicon Ultra (50,000 MWCO, Millipore Co.) container, a solution of antibody or antibody-drug conjugate was added and the solution of the antibody or antibody-drug conjugate was concentrated by centrifugation (centrifuge for 5 to 20 minutes at 2000 G to 3800 G) using a centrifuge (Allegra X-15R, Beckman Coulter, Inc.).

Common Procedure B: Measurement of Antibody Concentration

Using a UV detector (Nanodrop 1000, Thermo Fisher Scientific Inc.), measurement of the antibody concentration was performed according to the method defined by the manufacturer. At that time, a 280 nm absorption coefficient different for each antibody was used (1.3 mLmg$^{-1}$ cm$^{-1}$ to 1.8 mLmg$^{-1}$ cm$^{-1}$)

Common Procedure C-1: Buffer Exchange for Antibody

NAP-25 column (Cat. No. 17-0852-02, GE Healthcare Japan Corporation) using Sephadex G-25 carrier was equilibrated with phosphate buffer (10 mM, pH 6.0; it is referred to as PBS6.0/EDTA in the specification) containing sodium chloride (137 mM) and ethylene diamine tetraacetic acid (EDTA, 5 mM) according to the method defined by the manufacturer. Aqueous solution of the antibody was applied in an amount of 2.5 mL to single NAP-25 column, and then the fraction (3.5 mL) eluted with 3.5 mL of PBS6.0/EDTA was collected. The resulting fraction was concentrated by the Common procedure A. After measuring the concentration of the antibody using the Common procedure B, the antibody concentration was adjusted to 10 mg/mL using PBS6.0/EDTA.

Common Procedure C-2: Buffer Exchange for Antibody

NAP-25 column (Cat. No. 17-0852-02, GE Healthcare Japan Corporation) using Sephadex G-25 carrier was equilibrated with phosphate buffer (50 mM, pH 6.5; it is referred to as PBS6.5/EDTA in the specification) containing sodium chloride (50 mM) and EDTA (2 mM) according to the method defined by the manufacturer. Aqueous solution of the antibody was applied in an amount of 2.5 mL to single NAP-25 column, and then the fraction (3.5 mL) eluted with 3.5 mL of PBS6.5/EDTA was collected. The resulting fraction was concentrated by the Common procedure A. After measuring the concentration of the antibody using the Common procedure B, the antibody concentration was adjusted to 20 mg/mL using PBS6.5/EDTA.

Common Procedure D: Purification of Antibody-Drug Conjugate

NAP-25 column was equilibrated with any buffer selected from commercially available phosphate buffer (PBS7.4, Cat. No. 10010-023, Invitrogen), sodium phosphate buffer (10 mM, pH 6.0; it is referred to as PBS6.0) containing sodium chloride (137 mM), and acetate buffer containing sorbitol (5%) (10 mM, pH 5.5; it is referred to as ABS in the specification). Aqueous solution of the antibody-drug conjugate reaction was applied in an amount of about 1.5 mL to the NAP-25 column, and then eluted with the buffer in an amount defined by the manufacturer to collect the antibody fraction. The collected fraction was again applied to the NAP-25 column and, by repeating 2 to 3 times in total the gel filtration purification process for eluting with buffer, the antibody-drug conjugate excluding non-conjugated drug linker and a low-molecular-weight compound (tris(2-carboxyethyl)phosphine hydrochloride (TCEP), N-acetyl-L-cysteine (NAC), and dimethyl sulfoxide) was obtained.

Common Procedure E: Measurement of Antibody Concentration in Antibody-Drug Conjugate and Average Number of Conjugated Drug Molecules Per Antibody Molecule (1).

The conjugated drug concentration in the antibody-drug conjugate can be calculated by measuring UV absorbance of an aqueous solution of the antibody-drug conjugate at two wavelengths of 280 nm and 370 nm, followed by performing the calculation shown below.

Because the total absorbance at any wavelength is equal to the sum of the absorbance of every light-absorbing chemical species that are present in the system (additivity of absorbance), when the molar absorption coefficients of the antibody and the drug remain the same before and after conjugation between the antibody and the drug, the antibody concentration and the drug concentration in the antibody-drug conjugate are expressed by the following equations.

$$A_{280}=A_{D,280}+A_{A,280}=\varepsilon_{D,280}C_D+\varepsilon_{A,280}C_A \quad \text{Equation (I)}$$

$$A_{370}=A_{D,370}+A_{A,370}=\varepsilon_{D,370}C_D+\varepsilon_{A,370}C_A \quad \text{Equation (II)}$$

In the above, $A_{280}$ represents the absorbance of an aqueous solution of the antibody-drug conjugate at 280 nm, $A_{370}$ represents the absorbance of an aqueous solution of the antibody-drug conjugate at 370 nm, $A_{A,280}$ represents the absorbance of an antibody at 280 nm, $A_{A,370}$ represents the absorbance of an antibody at 370 nm, $A_{D,280}$ represents the absorbance of a conjugate precursor at 280 nm, $A_{D,370}$ represents the absorbance of a conjugate precursor at 370 nm, $\varepsilon_{A,280}$ represents the molar absorption coefficient of an antibody at 280 nm, $\varepsilon_{A,370}$ represents the molar absorption coefficient of an antibody at 370 nm, $\varepsilon_{D,280}$ represents the molar absorption coefficient of a conjugate precursor at 280 nm, $\varepsilon_{D,370}$ represents the molar absorption coefficient of a conjugate precursor at 370 nm, $C_A$ represents the antibody concentration in an antibody-drug conjugate, and $C_D$ represent the drug concentration in an antibody-drug conjugate.

As for $\varepsilon_{A,280}$, $\varepsilon_{A,370}$, $\varepsilon_{D,280}$, and $\varepsilon_{D,370}$ in the above, previously prepared values (estimated values based on calculation or measurement values obtained by UV measurement of the compounds) are used. For example, $\varepsilon_{A,280}$ can be estimated from the amino acid sequence of an antibody using a known calculation method (Protein Science, 1995, vol. 4, 2411-2423). $\varepsilon_{A,370}$ is generally zero. In Examples, as for the molar absorption coefficient of trastuzumab, $\varepsilon_{A,280}=215400$ (estimated value based on calculation) and $\varepsilon_{A,370}=0$ were used. $\varepsilon_{D,280}$ and $\varepsilon_{D,370}$ can be obtained based on Lambert-Beer's law (Absorbance=molar concentration× molar absorption coefficient×cell path length) by measuring the absorbance of a solution in which the conjugate precursor to be used is dissolved at a certain molar concentration. As for the molar absorption coefficient of a drug linker in the Examples, $\varepsilon_{D,280}=5000$ (measured average value) and $\varepsilon_{D,370}=19000$ (measured average value) were used, unless otherwise specified. By measuring $A_{280}$ and $A_{370}$ of an aqueous solution of the antibody-drug conjugate and solving the simultaneous equations (I) and (II) using the values, $C_A$ and $C_D$ can be obtained. Further, by dividing $C_D$ by $C_A$, the average number of conjugated drug molecules per antibody molecule can be obtained.

Common Procedure F: Measurement (2) of Average Number of Conjugated Drug Molecules Per Antibody Molecule in Antibody-Drug Conjugate.

The average number of conjugated drug molecules per antibody molecule in the antibody-drug conjugate can also be determined by high-performance liquid chromatography (HPLC) analysis using the following method in addition to the aforementioned Common procedure E.

[F-1. Preparation of Sample for HPLC Analysis (Reduction of Antibody-Drug Conjugate)]

An antibody-drug conjugate solution (about 1 mg/mL, 60 μL) is mixed with an aqueous solution of dithiothreitol (DTT) (100 mM, 15 μL). A sample in which the disulfide bond between the L chain and the H chain of the antibody-drug conjugate has been cleaved by incubating the mixture for 30 minutes at 37° C. is used in HPLC analysis.

[F-2. HPLC Analysis]

The HPLC analysis is performed under the following measurement conditions:

HPLC system: Agilent 1290 HPLC system (Agilent Technologies, Inc.)

Detector: ultraviolet absorption spectrometer (measurement wavelength: 280 nm)

Column: PLRP-S (2.1×50 mm, 8 m, 1000 angstroms; Agilent Technologies, Inc., P/N PL1912-1802)

Column temperature: 80° C.

Mobile phase A: aqueous solution containing 0.04% trifluoroacetic acid (TFA)

Mobile phase B: acetonitrile solution containing 0.04% TFA

Gradient program: 29%-36% (0-12.5 min), 36%-42% (12.5-15 min), 42%-29% (15-15.1 min), and 29%-29% (15.1-25 min) Sample injection volume: 15 μL

[F-3. Data Analysis]

[F-3-1] Compared with non-conjugated antibody L ($L_0$) and H ($H_0$) chains, drug-conjugated L (L chain connected to one drug molecule: $L^1$) and H (H chain connected to one drug molecule: $H_1$, H chain connected to two drug molecule: $H_2$, H chain connected to three drug molecules: $H_3$) chains exhibit higher hydrophobicity in proportion to the number of conjugated drug molecules and thus have a larger retention time. These chains are therefore eluted in the order of $L_0$ and $L_1$ or $H_0$, $H_1$, $H_2$, and $H_3$. Detection peaks can be assigned to any of $L_0$, $L_1$, $H_0$, $H_1$, $H_2$, and $H_3$ by the comparison of retention times with $L_0$ and $H_0$.

[F-3-2] Since the drug linker has UV absorption, peak area values are corrected in response to the number of conjugated drug linker molecules according to the following expression using the molar absorption coefficients of the L or H chain and the drug linker.

[Expression 1]

Corrected value of the peak area of the $L$ chain ($L_i$) =

$$\text{Peak area} \times \frac{\text{Molar absorption coefficient of the } L \text{ chain}}{\text{Molar absorption coefficient of the } L \text{ chain} + \text{The number of conjugated drug molecules} \times \text{Molar absorption coefficient of the drug linker}}$$

[Expression 2]

Corrected value of the peak area of the $H$ chain ($H_i$) =

$$\text{Peak area} \times \frac{\text{Molar absorption coefficient of the } H \text{ chain}}{\text{Molar absorption coefficient of the } H \text{ chain} + \text{The number of conjugated drug molecules} \times \text{Molar absorption coefficient of the drug linker}}$$

Here, as for the molar absorption coefficient (280 nm) of the L or H chain of each antibody, a value estimated from the amino acid sequence of the L or H chain of each antibody by a known calculation method (Protein Science, 1995, vol. 4, 2411-2423) can be used. In the case of trastuzumab, a molar absorption coefficient of 26150 and a molar absorption coefficient of 81290 were used as estimated values for the L and H chains, respectively, according to its amino acid sequence. As for the molar absorption coefficient (280 nm) of the drug linker, the measured molar absorption coefficient (280 nm) of a compound in which the maleimide group was converted to succinimide thioether by the reaction of each drug linker with mercaptoethanol or N-acetylcysteine was used.

[F-3-3] The peak area ratio (%) of each chain is calculated for the total of the corrected values of peak areas according to the following expression.

[Expression 3]

$$\text{Peak area ratio of the } L \text{ chain} = \frac{A_{Li}}{A_{L0} + A_{L1}} \times 100$$

$$\text{Peak area ratio of the } H \text{ chain} = \frac{A_{Hi}}{A_{H0} + A_{H1} + A_{H2} + A_{H3}} \times 100$$

Corrected values of respective peak areas of $A_{Li}$, $A_{Hi}$: $L_i H_i$

[F-3-4] The average number of conjugated drug molecules per antibody molecule in the antibody-drug conjugate is calculated according to the following expression.

Average number of conjugated drug molecules=($L_0$ peak area ratio×0+$L_0$ peak area ratio×1+$H_0$ peak area ratio×0+$H_1$ peak area ratio×1+$H_2$ peak area ratio×2+$H_3$ peak area ratio×3)/100×2

The production intermediate compound used in Production method 1 is described below. The compound represented by the formula (2) in Production method 1 is a compound represented by the following formula:

(maleimid-N-yl)-(CH$_2$)$n^3$-C(=O)-L$^2$-L$^P$-NH—(CH$_2$) $n^1$-L$^a$-(CH$_2$)$n^2$-C(=O)—(NH-DX).

In the formula,
$n^3$ represents an integer of 2 to 8,
$L^2$ represents —NH—(CH$_2$CH$_2$—O)n$^4$-CH$_2$CH$_2$—C(=O)— or a single bond,
wherein $n^4$ represents an integer of 1 to 6,
$L^P$ represents a peptide residue consisting of 2 to 7 amino acids selected from phenylalanine, glycine, valine, lysine, citrulline, serine, glutamic acid, and aspartic acid,
$n^1$ represents an integer of 0 to 6,
$n^2$ represents an integer of 0 to 5,
$L^a$ represents —O— or a single bond,
(maleimid-N-yl)- is a maleimidyl group (2,5-dioxo-2,5-dihydro-1H-pyrrol-1-yl group) represented by the following formula:

[Formula 20]

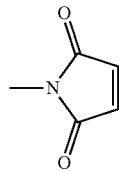

wherein the nitrogen atom is the connecting position, and —(NH-DX) is a group represented by the following formula:

[Formula 21]

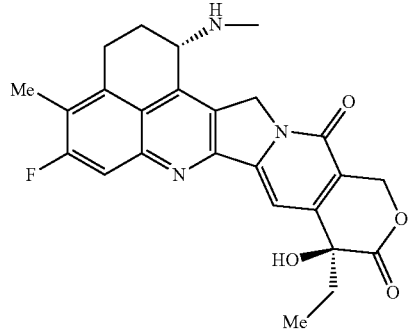

wherein the nitrogen atom of the amino group at position 1 is the connecting position.

When $L^2$ is a single bond or —NH—(CH$_2$CH$_2$—O)n$^4$-CH$_2$CH$_2$—C(=O)—, it is preferred as a production intermediate that $n^4$ should be an integer of 2 to 4.

As for the peptide residue of $L^P$, a compound having a peptide residue consisting of an amino acid selected from phenylalanine, glycine, valine, lysine, citrulline, serine, glutamic acid, and aspartic acid is preferred as a production intermediate. Among those peptide residues, a compound in which $L^P$ is a peptide residue consisting of 4 amino acids is preferred as a production intermediate. More specifically, a compound in which $L^P$ is the tetrapeptide residue -GGFG- (SEQ ID NO: 3) is preferred as a production intermediate.

Further, as for the —NH—(CH$_2$)n$^1$-L$^a$-(CH$_2$)n$^2$-, a compound having —NH—CH$_2$CH$_2$—, —NH—CH$_2$CH$_2$CH$_2$—, —NH—CH$_2$CH$_2$CH$_2$CH$_2$—, —NH—CH$_2$CH$_2$CH$_2$CH$_2$CH$_2$—, —NH—CH$_2$—O—CH$_2$—, or —NH—CH$_2$CH$_2$—O—CH$_2$— is preferred as a production intermediate. A compound having —NH—CH$_2$CH$_2$CH$_2$—, —NH—CH$_2$—O—CH$_2$—, or —NH—CH$_2$CH$_2$—O—CH$_2$ is more preferred.

A compound represented by the formula (2) in which $n^3$ is an integer of 2 to 5, $L^2$ is a single bond, and —NH—(CH$_2$)n$^1$-L$^a$-(CH$_2$)n$^2$- is —NH—CH$_2$CH$_2$—, —NH—CH$_2$CH$_2$CH$_2$—, —NH—CH$_2$CH$_2$CH$_2$CH$_2$—, —NH—CH$_2$CH$_2$CH$_2$CH$_2$CH$_2$—, —NH—CH$_2$—O—CH$_2$—, or —NH—CH$_2$CH$_2$—O—CH$_2$— is preferred as a production intermediate. A compound in which —NH—(CH$_2$)n$^1$-L$^a$-(CH$_2$)n$^2$- is —NH—CH$_2$CH$_2$—, —NH—CH$_2$CH$_2$CH$_2$—, —NH—CH$_2$—O—CH$_2$—, or —NH—CH$_2$CH$_2$—O—CH$_2$— is more preferred. A compound in which $n^3$ is an integer of 2 or 5 is further preferred.

A compound represented by the formula (2) in which $n^3$ is an integer of 2 to 5, $L^2$ is —NH—(CH$_2$CH$_2$—O)n$^4$-CH$_2$CH$_2$—C(=O)—, $n^4$ is an integer of 2 to 4, and —NH—(CH$_2$)n$^1$-L$^a$-(CH$_2$)n$^2$- is —NH—CH$_2$CH$_2$—, —NH—CH$_2$CH$_2$CH$_2$—, —NH—CH$_2$CH$_2$CH$_2$CH$_2$—, —NH—CH$_2$CH$_2$CH$_2$CH$_2$CH$_2$—, —NH—CH$_2$—O—CH$_2$—, or —NH—CH$_2$CH$_2$—O—CH$_2$— is preferred as a production intermediate. A compound in which $n^4$ is an integer of 2 or 4 is more preferred. A compound in which —NH—(CH$_2$)n$^1$-L$^a$-(CH$_2$)n$^2$- is —NH—CH$_2$CH$_2$CH$_2$—, —NH—CH$_2$—O—CH$_2$—, or —NH—CH$_2$CH$_2$—O—CH$_2$— is further preferred.

Preferred examples of an intermediate useful in producing such a compound of the present invention can include the following.
(maleimid-N-yl)-CH$_2$CH$_2$—C(=O)-GGFG (SEQ ID NO: 3)-NH—CH$_2$CH$_2$—C(=O)—(NH-DX),
(maleimid-N-yl)-CH$_2$CH$_2$CH$_2$—C(=O)-GGFG (SEQ ID NO: 3)-NH—CH$_2$CH$_2$—C(=O)—(NH-DX),
(maleimid-N-yl)-CH$_2$CH$_2$CH$_2$CH$_2$—C(=O)-GGFG (SEQ ID NO: 3)-NH—CH$_2$CH$_2$—C(=O)—(NH-DX),
(maleimid-N-yl)-CH$_2$CH$_2$CH$_2$CH$_2$CH$_2$—C(=O)-GGFG (SEQ ID NO: 3)-NH—CH$_2$CH$_2$—C(=O)—(NH-DX),
(maleimid-N-yl)-CH$_2$CH$_2$—C(=O)-GGFG (SEQ ID NO: 3)-NH—CH$_2$CH$_2$CH$_2$—C(=O)—(NH-DX),
(maleimid-N-yl)-CH$_2$CH$_2$CH$_2$—C(=O)-GGFG (SEQ ID NO: 3)-NH—CH$_2$CH$_2$CH$_2$—C(=O)—(NH-DX),
(maleimid-N-yl)-CH$_2$CH$_2$CH$_2$CH$_2$—C(=O)-GGFG (SEQ ID NO: 3)-NH—CH$_2$CH$_2$CH$_2$—C(=O)—(NH-DX),
(maleimid-N-yl)-CH$_2$CH$_2$CH$_2$CH$_2$CH$_2$—C(=O)-GGFG (SEQ ID NO: 3)-NH—CH$_2$CH$_2$CH$_2$—C(=O)—(NH-DX),
(maleimid-N-yl)-CH$_2$CH$_2$—C(=O)-GGFG (SEQ ID NO: 3)-NH—CH$_2$CH$_2$CH$_2$CH$_2$—C(=O)—(NH-DX),
(maleimid-N-yl)-CH$_2$CH$_2$CH$_2$—C(=O)-GGFG (SEQ ID NO: 3)-NH—CH$_2$CH$_2$CH$_2$CH$_2$—C(=O)—(NH-DX),
(maleimid-N-yl)-CH$_2$CH$_2$CH$_2$CH$_2$—C(=O)-GGFG (SEQ ID NO: 3)-NH—CH$_2$CH$_2$CH$_2$CH$_2$—C(=O)—(NH-DX),
(maleimid-N-yl)-CH$_2$CH$_2$CH$_2$CH$_2$CH$_2$—C(=O)-GGFG (SEQ ID NO: 3)-NH—CH$_2$CH$_2$CH$_2$CH$_2$—C(=O)—(NH-DX),
(maleimid-N-yl)-CH$_2$CH$_2$—C(=O)-GGFG (SEQ ID NO: 3)-NH—CH$_2$CH$_2$CH$_2$CH$_2$CH$_2$—C(=O)—(NH-DX), (maleimid-N-yl)-CH$_2$CH$_2$CH$_2$—C(=O)-GGFG (SEQ ID NO: 3)-NH—CH$_2$CH$_2$CH$_2$CH$_2$CH$_2$—C(=O)—(NH-DX),
(maleimid-N-yl)-CH$_2$CH$_2$CH$_2$CH$_2$—C(=O)-GGFG (SEQ ID NO: 3)-NH—CH$_2$CH$_2$CH$_2$CH$_2$CH$_2$—C(=O)—(NH-DX),
(maleimid-N-yl)-CH$_2$CH$_2$CH$_2$CH$_2$CH$_2$—C(=O)-GGFG (SEQ ID NO: 3)-NH—CH$_2$CH$_2$CH$_2$CH$_2$CH$_2$—C(=O)—(NH-DX),
(maleimid-N-yl)-CH$_2$CH$_2$—C(=O)-GGFG (SEQ ID NO: 3)-NH—CH$_2$—O—CH$_2$—C(=O)—(NH-DX),
(maleimid-N-yl)-CH$_2$CH$_2$CH$_2$—C(=O)-GGFG (SEQ ID NO: 3)-NH—CH$_2$—O—CH$_2$—C(=O)—(NH-DX),
(maleimid-N-yl)-CH$_2$CH$_2$CH$_2$CH$_2$—C(=O)-GGFG (SEQ ID NO: 3)-NH—CH$_2$—O—CH$_2$—C(=O)—(NH-DX),
(maleimid-N-yl)-CH$_2$CH$_2$CH$_2$CH$_2$CH$_2$—C(=O)-GGFG (SEQ ID NO: 3)-NH—CH$_2$—O—CH$_2$—C(=O)—(NH-DX),
(maleimid-N-yl)-CH$_2$CH$_2$—C(=O)-GGFG (SEQ ID NO: 3)-NH—CH$_2$CH$_2$—O—CH$_2$—C(=O)—(NH-DX),
(maleimid-N-yl)-CH$_2$CH$_2$CH$_2$—C(=O)-GGFG (SEQ ID NO: 3)-NH—CH$_2$CH$_2$—O—CH$_2$—C(=O)—(NH-DX),
(maleimid-N-yl)-CH$_2$CH$_2$CH$_2$CH$_2$—C(=O)-GGFG (SEQ ID NO: 3)-NH—CH$_2$CH$_2$—O—CH$_2$—C(=O)—(NH-DX),
(maleimid-N-yl)-CH$_2$CH$_2$CH$_2$CH$_2$CH$_2$—C(=O)-GGFG (SEQ ID NO: 3)-NH—CH$_2$CH$_2$—O—CH$_2$—C(=O)—(NH-DX),
(maleimid-N-yl)-CH$_2$CH$_2$—C(=O)—NH—CH$_2$CH$_2$—O—CH$_2$CH$_2$—O—CH$_2$CH$_2$—C(=O)-GGFG (SEQ ID NO: 3)-NH—CH$_2$CH$_2$CH$_2$—C(=O)—(NH-DX),
(maleimid-N-yl)-CH$_2$CH$_2$—C(=O)—NH—CH$_2$CH$_2$—O—CH$_2$CH$_2$—O—CH$_2$CH$_2$—O—CH$_2$CH$_2$—C(=O)-GGFG (SEQ ID NO: 3)-NH—CH$_2$CH$_2$CH$_2$—C(=O)—(NH-DX),
(maleimid-N-yl)-CH$_2$CH$_2$—C(=O)—NH—CH$_2$CH$_2$—O—CH$_2$CH$_2$—O—CH$_2$CH$_2$—O—CH$_2$CH$_2$—C(=O)-GGFG (SEQ ID NO: 3)-NH—CH$_2$CH$_2$CH$_2$—C(=O)—(NH-DX).

The anti-HER2 antibody-drug conjugate of the present invention can be produced by reacting a drug-linker compound selected from the above-mentioned production intermediate compound group with an anti-HER2 antibody or a reactive derivative thereof to thereby form a thioether bond at a disulfide bond site present in the hinge part of the anti-HER2 antibody. In this case, the reactive derivative of the anti-HER2 antibody is preferably used, and a reactive derivative obtained by reducing the anti-HER2 antibody is particularly preferred.

The following are compounds more preferred as a production intermediate.

(maleimid-N-yl)-CH$_2$CH$_2$—C(=O)-GGFG (SEQ ID NO: 3)-NH—CH$_2$CH$_2$—C(=O)—(NH-DX),
(maleimid-N-yl)-CH$_2$CH$_2$—C(=O)-GGFG (SEQ ID NO: 3)-NH—CH$_2$CH$_2$CH$_2$—C(=O)—(NH-DX),
(maleimid-N-yl)-CH$_2$CH$_2$CH$_2$CH$_2$—C(=O)-GGFG (SEQ ID NO: 3)-NH—CH$_2$CH$_2$—C(=O)—(NH-DX),
(maleimid-N-yl)-CH$_2$CH$_2$CH$_2$CH$_2$—C(=O)-GGFG (SEQ ID NO: 3)-NH—CH$_2$CH$_2$CH$_2$—C(=O)—(NH-DX),
(maleimid-N-yl)-CH$_2$CH$_2$CH$_2$CH$_2$CH$_2$—C(=O)-GGFG (SEQ ID NO: 3)-NH—CH$_2$CH$_2$CH$_2$CH$_2$CH$_2$—C(=O)—(NH-DX),
(maleimid-N-yl)-CH$_2$CH$_2$CH$_2$CH$_2$CH$_2$—C(=O)-GGFG (SEQ ID NO: 3)-NH—CH$_2$—O—CH$_2$—C(=O)—(NH-DX),
(maleimid-N-yl)-CH$_2$CH$_2$CH$_2$CH$_2$CH$_2$—C(=O)-GGFG (SEQ ID NO: 3)-NH—CH$_2$CH$_2$—O—CH$_2$—C(=O)—(NH-DX),
(maleimid-N-yl)-CH$_2$CH$_2$—C(=O)—NH—CH$_2$CH$_2$—O—CH$_2$CH$_2$—O—CH$_2$CH$_2$—C(=O)-GGFG (SEQ ID NO: 3)-NH—CH$_2$CH$_2$—C(=O)— (NH-DX),
(maleimid-N-yl)-CH$_2$CH$_2$—C(=O)—NH—CH$_2$CH$_2$—O—CH$_2$CH$_2$—O—CH$_2$CH$_2$—C(=O)-GGFG (SEQ ID NO: 3)-NH—CH$_2$CH$_2$CH$_2$—C(=O)—(NH-DX),
(maleimid-N-yl)-CH$_2$CH$_2$—C(=O)—NH—CH$_2$CH$_2$—O—CH$_2$CH$_2$—O—CH$_2$CH$_2$—O—CH$_2$CH$_2$—C(=O)-GGFG (SEQ ID NO: 3)-NH—CH$_2$CH$_2$CH$_2$—C(=O)— (NH-DX).

Among the above-mentioned intermediate compound group, a compound represented by the following formula:
(maleimid-N-yl)-CH$_2$CH$_2$—C(=O)—NH—CH$_2$CH$_2$—O—CH$_2$CH$_2$—O—CH$_2$CH$_2$—C(=O)-GGFG (SEQ ID NO: 3)-NH—CH$_2$CH$_2$CH$_2$—C(=O)—(NH-DX),
(maleimid-N-yl)-CH$_2$CH$_2$CH$_2$CH$_2$CH$_2$—C(=O)-GGFG (SEQ ID NO: 3)-NH—CH$_2$—O—CH$_2$—C(=O)—(NH-DX), or
(maleimid-N-yl)-CH$_2$CH$_2$CH$_2$CH$_2$CH$_2$—C(=O)-GGFG (SEQ ID NO: 3)-NH—CH$_2$CH$_2$—O—CH$_2$—C(=O)—(NH-DX),
is a further preferred compound.

In order to secure the amount of the conjugate, a plurality of conjugates obtained under similar production conditions to have an equivalent number of drugs (e.g., about ±1) can be mixed to prepare new lots. In this case, the average number of drugs falls between the average numbers of drugs in the conjugates before the mixing.

2. Production Method 2

The compound represented by the formula (2) as an intermediate used in the previous production method and a pharmacologically acceptable salt thereof can be produced by the following method, for example.

[Formula 22]
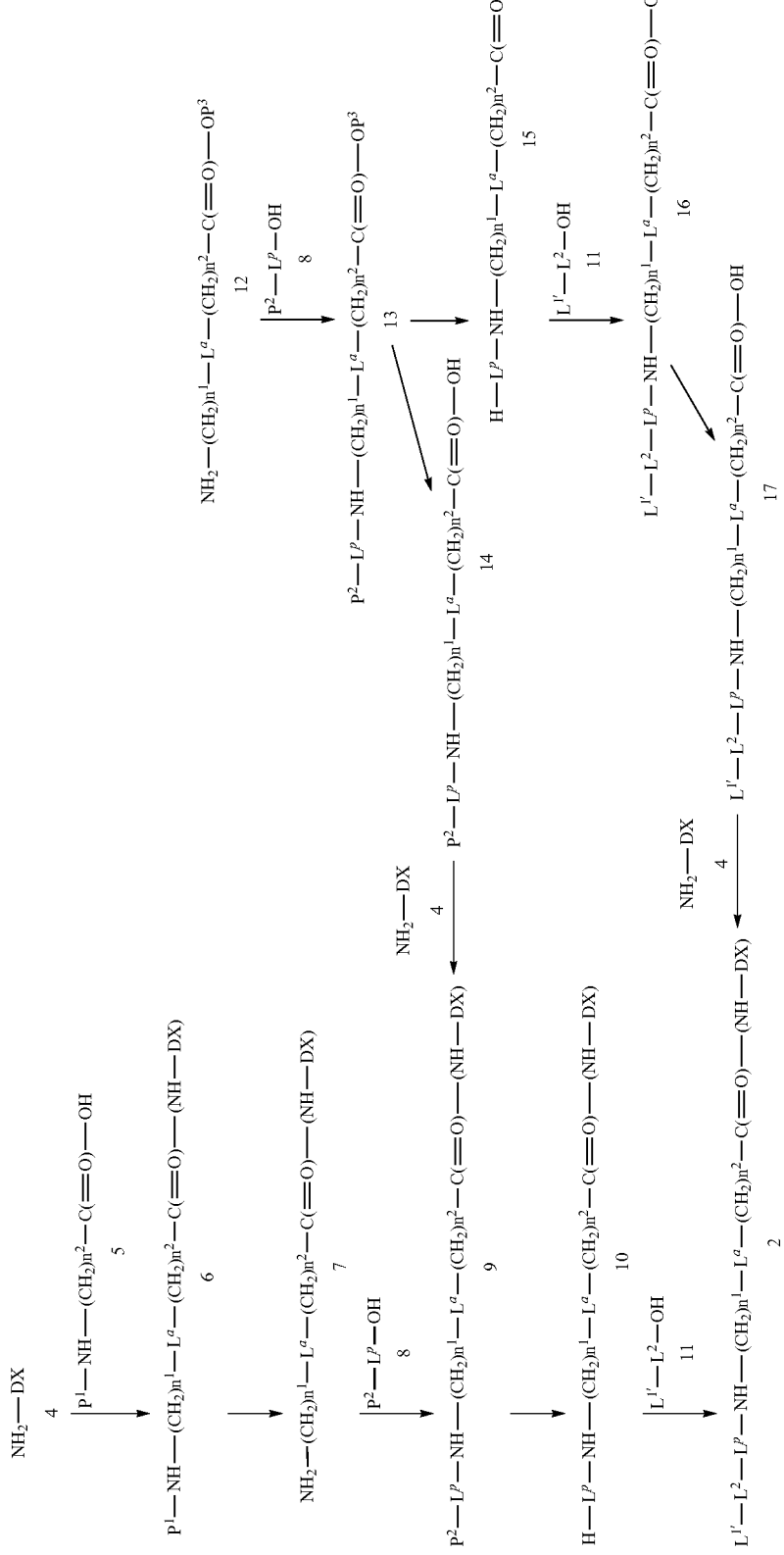

In the formula, $L^{1'}$ represents a terminal maleimidyl group, and $P^1$, $P^2$, and $P^3$ each represent a protecting group.

The compound (6) can be produced by derivatizing the carboxylic acid (5) into an active ester, mixed acid anhydride, acid halide, or the like and reacting it with $NH_2$-DX(4) or a pharmacologically acceptable salt thereof. $NH_2$-DX (4) indicates exatecan (chemical name: (1S,9S)-1-amino-9-ethyl-5-fluoro-2,3-dihydro-9-hydroxy-4-methyl-1H,12H-benzo[de]pyrano[3',4':6,7]indolizino[1,2-b]quinolin-10,13 (9H,15H)-dione).

Reaction reagents and conditions that are commonly used for peptide synthesis can be employed for the reaction. There are various kinds of active ester. For example, it can be produced by reacting phenols such as p-nitrophenol, N-hydroxy benzotriazole, N-hydroxy succinimide, or the like, with the carboxylic acid (5) using a condensing agent such as N,N'-dicyclohexylcarbodiimide or 1-ethyl-3-(3-dimethylaminopropyl)carbodiimide hydrochloride. Further, the active ester can be also produced by a reaction of the carboxylic acid (5) with pentafluorophenyl trifluoroacetate or the like; a reaction of the carboxylic acid (5) with 1-benzotriazolyl oxytripyrrolidinophosphonium hexafluorophosphite; a reaction of the carboxylic acid (5) with diethyl cyanophosphonate (salting-in method); a reaction of the carboxylic acid (5) with triphenylphosphine and 2,2'-dipyridyl disulfide (Mukaiyama's method); a reaction of the carboxylic acid (5) with a triazine derivative such as 4-(4,6-dimethoxy-1,3,5-triazin-2-yl)-4-methylmorpholinium chloride (DMTMM); or the like. Further, the reaction can be also performed by, e.g., an acid halide method by which the carboxylic acid (5) is treated with an acid halide such as thionyl chloride and oxalyl chloride in the presence of a base.

By reacting the active ester, mixed acid anhydride, or acid halide of the carboxylic acid (5) obtained as above with the compound (4) in the presence of a suitable base in an inert solvent at $-78°$ C. to $150°$ C., the compound (6) can be produced. (Meanwhile, "inert solvent" indicates a solvent which does not inhibit a reaction for which the solvent is used.)

Specific examples of the base used for each step described above include a carbonate, alkoxide, hydroxide or hydride of an alkali metal or an alkali earth metal such as sodium carbonate, potassium carbonate, sodium ethoxide, potassium butoxide, sodium hydroxide, potassium hydroxide, sodium hydride, and potassium hydride; an organometallic base represented by an alkyl lithium such as n-butyl lithium, or dialkylamino lithium such as lithium diisopropylamide; an organometallic base of bissilylamine such as lithium bis(trimethylsilyl)amide; and an organic base including a tertiary amine or a nitrogen-containing heterocyclic compound such as pyridine, 2,6-lutidine, collidine, 4-dimethylaminopyridine, triethylamine, N-methyl morpholine, diisopropylethylamine, and diazabicyclo[5.4.0]undec-7-ene (DBU).

Examples of the inert solvent which is used for the reaction of the present invention include a halogenated hydrocarbon solvent such as dichloromethane, chloroform, and carbon tetrachloride; an ether solvent such as tetrahydrofuran, 1,2-dimethoxyethane, and dioxane; an aromatic hydrocarbon solvent such as benzene and toluene; and an amide solvent such as N,N-dimethylformamide, N,N-dimethylacetamide, and N-methylpyrrolidin-2-one. In addition to these, a sulfoxide solvent such as dimethyl sulfoxide and sulfolane; and a ketone solvent such as acetone and methyl ethyl ketone and an alcohol solvent such as methanol and ethanol may be used in some cases. Further, a mixed solvent thereof can also be used.

As for the protecting group $P^1$ for the terminal amino group of the compound (6), a protecting group for an amino group which is generally used for peptide synthesis, for example, a tert-butyloxy carbonyl group, a 9-fluorenylmethyloxy carbonyl group, or a benzyloxy carbonyl group, can be used. Examples of other protecting groups for an amino group include an alkanoyl group such as an acetyl group; an alkoxycarbonyl group such as a methoxycarbonyl group and an ethoxycarbonyl group; an arylmethoxy carbonyl group such as a paramethoxybenzyloxy carbonyl group, and a para (or ortho)nitrobenzyloxy carbonyl group; an arylmethyl group such as a benzyl group and a triphenyl methyl group; an aroyl group such as a benzoyl group; and an aryl sulfonyl group such as a 2,4-dinitrobenzene sulfonyl group and a orthonitrobenzene sulfonyl group. The protecting group $P^1$ can be selected depending on, e.g., the properties of the compound having the amino group to be protected.

By deprotecting the protecting group $P^1$ for the terminal amino group of the compound (6) obtained, the compound (7) can be produced. In the deprotection, reagents and conditions can be selected depending on the protecting group.

The compound (9) can be produced by derivatizing the peptide carboxylic acid (8) having the N terminal protected with $P^2$ into an active ester, mixed acid anhydride, or the like and reacting it with the compound (7) obtained. The reaction conditions, reagents, base, and inert solvent used for forming a peptide bond between the peptide carboxylic acid (8) and the compound (7) can be suitably selected from those described for the synthesis of the compound (6). The protecting group $P^2$ can be suitably selected from those described for the protecting group of the compound (6), and the selection can be made based on, e.g., the properties of the compound having the amino group to be protected. As it is generally used for peptide synthesis, by repeating sequentially the reaction and deprotection of the amino acid or peptide constituting the peptide carboxylic acid (8) for elongation, the compound (9) can be also produced.

By deprotecting the protecting group $P^2$ for the amino group of the compound (9) obtained, the compound (10) can be produced. In the deprotection, reagents and conditions can be selected depending on the protecting group.

It is possible to produce the compound (2) by derivatizing the carboxylic acid (11) into an active ester, mixed acid anhydride, acid halide, or the like and reacting it with the compound (10) obtained. The reaction conditions, reagents, base, and inert solvent used for forming a peptide bond between the carboxylic acid (11) and the compound (10) can be suitably selected from those described for the synthesis of the compound (6).

The compound (9) can be also produced by the following method, for example.

The compound (13) can be produced by derivatizing the peptide carboxylic acid (8) having the N terminal protected with $P^2$ into an active ester, mixed acid anhydride, or the like and reacting it in the presence of a base with the amine compound (12) having the carboxy group protected with $P^3$. The reaction conditions, reagents, base, and inert solvent used for forming a peptide bond between the peptide carboxylic acid (8) and the compound (12) can be suitably selected from those described for the synthesis of the compound (6). The protecting group $P^2$ for the amino group of the compound (13) is not particularly limited as long as it is a protecting group generally used.

Specifically, examples of the protecting group for a hydroxyl group can include an alkoxymethyl group such as a methoxymethyl group; an arylmethyl group such as a benzyl group, a 4-methoxybenzyl group, and a triphenylmethyl group; an alkanoyl group such as an acetyl group; an aroyl group such as a benzoyl group; and a silyl group such as a tert-butyl diphenylsilyl group. Carboxy group can be protected, e.g., as an ester with an alkyl group such as a methyl group, an ethyl group, and a tert-butyl group, an allyl group, or an arylmethyl group such as a benzyl group. Examples of the protecting group for an amino group can include: an alkyloxy carbonyl group such as a tert-butyloxy carbonyl group, a methoxycarbonyl group, and an ethoxycarbonyl group; an allyloxycarbonyl group, or an arylmethoxy carbonyl group such as a 9-fluorenylmethyloxy carbonyl group, a benzyloxy carbonyl group, a paramethoxybenzyloxy carbonyl group, and a para (or ortho) nitrobenzyloxy carbonyl group; an alkanoyl group such as an acetyl group; an arylmethyl group such as a benzyl group and a triphenyl methyl group; an aroyl group such as a benzoyl group; and an aryl sulfonyl group such as a 2,4-dinitrobenzene sulfonyl group or an orthonitrobenzene sulfonyl group.

As for the protecting group $P^3$ for a carboxy group, a protecting group commonly used as a protecting group for a carboxy group in organic synthetic chemistry, in particular, peptide synthesis can be used. Specifically, it can be suitably selected from the protecting groups described above, for example, esters with an alkyl group such as a methyl group, an ethyl group, or a tert-butyl, allyl esters, and benzyl esters.

In such cases, the protecting group for an amino group and the protecting group for a carboxy group can be those preferably removed by a different method or different conditions. For example, a representative example includes a combination in which $P^2$ is a tert-butyloxy carbonyl group and $P^3$ is a benzyl group. The protecting groups can be selected from the aforementioned ones depending on, e.g., the properties of the compounds having the amino group and the carboxy group to be protected. For removal of the protecting groups, reagents and conditions can be selected depending on the protecting group.

By deprotecting the protecting group $P^3$ for the carboxy group of the compound (13) obtained, the compound (14) can be produced. In the deprotection, reagents and conditions are selected depending on the protecting group.

The compound (9) can be produced by derivatizing the compound (14) obtained into an active ester, mixed acid anhydride, acid halide, or the like and reacting with the compound (4) in the presence of a base. For the reaction, reaction reagents and conditions that are generally used for peptide synthesis can be also used, and the reaction conditions, reagents, base, and inert solvent used for the reaction can be suitably selected from those described for the synthesis of the compound (6).

The compound (2) can be also produced by the following method, for example.

By deprotecting the protecting group $P^2$ for the amino group of the compound (13), the compound (15) can be produced. In the deprotection, reagents and conditions can be selected depending on the protecting group.

The compound (16) can be produced by derivatizing the carboxylic acid derivative (11) into an active ester, mixed acid anhydride, acid halide, or the like and reacting it in the presence of a base with the compound (15) obtained. The reaction conditions, reagents, base, and inert solvent used for forming an amide bond between the peptide carboxylic acid (11) and the compound (15) can be suitably selected from those described for the synthesis of the compound (6).

By deprotecting the protecting group for the carboxy group of the compound (16) obtained, the compound (17) can be produced. The deprotection can be carried out similarly to the deprotection at the carboxy group for producing the compound (14).

The compound (2) can be produced by derivatizing the compound (17) into an active ester, mixed acid anhydride, acid halide, or the like and reacting it with the compound (4) in the presence of a base. For the reaction, reaction reagents and conditions that are generally used for peptide synthesis can be also used, and the reaction conditions, reagents, base, and inert solvent used for the reaction can be suitably selected from those described for the synthesis of the compound (6).

3. Production Method 3

The compound represented by the formula (2) of an intermediate can be also produced by the following method.

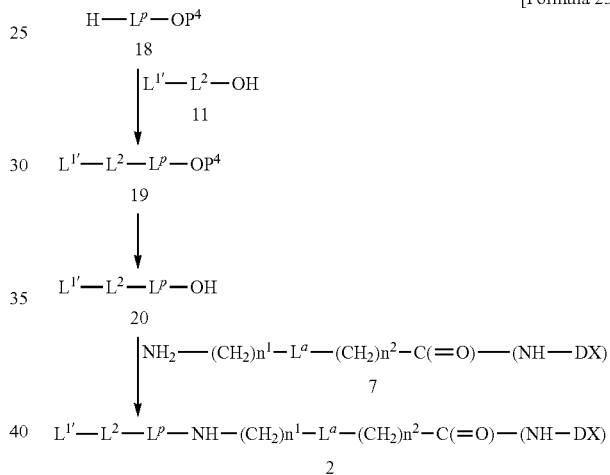

[Formula 23]

In the formula, $L^{1'}$ corresponds to $L^1$ having a structure in which the terminal is converted to a maleimidyl group, and $P^4$ represents a protecting group.

The compound (19) can be produced by derivatizing the compound (11) into an active ester, mixed acid anhydride, or the like and reacting it in the presence of a base with the peptide carboxylic acid (18) having the C terminal protected with $P^4$. The reaction conditions, reagents, base, and inert solvent used for forming a peptide bond between the peptide carboxylic acid (18) and the compound (11) can be suitably selected from those described for the synthesis of the compound (6). The protecting group $P^4$ for the carboxy group of the compound (18) can be suitably selected from the protecting groups described above.

By deprotecting the protecting group for the carboxy group of the compound (19) obtained, the compound (20) can be produced. The deprotection can be performed similar to the deprotection of the carboxy group for producing the compound (14).

The compound (2) can be produced by derivatizing the compound (20) obtained into an active ester, mixed acid anhydride, or the like and reacting it with the compound (7). For the reaction, reaction reagents and conditions that are generally used for peptide synthesis can be also used, and the reaction conditions, reagents, base, and inert solvent used for the reaction can be suitably selected from those described for the synthesis of the compound (6).

4. Production Method 4

Hereinbelow, the method for producing the compound (10b) having $n^1=1$, $L^a=0$ in the production intermediate (10) described in Production method 2 is described in detail. The compound represented by the formula (10b), a salt or a solvate thereof can be produced according to the following method, for example.

[Formula 24]

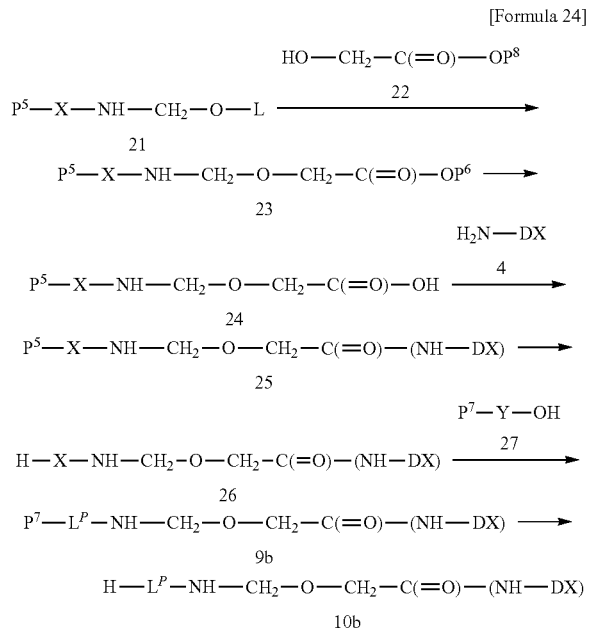

In the formula, $L^P$ is as defined above, $L^1$ represents an acyl group which is an alkanoyl group such as an acetyl group or an aroyl group such as benzoyl group, or a hydrogen atom, X and Y each represent an oligopeptide consisting of 1 to 3 amino acids, $P^5$ and $P^7$ each represent a protecting group for an amino group, and $P^6$ represents a protecting group for a carboxy group.

A compound represented by the formula (21) can be produced by using or applying the method described in Japanese Patent Laid-Open No. 2002-60351 or the literature (J. Org. Chem., Vol. 51, page 3196, 1986), and by conducting removal of the protecting groups or modification of the functional groups, if necessary. Furthermore, it can be also obtained by treating an amino acid with a protected terminal amino group or an acid amide of an oligopeptide with protected amino group with an aldehyde or a ketone.

By reacting the compound (21) with the compound (22) having a hydroxyl group at a temperature ranging from under temperature conditions of cooling to room temperature in an inert solvent in the presence of an acid or a base, the compound (23) can be produced.

Here, examples of the acid which may be used include an inorganic acid such as hydrofluoric acid, hydrochloric acid, sulfuric acid, nitric acid, phosphoric acid, and boric acid; an organic acid such as acetic acid, citric acid, paratoluene sulfonic acid, and methanesulfonic acid; and a Lewis acid such as tetrafluoroborate, zinc chloride, tin chloride, aluminum chloride, and iron chloride. Among these, a sulfonic acid, in particular, paratoluene sulfonic acid is preferable. As for the base, any one of the already mentioned bases can be suitably selected and used. Preferred examples thereof include an alkali metal alkoxide such as potassium tert-butoxide, an alkali metal hydroxide such as sodium hydroxide and potassium hydroxide; an alkali metal or alkaline earth metal hydride such as sodium hydride and potassium hydride; an organometallic base represented by dialkylamino lithium such as lithium diisopropylamide; and an organometallic base of bissilylamine such as lithium bis (trimethylsilyl)amide.

Examples of the solvent to be used for the reaction include an ether solvent such as tetrahydrofuran and 1,4-dioxane; and an aromatic hydrocarbon solvent such as benzene and toluene. Those solvents can be prepared as a mixture with water.

Further, the protecting group for an amino group as exemplified by $P^5$ is not particularly limited provided it is a group commonly used for protection of an amino group. Representative examples include the protecting groups for an amino group that are described in Production method 2. However, in the present reaction, there may be cases in which the protecting group for an amino group as exemplified by $P^5$ is cleaved off. In such cases, a protecting group can be introduced again by appropriately performing a reaction with a suitable reagent for protecting an amino group as may be required.

The compound (24) can be produced by removing the protecting group $P^6$ of the compound (23). Herein, representative examples of the protecting group for a carboxy group as exemplified by $P^6$ are described in Production method 2, and it can be appropriately selected from these. In the compound (23), it is desirable in this case that the protecting group $P^5$ for an amino group and protecting group $P^6$ for a carboxy group are the protecting groups that can be removed by a different method or different conditions. For example, a representative example includes a combination in which $P^5$ is a 9-fluorenylmethyloxy carbonyl group and $P^6$ is a benzyl group. The protecting groups can be selected depending on, e.g., the properties of a compound having the amino group and the carboxy group to be protected. For removal of the protecting groups, reagents and conditions are selected depending on the protecting group.

The compound (26) can be produced by derivatizing the carboxylic acid (24) into an active ester, mixed acid anhydride, acid halide, or the like and reacting it with the compound (4) or a pharmacologically acceptable salt thereof to produce the compound (25) followed by removing the protecting group $P^5$ of the compound (25) obtained. For the reaction between the compound (4) and the carboxylic acid (24) and the reaction for removing the protecting group $P^6$, the same reagents and reaction conditions as those described for Production method 2 can be used.

The compound (10b) can be produced by reacting the compound (26) with an amino acid with a protected terminal amino group or the oligopeptide (27) with a protected amino group to produce the compound (9b) and removing the protecting group $P^7$ of the compound (9b) obtained. The protecting group for an amino group as represented by $P^7$ is not particularly limited provided it is generally used for protection of an amino group. Representative examples thereof include the protecting groups for an amino group that are described in Production method 2. For removing the protecting group, reagents and conditions are selected depending on the protecting group. For the reaction between the compound (26) and the compound (27), reaction reagents and conditions that are commonly used for peptide synthesis can be employed. The compound (10b) produced by the aforementioned method can be derivatized into the compound (1) of the present invention according to the method described above.

5. Production Method 5

Hereinbelow, the method for producing the compound (2) having $n^1=1$, $n^2=1$, $L^a=O$ in the production intermediate (2) described in Production method 2 is described in detail. The compound represented by the formula (2), a salt or a solvate thereof can be produced according to the following method, for example.

[Formula 25]

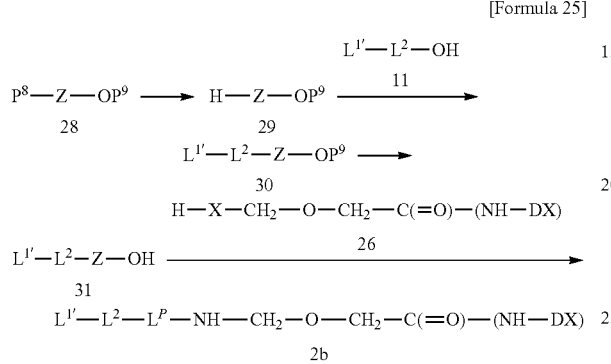

In the formula, $L^{1'}$, $L^2$, $L^P$ are as defined above, Z represents an oligopeptide consisting of 1 to 3 amino acids, $P^8$ represents a protecting group for an amino group, and $P^9$ represents a protecting group for a carboxy group.

The compound (30) can be produced by removing the protecting group $P^8$ of the amino acid or oligopeptide (28) with the protected terminal amino group and carboxy group to produce the compound (29) and reacting the obtained amine form (29) with the compound (11). The protecting group for an amino group as represented by $P^8$ is not particularly limited provided it is a group commonly used for protection of an amino group. Representative examples include the protecting groups for an amino group that are described in Production method 2. Further, for removing the protecting group $P^8$, reagents and conditions can be selected depending on the protecting group. For the reaction between the compound (29) and the carboxylic acid (11), the same reagents and reaction conditions as those described for Production method 2 can be used.

The production intermediate (2b) can be produced by removing the protecting group $P^9$ of the compound (30) to produce the compound (31) and reacting the obtained carboxylic acid (31) with the compound (26). The representative examples of the protecting group for a carboxy group as represented by $P^8$ are described in Production method 2. For the deprotection reaction thereof, the same reagents and reaction conditions as those described for Production method 2 can be used. For the reaction between the compound (26) and the carboxylic acid (31), reaction reagents and conditions that are generally used for peptide synthesis can be also used. The compound (2b) produced by the aforementioned method can be derivatized into the compound (1) of the present invention according to the method described above.

6. Production Method 6

Hereinbelow, a method for producing the compound (17b) having $n^1=1$, $n^2=1$, $L^a=O$ in the production intermediate (17) described in Production method 2 is described in detail. The compound represented by the formula (17b), a salt or a solvate thereof can be also produced according to the following method, for example.

[Formula 26]

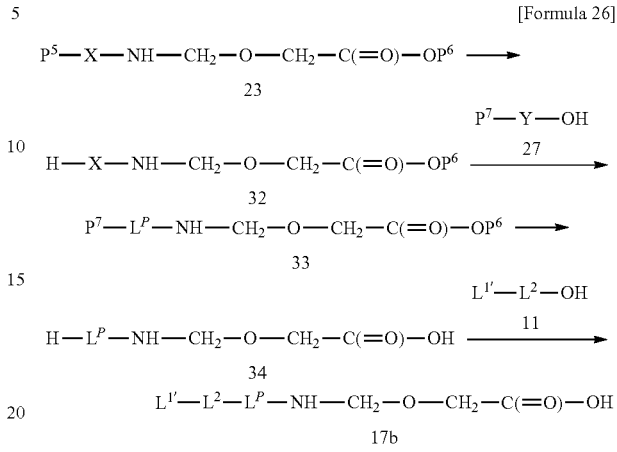

In the formula, $L^{1'}$, $L^2$, $L^P$, X, Y, $P^5$, $P^6$, and $P^7$ are as defined above.

The compound (33) can be produced by deprotecting the protecting group $P^5$ for the amino group of the compound (23) having the protected terminal amino group and carboxy group to produce the compound (32) and reacting the obtained amine derivative (32) with the oligopeptide (27) having a protected terminal amino group or a protected amino group. The protecting group for an amino group as represented by $P^5$ is not particularly limited provided it is a group commonly used for protection of an amino group. Representative examples include the protecting groups for an amino group that are described in Production method 2. Further, for removing the protecting group $P^5$, reagents and conditions can be selected depending on the protecting group. Herein, although representative examples of the protecting group for a carboxy group as represented by $P^6$ and the protecting group for an amino group as represented by $P^7$ include the protecting groups for a carboxy group and an amino group that are described in Production method 2. It is desirable that in the compound (33), the protecting group $P^6$ for a carboxy group and the protecting group $P^7$ for an amino group are protecting groups that can be removed by the same method or the same conditions. For example, a representative example includes a combination in which $P^6$ is a benzyl ester group and $P^7$ is a benzyloxy carbonyl group.

The compound (34) can be produced by removing the protecting group $P^6$ for the carboxy group of the compound (33) and the protecting group $P^7$ for the amino group of the compound (33). The compound (37) can be also produced by sequentially removing the protecting group $P^6$ for the carboxy group and the protecting group $P^7$ for the amino group, and furthermore, the compound (34) can be produced simply by removing at once both of the protecting groups $P^6$ and $P^7$ that can be removed by the same method or the same conditions.

The compound (17b) can be produced by reacting the obtained compound (34) with the compound (11). For the reaction between the compound (34) and the compound (11), the same reagents and reaction conditions as those described for Production method 2 can be used.

The anti-HER2 antibody-drug conjugate of the present invention, when it is left in air or recrystallized or purified, may absorb moisture or have adsorption water or turn into a hydrate, and such compounds or salts containing water are also included in the present invention.

Compounds labeled with various radioactive or non-radioactive isotopes are also included in the present invention. One or more atoms constituting the antibody-drug conjugate of the present invention may contain an atomic isotope at a non-natural ratio. Examples of atomic isotopes include deuterium ($^2$H), tritium ($^3$H), iodine-125 ($^{125}$I), and carbon-14 ($^{14}$C). Further, the compound of the present invention may be radioactive-labeled with a radioactive isotope such as tritium ($^3$H), iodine-125 ($^{125}$I), carbon-14 ($^{14}$C), copper-64 ($^{64}$Cu), zirconium-89 ($^{89}$Zr), iodine-124 ($^{124}$I), fluorine-18 ($^{18}$F), indium-ill ($^{111}$I), carbon-11 ($^{11}$C) and iodine-131 ($^{131}$I). The compound labeled with a radioactive isotope is useful as a therapeutic or prophylactic agent, a reagent for research such as an assay reagent and an agent for diagnosis such as an in vivo diagnostic imaging agent. Without being related to radioactivity, any isotope variant type of the antibody-drug conjugate of the present invention is within the scope of the present invention.

[Drugs]

The anti-HER2 antibody-drug conjugate of the present invention exhibits cytotoxic activity against cancer cells, and thus, it can be used as a drug, particularly as a therapeutic agent and/or prophylactic agent for cancer. That is, the anti-HER2 antibody-drug conjugate of the present invention can be selectively used as a drug for chemotherapy, which is a main method for treating cancer, and as a result, can delay development of cancer cells, inhibit growth thereof, and further kill cancer cells. This can allow cancer patients to be free from symptoms caused by cancer or achieve improvement in QOL of cancer patients and attains a therapeutic effect by sustaining the lives of the cancer patients. Even if the anti-HER2 antibody-drug conjugate of the present invention does not accomplish killing cancer cells, it can achieve higher QOL of cancer patients while achieving longer-term survival, by inhibiting or controlling the growth of cancer cells.

In such drug therapy, it can be used as a drug alone and in addition, it can be used as a drug in combination with an additional therapy in adjuvant therapy and can be combined with surgical operation, radiotherapy, hormone therapy, or the like. Furthermore, it can also be used as a drug for drug therapy in neoadjuvant therapy.

In addition to the therapeutic use as described above, an effect of suppressing the growth of small metastatic cancer cells and further killing them can also be expected. Particularly, when the expression of HER2 is confirmed in primary cancer cells, inhibition of cancer metastasis or a prophylactic effect can be expected by administering the anti-HER2 antibody-drug conjugate of the present invention. For example, an effect of inhibiting and killing cancer cells in a body fluid in the course of metastasis or an effect of, for example, inhibiting and killing small cancer cells immediately after implantation in any tissue can be expected. Accordingly, inhibition of cancer metastasis or a prophylactic effect can be expected, particularly, after surgical removal of cancer.

The anti-HER2 antibody-drug conjugate of the present invention can be expected to exert a therapeutic effect by administration as systemic therapy to patients, and additionally, by local administration to cancer tissues.

Examples of the cancer type to which the anti-HER2 antibody-drug conjugate of the present invention is applied can include lung cancer, urothelial cancer, colorectal cancer, prostate cancer, ovarian cancer, pancreatic cancer, breast cancer, bladder cancer, gastric cancer, gastrointestinal stromal tumor, uterine cervix cancer, esophageal cancer, squamous cell carcinoma, peritoneal cancer, liver cancer, hepatocellular cancer, colon cancer, rectal cancer, colorectal cancer, endometrial cancer, uterine cancer, salivary gland cancer, kidney cancer, vulval cancer, thyroid cancer, or penis cancer. The treatment subject of the anti-HER2 antibody-drug conjugate of the present invention is a cancer cell expressing, in a cancer cell as a treatment subject, HER2 protein which the antibody within the antibody-drug conjugate can recognize. The term "cancer expressing HER2 protein" as used in the present specification is a cancer containing cells having HER2 protein on their cell surface. The HER2 protein is overexpressed in various human tumors and can be evaluated using a method generally carried out in the art, such as immunohistochemical staining method (IHC) for evaluating the overexpression of the HER2 protein, or fluorescence in situ hybridization method (FISH) for evaluating amplification of the HER2 gene.

Further, the anti-HER2 antibody-drug conjugate of the present invention exhibits an antitumor effect by recognizing, through its anti-HER2 antibody, the HER2 protein expressed on the surface of cancer cells and internalizing in the cancer cells. Thus, the treatment subject of the anti-HER2 antibody-drug conjugate of the present invention is not limited to the "cancer expressing HER2 protein" and can also be, for example, leukemia, malignant lymphoma, plasmacytoma, myeloma, or sarcoma.

The anti-HER2 antibody-drug conjugate of the present invention can be preferably administered to a mammal, but it is more preferably administered to a human.

Substances used in a pharmaceutical composition containing anti-HER2 antibody-drug conjugate of the present invention can be suitably selected and applied from formulation additives or the like that are generally used in the art, in view of the dosage or administration concentration.

The anti-HER2 antibody-drug conjugate of the present invention can be administered as a pharmaceutical composition containing at least one pharmaceutically suitable ingredient. For example, the pharmaceutical composition above typically contains at least one pharmaceutical carrier (for example, sterilized liquid). Herein, the liquid includes, for example, water and oil (petroleum oil and oil of animal origin, plant origin, or synthetic origin. The oil may be, for example, peanut oil, soybean oil, mineral oil, or sesame oil. Water is a more typical carrier when the pharmaceutical composition above is intravenously administered. Saline solution, an aqueous dextrose solution, and an aqueous glycerol solution can be also used as a liquid carrier, in particular, for an injection solution. A suitable pharmaceutical vehicle can be selected from ones known in the art. If desired, the composition above may also contain a trace amount of a moisturizing agent, an emulsifying agent, or a pH buffering agent. Examples of suitable pharmaceutical carrier are disclosed in "Remington's Pharmaceutical Sciences" by E. W. Martin. The formulations correspond to an administration mode.

Various delivery systems are known and they can be used for administering the anti-HER2 antibody-drug conjugate of the present invention. Examples of the administration route can include intradermal, intramuscular, intraperitoneal, intravenous, and subcutaneous routes, but not limited thereto. The administration can be made by injection or bolus injection, for example. According to a specific preferred embodiment, the administration of the antibody-drug conjugate is performed by injection. Parenteral administration is a preferred administration route.

According to a representative embodiment, the pharmaceutical composition is prescribed, as a pharmaceutical composition suitable for intravenous administration to human, according to the conventional procedures. The composition for intravenous administration is typically a solution in a sterile and isotonic aqueous buffer solution. If necessary, the drug may contain a solubilizing agent and local anesthetics to alleviate pain at injection site (for example, lignocaine). Generally, the ingredient above is provided individually as any one of lyophilized powder or an anhydrous concentrate contained in a container which is obtained by sealing in an ampoule or a sachet having an amount of the active agent or as a mixture in a unit dosage form. When the drug is to be administered by injection, it may be administered from an injection bottle containing water or saline of sterile pharmaceutical grade. When the drug is administered by injection, an ampoule of sterile water or saline for injection may be provided such that the aforementioned ingredients are admixed with each other before administration.

The pharmaceutical composition of the present invention may be a pharmaceutical composition containing only the anti-HER2 antibody-drug conjugate of the present invention or a pharmaceutical composition containing the anti-HER2 antibody-drug conjugate and at least one cancer treating agent other than the conjugate. The anti-HER2 antibody-drug conjugate of the present invention can be administered with other cancer treating agents. The anti-cancer effect may be enhanced accordingly. Other anti-cancer agents used for such purpose may be administered to an individual simultaneously with, separately from, or subsequently to the antibody-drug conjugate, and may be administered while varying the administration interval for each. Examples of cancer treating agents include 5-FU, pertuzumab, paclitaxel, carboplatin, cisplatin, gemcitabine, capecitabine, irinotecan (CPT-11), paclitaxel, docetaxel, pemetrexed, sorafenib, vinblastin, vinorelbine, everolims, tanespimycin, bevacizumab, oxaliplatin, lapatinib, ado-trastuzumab emtansine(T-DM1), or drugs described in International Publication No. WO 2003/038043, LH-RH analogues (leuprorelin, goserelin, or the like), estramustine phosphate, estrogen antagonists (tamoxifen, raloxifene, or the like), and aromatase inhibitors (anastrozole, letrozole, exemestane, or the like), but are not limited as long as they are drugs having an antitumor activity.

The pharmaceutical composition can be formulated into a lyophilization formulation or a liquid formulation as a formulation having the desired composition and required purity. When formulated as a lyophilization formulation, it may be a formulation containing suitable formulation additives that are used in the art. Also for a liquid formulation, it can be formulated as a liquid formulation containing various formulation additives that are used in the art.

The composition and concentration of the pharmaceutical composition may vary depending on administration method. However, the anti-HER2 antibody-drug conjugate contained in the pharmaceutical composition of the present invention can exhibit a pharmaceutical effect even at a small dosage when the antibody-drug conjugate has a higher affinity for an antigen, that is, a higher affinity (=lower Kd value) in terms of the dissociation constant (that is, Kd value) for the antigen. Thus, for determining the dosage of the antibody-drug conjugate, the dosage can be determined in view of the situation relating to the affinity between the antibody-drug conjugate and antigen. When the antibody-drug conjugate of the present invention is administered to a human, for example, about 0.001 to 100 mg/kg can be administered once or administered several times with an interval of for 1 to 180 days.

at one time with an interval of 1 to 180 days

EXAMPLES

The present invention is specifically described in view of the examples shown below. However, the present invention is not limited to these. Further, it is by no means interpreted in a limited way. Further, unless specifically described otherwise, the reagent, solvent, and starting material described in the specification can be easily obtained from a commercial supplier.

Reference Example 1 Preparation of Trastuzumab

Fourteen vials of 440 mg/vial Herceptin (Genentech, Inc.) were dissolved in 2 L of cation-exchange chromatography buffer A (25 mM citrate buffer, 30 mM NaCl, pH 5.0) and filtered through a 0.2 μm filter (Millipore Corp.: Stericup 0.22 μm, GVPVDF Membrane). The samples were applied to a cation-exchange chromatography column (SP Sepharose HP 240 ml, XK50 column), followed by elution under a NaCl concentration linear gradient from 30 mM to 500 mM using cation-exchange chromatography buffer B (25 mM citrate buffer, 500 mM NaCl, pH 5.0) to separate IgG monomer fractions. Monomer samples having a higher purity over 98% by size exclusion chromatography analysis were combined and concentrated with UF30K (Millipore Corp.: PELLICON XL Filter, BIOMAX 30K, PXB030A50), and the buffer was replaced with CBS buffer (10 mM citrate/140 mM NaCl, pH 6.0). The CBS buffer-replaced samples were filtered through a 0.2 μm filter (Sartorius AG: Minisart-Plus 0.2 m, 17823K).

Reference Example 2 Production of Trastuzumab Emtansine T-DM1 SMCC Derivatization of Antibody By using the Common procedure C-2 (PBS6.5/EDTA was used as a buffer solution), Common procedure A, and Common procedure B (as absorption coefficient at 280 nm, 1.37 mLmg$^{-1}$ cm$^{-1}$ was used) described in Production method 1, replacement of buffer with PBS6.5/EDTA was conducted on the trastuzumab produced in Reference Example 1 to prepare a solution containing trastuzumab (160.0 mg) dissolved in PBS6.5/EDTA (7.60 mL) in a 15 mL polypropylene tube. Subsequently, SMCC (1.84 mg) DMSO solution (0.40 mL; which corresponds to about 5.1 equivalents per antibody molecule) was added at room temperature. The reaction mixture was adjusted to have an antibody concentration of 20 mg/mL, and the reaction was carried out at room temperature by using a tube rotator (MTR-103, manufactured by AS ONE Corporation) for 2 hours. This reaction solution was subjected to purification according to the Common procedure D-2 (PBS6.5/EDTA was used as a buffer solution) to yield 12 mL of a solution containing 154.9 mg of the SMCC-derivatized antibody.

Conjugation between antibody and drug linker: Adding PBS6.5/EDTA (2.56 mL) and N$^2$-deacetyl-N$^2$-(3-mercapto-1-oxopropyl)-maytansine (4.67 mg; DM1, Journal of Medicinal Chemistry, 2006, Vol. 49, No. 14, p. 4392) DMA (dimethylacetamide) solution (0.93 mL; which corresponds to about 5.8 equivalents per SMCC-derivatized antibody molecule) to the solution obtained above in the 50 mL polypropylene tube at room temperature, the reaction solution was adjusted to an antibody concentration of 10 mg/mL, and the reaction was carried out at room temperature by using a tube rotator for 16.5 hours.
Purification procedure: The above solution was subjected to purification using the Common procedure D-1 using a sodium phosphate buffer solution (10 mM, pH 6.5) containing sodium chloride (137 mM) to yield 35 mL of a solution containing the target Reference Example compound.
Physicochemical characterization: By using the Common procedure E using UV absorbance at two wavelengths of 252 nm and 280 nm, the following characteristic values were obtained. Antibody concentration: 4.14 mg/mL, antibody yield: 144.9 mg (91%), and average number of conjugated drug molecules (n) per antibody molecule: 3.0.

Example 1 Intermediate (1)

Process 1: tert-Butyl (4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl] amino}-4-oxobutyl) carbamate 4-(tert-Butoxycarbonylamino)butanoic acid (0.237 g, 1.13 mmol) was dissolved in dichloromethane (10 mL), N-hydroxysuccinimide (0.130 g, 1.13 mmol) and 1-ethyl-3-(3-dimethylaminopropyl)carbodiimide hydrochloride (0.216 g, 1.13 mmol) were added and stirred for 1 hour. The reaction solution was added dropwise to an N,N-dimethylformamide solution (10 mL) charged with methanesulfonic acid salt of exatecan (0.500 g, 0.94 mmol) and triethylamine (0.157 mL, 1.13 mmol), and stirred at room temperature for 1 day. The solvent was removed under reduced pressure and the residues obtained were purified by silica gel column

[Formula 27]

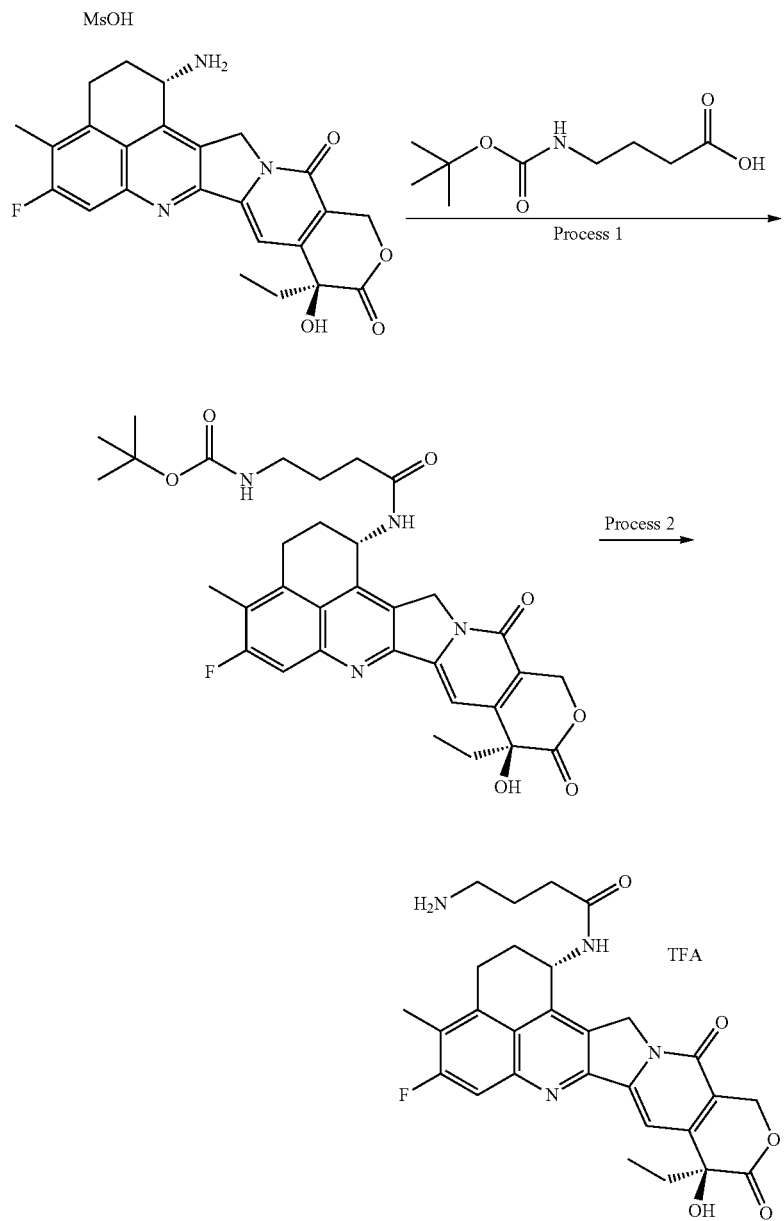

chromatography [chloroform-chloroform:methanol=8:2 (v/v)] to yield the titled compound (0.595 g, quantitative).

$^1$H-NMR (400 MHz, DMSO-$d_6$) δ: 0.87 (3H, t, J=7.2 Hz), 1.31 (9H, s), 1.58 (1H, t, J=7.2 Hz), 1.66 (2H, t, J=7.2 Hz), 1.82-1.89 (2H, m), 2.12-2.21 (3H, m), 2.39 (3H, s), 2.92 (2H, t, J=6.5 Hz), 3.17 (2H, s), 5.16 (1H, d, J=18.8 Hz), 5.24 (1H, d, J=18.8 Hz), 5.42 (2H, s), 5.59-5.55 (1H, m), 6.53 (1H, s), 6.78 (1H, t, J=6.3 Hz), 7.30 (1H, s), 7.79 (1H, d, J=11.0 Hz), 8.40 (1H, d, J=8.6 Hz).

MS (APCI) m/z: 621 (M+H)$^+$

Process 2: 4-Amino-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]butanamide The compound (0.388 g, 0.61 mmol) obtained in Process 1 above was dissolved in dichloromethane (9 mL). Trifluoroacetic acid (9 mL) was added and it was stirred for 4 hours. The solvent was removed under reduced pressure and the residues obtained were purified by silica gel column chromatography [chloroform-partitioned organic layer of chloroform:methanol:water=7:3:1 (v/v/v)] to yield trifluoroacetate of the titled compound (0.343 g, quantitative).

$^1$H-NMR (400 MHz, DMSO-$d_6$) δ: 0.87 (3H, t, J=7.2 Hz), 1.79-1.92 (4H, m), 2.10-2.17 (2H, m), 2.27 (2H, t, J=7.0 Hz), 2.40 (3H, s), 2.80-2.86 (2H, m), 3.15-3.20 (2H, m), 5.15 (1H, d, J=18.8 Hz), 5.26 (1H, d, J=18.8 Hz), 5.42 (2H, s), 5.54-5.61 (1H, m), 6.55 (1H, s), 7.32 (1H, s), 7.72 (3H, brs), 7.82 (1H, d, J=11.0 Hz), 8.54 (1H, d, J=8.6 Hz).

MS (APCI) m/z: 521 (M+H)$^+$

Example 2 Antibody-Drug Conjugate (2)

[Formula 28]

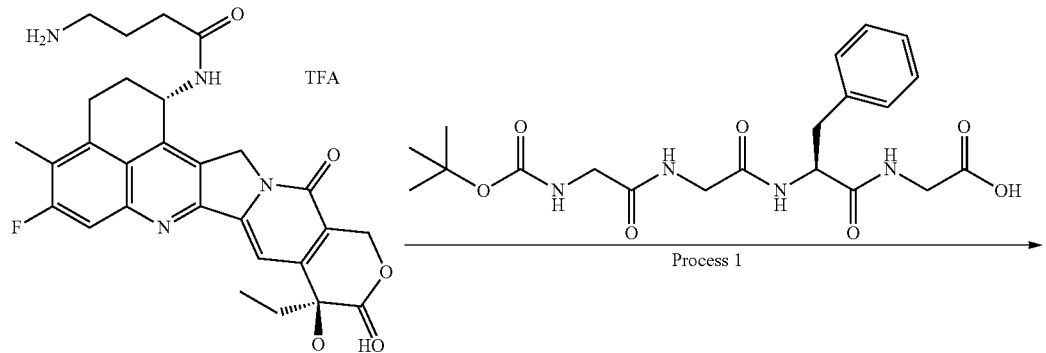

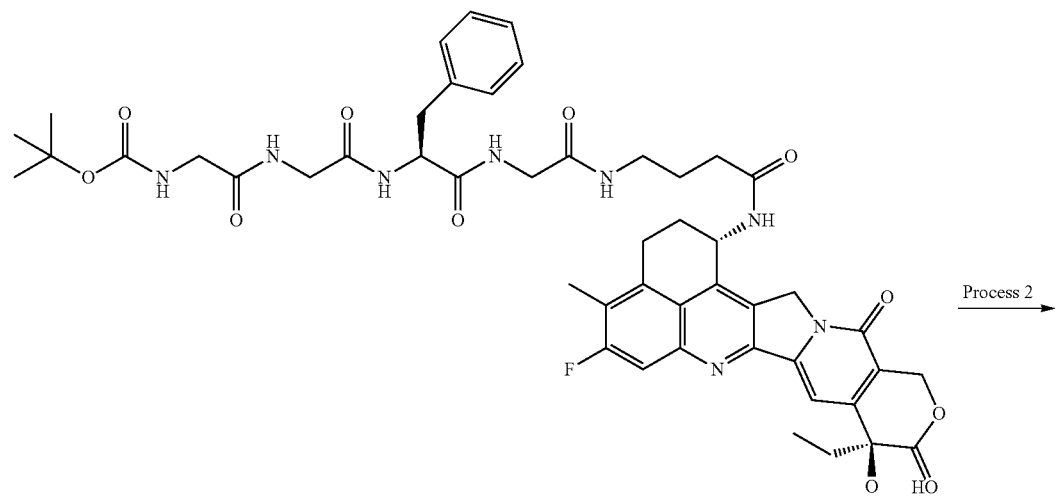

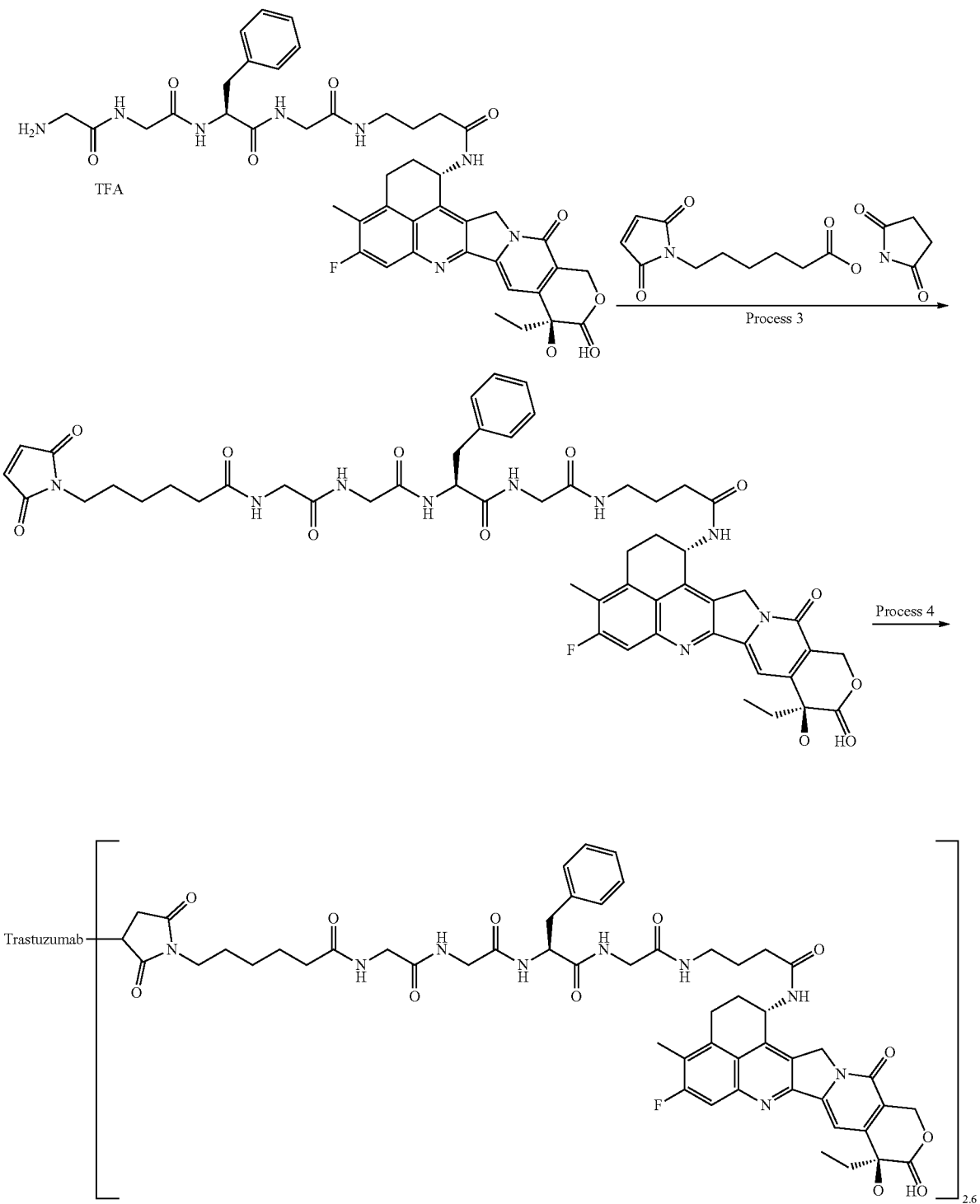

Process 1: N-(tert-Butoxycarbonyl)glycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide N-(tert-Butoxycarbonyl)glycylglycyl-L-phenylalanylglycine (0.081 g, 0.19 mmol) was dissolved in dichloromethane (3 mL), N-hydroxysuccinimide (0.021 g, 0.19 mmol) and 1-ethyl-3-(3-dimethylaminopropyl)carbodiimide hydrochloride (0.036 g, 0.19 mmol) were added and then stirred for 3.5 hours. The reaction solution was added dropwise to an N,N-dimethylformamide solution (1.5 mL) charged with the compound (0.080 g, 0.15 mmol) obtained in Process 2 of Example 1, and stirred at room temperature for 4 hours. The solvent was removed under reduced pressure and the residues obtained were purified by silica gel column chromatography [chloroform-chloroform:methanol=8:2 (v/v)] to yield the titled compound (0.106 g, 73%).

$^1$H-NMR (400 MHz, DMSO-$d_6$) δ: 0.87 (3H, t, J=7.4 Hz), 1.36 (9H, s), 1.71 (2H, m), 1.86 (2H, t, J=7.8 Hz), 2.15-2.19 (4H, m), 2.40 (3H, s), 2.77 (1H, dd, J=12.7, 8.8 Hz), 3.02 (1H, dd, J=14.1, 4.7 Hz), 3.08-3.11 (2H, m), 3.16-3.19 (2H, m), 3.54 (2H, d, J=5.9 Hz), 3.57-3.77 (4H, m), 4.46-4.48 (1H, m), 5.16 (1H, d, J=19.2 Hz), 5.25 (1H, d, J=18.8 Hz), 5.42 (2H, s), 5.55-5.60 (1H, m), 6.53 (1H, s), 7.00 (1H, t, J=6.3 Hz), 7.17-7.26 (5H, m), 7.31 (1H, s), 7.71 (1H, t, J=5.7 Hz), 7.80 (1H, d, J=11.0 Hz), 7.92 (1H, t, J=5.7 Hz), 8.15 (1H, d, J=8.2 Hz), 8.27 (1H, t, J=5.5 Hz), 8.46 (1H, d, J=8.2 Hz).

MS (APCI) m/z: 939 (M+H)$^+$

Process 2: Glycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide The compound (1.97 g, 2.10 mmol) obtained in Process 1 above was dissolved in dichloromethane (7 mL). After adding trifluoroacetic acid (7 mL), it was stirred for 1 hour. The solvent was removed under reduced pressure, and the residues were charged with toluene for azeotropic distillation. The residues obtained were purified by silica gel column chromatography [chloroform-partitioned organic layer of chloroform:methanol:water=7:3:1 (v/v/v)] to yield trifluoroacetate of the titled compound (1.97 g, 99%).

$^1$H-NMR (400 MHz, DMSO-$d_6$) δ: 0.87 (3H, t, J=7.4 Hz), 1.71-1.73 (2H, m), 1.82-1.90 (2H, m), 2.12-2.20 (4H, m), 2.40 (3H, s), 2.75 (1H, dd, J=13.7, 9.4 Hz), 3.03-3.09 (3H, m), 3.18-3.19 (2H, m), 3.58-3.60 (2H, m), 3.64 (1H, d, J=5.9 Hz), 3.69 (1H, d, J=5.9 Hz), 3.72 (1H, d, J=5.5 Hz), 3.87 (1H, dd, J=16.8, 5.9 Hz), 4.50-4.56 (1H, m), 5.16 (1H, d, J=19.2 Hz), 5.25 (1H, d, J=18.8 Hz), 5.42 (2H, s), 5.55-5.60 (1H, m), 7.17-7.27 (5H, m), 7.32 (1H, s), 7.78-7.81 (2H, m), 7.95-7.97 (3H, m), 8.33-8.35 (2H, m), 8.48-8.51 (2H, m).

MS (APCI) m/z: 839 (M+H)$^+$

Process 3: N-[6-(2,5-Dioxo-2,5-dihydro-1H-pyrrol-1-yl)hexanoyl]glycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide To an N,N-dimethylformamide (1.2 mL) solution of the compound (337 mg, 0.353 mmol) obtained in Process 2 above, triethylamine (44.3 mL, 0.318 mmol) and N-succinimidyl 6-maleimide hexanoate (119.7 mg, 0.388 mmol) were added and stirred at room temperature for 1 hour. The solvent was removed under reduced pressure and the residues obtained were purified by silica gel column chromatography [chloroform -chloroform:methanol=5:1 (v/v)] to yield the titled compound as a pale yellow solid (278.0 mg, 76%).

$^1$H-NMR (400 MHz, DMSO-$d_6$) δ: 0.87 (3H, t, J=7.3 Hz), 1.12-1.22 (2H, m), 1.40-1.51 (4H, m), 1.66-1.76 (2H, m), 1.80-1.91 (2H, m), 2.05-2.21 (6H, m), 2.39 (3H, s), 2.79 (1H, dd, J=14.0, 9.8 Hz), 2.98-3.21 (5H, m), 3.55-3.77 (8H, m), 4.41-4.48 (1H, m), 5.15 (1H, d, J=18.9 Hz), 5.24 (1H, d, J=18.9 Hz), 5.40 (1H, d, J=17.1 Hz), 5.44 (1H, d, J=17.1 Hz), 5.54-5.60 (1H, m), 6.53 (1H, s), 6.99 (2H, s), 7.20-7.27 (5H, m), 7.30 (1H, s), 7.70 (1H, t, J=5.5 Hz), 7.80 (1H, d, J=11.0 Hz), 8.03 (1H, t, J=5.8 Hz), 8.08 (1H, t, J=5.5 Hz), 8.14 (1H, d, J=7.9 Hz), 8.25 (1H, t, J=6.1 Hz), 8.46 (1H, d, J=8.5 Hz).

MS (APCI) m/z: 1032 (M+H)$^+$

Process 4: Antibody-Drug Conjugate (2)

Reduction of the antibody: The trastuzumab produced in Reference Example 1 was prepared to have an antibody concentration of 10 mg/mL with PBS6.0/EDTA by using the Common procedure C-1 and Common procedure B (as absorption coefficient at 280 nm, 1.37 mLmg$^{-1}$ cm$^{-1}$ was used) described in Production method 1. The solution (3.0 mL) was placed in a 15 mL polypropylene tube and charged with an aqueous solution of 10 mM tris(2-carboxyethyl)phosphine hydrochloride (TCEP, Tokyo Chemical Industry Co., Ltd.) (0.0934 mL; 4.6 equivalents per antibody molecule) and an aqueous solution of 1 M dipotassium hydrogen phosphate (Nacalai Tesque, Inc.; 0.150 mL). After confirming that the solution had a pH of 7.4±0.1, the disulfide bond at the hinge part in the antibody was reduced by incubating at 37° C. for 1 hour.

Conjugation between antibody and drug linker: After incubating the solution above at 22° C. for 10 minutes, a DMSO solution (0.187 mL; 9.2 equivalents per antibody molecule) containing 10 mM of the compound obtained in Process 3 was added thereto and incubated for conjugating the drug linker to the antibody at 22° C. for 40 minutes. Next, an aqueous solution (0.0374 mL; 18.4 equivalents per antibody molecule) of N-acetylcysteine (NAC, Sigma-Aldrich Co. LLC) was added thereto and incubated at 22° C. to terminate the reaction of the drug linker for another 20 minutes.

Purification: The above solution was subjected to purification using the Common procedure D-1 (PBS6.0 was used as buffer solution) described in Production method 1 to yield 6 mL of a solution containing the titled antibody-drug conjugate. After that, the solution was concentrated by the Common procedure A. Physicochemical characterization: By using the Common procedure E described in Production method 1, the following characteristic values were obtained.

Antibody concentration: 3.21 mg/mL, antibody yield: 22.5 mg (75%), and average number of conjugated drug molecules (n) per antibody molecule: 2.6.

Example 3 Antibody-Drug Conjugate (3)

[Formula 29]

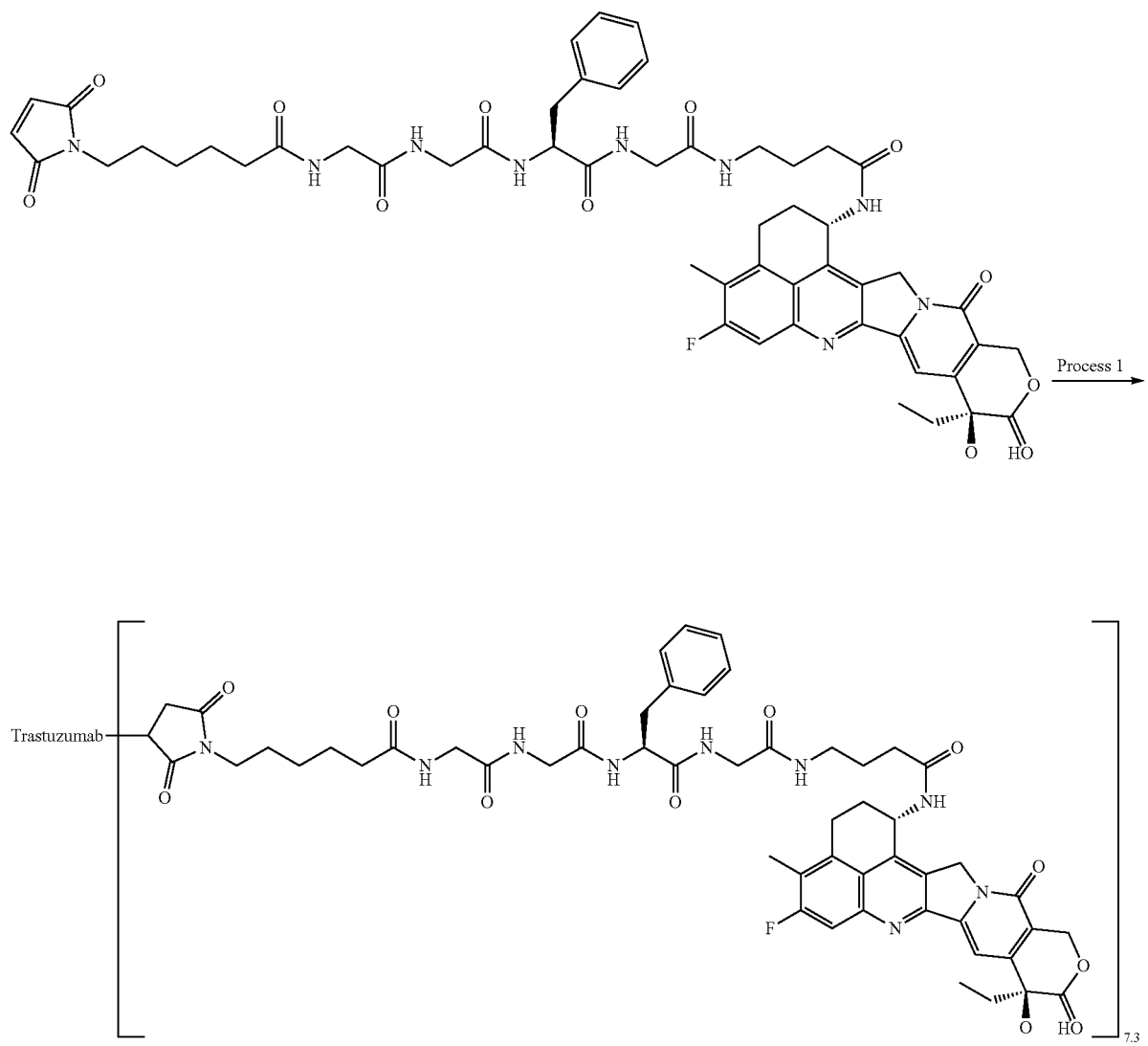

Process 1: Antibody-Drug Conjugate (3)

Reduction of the antibody: The trastuzumab produced in Reference Example 1 was prepared to have an antibody concentration of 10 mg/mL by replacing the medium with PBS6.0/EDTA by using the Common procedure C-1 and Common procedure B (as absorption coefficient at 280 nm, 1.487 mL mg$^{-1}$ cm$^{-1}$ was used). The solution (1.25 mL) was placed in a 1.5 mL polypropylene tube and charged with an aqueous solution of 10 mM TCEP (0.039 mL; 4.6 equivalents per antibody molecule) and an aqueous solution of 1 M dipotassium hydrogen phosphate (0.0625 mL). After confirming that the solution had a pH of 7.4±0.1, the disulfide bond at the hinge part in the antibody was reduced by incubating at 37° C. for 1 hour. Conjugation between antibody and drug linker: After adding DMSO (0.072 mL) and a DMSO solution containing 10 mM of the compound of Process 3 of Example 2 (0.078 mL; 9.2 equivalents per antibody molecule) to the above solution at room temperature, it was stirred by using a tube rotator for conjugating the drug linker to the antibody at room temperature for 40 minutes. Next, an aqueous solution (0.0155 mL; 18.4 equivalents per antibody molecule) of 100 mM NAC was added thereto and stirred at room temperature to terminate the reaction of the drug linker for another 20 minutes.

Purification: The above solution was subjected to purification using the Common procedure D (ABS was used as buffer solution) described in Production method 1 to yield 6 mL of a solution containing the compound of interest. The solution was further concentrated by the Common procedure A. After that, by using the Common procedure E, the following characteristic values were obtained.

Antibody concentration: 9.85 mg/mL, antibody yield: 6.9 mg (55%), and average number of conjugated drug molecules (n) per antibody molecule: 7.3.

Example 4 Antibody-Drug Conjugate (4)
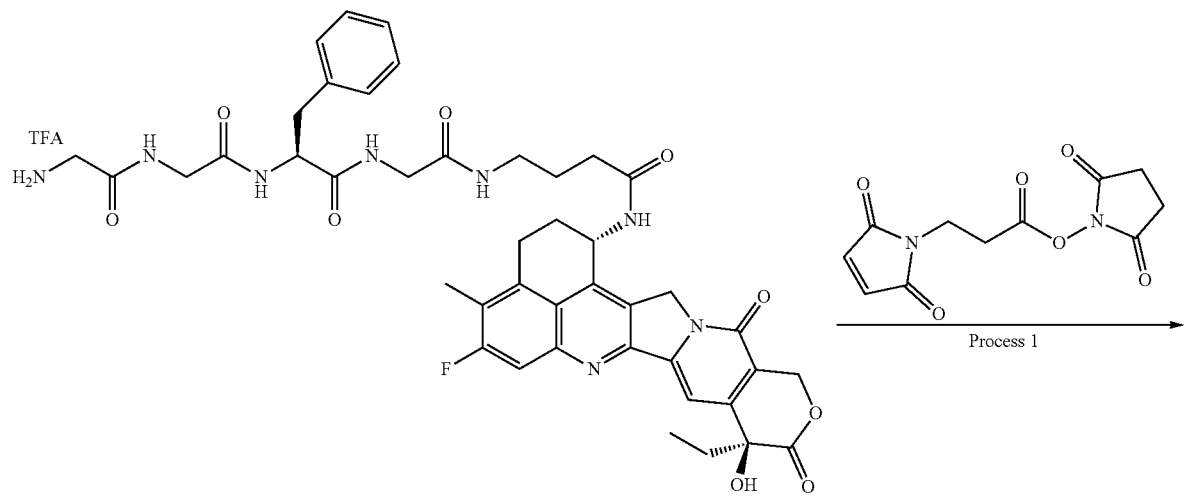
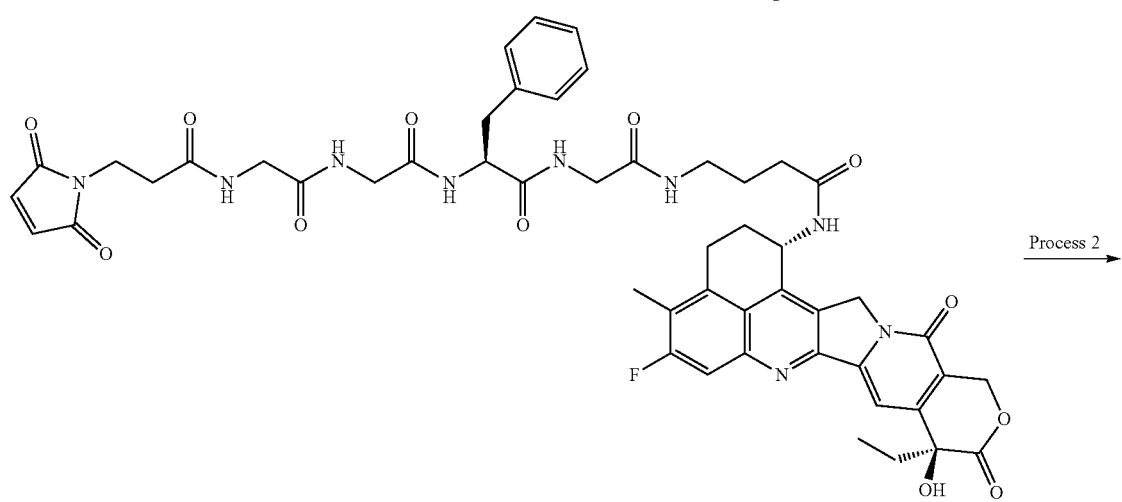
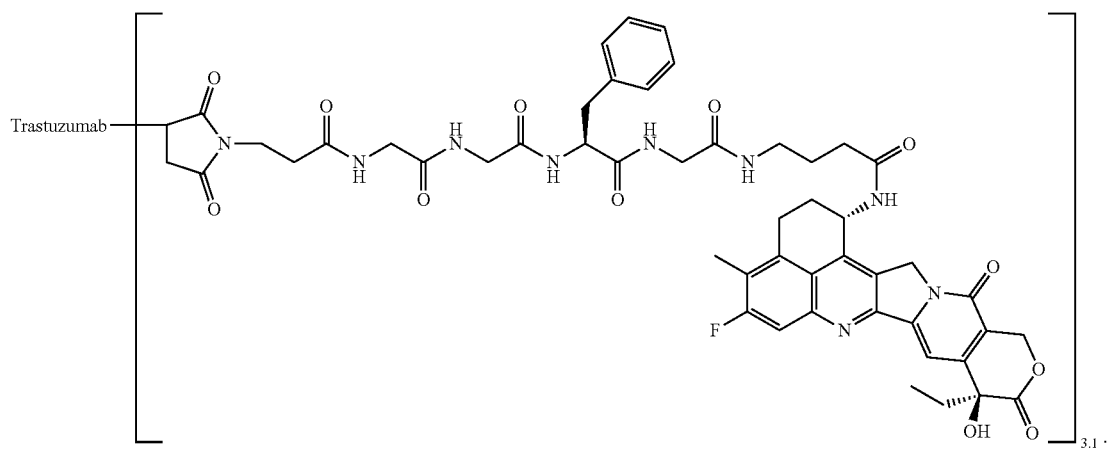

Process 1: N-[3-(2,5-Dioxo-2,5-dihydro-1H-pyrrol-1-yl)propanoyl]glycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide The compound (80 mg, 0.084 mmol) of Example 1 was reacted in the same manner as Process 3 of Example 2 by using N-succinimidyl 3-maleimide propioate (24.6 mg, 0.0924 mmol) instead of N-succinimidyl 6-maleimide hexanoate to yield the titled compound as a pale yellow solid (60.0 mg, 73%).

$^1$H-NMR (400 MHz, DMSO-d$_6$) δ: 0.89 (3H, t, J=7.3 Hz), 1.70-1.78 (2H, m), 1.81-1.94 (2H, m), 2.12-2.23 (4H, m), 2.42 (3H, s), 2.81 (1H, dd, J=13.7, 9.8 Hz), 3.01-3.15 (3H, m), 3.16-3.23 (2H, m), 3.30-3.35 (1H, m), 3.58-3.71 (6H, m), 3.71-3.79 (1H, m), 4.44-4.51 (1H, m), 5.19 (1H, d, J=19.0 Hz), 5.27 (1H, d, J=19.0 Hz), 5.43 (1H, d, J=17.6 Hz), 5.47 (1H, d, J=17.6 Hz), 5.57-5.63 (1H, m), 6.56 (1H, s), 7.02 (2H, s), 7.17-7.22 (1H, m), 7.22-7.30 (5H, m), 7.34 (1H, s), 7.73 (1H, t, J=5.6 Hz), 7.83 (1H, d, J=10.7 Hz), 8.08 (1H, t, J=5.6 Hz), 8.15 (1H, d, J=7.8 Hz), 8.30 (2H, dt, J=18.7, 5.7 Hz), 8.49 (1H, d, J=8.8 Hz).

MS (APCI) m/z: 990 (M+H)$^+$

Process 2: Antibody-Drug Conjugate (4)

Reduction of the antibody: The trastuzumab produced in Reference Example 1 was prepared to have an antibody concentration of 10 mg/mL by replacing the medium with PBS6.0/EDTA by using the Common procedure C-1 and Common procedure B (as absorption coefficient at 280 nm, 1.48 mLmg$^{-1}$ cm$^{-1}$ was used). The solution (1 mL) was placed in a 1.5 mL polypropylene tube and charged with an aqueous solution of 10 mM TCEP (0.0155 mL; 2.3 equivalents per antibody molecule) and an aqueous solution of 1 M dipotassium hydrogen phosphate (0.050 mL). After confirming that the solution had a pH of 7.4±0.1, the disulfide bond at the hinge part in the antibody was reduced by incubating at 37° C. for 1 hour.

Conjugation between antibody and drug linker: After adding DMSO (0.072 mL) and a DMSO solution containing 10 mM of the compound of Process 3 of Example 2 (0.031 mL; 4.6 equivalents per antibody molecule) to the above solution at room temperature, it was stirred by using a tube rotator for conjugating the drug linker to the antibody at room temperature for 40 minutes. Next, an aqueous solution (0.0078 mL; 9.2 equivalents per antibody molecule) of 100 mM NAC was added thereto and stirred at room temperature to terminate the reaction of the drug linker for another 20 minutes.

Purification: The above solution was subjected to purification using the Common procedure D (ABS was used as buffer solution) to yield 6 mL of a solution containing the compound of interest. By using the Common procedure E, the following characteristic values were obtained.

Antibody concentration: 1.32 mg/mL, antibody yield: 7.9 mg (79%), and average number of conjugated drug molecules (n) per antibody molecule: 3.1.

Example 5 Antibody-Drug Conjugate (5)

[Formula 31]

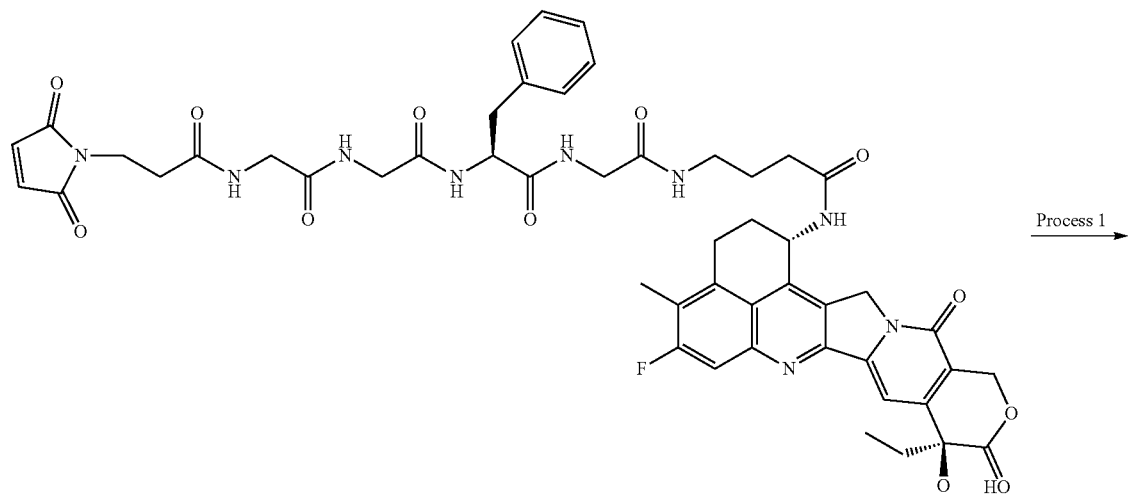

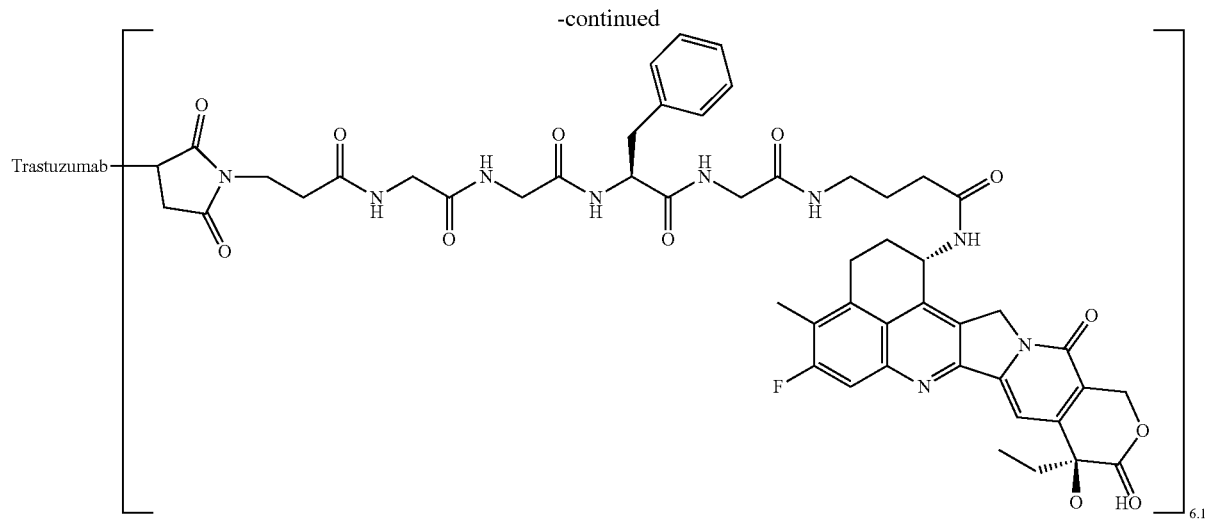

Process 1: Antibody-Drug Conjugate (5)

The amount of the aqueous solution of 10 mM TCEP was adjusted such that the molar ratio of TCEP to the antibody at the antibody reduction was 4.6. And the amount of the 10 mM drug linker solution added was adjusted such that the molar ratio of the compound of Process 1 of Example 4 to the antibody at the drug linker conjugation was 9.2. Then the amount of the aqueous solution of 100 mM NAC added was adjusted such that the molar ratio of NAC to the antibody at the termination of the reaction was 18.4. By the same procedures as Process 2 of Example 4, 6 mL of a solution containing the titled antibody-drug conjugate was obtained, and the following characteristic values were obtained.

Antibody concentration: 1.23 mg/mL, antibody yield: 7.4 mg (74%), and average number of conjugated drug molecules (n) per antibody molecule: 6.1.

Example 6: Antibody-Drug Conjugate (6)

[Formula 32]

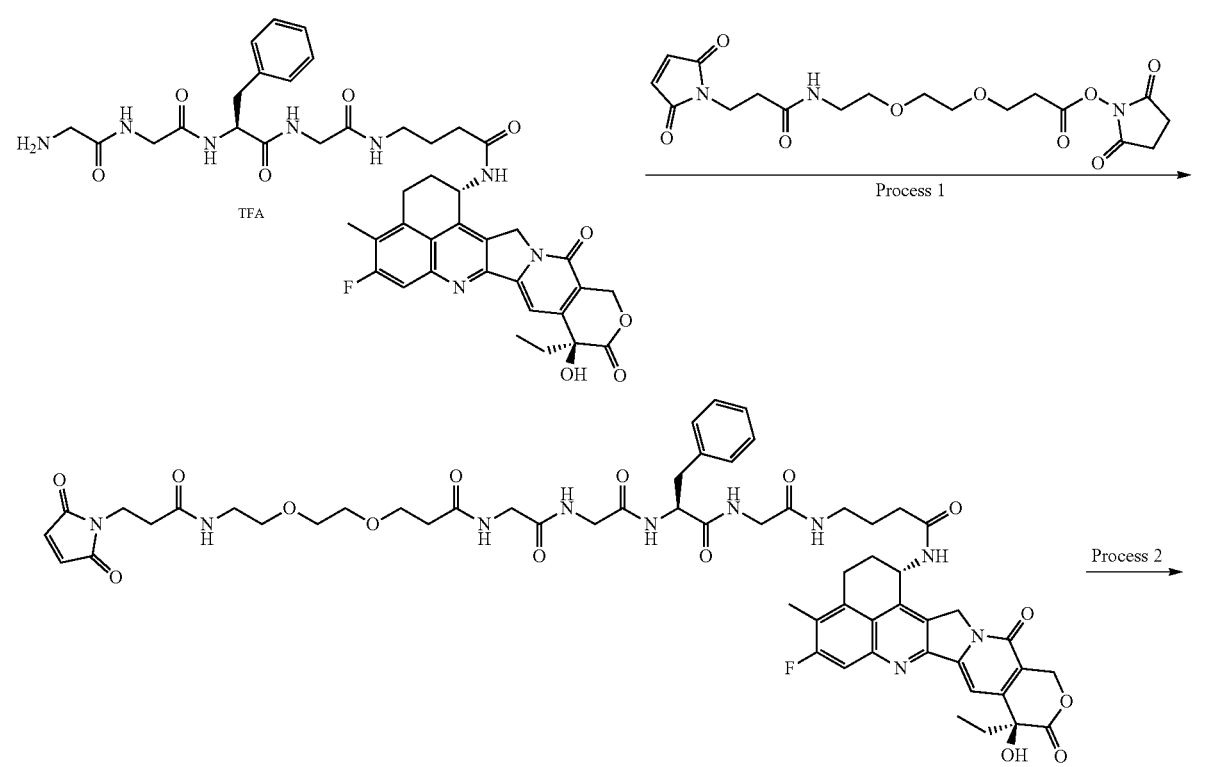

-continued

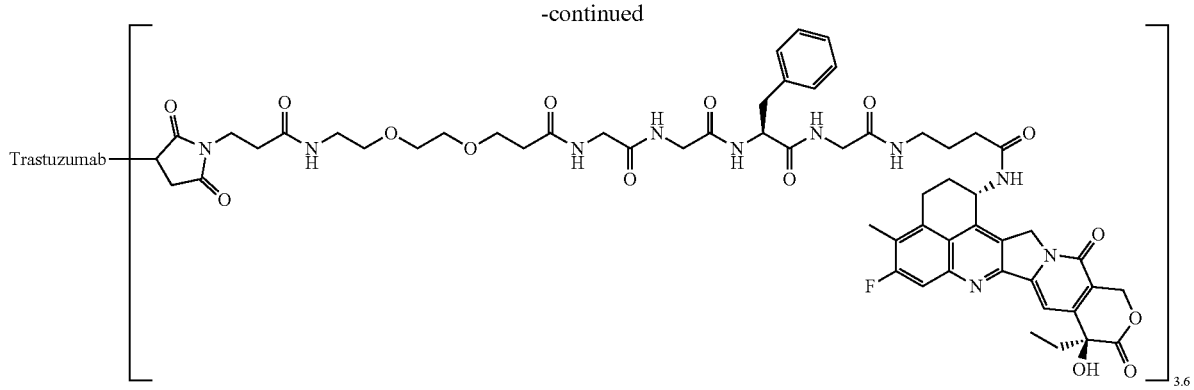

Process 1: N-{3-[2-(2-{[3-(2,5-Dioxo-2,5-dihydro-1H-pyrrol-1-yl)propanoyl]amino}ethoxy)ethoxy]propanoyl}glycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide The compound (100 mg, 0.119 mmol) obtained in Process 2 of Example 2 was reacted in the same manner as Process 3 of Example 2 by using diisopropylethylamine (20.8 μL, 0.119 mmol) instead of triethylamine and N-succinimidyl 3-(2-(2-(3-maleinimidepropanamide)ethoxy)ethoxy)propanoate (50.7 mg, 0.119 mmol) instead of N-succinimidyl 6-maleimide hexanoate to yield the titled compound as a pale yellow solid (66.5 mg, 48%).

$^1$H-NMR (400 MHz, DMSO-d$_6$) δ: 0.85 (3H, t, J=7.4 Hz), 1.65-1.74 (2H, m), 1.77-1.90 (2H, m), 2.07-2.19 (4H, m), 2.30 (2H, t, J=7.2 Hz), 2.33-2.36 (2H, m), 2.38 (3H, s), 2.76 (1H, dd, J=13.7, 9.8 Hz), 2.96-3.18 (9H, m), 3.42-3.44 (4H, m), 3.53-3.76 (10H, m), 4.43 (1H, td, J=8.6, 4.7 Hz), 5.14 (1H, d, J=18.8 Hz), 5.23 (1H, d, J=18.8 Hz), 5.38 (1H, d, J=17.2 Hz), 5.42 (1H, d, J=17.2 Hz), 5.52-5.58 (1H, m), 6.52 (1H, s), 6.98 (2H, s), 7.12-7.17 (1H, m), 7.18-7.25 (4H, m), 7.29 (1H, s), 7.69 (1H, t, J=5.5 Hz), 7.78 (1H, d, J=11.3 Hz), 7.98-8.03 (2H, m), 8.11 (1H, d, J=7.8 Hz), 8.16 (1H, t, J=5.7 Hz), 8.23 (1H, t, J=5.9 Hz), 8.44 (1H, d, J=9.0 Hz).

MS (APCI) m/z: 1149 (M+H)$^+$

Process 2: Antibody-Drug Conjugate (6)

Reduction of the antibody: The trastuzumab produced in Reference Example 1 was prepared to have an antibody concentration of 10 mg/mL by replacing the medium with PBS6.0/EDTA by using the Common procedure C-1 and Common procedure B (as absorption coefficient at 280 nm, 1.48 mLmg$^{-1}$ cm$^{-1}$ was used). The solution (1.25 mL) was placed in a 1.5 mL polypropylene tube and charged with an aqueous solution of 10 mM TCEP (0.019 mL; 2.3 equivalents per antibody molecule) and an aqueous solution of 1 M dipotassium hydrogen phosphate (0.0625 mL). After confirming that the solution had a pH of 7.4±0.1, the disulfide bond at the hinge part in the antibody was reduced by incubating at 37° C. for 1 hour. Conjugation between antibody and drug linker: After adding DMSO (Sigma-Aldrich Co. LLC; 0.109 mL) and a DMSO solution containing 10 mM of the compound of Process 1 (0.039 mL; 4.6 equivalents per antibody molecule) to the above solution at room temperature, it was stirred by using a tube rotator for conjugating the drug linker to the antibody at room temperature for 40 minutes. Next, an aqueous solution (0.008 mL) of 100 mM NAC was added thereto and stirred at room temperature to terminate the reaction of the drug linker for another 20 minutes.

Purification: The above solution was subjected to purification using the Common procedure D (ABS was used as buffer solution) described in Production method 1 to yield 6 mL of a solution containing the compound of interest.

Physicochemical characterization: By using the Common procedure E, the following characteristic values were obtained. Antibody concentration: 1.76 mg/mL, antibody yield: 10.6 mg (85%), and average number of conjugated drug molecules (n) per antibody molecule: 3.6.

Example 7 Antibody-Drug Conjugate (7)

[Formula 33]

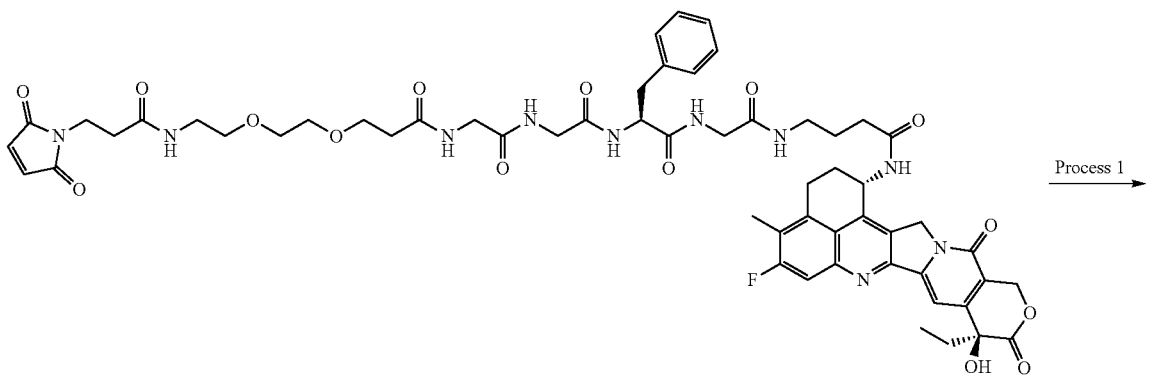

Process 1

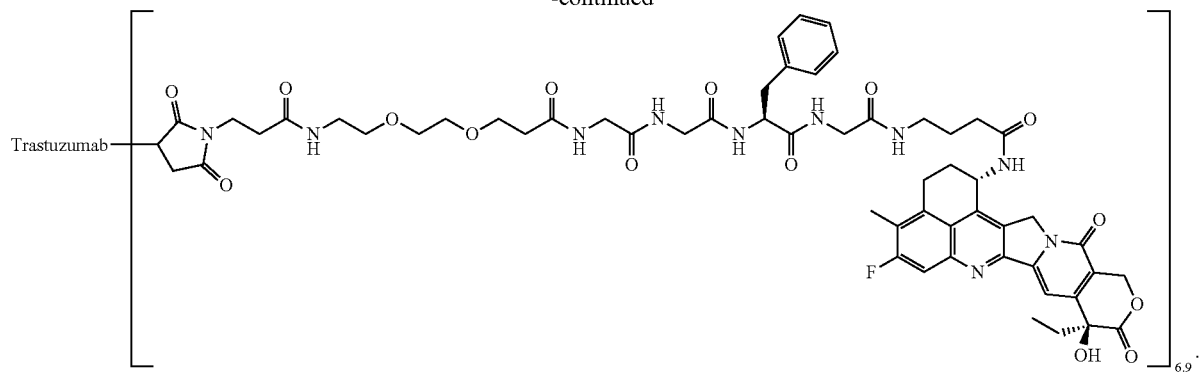

Process 1: Antibody-Drug Conjugate (7)

Reduction of the antibody: The trastuzumab produced in Reference Example 1 was prepared to have an antibody concentration of 10 mg/mL by replacing the medium with PBS6.0/EDTA by using the Common procedure C-1 and Common procedure B (as absorption coefficient at 280 nm, 1.48 mLmg$^{-1}$ cm$^{-1}$ was used). The solution (1.25 mL) was placed in a 1.5 mL polypropylene tube and charged with an aqueous solution of 10 mM TCEP (0.039 mL; 4.6 equivalents per antibody molecule) and an aqueous solution of 1 M dipotassium hydrogen phosphate (0.0625 mL). After confirming that the solution had a pH of 7.4±0.1, the disulfide bond at the hinge part in the antibody was reduced by incubating at 37° C. for 1 hour. Conjugation between antibody and drug linker: After adding DMSO (0.072 mL) and a DMSO solution containing 10 mM of the compound of Process 1 of Example 6 (0.078 mL; 9.2 equivalents per antibody molecule) to the above solution at room temperature, it was stirred by using a tube rotator for conjugating the drug linker to the antibody at room temperature for 40 minutes. Next, an aqueous solution (0.0155 mL) of 100 mM NAC was added thereto and stirred at room temperature to terminate the reaction of the drug linker for another 20 minutes.

Purification: The above solution was subjected to purification using the Common procedure D (ABS was used as buffer solution) to yield 6 mL of a solution containing the compound of interest.

Physicochemical characterization: By using the Common procedure E, the following characteristic values were obtained. Antibody concentration: 1.93 mg/mL, antibody yield: 11.6 mg (93%), and average number of conjugated drug molecules (n) per antibody molecule: 6.9.

Example 8 Antibody-Drug Conjugate (8)

[Formula 34]

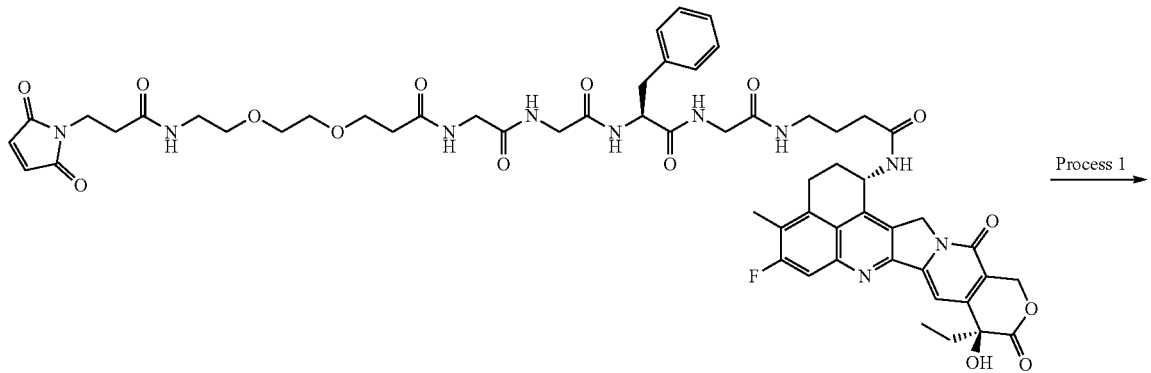

Process 1 →

-continued

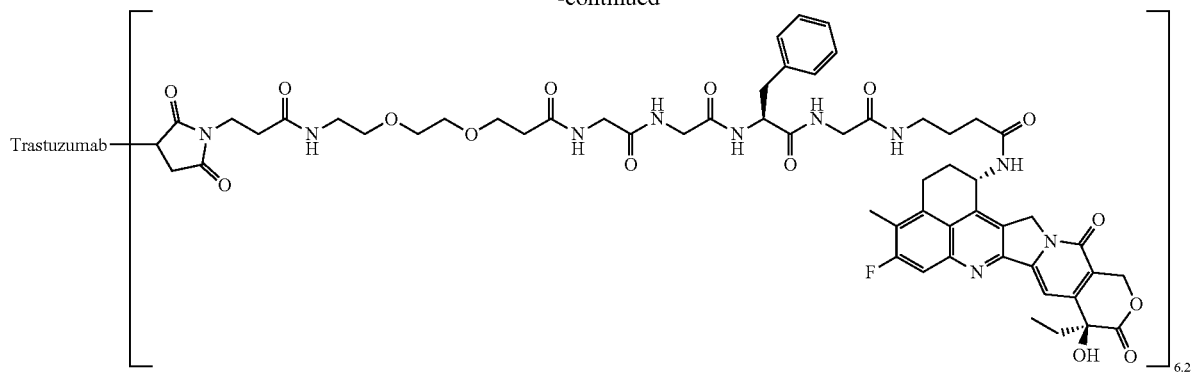

Process 1: Antibody-Drug Conjugate (8)

Reduction of the antibody: The trastuzumab produced in Reference Example 1 was prepared to have an antibody concentration of 10 mg/mL by replacing the medium with PBS6.0/EDTA by using the Common procedure C-1 and Common procedure B (as absorption coefficient at 280 nm, 1.48 mLmg$^{-1}$ cm$^{-1}$ was used). The solution (1.25 mL) was placed in a 1.5 mL polypropylene tube and charged with an aqueous solution of 10 mM TCEP (0.039 mL; 4.6 equivalents per antibody molecule) and an aqueous solution of 1 M dipotassium hydrogen phosphate (0.0625 mL). After confirming that the solution had a pH of 7.4±0.1, the disulfide bond at the hinge part in the antibody was reduced by incubating at 37° C. for 1 hour. Conjugation between antibody and drug linker: After adding DMSO (0.072 mL) and a DMSO solution containing 10 mM of the compound of Process 1 of Example 6 (0.078 mL; 9.2 equivalents per antibody molecule) to the above solution at room temperature, it was stirred by using a tube rotator for conjugating the drug linker to the antibody at room temperature for 40 minutes. Next, an aqueous solution (0.0155 mL) of 100 mM NAC was added thereto and stirred at room temperature to terminate the reaction of the drug linker for another 20 minutes.

Purification: The above solution was subjected to purification using the Common procedure D-1 (ABS was used as buffer solution) to yield 5.7 mL of a solution containing the compound of interest.

Physicochemical characterization: By using the Common procedure E, the following characteristic values were obtained. Antibody concentration: 1.50 mg/mL, antibody yield: 8.55 mg (86%), and average number of conjugated drug molecules (n) per antibody molecule: 6.2.

Example 9 Antibody-Drug Conjugate (9)

[Formula 35]

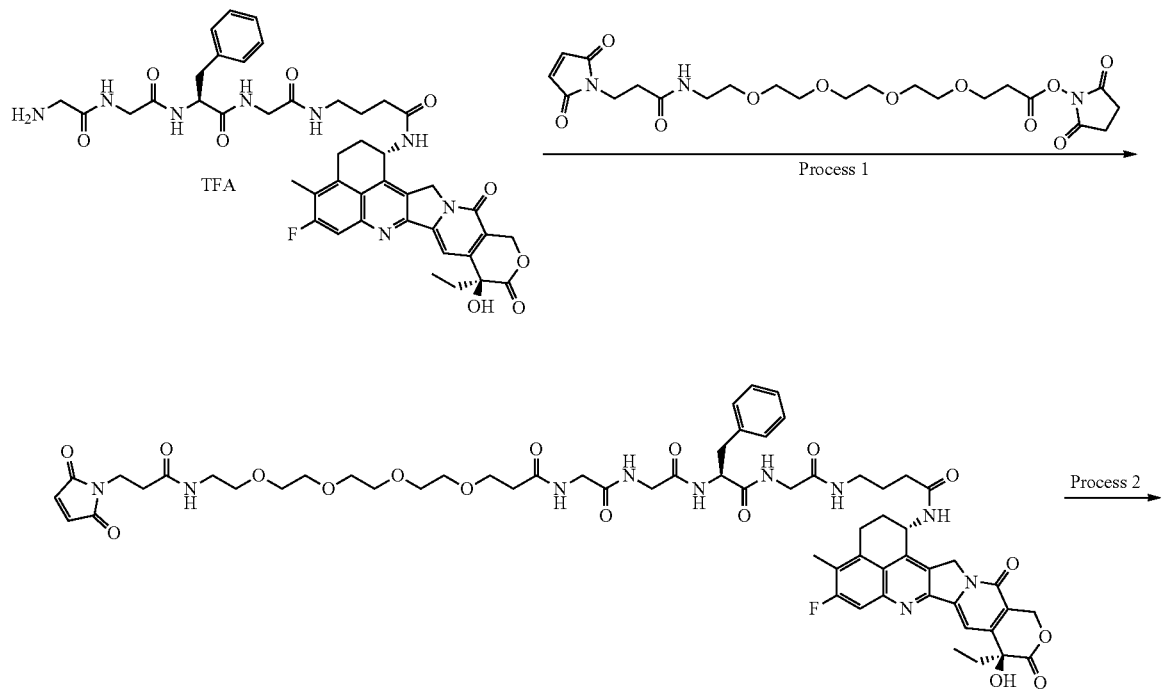

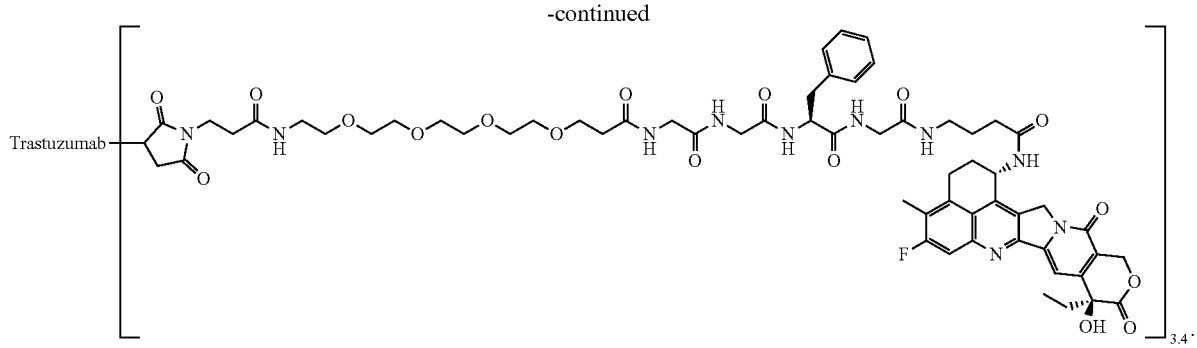

Process 1: N-[19-(2,5-Dioxo-2,5-dihydro-1H-pyrrol-1-yl)-17-oxo-4,7,10,13-tetraoxo-16-azanonadecan-1-oyl]glycylglycyl-L-phenylalanyl-N-(4-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-4-oxobutyl)glycinamide The compound (90 mg, 0.107 mmol) obtained in Process 2 of Example 2 was reacted in the same manner as Process 3 of Example 2 by using diisopropylethylamine (18.7 µL, 0.107 mmol) instead of triethylamine and N-succinimidyl 1-maleinimide-3-oxo-7,10,13,16-tetraoxa-4-azanonadecan-19-oate (55.1 mg, 0.107 mmol) instead of N-succinimidyl 6-maleimide hexanoate to yield the titled compound as a pale yellow solid (50 mg, 37%).

$^1$H-NMR (400 MHz, DMSO-$d_6$) δ: 0.85 (3H, t, J=7.2 Hz), 1.64-1.74 (2H, m), 1.77-1.90 (2H, m), 2.06-2.19 (4H, m), 2.27-2.32 (2H, m), 2.33-2.37 (2H, m), 2.38 (3H, s), 2.72-2.80 (3H, m), 2.96-3.19 (6H, m), 3.39-3.48 (10H, m), 3.52-3.75 (10H, m), 4.39-4.48 (1H, m), 5.14 (1H, d, J=18.8 Hz), 5.23 (1H, d, J=18.8 Hz), 5.38 (1H, d, J=17.0 Hz), 5.42 (1H, d, J=17.0 Hz), 5.52-5.58 (1H, m), 6.52 (1H, s), 6.98 (1H, s), 7.13-7.24 (5H, m), 7.29 (1H, s), 7.69 (1H, t, J=5.5 Hz), 7.78 (1H, d, J=10.9 Hz), 7.98-8.03 (2H, m), 8.10 (1H, d, J=7.8 Hz), 8.16 (1H, t, J=5.7 Hz), 8.23 (1H, t, J=5.7 Hz), 8.44 (1H, d, J=8.6 Hz).

MS (APCI) m/z: 1237 (M+H)$^+$

Process 2: Antibody-Drug Conjugate (9)

By using the trastuzumab produced in Reference Example 1 and the compound obtained in Process 1, the titled antibody-drug conjugate was obtained in the same manner as Process 2 of Example 6.

Antibody concentration: 1.75 mg/mL, antibody yield: 10.5 mg (84%), and average number of conjugated drug molecules (n) per antibody molecule: 3.4.

Example 10 Antibody-Drug Conjugate (10)

[Formula 36]

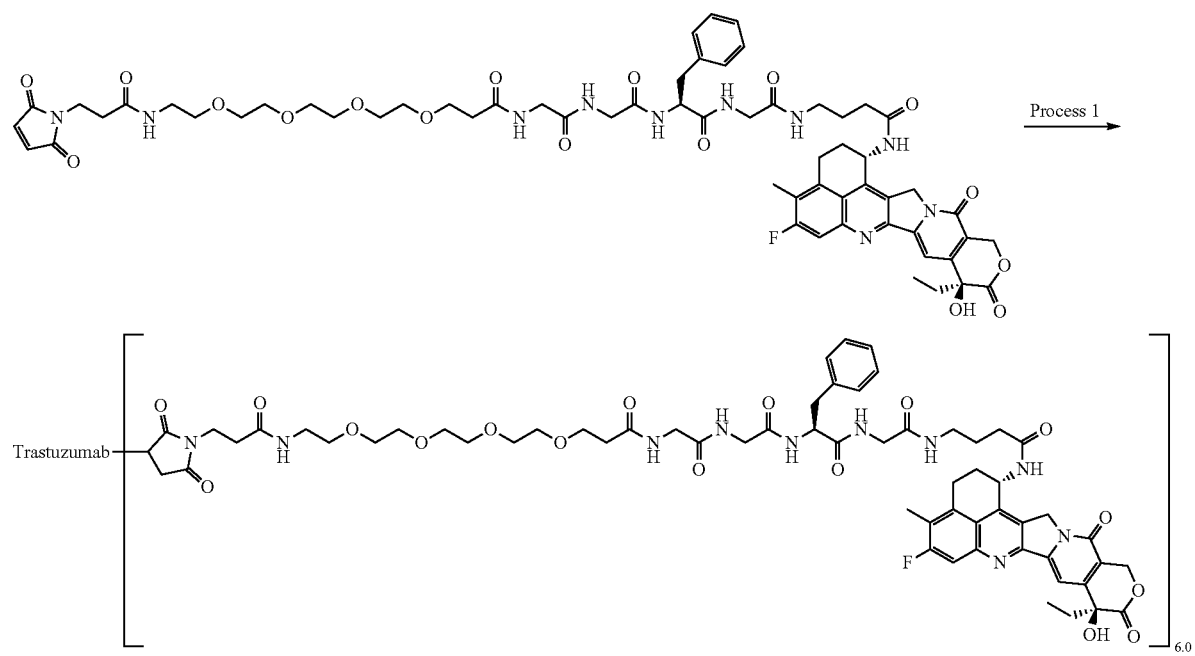

Process 1: Antibody-Drug Conjugate (10)

By using the trastuzumab produced in Reference Example 1 and the compound obtained in Process 1 of Example 9, the titled antibody-drug conjugate was obtained in the same manner as Process 1 of Example 7.
Antibody concentration: 1.79 mg/mL, antibody yield: 10.7 mg (86%), and average number of conjugated drug molecules (n) per antibody molecule: 6.0.

Example 11 Intermediate (11)

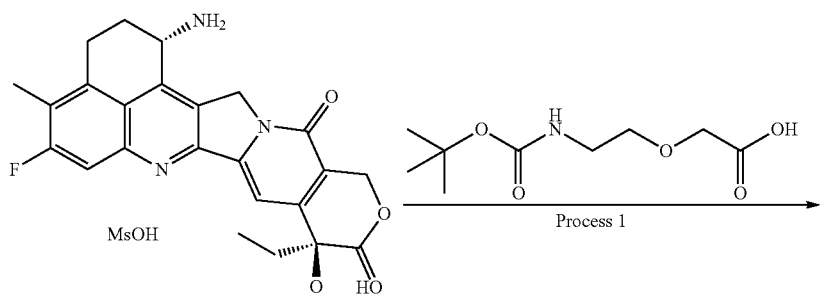

[Formula 37]

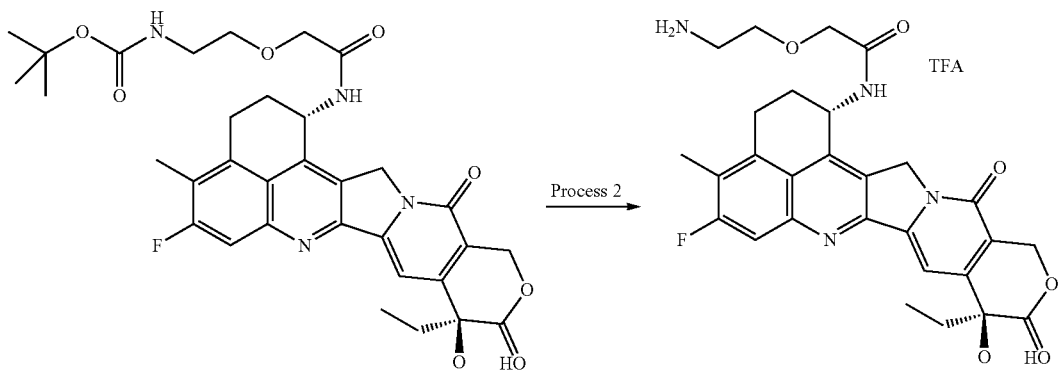

Process 1: tert-Butyl [2-(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)ethyl]carbamate Methanesulfonic acid salt of exatecan (3.10 g, 5.47 mol) was reacted in the same manner as Process 1 of Example 1 by using {2-[(tert-butoxycarbonyl)amino]ethoxy}acetic acid (J. Med. Chem., 1992, vol. 35, pp. 292; 1.55 g, 6.01 mmol) instead of 4-(tert-butoxycarbonylamino)butanoic acid to yield the titled compound as a pale yellow solid (2.56 g, 73%).

$^1$H-NMR (400 MHz, DMSO-$d_6$) δ: 0.87 (3H, t, J=7.3 Hz), 1.26 (9H, s), 1.81-1.91 (2H, m), 2.13-2.22 (2H, m), 2.40 (3H, s), 3.08-3.26 (4H, m), 3.43-3.53 (2H, m), 4.00 (1H, d, J=15.1 Hz), 4.05 (1H, d, J=15.1 Hz), 5.14 (1H, d, J=18.7 Hz), 5.22 (1H, d, J=18.7 Hz), 5.40 (1H, d, J=16.6 Hz), 5.44 (1H, d, J=16.6 Hz), 5.59-5.66 (1H, m), 6.53 (1H, s), 6.86 (1H, t, J=5.4 Hz), 7.31 (1H, s), 7.79 (1H, d, J=10.9 Hz), 8.49 (1H, d, J=9.1 Hz).

MS (APCI) m/z: 637 (M+H)$^+$

Process 2: 2-(2-Aminoethoxy)-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]acetamide The compound (1.50 g, 2.36 mol) obtained in Process 1 above was reacted in the same manner as Process 2 of Example 1 to yield trifluoroacetic acid salt of the titled compound as a pale yellow solid (1.50 g, quantitative).

$^1$H-NMR (400 MHz, DMSO-$d_6$) δ: 0.87 (3H, t, J=7.5 Hz), 1.81-1.92 (2H, m), 2.15-2.23 (2H, m), 2.41 (3H, s), 3.05 (2H, t, J=5.1 Hz), 3.15-3.23 (2H, m), 3.71 (2H, t, J=5.1 Hz), 4.10 (2H, s), 5.19 (1H, d, J=18.7 Hz), 5.24 (1H, d, J=18.7 Hz), 5.43 (2H, s), 5.58-5.66 (1H, m), 6.55 (1H, s), 7.33 (1H, s), 7.73-7.84 (4H, m), 8.55 (1H, d, J=9.1 Hz).

MS (APCI) m/z: 537 (M+H)$^+$

Example 12 Antibody-Drug Conjugate (12)
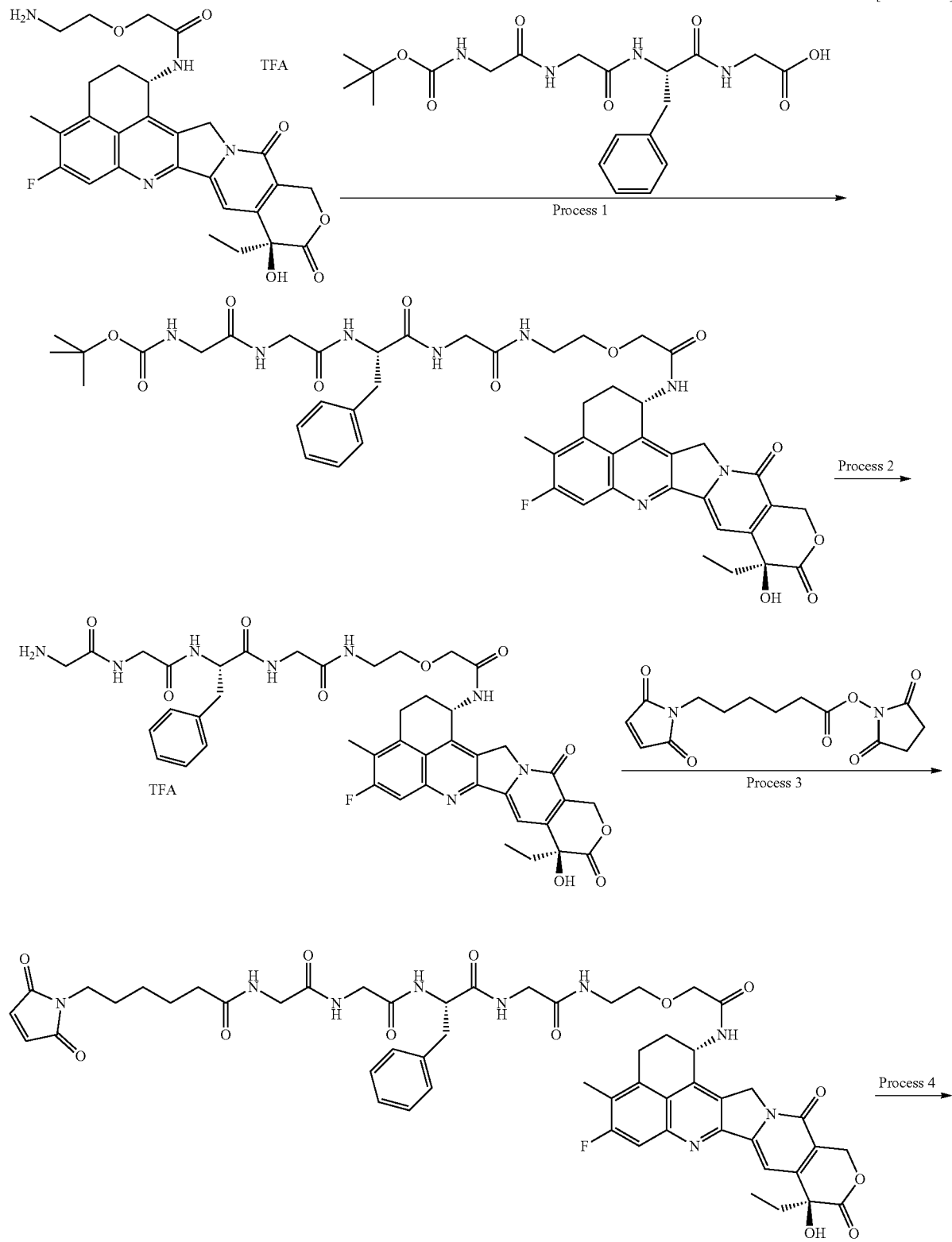
[Formula 38]

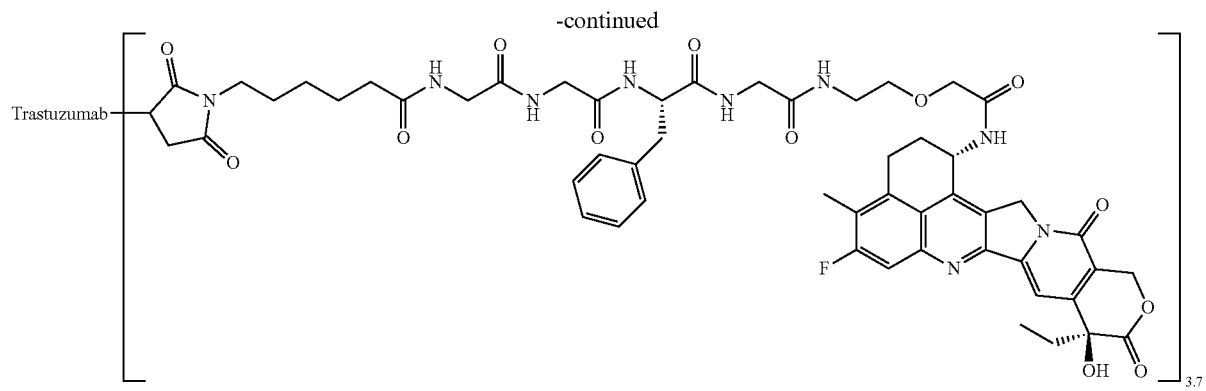

Process 1: N-(tert-Butoxycarbonyl)glycylglycyl-L-phenylalanyl-N-[2-(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl] amino}-2-oxoethoxy)ethyl]glycinamide The compound (554 mg, 0.85 mmol) of Process 2 of Example 11 was reacted in the same manner as Process 1 of Example 2 to yield the titled compound (775 mg, 95%).

$^1$H-NMR (400 MHz, DMSO-$d_6$) δ: 0.85 (3H, t, J=7.3 Hz), 1.36 (9H, s), 1.78-1.89 (2H, m), 2.13-2.22 (2H, m), 2.39 (3H, s), 2.71 (1H, dd, J=13.4, 9.8 Hz), 2.95 (1H, dd, J=13.4, 4.3 Hz), 3.09-3.23 (1H, m), 3.23-3.32 (2H, m), 3.40-3.62 (8H, m), 3.73 (1H, dd, J=16.5, 5.5 Hz), 4.03 (2H, s), 4.39-4.47 (1H, m), 5.17 (1H, d, J=18.9 Hz), 5.25 (1H, d, J=18.9 Hz), 5.41 (1H, d, J=16.8 Hz), 5.45 (1H, d, J=16.8 Hz), 5.57-5.64 (1H, m), 6.54 (1H, s), 6.99 (1H, t, J=5.8 Hz), 7.13-7.26 (5H, m), 7.31 (1H, s), 7.76-7.82 (2H, m), 7.90 (1H, t, J=5.2 Hz), 8.13 (1H, d, J=7.9 Hz), 8.27 (1H, t, J=5.8 Hz), 8.49 (1H, d, J=8.5 Hz).

MS (APCI) m/z: 955 (M+H)$^+$

Process 2: Glycylglycyl-L-phenylalanyl-N-[2-(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl] amino}-2-oxoethoxy)ethyl]glycinamide The compound (630 mg, 0.659 mmol) obtained in Process 1 above was reacted in the same manner as Process 2 of Example 2 to yield trifluoroacetic acid salt of the titled compound (588 mg, 92%).

$^1$H-NMR (400 MHz, DMSO-$d_6$) δ: 0.86 (3H, t, J=7.3 Hz), 1.79-1.90 (2H, m), 2.13-2.22 (2H, m), 2.39 (3H, s), 2.71 (1H, dd, J=13.4, 10.1 Hz), 2.99 (1H, dd, J=13.4, 4.3 Hz), 3.09-3.23 (1H, m), 3.24-3.32 (3H, m), 3.41-3.71 (7H, m), 3.86 (1H, dd, J=16.8, 5.8 Hz), 4.04 (2H, s), 4.52 (1H, td, J=9.0, 4.1 Hz), 5.17 (1H, d, J=18.9 Hz), 5.25 (1H, d, J=18.9 Hz), 5.41 (1H, d, J=16.5 Hz), 5.45 (1H, d, J=16.5 Hz), 5.56-5.65 (1H, m), 6.55 (1H, s), 7.13-7.26 (5H, m), 7.32 (1H, s), 7.80 (1H, d, J=11.0 Hz), 7.87-8.01 (4H, m), 8.29-8.36 (2H, m), 8.46-8.55 (2H, m).

MS (APCI) m/z: 855 (M+H)$^+$

Process 3: N-[6-(2,5-Dioxo-2,5-dihydro-1H-pyrrol-1-yl)hexanoyl]glycylglycyl-L-phenylalanyl-N-[2-(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl] amino}-2-oxoethoxy)ethyl]glycinamide The compound (240 mg, 0.247 mmol) obtained in Process 2 above was reacted in the same manner as Process 3 of Example 2 to yield the titled compound (162 mg, 62%).

$^1$H-NMR (400 MHz, DMSO-$d_6$) δ: 0.86 (3H, t, J=7.6 Hz), 1.13-1.22 (2H, m), 1.40-1.51 (4H, m), 1.78-1.90 (2H, m), 2.09 (2H, t, J=7.6 Hz), 2.14-2.21 (2H, m), 2.39 (3H, s), 2.74 (1H, dd, J=13.6, 9.7 Hz), 2.96 (1H, dd, J=13.6, 4.5 Hz), 3.08-3.24 (1H, m), 3.24-3.30 (1H, m), 3.33-3.40 (4H, m), 3.47-3.68 (7H, m), 3.72 (1H, dd, J=16.6, 5.7 Hz), 4.03 (2H, s), 4.42 (1H, td, J=8.6, 4.2 Hz), 5.17 (1H, d, J=18.7 Hz), 5.25 (1H, d, J=18.7 Hz), 5.40 (1H, d, J=17.2 Hz), 5.44 (1H, d, J=17.2 Hz), 5.57-5.64 (1H, m), 6.52 (1H, s), 6.99 (2H, s), 7.13-7.25 (5H, m), 7.31 (1H, s), 7.74-7.81 (2H, m), 7.99 (1H, t, J=5.7 Hz), 8.03-8.11 (2H, m), 8.22 (1H, t, J=5.7 Hz), 8.47 (1H, d, J=9.1 Hz)

MS (APCI) m/z: 1048 (M+H)$^+$

Process 4: Antibody-Drug Conjugate (12)

By using the trastuzumab produced in Reference Example 1 and the compound obtained in Process 3, the titled antibody-drug conjugate was obtained in the same manner as Process 2 of Example 6. The solution was further concentrated by the Common procedure A. After that, by using the Common procedure E, the following characteristic values were obtained.

Antibody concentration: 10.77 mg/mL, antibody yield: 7.5 mg (60%), and average number of conjugated drug molecules (n) per antibody molecule: 3.7.

Example 13 Antibody-Drug Conjugate (13)

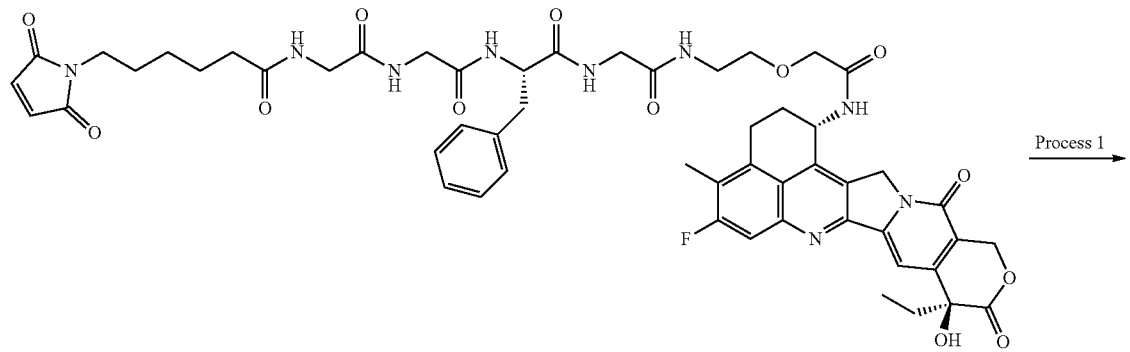

[Formula 39]

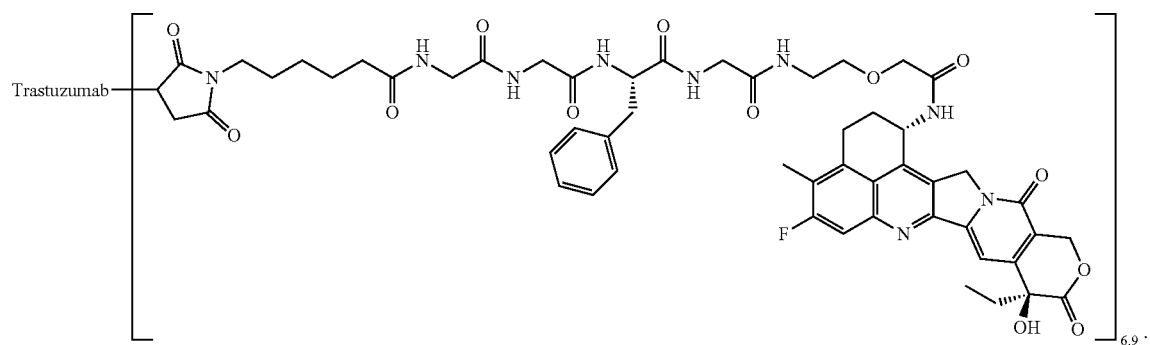

Process 1: Antibody-Drug Conjugate (13)

By using the trastuzumab produced in Reference Example 1 and the compound obtained in Process 3 of Example 12, the titled antibody-drug conjugate was obtained in the same manner as Process 1 of Example 7. The solution was further concentrated by the Common procedure A. After that, by using the Common procedure E, the following characteristic values were obtained.

Antibody concentration: 10.69 mg/mL, antibody yield: 7.5 mg (60%), and average number of conjugated drug molecules (n) per antibody molecule: 6.9.

Example 14 Intermediate (14)

[Formula 40]

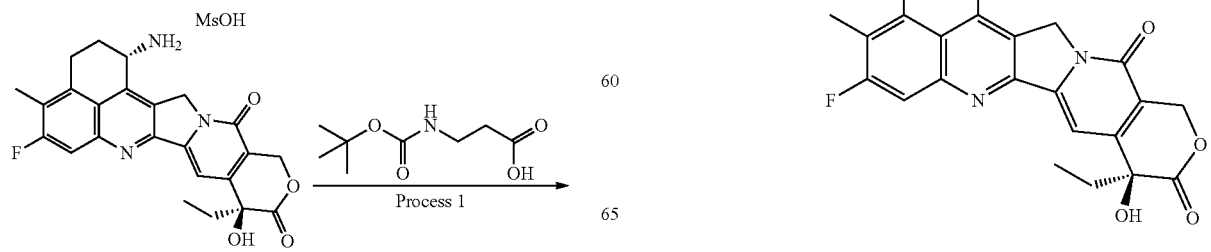

-continued

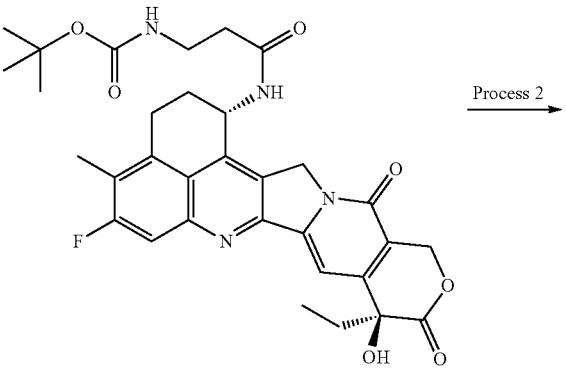

Process 1: tert-Butyl (3-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl] amino}-3-oxopropyl) carbamate Methanesulfonic acid salt of exatecan (500 mg, 0.941 mmol) was reacted in the same manner as Process 1 of Example 1 by using N-(tert-butoxycarbonyl)-β-alanine instead of 4-(tert-butoxycarbonylamino)butanoic acid to yield the titled compound as a yellow-brown solid (616 mg, quantitative).

$^1$H-NMR (400 MHz, DMSO-d$_6$) δ: 0.87 (3H, t, J=7.2 Hz), 1.29 (9H, s), 1.86 (2H, dt, J=15.1, 7.3 Hz), 2.04-2.22 (2H, m), 2.31 (2H, t, J=6.8 Hz), 2.40 (3H, s), 3.10-3.26 (4H, m), 5.15 (1H, d, J=18.8 Hz), 5.26 (1H, d, J=19.2 Hz), 5.42 (2H, dd, J=18.8, 16.4 Hz), 5.57 (1H, dt, J=8.5, 4.2 Hz), 6.53 (1H, s), 6.78 (1H, t, J=5.5 Hz), 7.30 (1H, s), 7.80 (1H, d, J=11.0 Hz), 8.46 (1H, d, J=8.6 Hz).

MS (ESI) m/z: 607 (M+H)$^+$

Process 2: N-[(1S,9S)-9-Ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-3-alaninamide The compound obtained in Process 1 above was reacted in the same manner as Process 2 of Example 1 to yield trifluoroacetic acid salt of the titled compound as a yellow solid (499 mg, 86%).

$^1$H-NMR (400 MHz, DMSO-d$_6$) δ: 0.87 (3H, t, J=7.2 Hz), 1.86 (2H, dquin, J=14.6, 7.2, 7.2, 7.2, 7.2 Hz), 2.06-2.27 (1H, m), 2.41 (3H, s), 2.46-2.57 (2H, m), 3.08 (2H, t, J=6.8 Hz), 3.14-3.24 (2H, m), 5.22 (1H, d, J=18.8 Hz), 5.29 (1H, d, J=18.8 Hz), 5.43 (2H, s), 5.58 (1H, dt, J=8.5, 4.5 Hz), 6.55 (1H, s), 7.32 (1H, s), 7.74 (3H, brs), 7.82 (1H, d, J=11.0 Hz), 8.67 (1H, d, J=8.6 Hz).

MS (ESI) m/z: 507 (M+H)$^+$

Example 15 Antibody-Drug Conjugate (15)

[Formula 41]

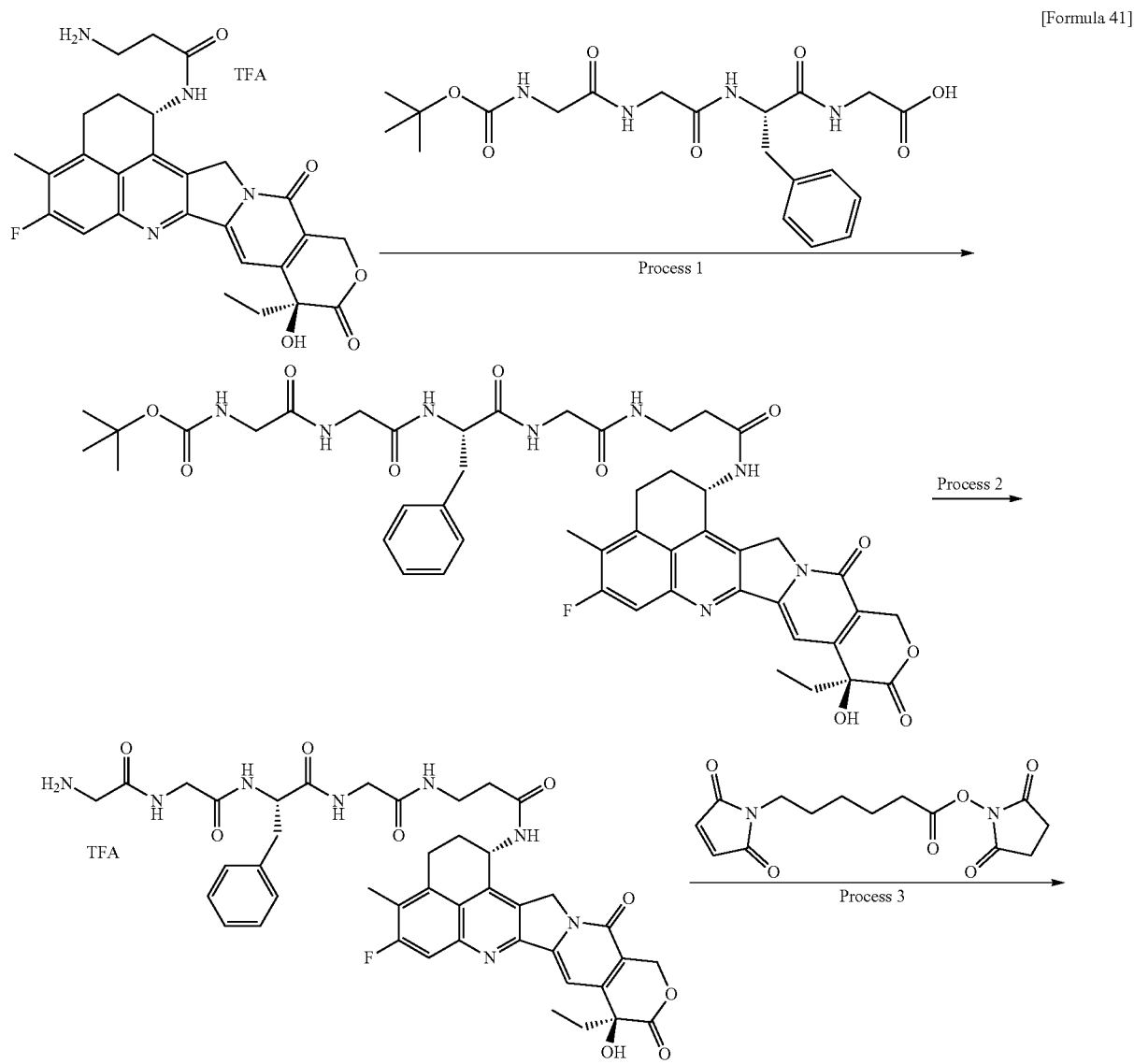

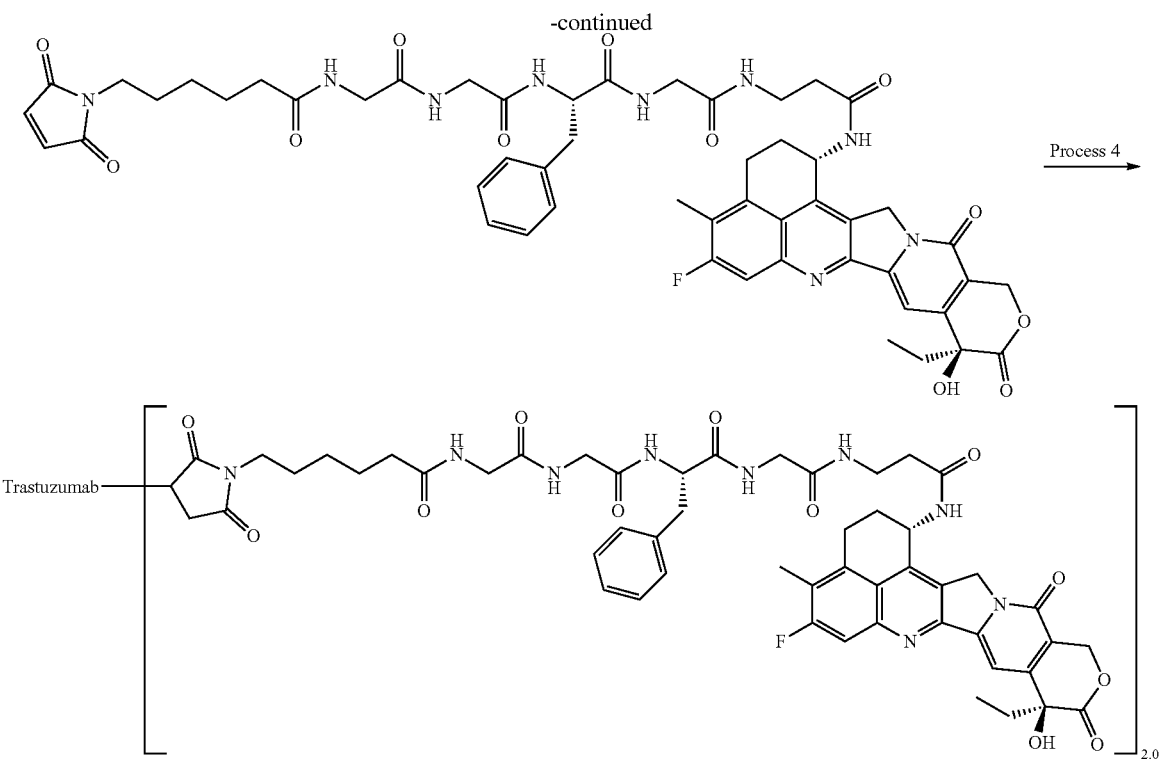

Process 1: N-(tert-Butoxycarbonyl)glycylglycyl-L-phenylalanylglycyl-N-[(1S,9S)-9-ethyl-5-fluoro-9-hydroxy-4-methyl-10,13-dioxo-2,3,9,10,13,15-hexahydro-1H, 12H-benzo[de]pyrano[3',4':6,7]indolizino[1,2-b]quinolin-1-yl]-β-alaninamide The compound (484 mg, 0.780 mmol) obtained in Process 2 of Example 14 was reacted in the same manner as Process 1 of Example 2 to yield the titled compound as a pale yellow solid (626 mg, 87%).

$^1$H-NMR (400 MHz, DMSO-$d_6$) δ: 0.87 (3H, t, J=7.4 Hz), 1.27-1.42 (9H, m), 1.77-1.93 (2H, m), 2.06-2.22 (2H, m), 2.36 (2H, t, J=7.2 Hz), 2.40 (3H, d, J=1.6 Hz), 2.44-2.54 (2H, m), 2.76 (1H, dd, J=14.5, 10.2 Hz), 3.02 (1H, dd, J=13.9, 4.5 Hz), 3.12-3.22 (2H, m), 3.52 (6H, d, J=6.3 Hz), 4.42-4.54 (1H, m), 5.19 (1H, d, J=19.2 Hz), 5.26 (1H, d, J=18.4 Hz), 5.42 (1H, dd, J=18.4, 16.4 Hz), 5.57 (1H, dt, J=8.7, 4.4 Hz), 6.53 (1H, s), 6.98 (1H, t, J=5.9 Hz), 7.14-7.28 (5H, m), 7.31 (1H, s), 7.77-7.84 (1H, m), 7.91 (1H, t, J=5.5 Hz), 8.16 (1H, d, J=7.8 Hz), 8.27 (1H, t, J=5.1 Hz), 8.52 (1H, d, J=9.0 Hz).

Process 2: Glycylglycyl-L-phenylalanylglycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-β-alaninamide trifluoroacetate The compound (624 mg, 0.675 mmol) obtained in Process 1 above was reacted in the same manner as Process 2 of Example 2 to yield the titled compound as a yellow solid (626 mg, 92%).

$^1$H-NMR (400 MHz, DMSO-$d_6$) δ: 0.87 (3H, t, J=7.4 Hz), 1.86 (2H, tt, J=14.5, 7.2 Hz), 2.07-2.22 (2H, m), 2.36 (2H, t, J=7.2 Hz), 2.40 (3H, s), 2.44-2.54 (2H, m), 2.75 (1H, dd, J=13.7, 9.8 Hz), 3.04 (1H, dd, J=13.7, 4.3 Hz), 3.12-3.22 (2H, m), 3.58 (2H, d, J=4.7 Hz), 3.69 (3H, td, J=11.2, 5.7 Hz), 3.87 (1H, dd, J=17.0, 5.7 Hz), 4.54 (1H, m, J=17.8, 4.5 Hz), 5.19 (1H, d, J=19.2 Hz), 5.26 (1H, d, J=18.8 Hz), 5.43 (2H, s), 5.51-5.60 (1H, m), 6.55 (1H, s), 7.14-7.29 (5H, m), 7.32 (1H, s), 7.81 (1H, d, J=10.9 Hz), 7.88 (1H, t, J=5.7 Hz), 7.97 (3H, brs), 8.29-8.38 (2H, m), 8.50 (1H, t, J=5.7 Hz), 8.55 (1H, d, J=8.6 Hz).

MS (ESI) m/z: 825 (M+H)$^+$

Process 3: N-[6-(2,5-Dioxo-2,5-dihydro-1H-pyrrol-1-yl)hexanoyl]glycylglycyl-L-phenylalanylglycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-β-alaninamide The compound (60.0 mg, 0.0646 mmol) obtained in Process 2 above was reacted in the same manner as Process 3 of Example 2 to yield the titled compound as a solid (14.0 mg, 21%).

$^1$H-NMR (400 MHz, DMSO-$d_6$) δ: 0.86 (3H, t, J=7.2 Hz), 1.12-1.22 (2H, m), 1.39-1.51 (4H, m), 1.79-1.91 (2H, m), 2.02-2.20 (2H, m), 2.07 (2H, t, J=7.4 Hz), 2.30-2.42 (4H, m), 2.40 (3H, s), 2.78 (1H, dd, J=14.1, 9.4 Hz), 3.02 (1H, dd, J=14.7, 4.9 Hz), 3.12-3.21 (2H, m), 3.26-3.42 (2H, m), 3.50-3.80 (6H, m), 4.40-4.51 (1H, m), 5.19 (1H, d, J=19.6 Hz), 5.26 (1H, d, J=19.2 Hz), 5.42 (2H, brs), 5.51-5.62 (1H, m), 6.53 (1H, s), 6.99 (2H, s), 7.13-7.28 (5H, m), 7.31 (1H, s), 7.74-7.84 (2H, m), 8.01 (1H, t, J=5.3 Hz), 8.06 (1H, t, J=5.7 Hz), 8.14 (1H, d, J=8.2 Hz), 8.25 (1H, t, J=5.7 Hz), 8.53 (1H, d, J=8.6 Hz).

MS (ESI) m/z: 1018 (M+H)$^+$

Process 4: Antibody-Drug Conjugate (15)

Reduction of the antibody: The trastuzumab produced in Reference Example 1 was prepared to have an antibody concentration of 10 mg/mL with PBS6.0/EDTA by using the Common procedure C-1 and Common procedure B (as absorption coefficient at 280 nm, 1.37 mLmg$^{-1}$ cm$^{-1}$ was used). The solution (1.0 mL) was collected into a 2 mL tube and charged with an aqueous solution of 10 mM TCEP (0.0155 mL; 2.3 equivalents per antibody molecule) and an aqueous solution of 1 M dipotassium hydrogen phosphate (0.050 mL). After confirming that the solution had a pH of 7.4±0.1, the disulfide bond at the hinge part in the antibody was reduced by incubating at 37° C. for 1 hour.

Conjugation between antibody and drug linker: After incubating the solution at 22° C. for 10 minutes, a DMSO solution (0.0311 mL; 4.6 equivalents per antibody molecule) containing 10 mM of the compound obtained in Process 3 was added thereto and incubated for conjugating the drug linker to the antibody at 22° C. for 40 minutes. Next, an aqueous solution (0.00622 mL; 9.2 equivalents per antibody molecule) of 100 mM NAC was added thereto and incubated at 22° C. to terminate the reaction of the drug linker for another 20 minutes.

Purification: The above solution was subjected to purification using the Common procedure D-1 (PBS6.0 was used as buffer solution) to yield 6 mL of a solution containing the titled antibody-drug conjugate.

Physicochemical characterization: By using the Common procedure E, the following characteristic values were obtained. Antibody concentration: 1.18 mg/mL, antibody yield: 7.08 mg (71%), and average number of conjugated drug molecules (n) per antibody molecule: 2.0.

Example 16 Antibody-Drug Conjugate (16)

Process 1: Antibody-Drug Conjugate (16)

Reduction of the antibody: The trastuzumab produced in Reference Example 1 was prepared to have an antibody concentration of 10 mg/mL with PBS6.0/EDTA by using the Common procedure C-1 and Common procedure B (as absorption coefficient at 280 nm, 1.37 mLmg$^{-1}$ cm$^{-1}$ was used). The solution (1.0 mL) was collected into a 2 mL tube and charged with an aqueous solution of 10 mM TCEP (0.0311 mL; 4.6 equivalents per antibody molecule) and an aqueous solution of 1 M dipotassium hydrogen phosphate (0.050 mL). After confirming that the solution had a pH of 7.4±0.1, the disulfide bond at the hinge part in the antibody was reduced by incubating at 37° C. for 1 hour.

Conjugation between antibody and drug linker: After incubating the solution at 22° C. for 10 minutes, a DMSO solution (0.0622 mL; 9.2 equivalents per antibody molecule) containing 10 mM of the compound obtained in Process 3 of Example 15 was added thereto and incubated for conjugating the drug linker to the antibody at 22° C. for 40 minutes. Next, an aqueous solution (0.0124 mL; 18.4 equivalents per antibody molecule) of 100 mM NAC was added thereto and incubated at 22° C. to terminate the reaction of the drug linker for another 20 minutes.

Purification: The above solution was subjected to purification using the Common procedure D-1 (PBS6.0 was used as buffer solution) to yield 6 mL of a solution containing the titled antibody-drug conjugate.

Physicochemical characterization: By using the Common procedure E, the following characteristic values were obtained. Antibody concentration: 1.03 mg/mL, antibody yield: 6.18 mg (62%), and average number of conjugated drug molecules (n) per antibody molecule: 3.8.

[Formula 42]

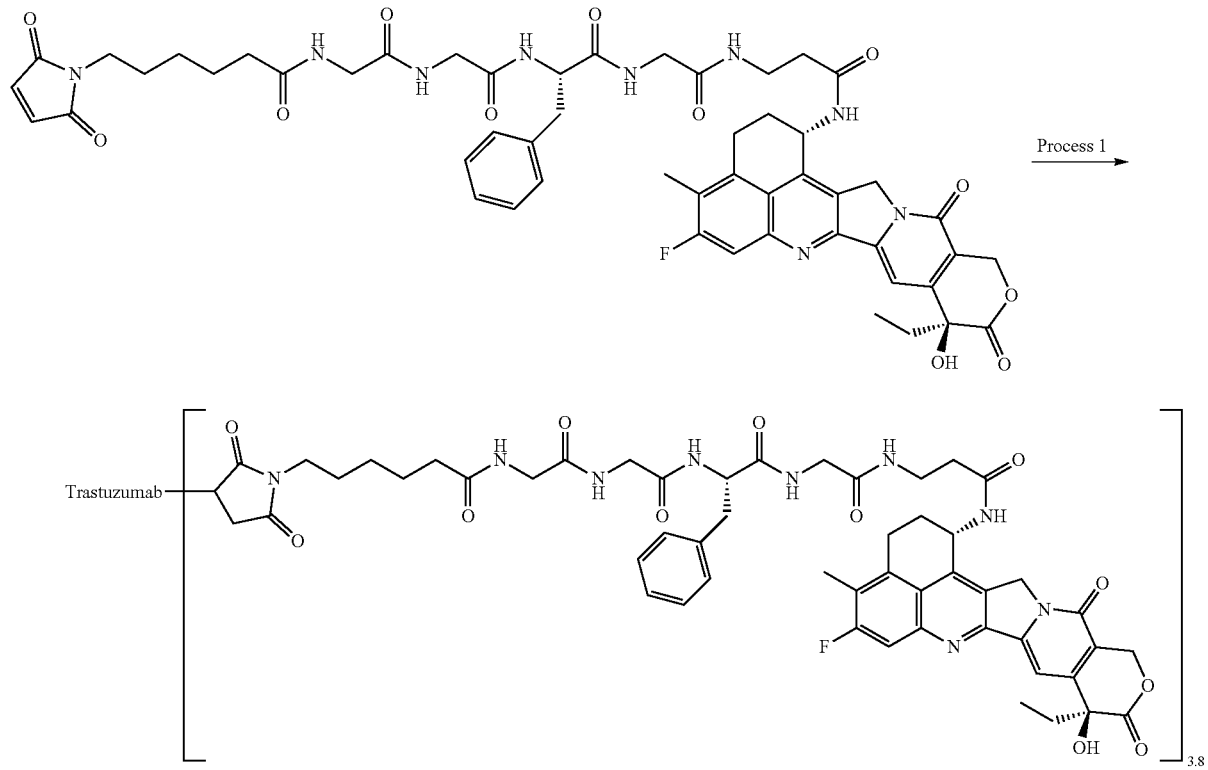

Example 17 Antibody-Drug Conjugate (17)

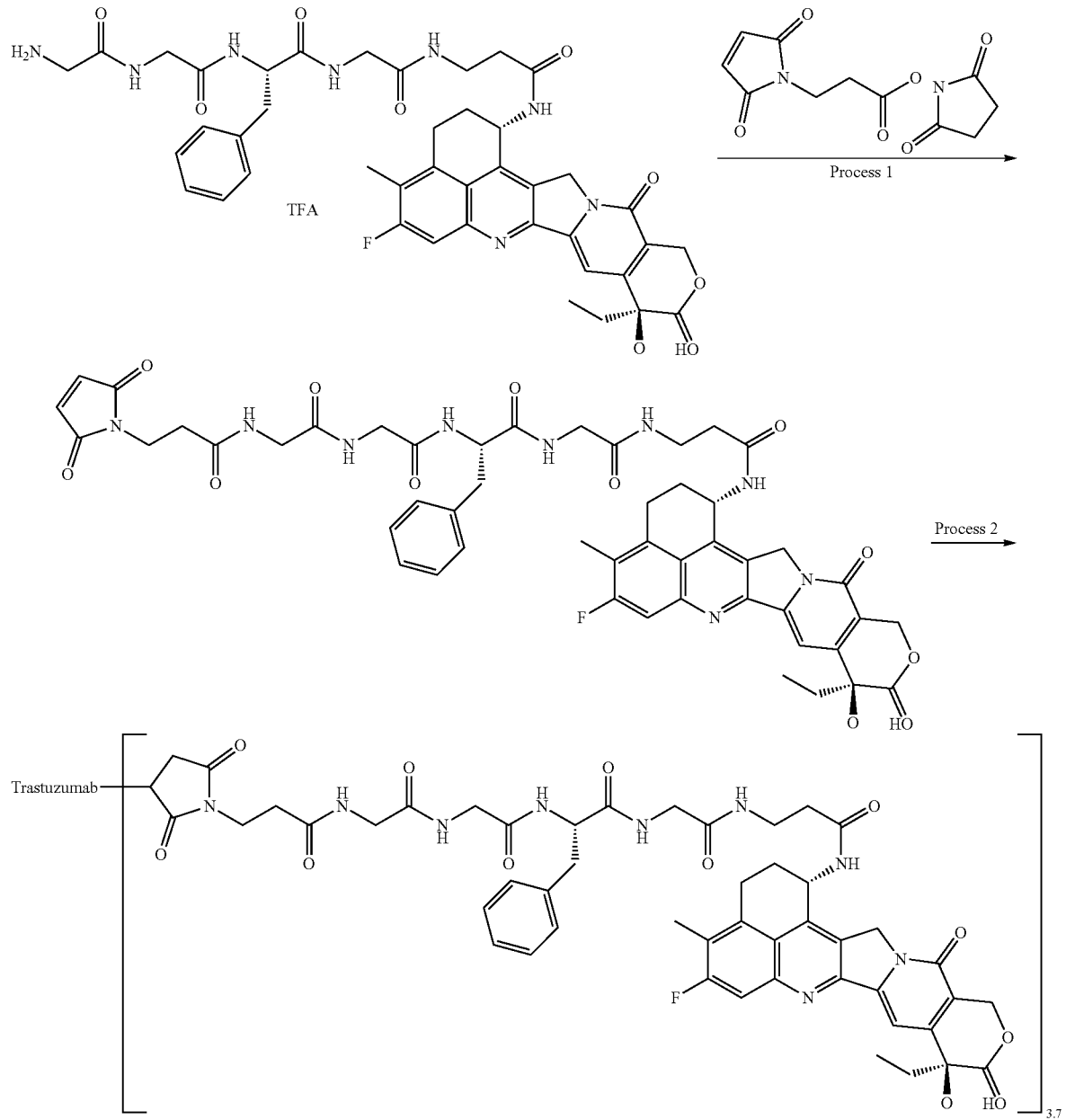

Process 1: N-[3-(2,5-Dioxo-2,5-dihydro-1H-pyrrol-1-yl)propanoyl]glycylglycyl-L-phenylalanylglycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-β-alaninamide The compound (60.0 mg, 0.0646 mmol) obtained in Process 2 of Example 15 was reacted in the same manner as Process 3 of Example 2 by using N-succinimidyl 3-maleimide propionate instead of N-succinimidyl 6-maleimide hexanoate to yield the titled compound as a pale yellow solid (36.0 mg, 57%).

$^1$H-NMR (400 MHz, DMSO-$d_6$) δ: 0.86 (3H, t, J=7.4 Hz), 1.85 (2H, dt, J=14.4, 7.5 Hz), 2.05-2.22 (2H, m), 2.40 (3H, s), 2.30-2.44 (5H, m), 2.73-2.84 (1H, m), 3.02 (1H, dd, J=13.9, 4.5 Hz), 3.17 (3H, d, J=5.1 Hz), 3.26-3.40 (2H, m), 3.41-3.81 (6H, m), 4.40-4.51 (1H, m), 5.19 (1H, d, J=19.2 Hz), 5.26 (1H, d, J=18.8 Hz), 5.42 (2H, brs), 5.52-5.61 (1H, m), 6.53 (1H, s), 6.99 (2H, s), 7.13-7.28 (5H, m), 7.31 (1H, s), 7.80 (2H, d, J=10.2 Hz), 8.03 (1H, t, J=5.5 Hz), 8.12 (1H, d, J=8.2 Hz), 8.20-8.31 (2H, m), 8.52 (1H, d, J=8.6 Hz).

MS (ESI) m/z: 976 (M+H)$^+$

Process 2: Antibody-Drug Conjugate (17)

By using the trastuzumab produced in Reference Example 1 and the compound obtained in Process 1 above, the titled antibody-drug conjugate was obtained in the same manner as Process 2 of Example 6.
Antibody concentration: 1.74 mg/mL, antibody yield: 10.4 mg (83%), and average number of conjugated drug molecules (n) per antibody molecule: 3.7.

Example 18 Antibody-Drug Conjugate (18)

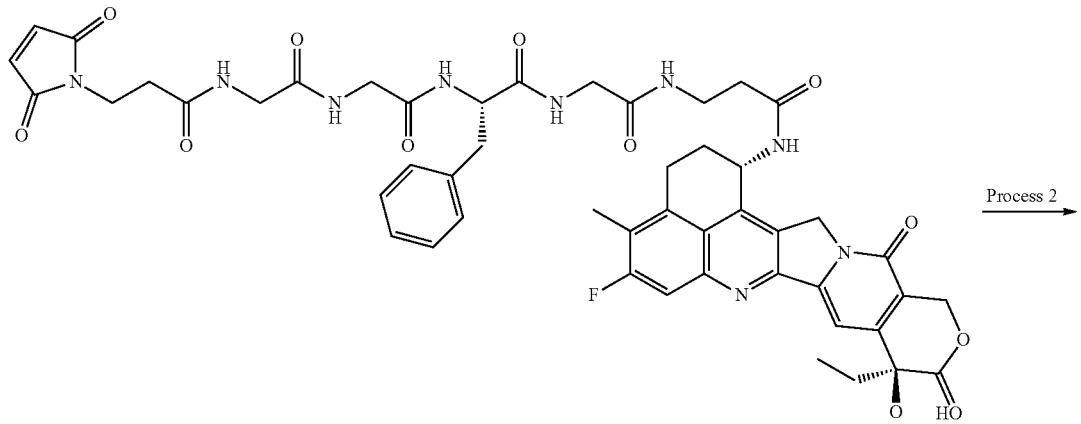

[Formula 44]

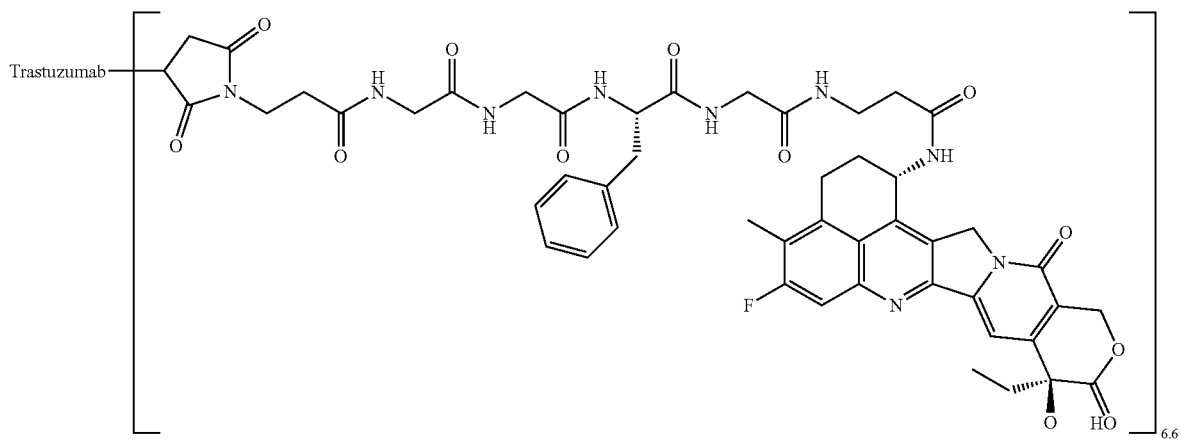

Process 1: Antibody-Drug Conjugate (18)

By using the trastuzumab produced in Reference Example 1 and the compound obtained in Process 1 of Example 17, the titled antibody-drug conjugate was obtained in the same manner as Process 1 of Example 7.

Antibody concentration: 1.98 mg/mL, antibody yield: 11.9 mg (95%), and average number of conjugated drug molecules (n) per antibody molecule: 6.6.

Example 19 Antibody-Drug Conjugate (19)

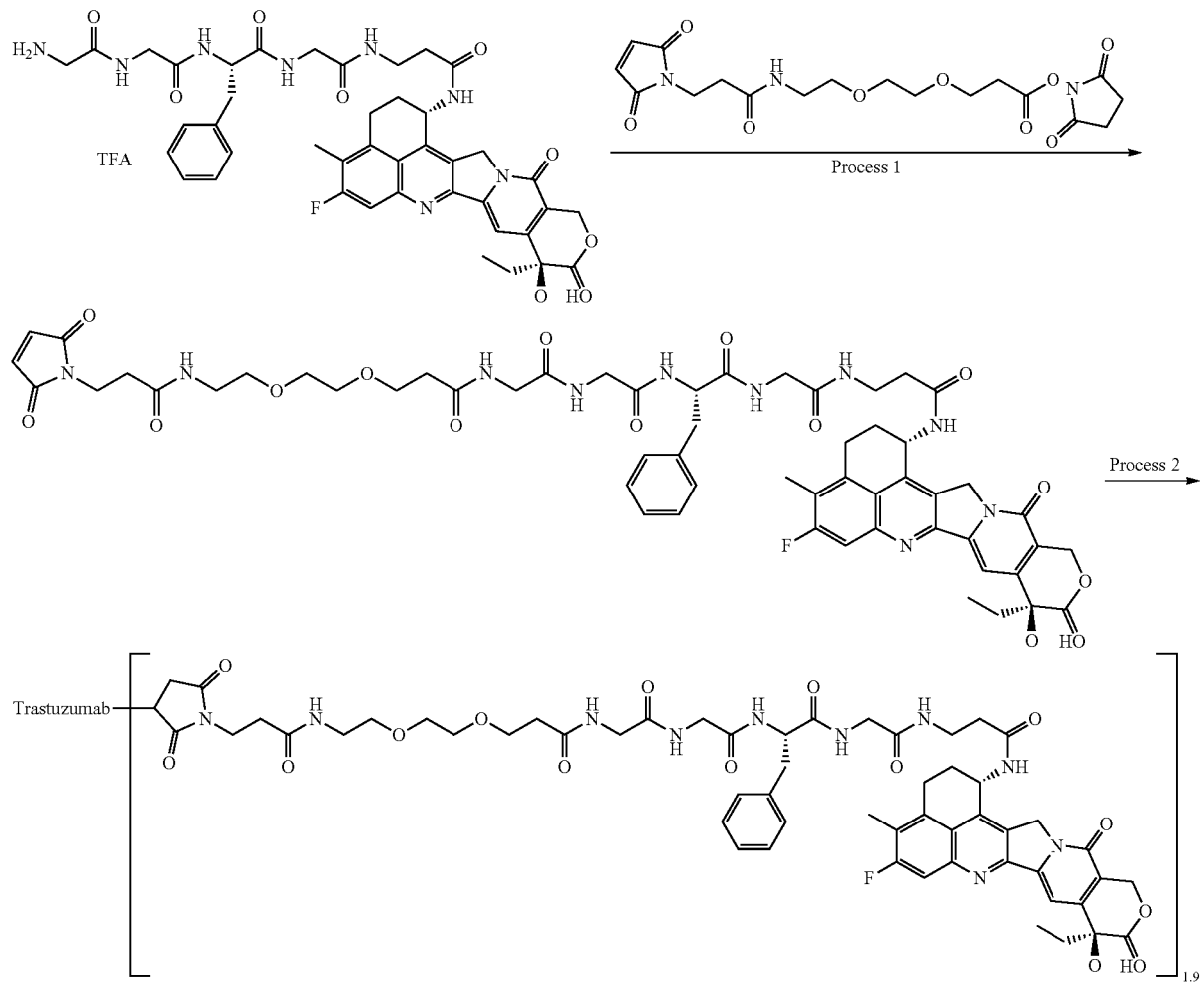

Process 1: N-{3-[2-(2-{[3-(2,5-Dioxo-2,5-dihydro-1H-pyrrol-1-yl)propanoyl]amino}ethoxy]propanoyl}glycylglycyl-L-phenylalanylglycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-3-alaninamide The compound (60.0 mg, 0.0646 mmol) obtained in Process 2 of Example 15 was reacted in the same manner as Process 3 of Example 2 by using N-succinimidyl 3-(2-(2-(3-maleinimidepropanamide)ethoxy)ethoxy)propanoate instead of N-succinimidyl 6-maleimide hexanoate to yield the titled compound as a solid (23.0 mg, 31%).

$^1$H-NMR (400 MHz, DMSO-$d_6$) δ: 0.86 (3H, t, J=7.4 Hz), 1.77-1.92 (2H, m), 2.07-2.21 (2H, m), 2.27-2.42 (6H, m), 2.40 (3H, s), 2.74-2.84 (1H, m), 2.97-3.06 (1H, m), 3.09-3.21 (4H, m), 3.25-3.39 (6H, m), 3.45 (4H, s), 3.50-3.80 (8H, m), 4.41-4.51 (1H, m), 5.19 (1H, d, J=18.4 Hz), 5.26 (1H, m, J=18.4 Hz), 5.42 (2H, brs), 5.51-5.61 (1H, m), 6.54 (1H, s), 7.00 (2H, s), 7.13-7.28 (5H, m), 7.31 (1H, s), 7.74-7.87 (2H, m), 7.93-8.07 (2H, m), 8.09-8.21 (2H, m), 8.26 (1H, brs), 8.54 (1H, d, J=8.6 Hz).

MS (ESI) m/z: 1135 (M+H)$^+$

Process 2: Antibody-Drug Conjugate (19)

By using the trastuzumab produced in Reference Example 1 and the compound obtained in Process 1 above, the titled antibody-drug conjugate was obtained in the same manner as Process 2 of Example 6.

Antibody concentration: 1.60 mg/mL, antibody yield: 9.6 mg (77%), and average number of conjugated drug molecules (n) per antibody molecule: 1.9.

Example 20 Antibody-Drug Conjugate (20)

[Formula 46]

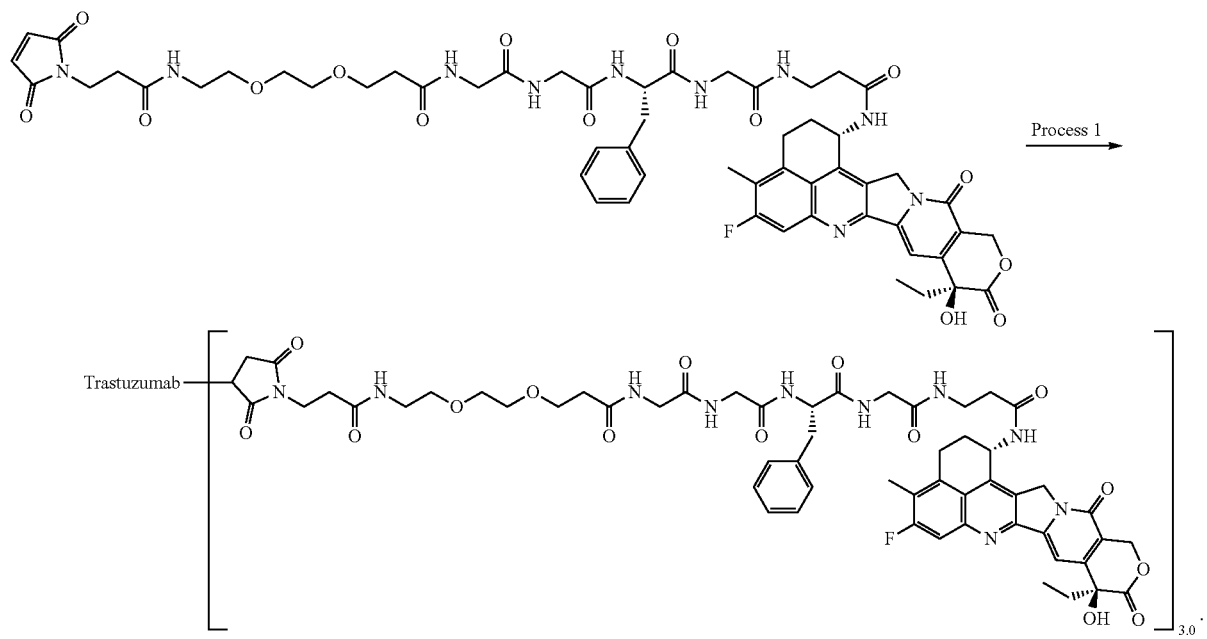

Process 1: Antibody-Drug Conjugate (20)

By using the trastuzumab produced in Reference Example 1 and the compound obtained in Process 1 of Example 19, the titled antibody-drug conjugate was obtained in the same manner as Process 1 of Example 7.

Antibody concentration: 1.69 mg/mL, antibody yield: 10.1 mg (81%), and average number of conjugated drug molecules (n) per antibody molecule: 3.0.

Example 21 Antibody-Drug Conjugate (21)

[Formula 47]

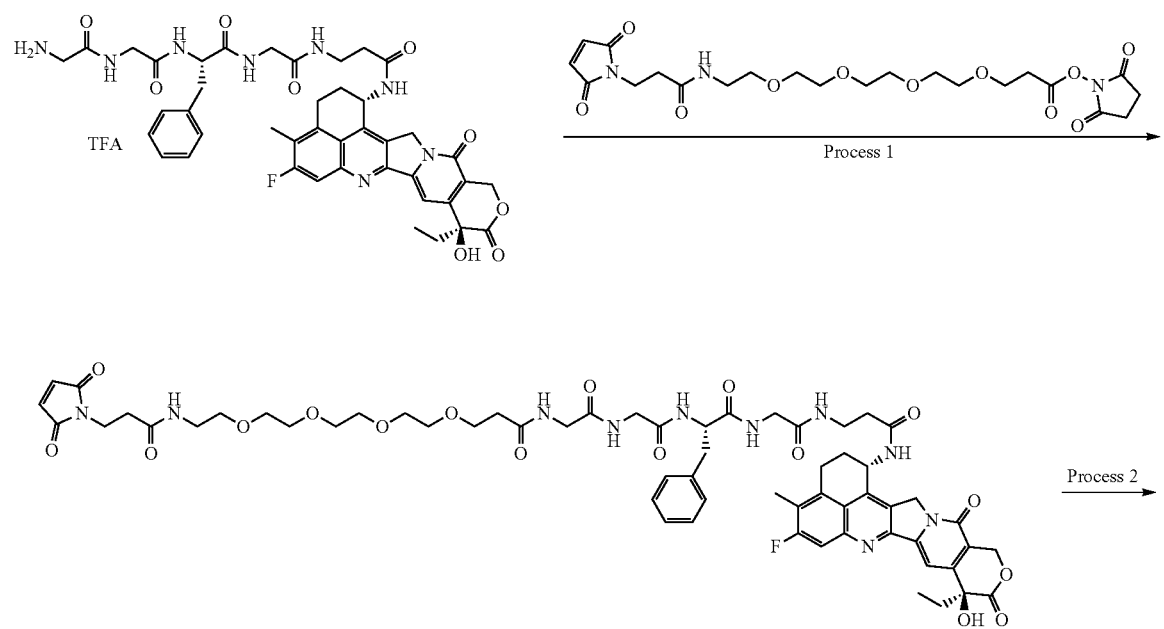

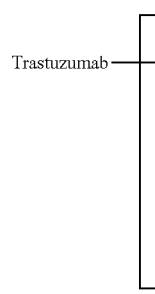
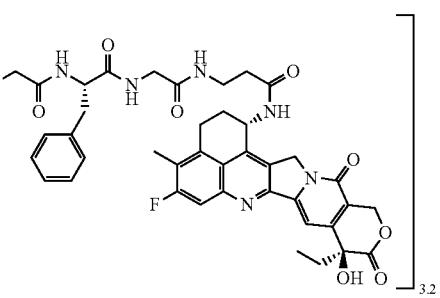

Process 1: N-[19-(2,5-Dioxo-2,5-dihydro-1H-pyrrol-1-yl)-17-oxo-4,7,10,13-tetraoxa-16-azanonadecan-1-oyl]glycylglycyl-L-phenylalanylglycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-3-alaninamide The compound (60.0 mg, 0.0646 mmol) obtained in Process 2 of Example 15 was reacted in the same manner as Process 3 of Example 2 by using N-succinimidyl 1-maleinimide-3-oxo-7,10,13,16-tetraoxa-4-azanonadecanoate instead of N-succinimidyl 6-maleimide hexanoate to yield the titled compound as a solid (23.0 mg, 290)

$^1$H-NMR (400 MHz, DMSO-$d_6$) δ: 0.86 (3H, t, J=7.0 Hz), 1.85 (2H, tt, J=14.6, 7.1 Hz), 2.06-2.22 (2H, m), 2.40 (3H, s), 2.28-2.43 (6H, m), 2.78 (1H, dd, J=13.7, 9.4 Hz), 3.02 (1H, dd, J=14.1, 3.9 Hz), 3.09-3.22 (4H, m), 3.27-3.41 (4H, m), 3.47 (12H, d, J=8.6 Hz), 3.53-3.81 (10H, m), 4.41-4.51 (1H, m), 5.19 (1H, d, J=19.2 Hz), 5.26 (1H, d, J=18.8 Hz), 5.42 (2H, brs), 5.53-5.61 (1H, m), 6.54 (1H, s), 7.00 (2H, s), 7.12-7.29 (5H, m), 7.31 (1H, s), 7.74-7.85 (2H, m), 8.03 (2H, d, J=6.6 Hz), 8.11-8.21 (2H, m), 8.27 (1H, t, J=5.9 Hz), 8.54 (1H, d, J=8.6 Hz).

MS (ESI) m/z: 1224 (M+H)$^+$

Process 2: Antibody-Drug Conjugate (21)

By using the trastuzumab produced in Reference Example 1 and the compound obtained in Process 1, the titled antibody-drug conjugate was obtained in the same manner as Process 2 of Example 6.

Antibody concentration: 1.77 mg/mL, antibody yield: 10.6 mg (85%), and average number of conjugated drug molecules (n) per antibody molecule: 3.2.

Example 22 Antibody-Drug Conjugate (22)

[Formula 48]

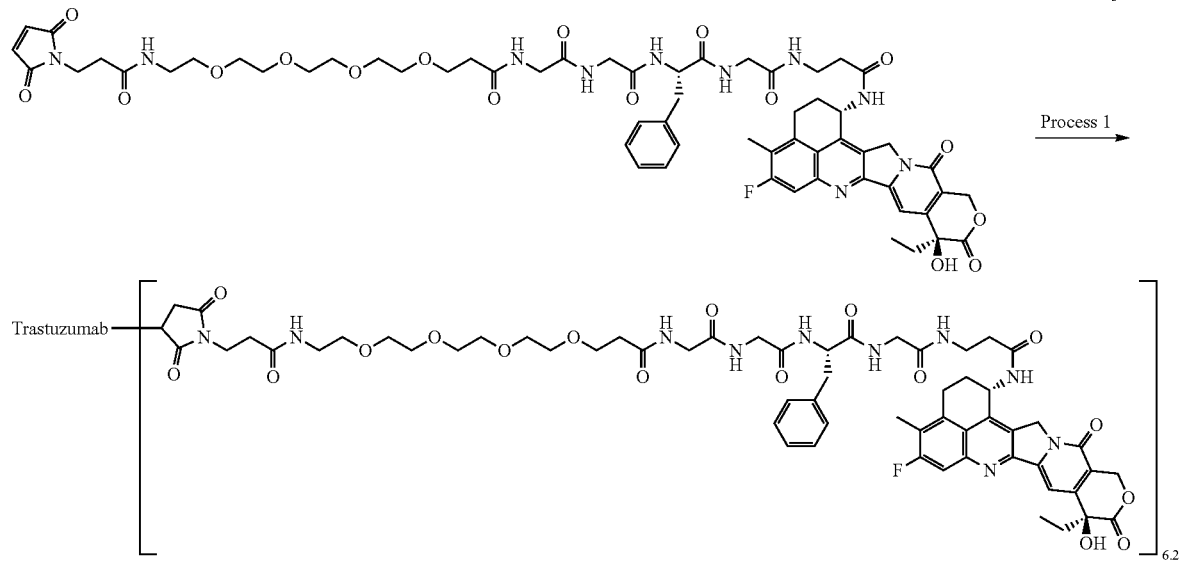

Process 1: Antibody-Drug Conjugate (22)

By using the trastuzumab produced in Reference Example 1 and the compound obtained in Process 1 of Example 21, the titled antibody-drug conjugate was obtained in the same manner as Process 1 of Example 7.

Antibody concentration: 1.89 mg/mL, antibody yield: 11.3 mg (90%), and average number of conjugated drug molecules (n) per antibody molecule: 6.2.

Example 23 Intermediate (23)

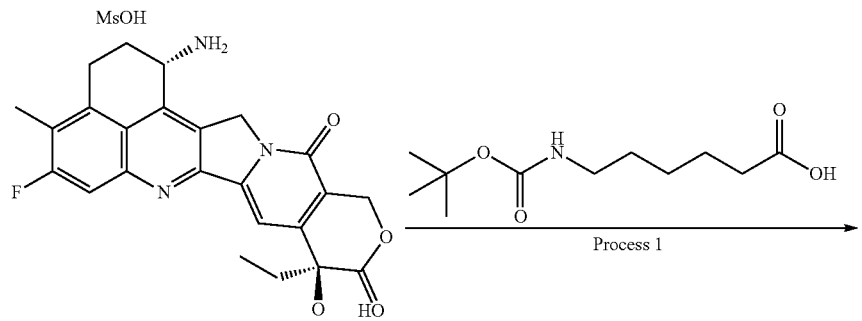

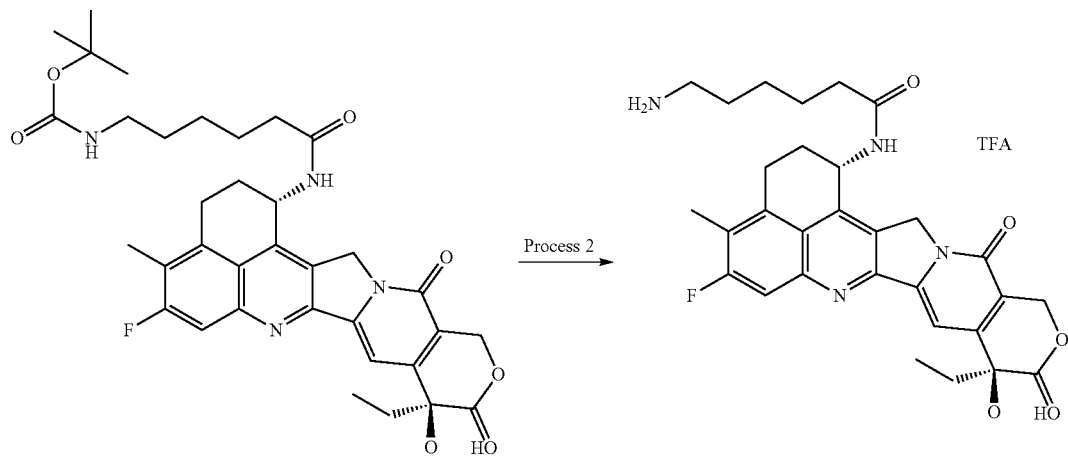

Process 1: tert-Butyl (6-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl] amino}-6-oxohexyl) carbamate Methanesulfonic acid salt of exatecan (0.500 g, 0.882 mmol) was reacted in the same manner as Process 1 of Example 1 by using 6-(tert-butoxycarbonylamino)hexanoic acid instead of 4-(tert-butoxycarbonylamino)butanoic acid to yield the titled compound (0.620 g, quantitative).

$^1$H-NMR (DMSO-$d_6$) δ: 0.83 (3H, t, J=7.8 Hz), 1.14-1.28 (2H, m), 1.31 (9H, s), 1.47-1.61 (2H, m), 1.75-1.89 (2H, m), 2.04-2.17 (4H, m), 2.35 (3H, s), 2.81-2.88 (2H, m), 3.09-3.16 (2H, m), 5.10 (1H, d, J=19.4 Hz), 5.16 (1H, d, J=19.4 Hz), 5.39 (2H, s), 5.48-5.55 (1H, m), 6.50 (1H, s), 6.73-6.78 (1H, m), 7.26 (1H, s), 7.74 (1H, d, J=10.9 Hz), 8.39 (1H, d, J=9.0 Hz).

Process 2: 6-Amino-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]hexanamide The compound (0.397 g, 0.611 mmol) obtained in Process 1 above was reacted in the same manner as Process 2 of Example 1 to yield trifluoroacetic acid salt of the titled compound (0.342 g, 84%).

$^1$H-NMR (DMSO-$d_6$) δ: 0.88 (3H, t, J=7.2 Hz), 1.31-1.41 (2H, m), 1.52-1.70 (4H, m), 1.80-1.94 (2H, m), 2.05-2.18 (2H, m), 2.21 (2H, t, J=7.4 Hz), 2.40 (3H, s), 2.81 (2H, t, J=7.4 Hz), 3.10-3.25 (2H, m), 3.33 (2H, brs), 5.18 (1H, d, J=19.8 Hz), 5.22 (1H, d, J=19.8 Hz), 5.41 (2H, d, J=16.6 Hz), 5.45 (2H, d, J=16.6 Hz), 5.53-5.60 (1H, m), 6.55 (1H, s), 7.32 (1H, s), 7.80 (1H, d, J=10.9 Hz), 8.49 (1H, d, J=9.2 Hz)

Example 24 Antibody-Drug Conjugate (24)
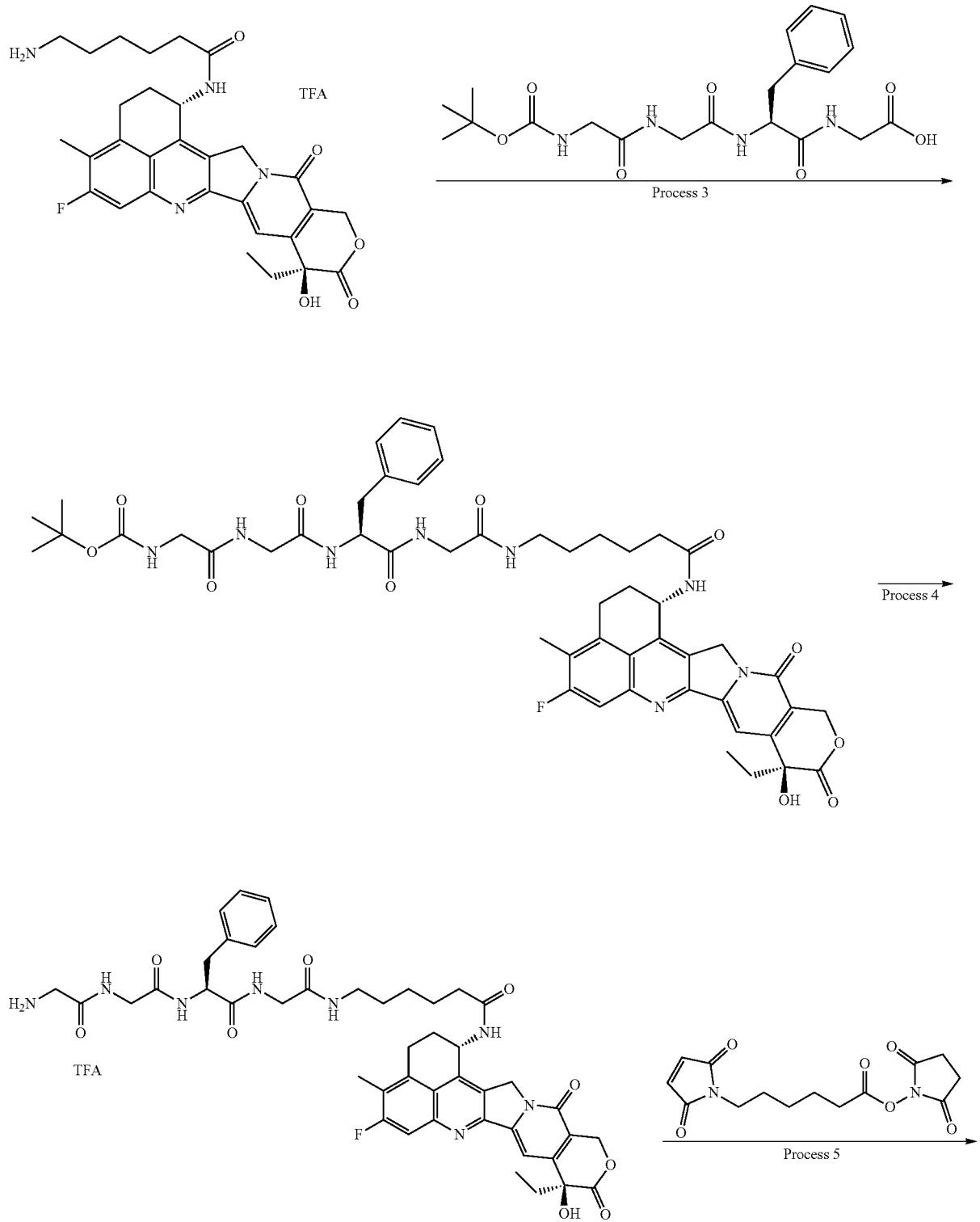

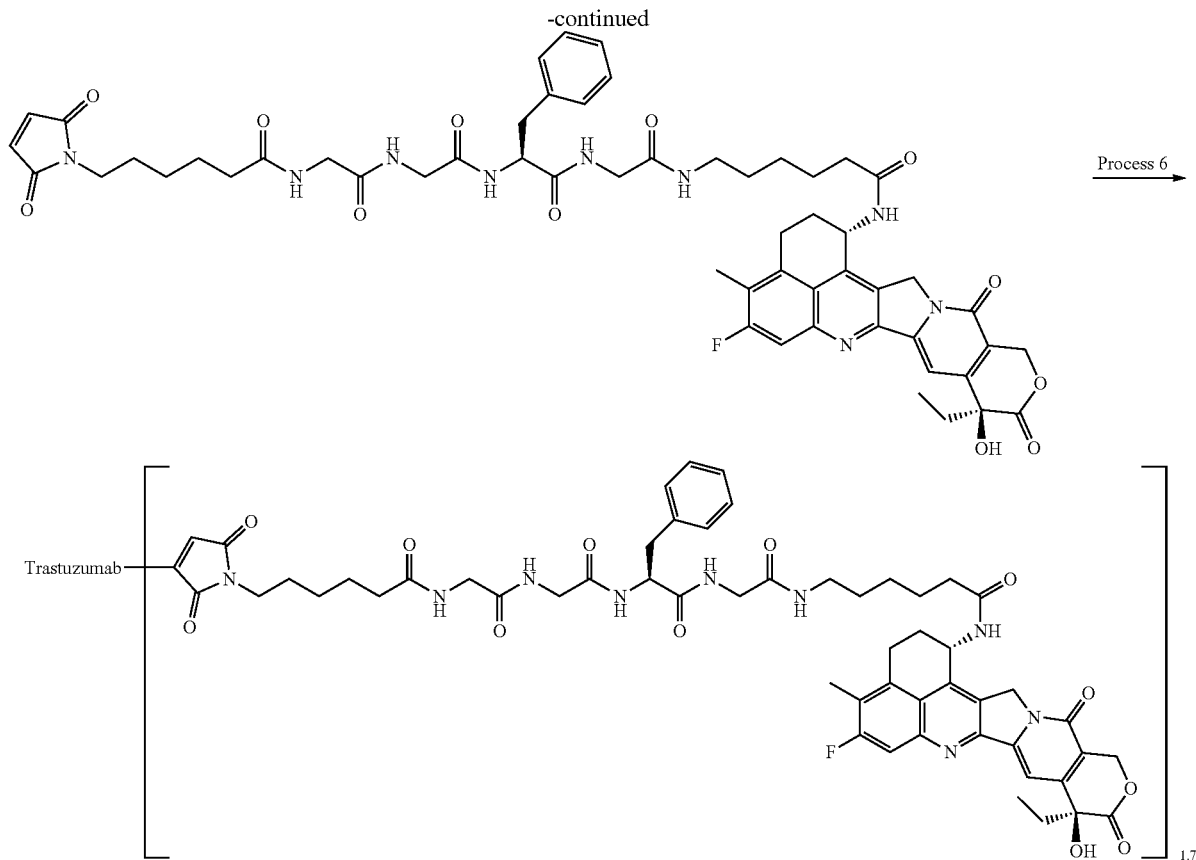

Process 1: N-(tert-Butoxycarbonyl)glycylglycyl-L-phenylalanyl-N-(6-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl] amino}-6-oxohexyl) glycinamide The compound (0.170 g, 0.516 mmol) obtained in Process 2 of Example 23 was reacted in the same manner as Process 1 of Example 2 to yield the titled compound (0.225 g, 91%).

$^1$H-NMR (DMSO-$d_6$) δ: 0.88 (3H, t, J=7.4 Hz), 1.43-1.70 (6H, m), 1.87 (2H, td, J=15.0, 7.4 Hz), 2.10-2.22 (3H, m), 2.28-2.37 (1H, m), 2.42 (3H, s), 2.78-2.85 (1H, m), 3.01-3.10 (3H, m), 3.15-3.22 (2H, m), 3.54-3.61 (5H, m), 3.62-3.69 (1H, m), 4.44-4.53 (1H, m), 5.17 (1H, d, J=19.2 Hz), 5.25 (1H, d, J=19.2 Hz), 5.45 (2H, s), 5.54-5.61 (1H, m), 6.55 (1H, s), 7.02 (1H, t, J=6.1 Hz), 7.11-7.28 (5H, m), 7.33 (1H, s), 7.63-7.69 (1H, m), 7.82 (1H, d, J=11.0 Hz), 7.90-7.96 (1H, m), 8.17 (1H, d, J=7.8 Hz), 8.28 (1H, t, J=5.5 Hz), 8.46 (1H, d, J=9.0 Hz).

Process 2: Glycylglycyl-L-phenylalanyl-N-(6-{[(1S,9S)-9-ethyl-5-fluoro-9-hydroxy-10,13-dioxo-2,3,9,10,13,15-hexahydro-1H,12H-benzo[de]pyrano[3',4':6,7]indolizino[1,2-b]quinolin-1-yl]amino}-6-oxohexyl)glycinamide The compound (0.105 g, 0.108 mmol) obtained in Process 1 above was reacted in the same manner as Process 2 of Example 2 to yield the titled compound (0.068 mg, 65%).

$^1$H-NMR (DMSO-$d_6$) δ: 0.89 (3H, t, J=7.4 Hz), 1.15-1.67 (6H, m), 1.79-1.97 (2H, m), 2.08-2.24 (4H, m), 2.42 (3H, s), 2.76-2.82 (1H, m), 3.00-3.10 (5H, m), 3.19 (1H, s), 3.50-3.63 (2H, m), 3.64-3.76 (3H, m), 3.84-3.92 (1H, m), 4.51-4.59 (1H, m), 5.17 (1H, d, J=19.4 Hz), 5.24 (1H, d, J=19.4 Hz), 5.44 (2H, s), 5.53-5.61 (1H, m), 6.55 (1H, brs), 7.15-7.29 (5H, m), 7.33 (1H, s), 7.72-7.78 (1H, m), 7.82 (1H, d, J=11.0 Hz), 7.96-8.08 (2H, m), 8.30-8.38 (2H, m), 8.46-8.56 (2H, m).

Process 3: N-[6-(2,5-Dioxo-2,5-dihydro-1H-pyrrol-1-yl)hexanoyl]glycylglycyl-L-phenylalanyl-N-(6-{[(1S,9S)-9-ethyl-5-fluoro-9-hydroxy-10,13-dioxo-2,3,9,10,13,15-hexahydro-1H,12H-benzo[de]pyrano[3',4':6,7]indolizino[1,2-b]quinolin-1-yl] amino}-6-oxohexyl)glycinamide The compound (58 mg, 0.060 mmol) obtained in Process 2 above was reacted in the same manner as Process 3 of Example 2 to yield the titled compound (39 mg, 62%).

$^1$H-NMR (CD$_3$OD) δ: 0.99 (3H, t, J=7.4 Hz), 1.27 (2H, td, J=11.6, 6.1 Hz), 1.38-1.44 (2H, m), 1.50-1.63 (6H, m), 1.65-1.80 (2H, m), 1.89-1.98 (2H, m), 2.17-2.25 (3H, m), 2.26-2.36 (3H, m), 2.40 (3H, s), 2.95 (1H, dd, J=14.3, 9.2 Hz), 3.12 (1H, dd, J=13.7, 5.7 Hz), 3.15-3.25 (4H, m), 3.44 (2H, t, J=7.2 Hz), 3.65 (1H, d, J=17.2 Hz), 3.76 (1H, d, J=17.2 Hz), 3.79-3.86 (4H, m), 4.43 (1H, dd, J=8.9, 6.0 Hz), 5.10 (1H, d, J=18.9 Hz), 5.25 (1H, d, J=18.9 Hz), 5.35 (1H, d, J=16.6 Hz), 5.56 (1H, d, J=16.0 Hz), 5.60-5.64 (1H, m), 6.76 (2H, s), 7.12-7.24 (6H, m), 7.58 (1H, s), 7.60 (1H, d, J=10.9 Hz), 7.68 (1H, t, J=5.7 Hz).

MS (ESI) m/z: 1060 (M+H)$^+$

Process 4: Antibody-Drug Conjugate (24)

Reduction of the antibody: The trastuzumab produced in Reference Example 1 was prepared to have an antibody concentration of 10 mg/mL with PBS6.0/EDTA by using the Common procedure C-1 and Common procedure B (as absorption coefficient at 280 nm, 1.37 mLmg$^{-1}$ cm$^{-1}$ was used). The solution (9.0 mL) was collected into a 50 mL tube and charged with an aqueous solution of 10 mM TCEP (0.140 mL; 2.3 equivalents per antibody molecule) and an aqueous solution of 1 M dipotassium hydrogen phosphate (0.450 mL). After confirming that the solution had a pH of 7.4±0.1, the disulfide bond at the hinge part in the antibody was reduced by incubating at 37° C. for 1 hour.

Conjugation between antibody and drug linker: After incubating the solution at 22° C. for 10 minutes, a DMSO solution (0.280 mL; 4.6 equivalents per antibody molecule) containing 10 mM of the compound in Process 3 was added thereto and incubated for conjugating the drug linker to the antibody at 22° C. for 40 minutes. Next, an aqueous solution (0.0559 mL; 9.2 equivalents per antibody molecule) of 100 mM NAC was added thereto and incubated at 22° C. to terminate the reaction of the drug linker for another 20 minutes.

Purification: The above solution was subjected to purification using the Common procedure D-1 (PBS7.4 was used as buffer solution) to yield a solution containing the titled antibody-drug conjugate.

Physicochemical characterization: By using the Common procedure E, the following characteristic values were obtained. Antibody concentration: 3.30 mg/mL, antibody yield: 53.5 mg (59%), and average number of conjugated drug molecules (n) per antibody molecule: 1.7.

Example 25 Antibody-Drug Conjugate (25)

[Formula 51]

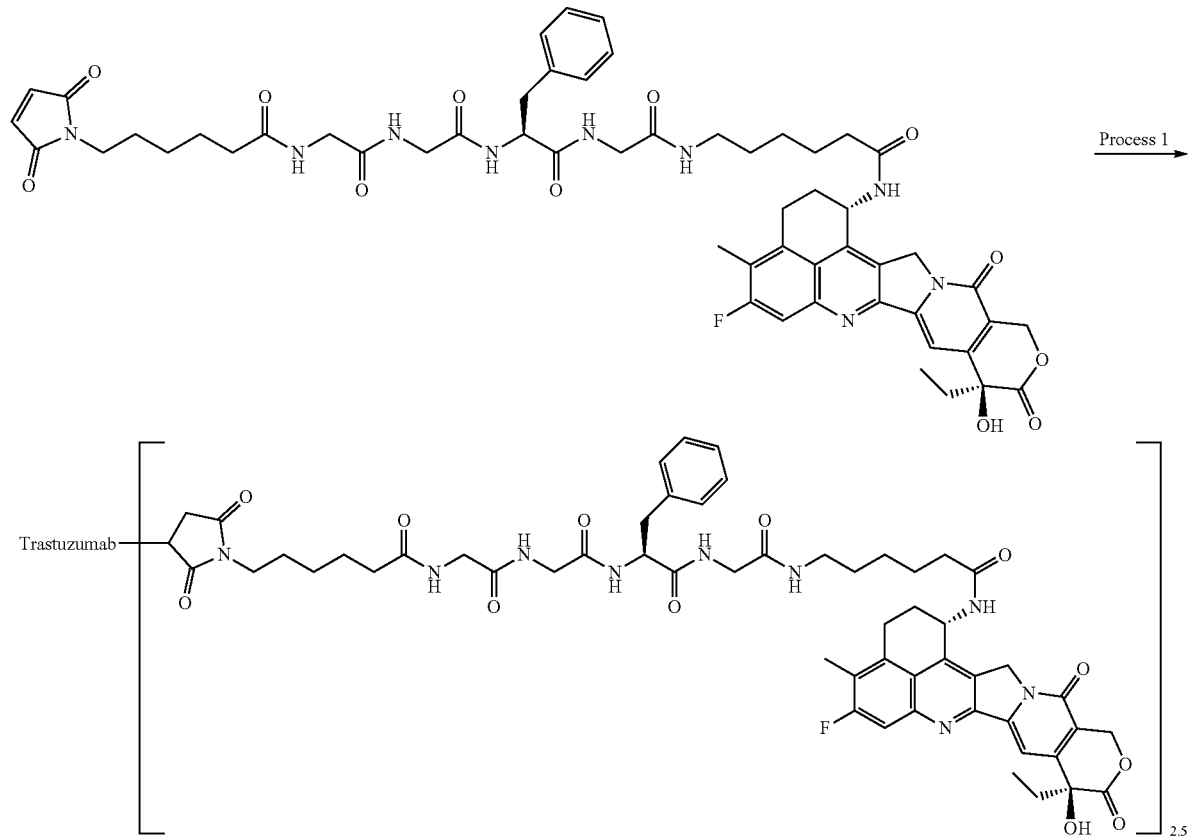

Process 1: Antibody-Drug Conjugate (25)

Reduction of the antibody: The trastuzumab produced in Reference Example 1 was prepared to have an antibody concentration of 10 mg/mL with PBS6.0/EDTA by using the Common procedure C-1 and Common procedure B (as absorption coefficient at 280 nm, 1.37 mLmg$^{-1}$ cm$^{-1}$ was used). The solution (9.0 mL) was collected into a 50 mL tube and charged with an aqueous solution of 10 mM TCEP (0.280 mL; 4.6 equivalents per antibody molecule) and an aqueous solution of 1 M dipotassium hydrogen phosphate (0.450 mL). After confirming that the solution had a pH of 7.4±0.1, the disulfide bond at the hinge part in the antibody was reduced by incubating at 37° C. for 1 hour.

Conjugation between antibody and drug linker: After incubating the solution at 22° C. for 10 minutes, a DMSO solution (0.559 mL; 9.2 equivalents per antibody molecule) containing 10 mM of the compound in Process 3 of Example 24 was added thereto and incubated for conjugating the drug linker to the antibody at 22° C. for 40 minutes. Next, an aqueous solution (0.112 mL; 18.4 equivalents per antibody molecule) of 100 mM NAC was added thereto and incubated at 22° C. to terminate the reaction of the drug linker for another 20 minutes.
Purification: The above solution was subjected to purification using the Common procedure D-1 (PBS6.0 was used as buffer solution) to yield a solution containing the titled antibody-drug conjugate.
Physicochemical characterization: By using the Common procedure E, the following characteristic values were obtained. Antibody concentration: 10.65 mg/mL, antibody yield: 55.1 mg (61%), and average number of conjugated drug molecules (n) per antibody molecule: 2.5.

Example 26 Antibody-Drug Conjugate (26)

[Formula 52]

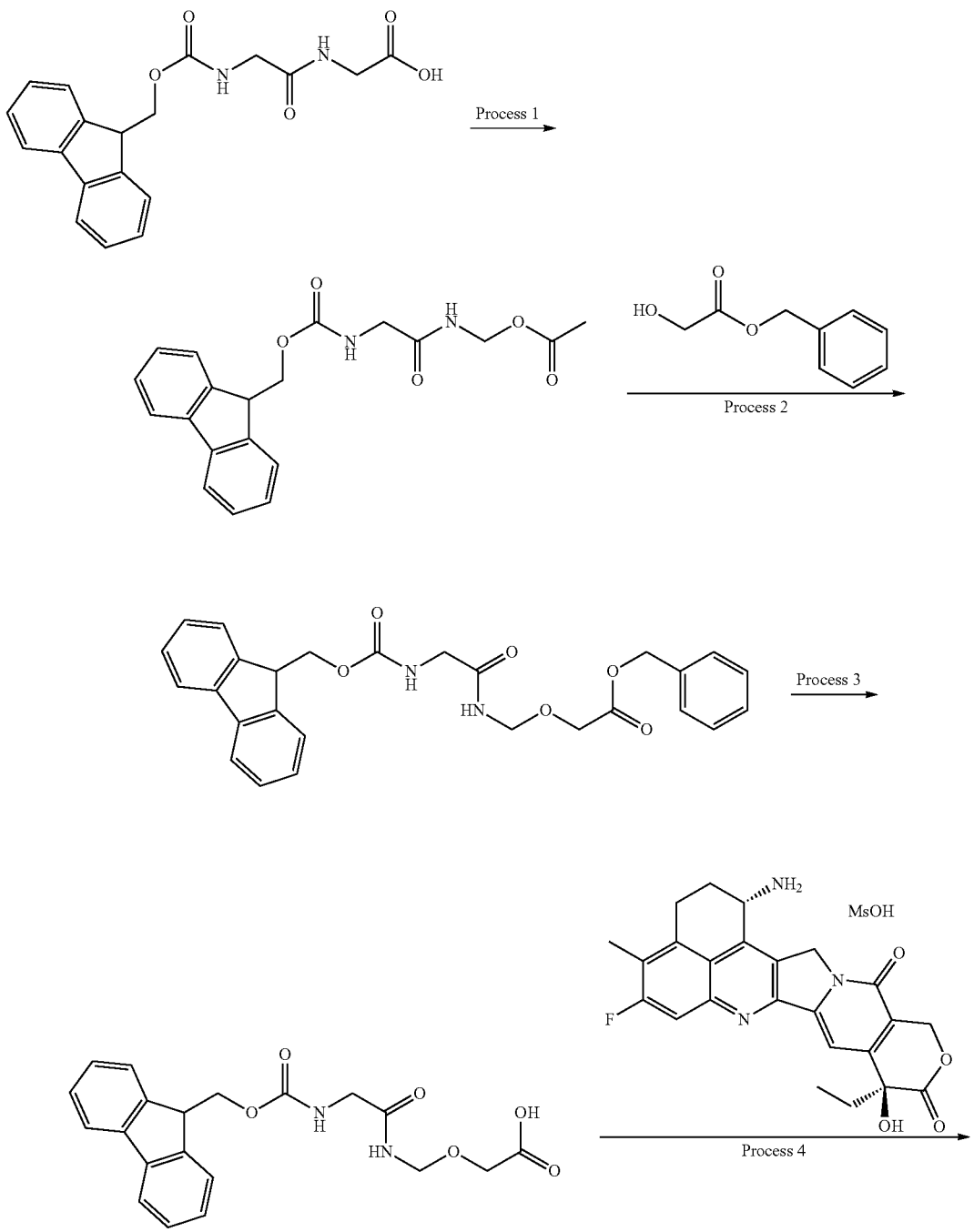

-continued
121
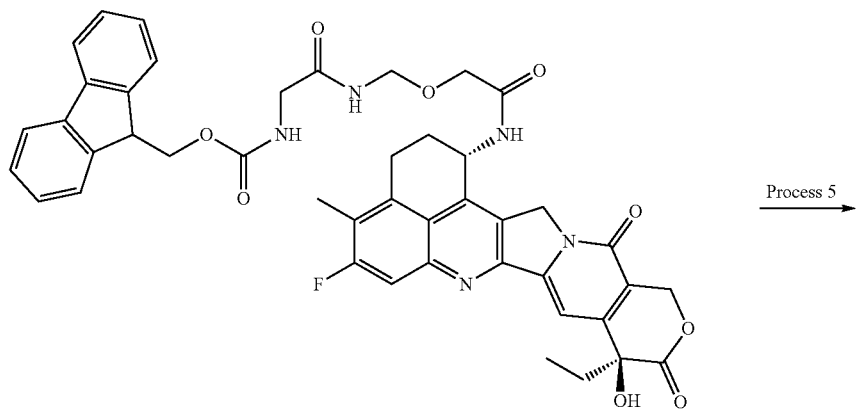
122
Process 5 →
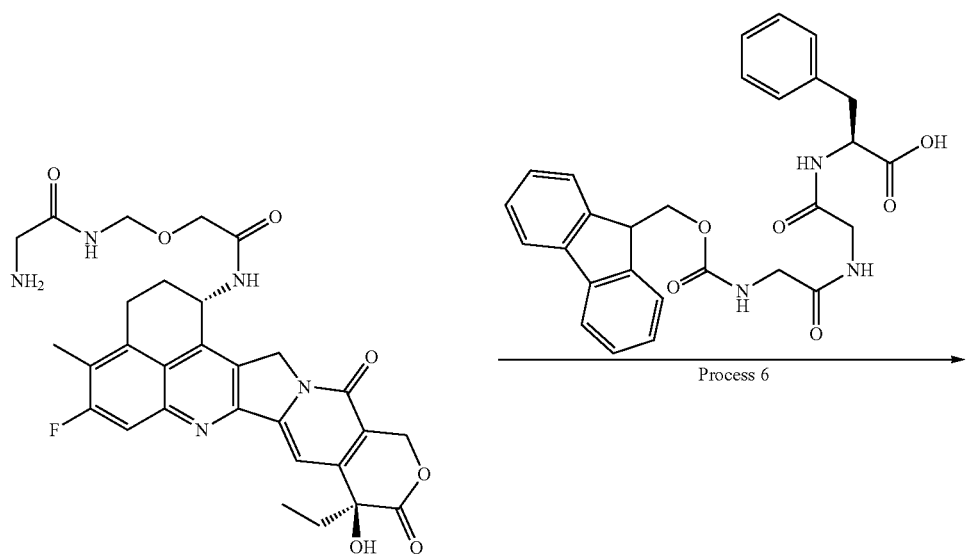
Process 6 →
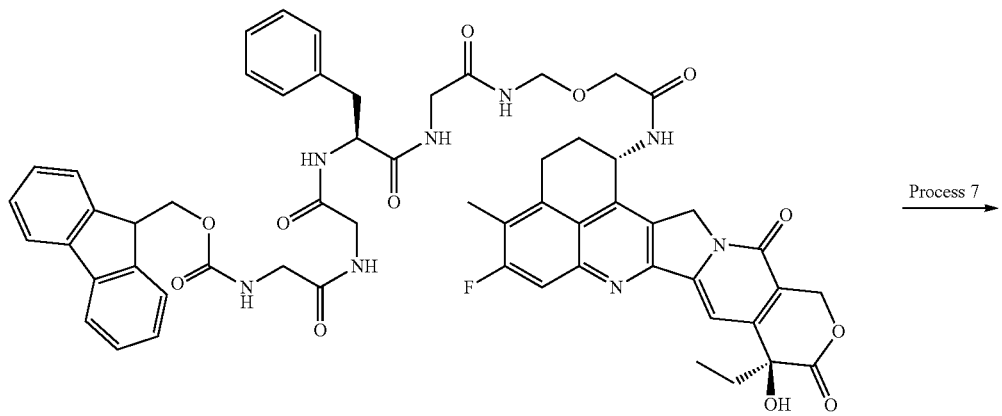
Process 7 →

123 124

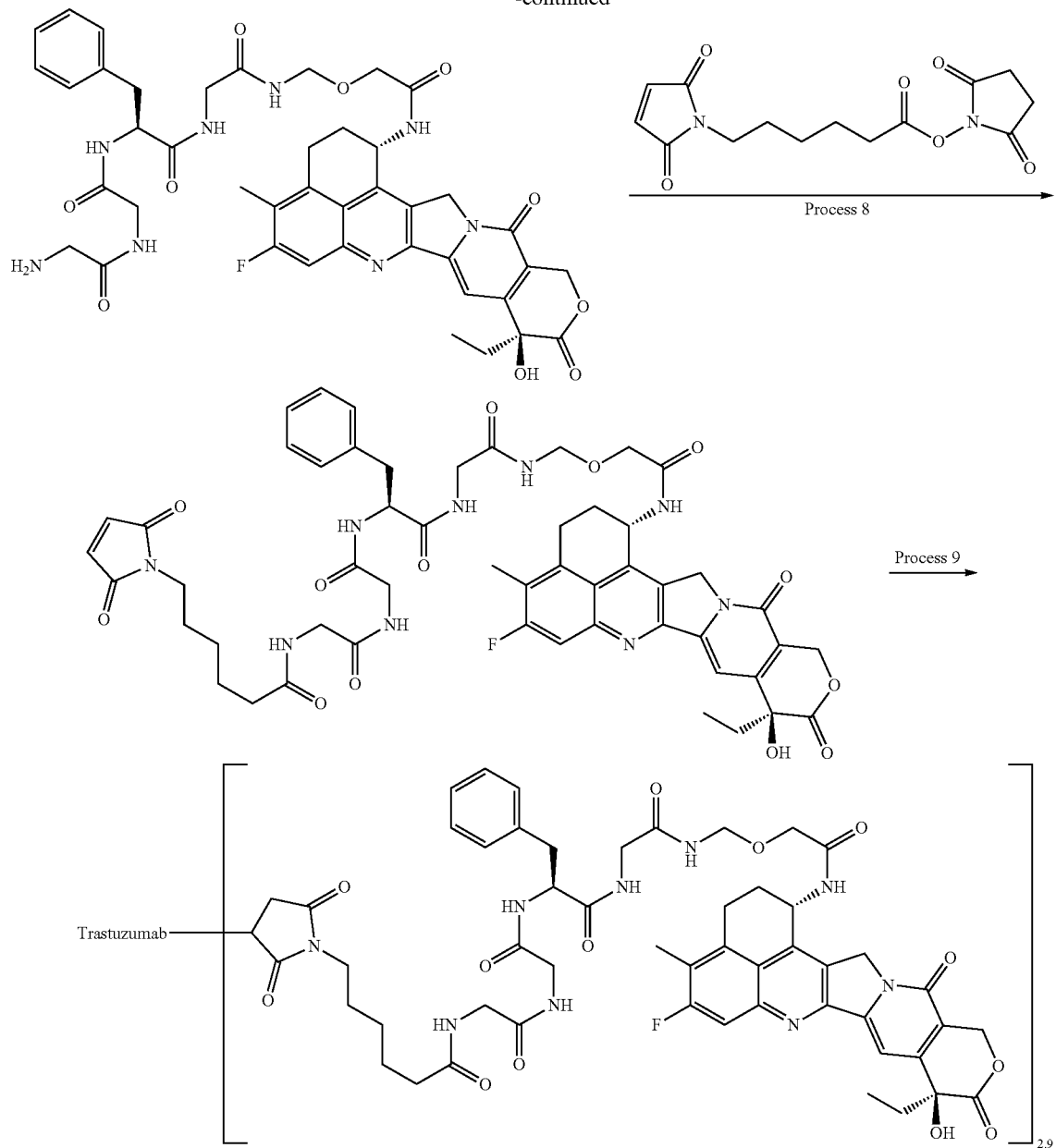

Process 1: ({N-[(9H-Fluoren-9-ylmethoxy)carbonyl]glycyl}amino)methyl acetate

To a mixture containing N-9-fluorenylmethoxycarbonylglycylglycine (4.33 g, 12.2 mmol), tetrahydrofuran (THF; 120 ml), and toluene (40.0 ml), pyridine (1.16 ml, 14.7 mmol) and lead tetraacetate (6.84 g, 14.7 mmol) were added and heated under reflux for 5 hours. After the reaction solution was cooled to room temperature, the insolubles were removed by filtration through Celite, and concentrated under reduced pressure. The residues obtained were dissolved in ethyl acetate and washed with water and saturated brine, and then the organic layer was dried over anhydrous magnesium sulfate. After the solvent was removed under reduced pressure, the residues obtained were purified by silica gel column chromatography [hexane:ethyl acetate=9:1 (v/v)-ethyl acetate] to yield the titled compound as a colorless solid (3.00 g, 67%).

$^1$H-NMR (400 MHz, $CDCl_3$) δ: 2.07 (3H, s), 3.90 (2H, d, J=5.1 Hz), 4.23 (1H, t, J=7.0 Hz), 4.46 (2H, d, J=6.6 Hz), 5.26 (2H, d, J=7.0 Hz), 5.32 (1H, brs), 6.96 (1H, brs), 7.32 (2H, t, J=7.3 Hz), 7.41 (2H, t, J=7.3 Hz), 7.59 (2H, d, J=7.3 Hz), 7.77 (2H, d, J=7.3 Hz).

Process 2: Benzyl [({N-[(9H-fluoren-9-ylmethoxy)carbonyl]glycyl}amino)methoxy]acetate To a THF (40.0 mL) solution of the compound (3.68 g, 10.0 mmol) obtained in Process 1 above and benzyl glycolate (4.99 g, 30.0 mmol), potassium tert-butoxide (2.24 g, 20.0 mmol) was added at 0° C. and stirred at room temperature for 15 minutes. The reaction solution was charged with ethyl acetate and water at 0° C. and extracted with ethyl acetate and chloroform. The obtained organic layer was dried over sodium sulfate and filtered. The solvent was removed under reduced pressure. The residues obtained were dissolved in dioxane (40.0 mL) and water (10.0 mL), charged with sodium hydrogen carbonate (1.01 g, 12.0 mmol) and 9-fluorenylmethyl chloroformate (2.59 g, 10.0 mmol), and stirred at room temperature for 2 hours. The reaction solution was charged with water and extracted with ethyl acetate. The obtained organic layer was dried over sodium sulfate and filtered. The solvent was removed under reduced pressure and the residues obtained were purified by silica gel column chromatography [hexane ethyl acetate=100:0 (v/v)-0:100] to yield the titled compound as a colorless oily substance (1.88 g, 40%).

$^1$H-NMR (400 MHz, CDCl$_3$) δ: 3.84 (2H, d, J=5.5 Hz), 4.24 (3H, t, J=6.5 Hz), 4.49 (2H, d, J=6.7 Hz), 4.88 (2H, d, J=6.7 Hz), 5.15-5.27 (1H, m), 5.19 (2H, s), 6.74 (1H, brs), 7.31-7.39 (7H, m), 7.43 (2H, t, J=7.4 Hz), 7.61 (2H, d, J=7.4 Hz), 7.79 (2H, d, J=7.4 Hz).

Process 3: [({N-[(9H-Fluoren-9-ylmethoxy)carbonyl]glycyl}amino)methoxy]acetic acid The compound (1.88 g, 3.96 mmol) obtained in Process 2 above was dissolved in ethanol (40.0 mL) and ethyl acetate (20.0 ml). After adding palladium carbon catalyst (376 mg), it was stirred under hydrogen atmosphere at room temperature for 2 hours. The insolubles were removed by filtration through Celite, and the solvent was removed under reduced pressure to yield the titled compound as a colorless solid (1.52 g, quantitative).

$^1$H-NMR (400 MHz, DMSO-d$_6$) δ: 3.62 (2H, d, J=6.3 Hz), 3.97 (2H, s), 4.18-4.32 (3H, m), 4.60 (2H, d, J=6.7 Hz), 7.29-7.46 (4H, m), 7.58 (1H, t, J=5.9 Hz), 7.72 (2H, d, J=7.4 Hz), 7.90 (2H, d, J=7.4 Hz), 8.71 (1H, t, J=6.5 Hz).

Process 4: 9H-Fluoren-9-ylmethyl(2-{[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]amino}-2-oxoethyl)carbamate Under ice cooling, to an N,N-dimethylformamide (10.0 mL) solution of methanesulfonic acid salt of exatecan (0.283 g, 0.533 mmol), N-hydroxysuccinimide (61.4 mg, 0.533 mmol), and the compound (0.205 g, 0.533 mmol) obtained in Process 3 above, N,N-diisopropylethylamine (92.9 µL, 0.533 mmol) and N,N'-dicyclohexylcarbodiimide (0.143 g, 0.693 mmol) were added and stirred at room temperature for 3 days. The solvent was removed under reduced pressure and the residues obtained were purified by silica gel column chromatography [chloroform -partitioned organic layer of chloroform:methanol:water=7:3:1 (v/v/v)] to yield the titled compound as a pale brown solid (0.352 g, 82%).

$^1$H-NMR (400 MHz, DMSO-d$_6$) δ: 0.81 (3H, t, J=7.4 Hz), 1.73-1.87 (2H, m), 2.06-2.20 (2H, m), 2.34 (3H, s), 3.01-3.23 (2H, m), 3.58 (2H, d, J=6.7 Hz), 3.98 (2H, s), 4.13-4.25 (3H, m), 4.60 (2H, d, J=6.7 Hz), 5.09-5.22 (2H, m), 5.32-5.42 (2H, m), 5.50-5.59 (1H, m), 6.49 (1H, s), 7.24-7.30 (3H, m), 7.36 (2H, t, J=7.4 Hz), 7.53 (1H, t, J=6.3 Hz), 7.66 (2H, d, J=7.4 Hz), 7.75 (1H, d, J=11.0 Hz), 7.84 (2H, d, J=7.4 Hz), 8.47 (1H, d, J=8.6 Hz), 8.77 (1H, t, J=6.7 Hz).

MS (ESI) m/z: 802 (M+H)$^+$

Process 5: N-[(2-{[(1S,9S)-9-Ethyl-5-fluoro-9-hydroxy-4-methyl-10,13-dioxo-2,3,9,10,13, 15-hexahydro-1H,12H-benzo[de]pyrano[3',4':6,7]indolizino[1,2-b]quinolin-1-yl] amino}-2-oxoethoxy)methyl]glycinamide To an N,N-dimethylformamide (11.0 mL) solution of the compound (0.881 g, 1.10 mmol) obtained in Process 4 above, piperidine (1.1 mL) was added and stirred at room temperature for 2 hours. The solvent was removed under reduced pressure to yield a mixture containing the titled compound. The mixture was used for the next reaction without further purification.

Process 6: N-[(9H-Fluoren-9-ylmethoxy) carbonyl] glycylglycyl-L-phenylalanyl-N-[(2-{[(1S,9S)-9-ethyl-5-fluoro-9-hydroxy-4-methyl-10,13-dioxo-2,3, 9,10,13,15-hexahydro-1H,12H-benzo[de]pyrano[3', 4':6,7]indolizino[1,2-b]quinolin-1-yl] amino}-2-oxoethoxy)methyl]glycinamide Under ice cooling, to an N,N-dimethylformamide (50.0 mL) solution of the mixture (0.439 mmol) obtained in Process 5 above, N-hydroxysuccinimide (0.101 g, 0.878 mmol), and N-[(9H-fluoren-9-ylmethoxy)carbonyl]glycylglycyl-L-phenylalanine (the compound described in Japanese Patent Laid-Open No. 2002-60351; 0.440 g, 0.878 mmol), N,N'-dicyclohexylcarbodiimide (0.181 g, 0.878 mmol) was added and stirred at room temperature for 4 days. The solvent was removed under reduced pressure and the residues obtained were purified by silica gel column chromatography [chloroform-chloroform:methanol=9:1 (v/v)] to yield the titled compound as a pale orange solid (0.269 g, 58%).

MS (ESI) m/z: 1063 (M+H)$^+$

Process 7: Glycylglycyl-L-phenylalanyl-N-[(2-{[(1S,9S)-9-ethyl-5-fluoro-9-hydroxy-4-methyl-10, 13-dioxo-2,3,9,10,13,15-hexahydro-1H,12H-benzo [de]pyrano[3',4':6,7]indolizino[1,2-b]quinolin-1-yl] amino}-2-oxoethoxy)methyl]glycinamide To an N,N-dimethylformamide (4.00 mL) solution of the compound (0.269 g, 0.253 mmol) obtained in Process 6 above, piperidine (0.251 mL, 2.53 mmol) was added and stirred at room temperature for 2 hours. The solvent was removed under reduced pressure to yield a mixture containing the titled compound. The mixture was used for the next reaction without further purification.

Process 8: N-[6-(2,5-Dioxo-2,5-dihydro-1H-pyrrol-1-yl)hexanoyl]glycylglycyl-L-phenylalanyl-N-[(2-{[(1S,9S)-9-ethyl-5-fluoro-9-hydroxy-4-methyl-10, 13-dioxo-2,3,9,10,13,15-hexahydro-1H,12H-benzo [de]pyrano[3',4':6,7]indolizino[1,2-b]quinolin-1-yl] amino}-2-oxoethoxy)methyl]glycinamide To an N,N-dimethylformamide (10.0 mL) solution of the compound (0.253 mmol) obtained in Process 7 above, N-succinimidyl 6-maleimide hexanoate (0.156 g, 0.506 mmol) was added and stirred at room temperature for 3 days. The solvent was removed under reduced pressure and the residues obtained were purified by silica gel column chromatography [chloroform-chloroform:methanol=9:1 (v/v)] to yield the titled compound as a pale yellow solid (0.100 g, 38%).

$^1$H-NMR (400 MHz, DMSO-d$_6$) δ: 0.83 (3H, t, J=7.2 Hz), 1.09-1.21 (2H, m), 1.33-1.47 (4H, m), 1.75-1.90 (2H, m), 2.00-2.23 (4H, m), 2.36 (3H, s), 2.69-2.81 (1H, m), 2.94-3.03 (1H, m), 3.06-3.22 (2H, m), 3.23-3.74 (6H, m), 3.98 (2H, s), 4.39-4.50 (1H, m), 4.60 (2H, d, J=6.7 Hz), 5.17 (2H, s), 5.39 (2H, s), 5.53-5.61 (1H, m), 6.50 (1H, s), 6.96 (2H, s), 7.11-7.24 (5H, m), 7.28 (1H, s), 7.75 (1H, d, J=11.0 Hz), 7.97 (1H, t, J=5.7 Hz), 8.03 (1H, t, J=5.9 Hz), 8.09 (1H, d, J=7.8 Hz), 8.27 (1H, t, J=6.5 Hz), 8.48 (1H, d, J=9.0 Hz), 8.60 (1H, t, J=6.5 Hz).

MS (ESI) m/z: 1034 (M+H)$^+$

Process 9: Antibody-Drug Conjugate (26)

By using the trastuzumab produced in Reference Example 1 and the compound obtained in Process 8 above, the titled antibody-drug conjugate was obtained in the same manner as Process 2 of Example 6.
Antibody concentration: 1.61 mg/mL, antibody yield: 9.7 mg (77%), and average number of conjugated drug molecules (n) per antibody molecule: 2.9.

Example 27 Antibody-Drug Conjugate (27)

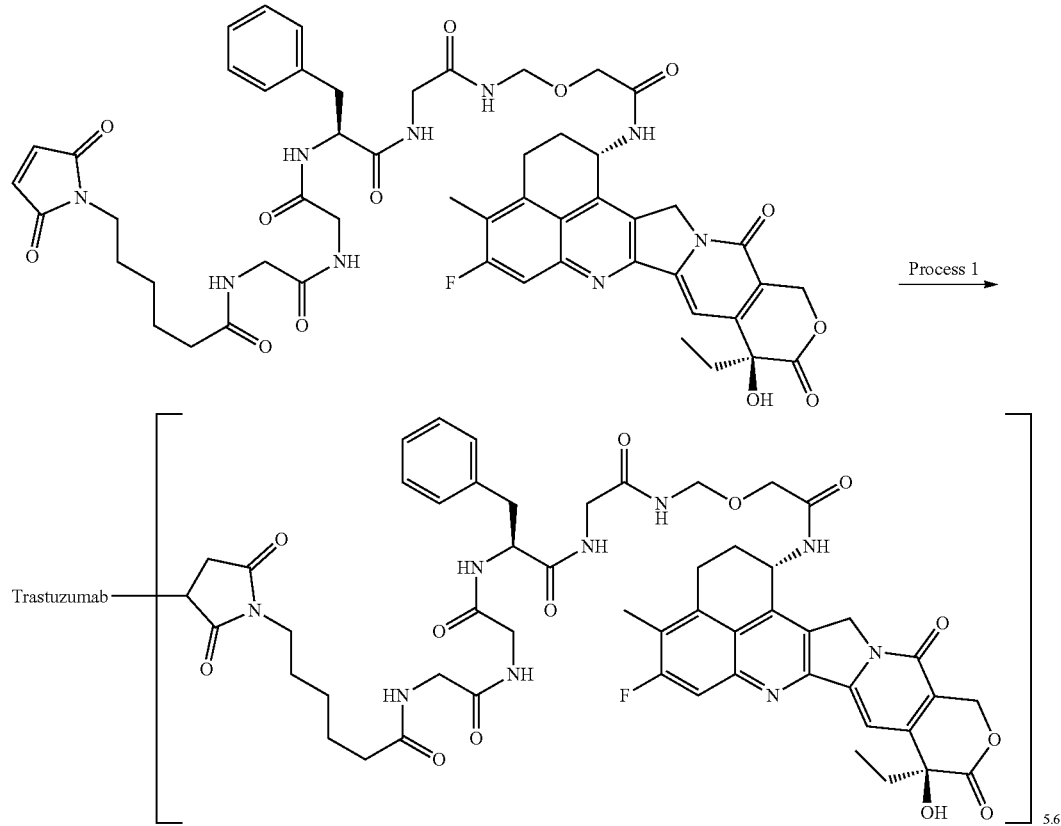

[Formula 53]

Process 1: Antibody-Drug Conjugate (27)

By using the trastuzumab produced in Reference Example 1 and the compound obtained in Process 8 of Example 26, the titled antibody-drug conjugate was obtained in the same manner as Process 1 of Example 7.

Antibody concentration: 1.58 mg/mL, antibody yield: 9.5 mg (76%), and average number of conjugated drug molecules (n) per antibody molecule: 5.6.

Example 28 Antibody-Drug Conjugate (28)

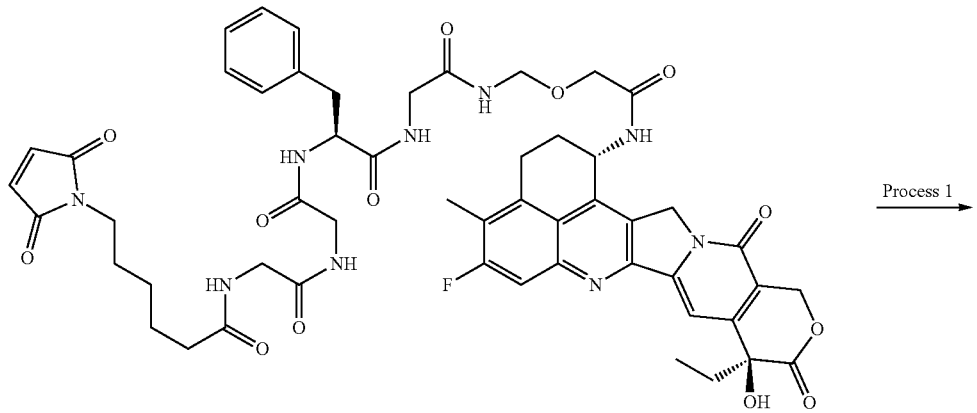

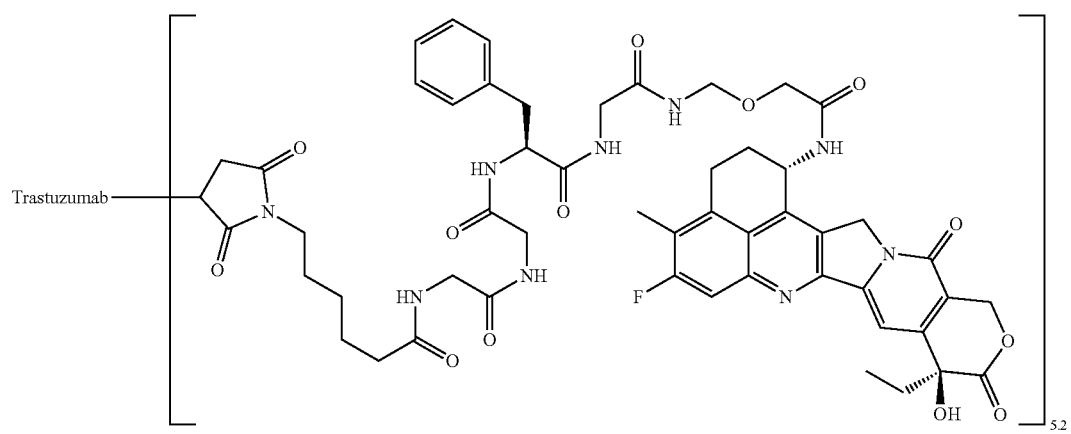

Process 1: Antibody-Drug Conjugate (28)

Reduction of the antibody: The trastuzumab produced in Reference Example 1 was prepared to have an antibody concentration of 10 mg/mL by replacing the medium with PBS6.0/EDTA by using the Common procedure C-1 and Common procedure B (as absorption coefficient at 280 nm, 1.48 mLmg$^{-1}$ cm$^{-1}$ was used). The solution (1.25 mL) was placed in two 1.5 mL polypropylene tubes and charged with an aqueous solution of 10 mM TCEP (0.039 mL; 4.6 equivalents per antibody molecule) and an aqueous solution of 1 M dipotassium hydrogen phosphate (0.0625 mL). After confirming that the solution had a pH of 7.4±0.1, the disulfide bond at the hinge part in the antibody was reduced by incubating at 37° C. for 1 hour. Conjugation between antibody and drug linker: After adding DMSO (0.072 mL) and a DMSO solution containing 10 mM of the compound of Process 8 of Example 26 (0.078 mL; 9.2 equivalents per antibody molecule) to the above solution at room temperature, it was stirred by using a tube rotator for conjugating the drug linker to the antibody at room temperature for 40 minutes. Next, an aqueous solution of 100 mM NAC (0.0155 mL) was added thereto and stirred at room temperature to terminate the reaction of the drug linker for another 20 minutes.

Purification: The above solution was subjected to purification using the Common procedure D-1 (ABS was used as a buffer solution) to yield 11.7 mL in total of a solution containing the compound of interest.

Physicochemical characterization: By using the Common procedure E, the following characteristic values were obtained. Antibody concentration: 1.60 mg/mL, antibody yield: 18.7 mg (94%), and average number of conjugated drug molecules (n) per antibody molecule: 5.2.

Example 29 Antibody-Drug Conjugate (29)

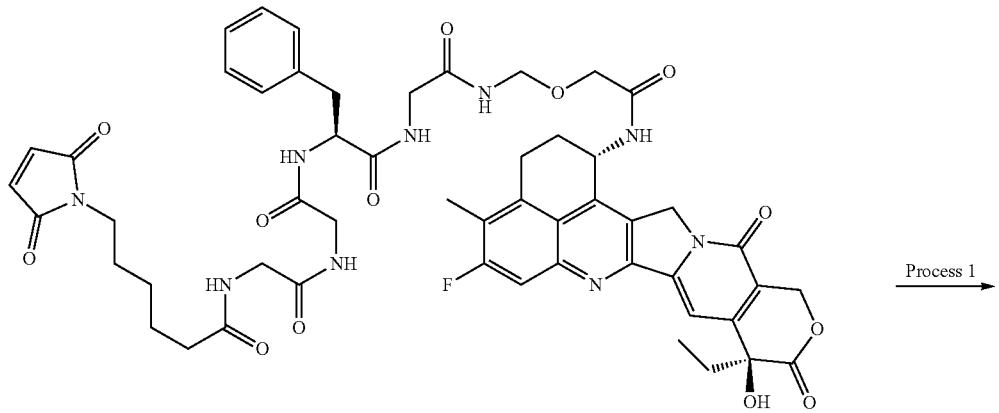

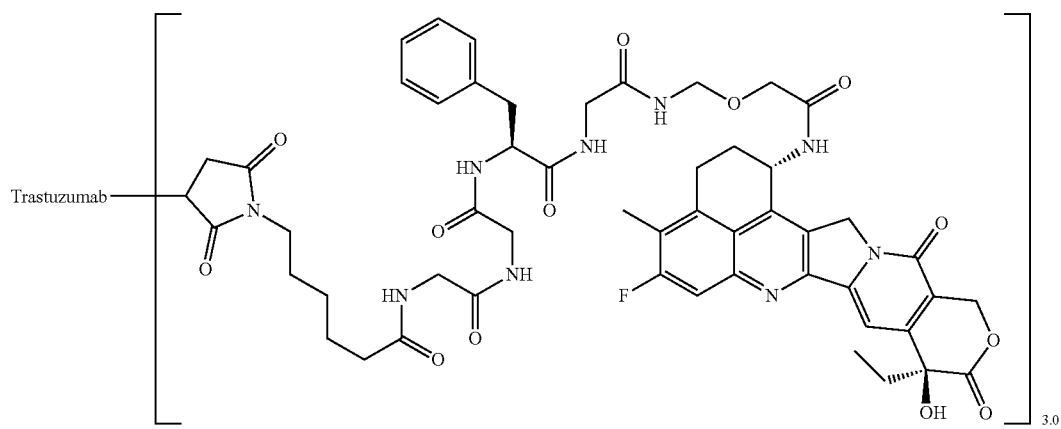

Process 1: Antibody-Drug Conjugate (29)

Reduction of the antibody: The trastuzumab produced in Reference Example 1 was prepared to have an antibody concentration of 10 mg/mL by replacing the medium with PBS6.0/EDTA by using the Common procedure C-1 and Common procedure B (as absorption coefficient at 280 nm, 1.48 mLmg$^{-1}$ cm$^{-1}$ was used). The solution (6 mL) was placed in a polypropylene tube and charged with an aqueous solution of 10 mM TCEP (0.108 mL; 2.5 equivalents per antibody molecule) and an aqueous solution of 1 M dipotassium hydrogen phosphate (0.091 mL). After confirming that the solution had a pH of 7.0±0.1, the disulfide bond at the hinge part in the antibody was reduced by incubating at 37° C. for 1 hour.

Conjugation between antibody and drug linker: After adding DMSO (0.146 mL) and a DMSO solution containing 10 mM of the compound of Process 8 of Example 26 (0.193 mL; 4.5 equivalents per antibody molecule) to the above solution at room temperature, it was incubated for conjugating the drug linker to the antibody at 15° C. for 1 hour. Next, an aqueous solution (0.029 mL) of 100 mM NAC was added thereto and stirred at room temperature to terminate the reaction of the drug linker for another 20 minutes.

Purification: The above solution was subjected to purification using the Common procedure D (ABS was used as buffer solution) to yield 24 mL of a solution containing the compound of interest.

Physicochemical characterization: By using the Common procedures E and F ($\varepsilon_{D,280}$=5178 (measured value), and $\varepsilon_{D,370}$=20217 (measured value) were used), the following characteristic values were obtained.

Antibody concentration: 1.77 mg/mL, antibody yield: 42 mg (85%), average number of conjugated drug molecules (n) per antibody molecule measured by the Common procedure E: 3.0, and average number of conjugated drug molecules (n) per antibody molecule measured by the Common procedure F: 3.4.

Example 30 Antibody-Drug Conjugate (30)

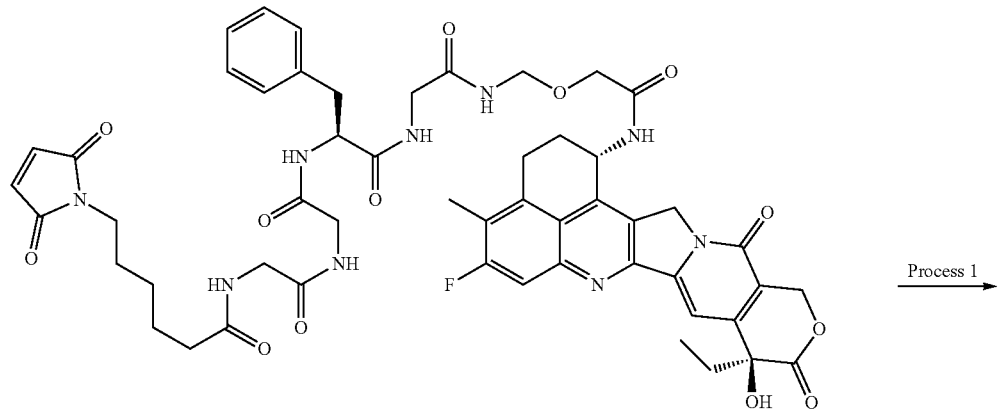

[Formula 56]

Process 1

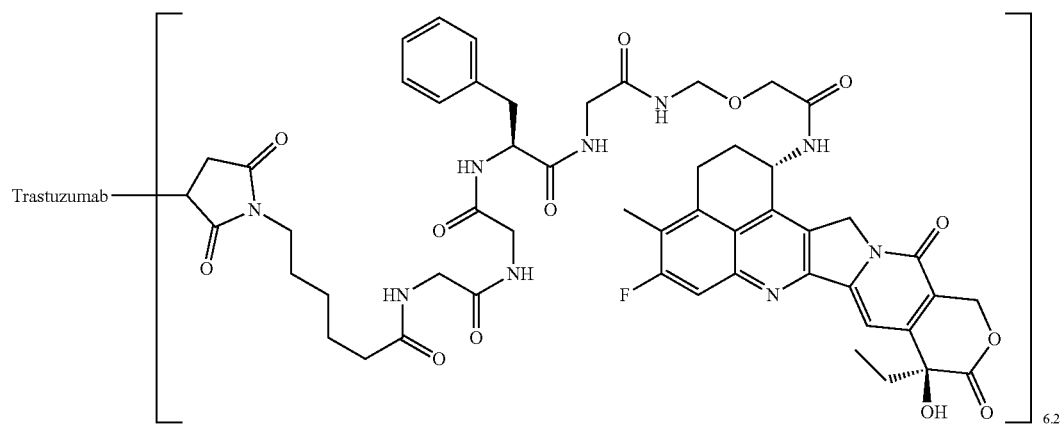

Process 1: Antibody-Drug Conjugate (30)

Reduction of the antibody: The trastuzumab produced in Reference Example 1 was prepared to have an antibody concentration of 10 mg/mL by replacing the medium with PBS6.0/EDTA by using the Common procedure C-1 and Common procedure B (as absorption coefficient at 280 nm, 1.48 mLmg$^{-1}$ cm$^{-1}$ was used). The solution (6 mL) was placed in a polypropylene tube and charged with an aqueous solution of 10 mM TCEP (0.215 mL; 5 equivalents per antibody molecule) and an aqueous solution of 1 M dipotassium hydrogen phosphate (0.094 mL). After confirming that the solution had a pH of 7.0±0.1, the disulfide bond at the hinge part in the antibody was reduced by incubating at 37° C. for 1 hour.

Conjugation between antibody and drug linker: After adding a DMSO solution containing 10 mM of the compound of Process 8 of Example 26 (0.370 mL; 8.6 equivalents per antibody molecule) to the above solution at room temperature, it was incubated for conjugating the drug linker to the antibody at 15° C. for 1 hour. Next, an aqueous solution (0.056 mL) of 100 mM NAC was added thereto and stirred at room temperature to terminate the reaction of the drug linker for another 20 minutes.

Purification: The above solution was subjected to purification using the Common procedure D (ABS was used as buffer solution) to yield 24 mL of a solution containing the compound of interest.

Physicochemical characterization: By using the Common procedures E and F ($\varepsilon_{D,280}$=5178 (measured value), and $\varepsilon_{D,370}$=20217 (measured value) were used), the following characteristic values were obtained.

Antibody concentration: 1.92 mg/mL, antibody yield: 46 mg (92%), average number of conjugated drug molecules (n) per antibody molecule measured by the Common procedure E: 6.2, and average number of conjugated drug molecules (n) per antibody molecule measured by the Common procedure F: 7.1.

Example 31 Antibody-Drug Conjugate (31)

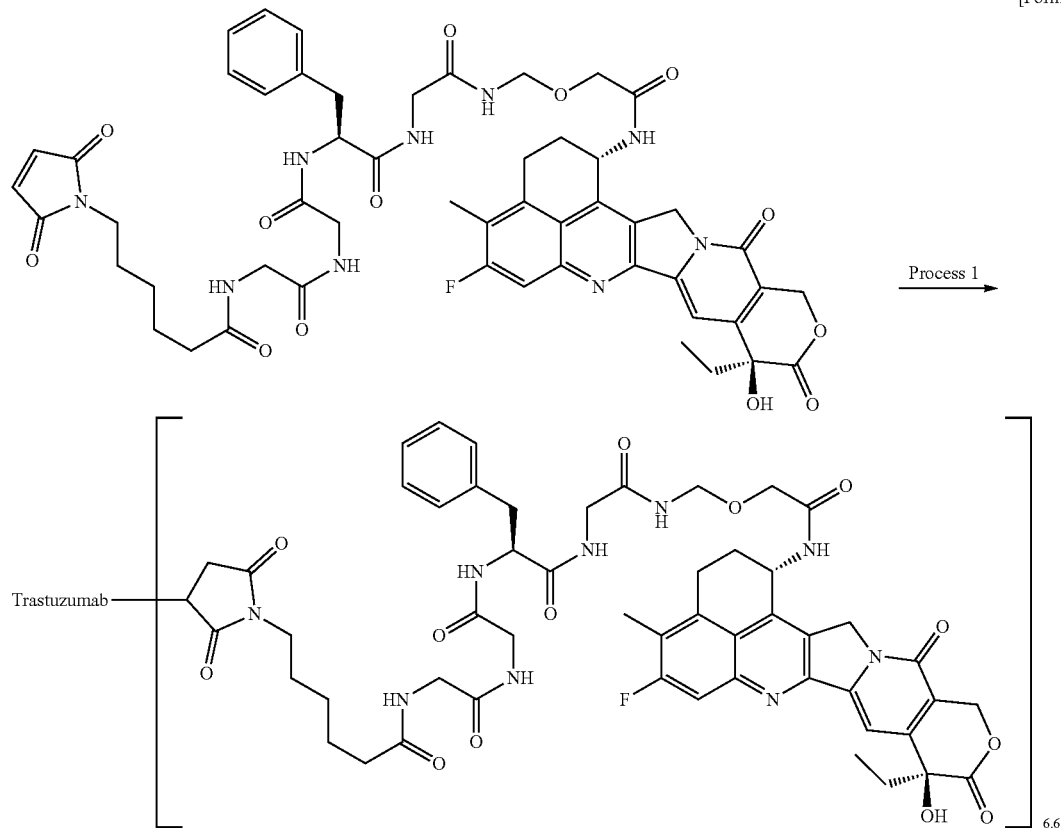

[Formula 57]

Process 1

Process 1: Antibody-Drug Conjugate (31)

Reduction of the antibody: The trastuzumab produced in Reference Example 1 was prepared to have an antibody concentration of 10 mg/mL by replacing the medium with PBS6.0/EDTA by using the Common procedure C-1 and Common procedure B (as absorption coefficient at 280 nm, 1.48 mLmg$^{-1}$ cm$^{-1}$ was used). The solution (50.00 mL) was placed in a polypropylene container and charged with an aqueous solution of 1 M dipotassium hydrogen phosphate (0.745 mL) at room temperature with stirring and then with an aqueous solution of 10 mM TCEP (1.868 mL; 5.4 equivalents per antibody molecule). After confirming that the solution had a pH of 7.0 medium 0.1, stirring was terminated, and the disulfide bond at the hinge part in the antibody was reduced by incubating at 37° C. for 1 hour. Conjugation between antibody and drug linker: After cooling the above solution to 15° C., a DMSO solution containing 10 mM of the compound of Process 8 of Example 26 (2.958 mL; 8.6 equivalents per antibody molecule) was gradually added dropwise thereto with stirring. While the temperature was kept at 15° C., the reaction solution was stirred for the first 30 minutes and incubated without stirring for conjugating the drug linker to the antibody for the next 1 hour. Next, an aqueous solution (0.444 mL) of 100 mM NAC was added thereto with stirring and stirred at room temperature to terminate the reaction of the drug linker for another 20 minutes.

Purification: By gradually adding 20% aqueous acetic acid solution (about 0.25 mL) and ABS (50 mL) to the above solution with stirring, the pH of the solution was adjusted to 5.5±0.1. This solution was subjected to microfiltration (Millipore Corp., Millex-HV filter, 0.45 μm, PVDF membrane) to remove whitish matter. This solution was subjected to ultrafiltration purification using an ultrafiltration apparatus composed of an ultrafiltration membrane (Merck Japan, Pellicon XL Cassette, Biomax 50 KDa), a tube pump (Cole-Parmer International, MasterFlex Pump model 77521-40, Pump Head model 7518-00), and a tube (Cole-Parmer International, MasterFlex Tube L/S16). Specifically, while ABS was added dropwise (a total of 800 mL) as a buffer solution for purification to the reaction solution, ultrafiltration purification was performed for removing unconjugated drug linkers and other low-molecular-weight reagents, also replacing the buffer solution with ABS, and further concentrating the solution. The purified solution obtained was subjected to microfiltration (0.22 m (Millipore Corp., Millex-GV filter, PVDF membrane) and 0.10 m (Millipore Corp., Millex-VV filter, PVDF membrane)) to yield a solution containing the titled antibody-drug conjugate.

Physicochemical characterization: By using the Common procedures E and F ($\varepsilon_{D,280}$=5178 (measured value), and $\varepsilon_{D,370}$=20217 (measured value) were used), the following characteristic values were obtained.

Antibody concentration: 11.28 mg/mL, antibody yield: 451 mg (90%), average number of conjugated drug molecules (n) per antibody molecule measured by the Common procedure E: 6.6, and average number of conjugated drug molecules (n) per antibody molecule measured by the Common procedure F: 7.7.

Example 32 (Alternative Method for Synthesizing Compound of Process 8 of Example 26)

Process 1: tert-Butyl N-[6-(2,5-Dioxo-2,5-dihydro-1H-pyrrol-1-yl)hexanoyl]glycylglycyl-L-phenyl alaninate Under ice cooling, to a THF (12.0 ml) solution of tert-butyl N-[(9H-fluoren-9-ylmethoxy)carbonyl]glycylglycyl-L-phenyl alaninate (J. Pept. Res., 1999, vol. 53, pp. 393; 0.400 g, 0.717 mmol), 1,8-diazabicyclo[5.4.0]-7-undecene

[Formula 58]

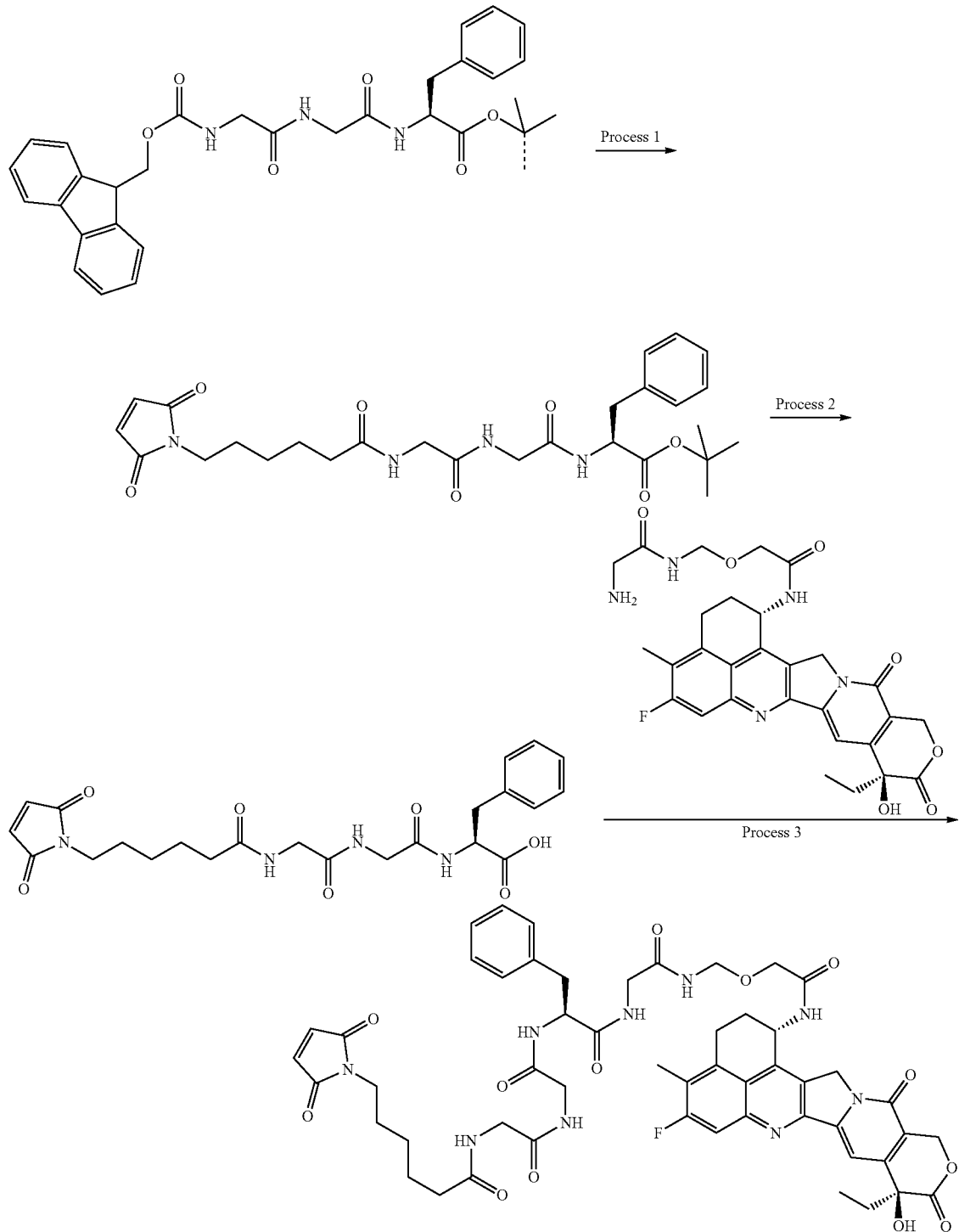

(0.400 ml) was added and stirred at room temperature for 4 days, and then N-succinimidyl 6-maleimide hexanoate (0.221 g, 0.717 mmol) was further added and stirred for 3 hours. The reaction solution was diluted with ethyl acetate and washed with an aqueous solution of 10% citric acid, a saturated aqueous solution of sodium hydrogen carbonate, and saturated brine, and then the organic layer was dried over anhydrous magnesium sulfate. After the solvent was removed under reduced pressure, the residues obtained were purified by silica gel column chromatography [chloroform-chloroform:methanol=9:1 (v/v)] to yield the titled compound as a pale yellow solid (0.295 g, 78%).

$^1$H-NMR (400 MHz, CDCl$_3$) δ: 1.28-1.36 (2H, m), 1.41 (9H, s), 1.57-1.71 (4H, m), 2.23 (2H, t, J=7.6 Hz), 3.09 (2H, d, J=6.0 Hz), 3.51 (2H, t, J=7.6 Hz), 3.85-4.02 (4H, m), 4.69-4.78 (1H, m), 6.15 (1H, t, J=4.6 Hz), 6.33 (1H, d, J=7.3 Hz), 6.60 (1H, t, J=5.0 Hz), 6.68 (2H, s), 7.10-7.16 (2H, m), 7.22-7.31 (3H, m).

MS (ESI) m/z: 529 (M+H)$^+$

Process 2: N-[6-(2,5-Dioxo-2,5-dihydro-1H-pyrrol-1-yl) hexanoyl] glycylglycyl-L-phenylalanine To a dichloromethane (8.00 ml) solution of the compound (0.295 g, 0.558 mmol) obtained in Process 1 above, trifluoroacetic acid (4.00 mL) was added and stirred at room temperature for 18 hours. The solvent was removed under reduced pressure to yield the titled compound as a pale yellow solid (0.240 g, 91%).

$^1$H-NMR (400 MHz, DMSO-d$_6$) δ: 1.15-1.23 (2H, m), 1.40-1.53 (4H, m), 2.10 (2H, t, J=7.6 Hz), 2.88 (1H, dd, J=13.7, 8.9 Hz), 3.04 (1H, dd, J=13.7, 5.0 Hz), 3.35-3.43 (2H, m), 3.58-3.77 (4H, m), 4.41 (1H, td, J=7.8, 5.0 Hz), 7.00 (2H, s), 7.16-7.31 (5H, m), 8.00 (1H, t, J=5.7 Hz), 8.06 (1H, t, J=5.7 Hz), 8.13 (1H, d, J=7.8 Hz).

Process 3: N-[6-(2,5-Dioxo-2,5-dihydro-1H-pyrrol-1-yl)hexanoyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide The compound (0.572 g, 1.21 mmol) obtained in Process 2 above was dissolved in dichloromethane (12.0 mL), charged with N-hydroxysuccinimide (0.152 g, 1.32 mmol) and 1-(3-dimethylaminopropyl)-3-ethylcarbodiimide hydrochloride (0.253 g, 1.32 mmol), and stirred for 1 hour. The reaction solution was added to an N,N-dimethylformamide (22.0 mL) solution of the mixture (1.10 mmol) obtained in Process 5 of Example 26, and stirred at room temperature for 3 hours. The reaction solution was charged with an aqueous solution of 10% citric acid and extracted with chloroform. The obtained organic layer was dried over sodium sulfate and filtered. The solvent was removed under reduced pressure and the residues obtained were purified by silica gel column chromatography [chloroform -chloroform:methanol=8:2 (v/v)] to yield the titled compound as a pale yellow solid (0.351 g, 31%). The instrumental data of the compound was the same as that of the compound of Process 8 of Example 26.

Example 33 (Alternative Method for Synthesizing Compound of Process 8 of Example 26)

[Formula 59]

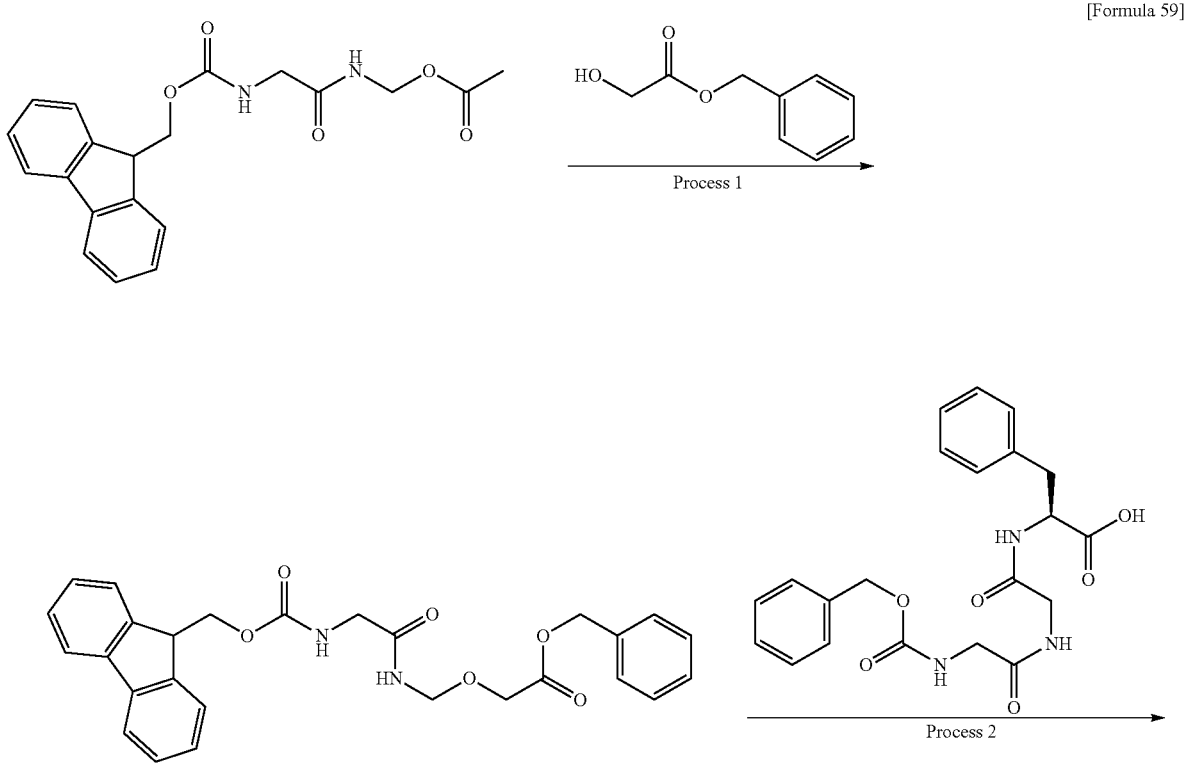

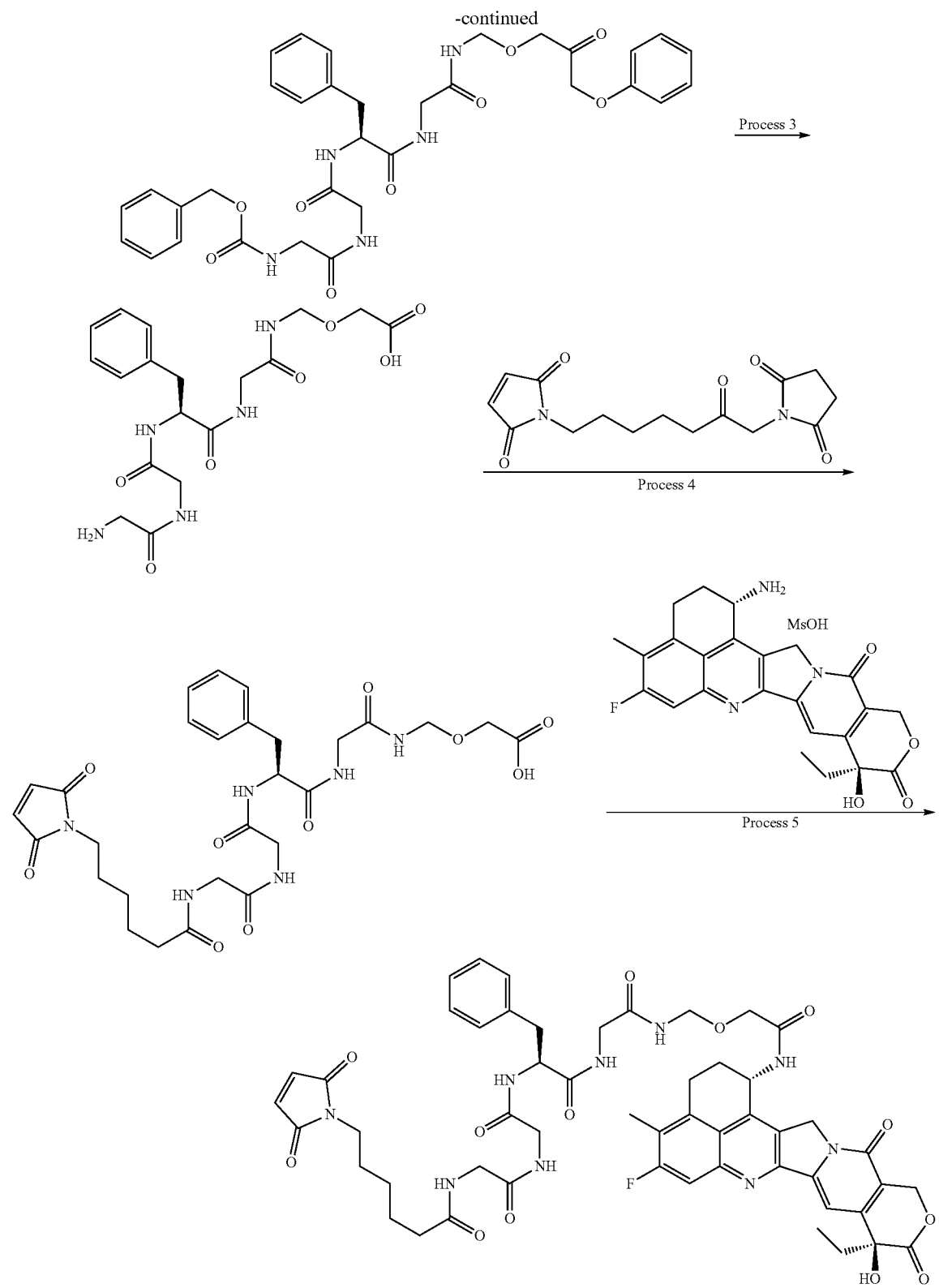

Process 1: Benzyl [({N-[(9H-fluoren-9-ylmethoxy)carbonyl]glycyl}amino)methoxy]acetate To a THF (200 ml) solution of the compound (7.37 g, 20.0 mmol) obtained in Process 1 of Example 26, benzyl glycolate (6.65 g, 40.0 mmol) and p-toluene sulfonic acid monohydrate (0.381 g, 2.00 mmol) were added at 0° C. and stirred at room temperature for 2 hours and 30 minutes. The reaction solution was charged with a saturated aqueous solution of sodium hydrogen carbonate and extracted with ethyl acetate. The obtained organic layer was dried over sodium sulfate and filtered. The solvent was removed under reduced pressure and the residues obtained were purified by silica gel column chromatography [hexane:ethyl acetate=100:0 (v/v)-0: 100] to yield the titled compound as a colorless solid (6.75 g, 71%). The instrumental data of the compound was the same as that of the compound of Process 2 of Example 26.

Process 2: N-[(Benzyloxy)carbonyl]glycylglycyl-L-phenylalanine-N-{[(2-(benzyloxy)-2-oxoethoxy]methyl}glycinamide To an N,N-dimethylformamide (140 mL) solution of the compound (6.60 g, 13.9 mmol) obtained in Process 1 above, 1,8-diazabicyclo[5.4.0]undec-7-ene (2.22 g, 14.6 mmol) was added at 0° C. and stirred at room temperature for 15 minutes. The reaction solution was charged with an N,N-dimethylformamide (140 mL) solution of N-[(benzyloxy)carbonyl]glycylglycyl-L-phenylalanine (6.33 g, 15.3 mmol), N-hydroxysuccinimide (1.92 g, 16.7 mmol), and 1-(3-dimethylaminopropyl)-3-ethylcarbodiimide hydrochloride (3.20 g, 16.7 mmol) stirred in advance at room temperature for 1 hour, and stirred at room temperature for 4 hours. The reaction solution was charged with 0.1 N hydrochloric acid and extracted with chloroform. The obtained organic layer was dried over sodium sulfate and filtered. The solvent was removed under reduced pressure and the residues obtained were purified by silica gel column chromatography [chloroform-chloroform:methanol=8:2 (v/v)] to yield the titled compound as a colorless solid (7.10 g, 79%).

$^1$H-NMR (DMSO-$d_6$) δ: 2.78 (1H, dd, J=13.9, 9.6 Hz), 3.05 (1H, dd, J=13.9, 4.5 Hz), 3.56-3.80 (6H, m), 4.15 (2H, s), 4.47-4.55 (1H, m), 4.63 (2H, d, J=6.6 Hz), 5.03 (2H, s), 5.15 (2H, s), 7.16-7.38 (15H, m), 7.52 (1H, t, J=5.9 Hz), 8.03 (1H, t, J=5.5 Hz), 8.17 (1H, d, J=8.2 Hz), 8.36 (1H, t, J=5.7 Hz), 8.61 (1H, t, J=6.6 Hz).

Process 3: Glycylglycyl-L-phenylalanyl-N-[(carboxymethoxy)methyl]glycinamide

To an N,N-dimethylformamide (216 mL) solution of the compound (7.00 g, 10.8 mmol) obtained in Process 2 above, palladium carbon catalyst (7.00 g) was added and stirred under a hydrogen atmosphere at room temperature for 24 hours. The insolubles were removed by filtration through Celite, and the solvent was removed under reduced pressure. The residues obtained were dissolved in water, the insoluble material was removed by filtration through Celite, and the solvent was removed under reduced pressure. This procedure was repeated twice to yield the titled compound as a colorless solid (3.77 g, 82%).

$^1$H-NMR (DMSO-$d_6$) δ: 2.84 (1H, dd, J=13.7, 9.8 Hz), 3.08 (1H, dd, J=13.7, 4.7 Hz), 3.50-3.72 (4H, m), 3.77-3.86 (2H, m), 3.87 (2H, s), 4.52-4.43 (1H, m), 4.61 (2H, d, J=6.6 Hz), 7.12-7.30 (5H, m), 8.43 (1H, t, J=5.9 Hz), 8.54 (1H, d, J=7.8 Hz), 8.70 (1H, t, J=6.3 Hz), 8.79 (1H, t, J=5.5 Hz).

Process 4: N-[6-(2,5-Dioxo-2,5-dihydro-1H-pyrrol-1-yl)hexanoyl]glycylglycyl-L-phenylalanyl-N-[(carboxymethoxy)methyl]glycinamide To an N,N-dimethylformamide (85.0 mL) solution of the compound (3.59 g, 8.48 mmol) obtained in Process 3 above, N-succinimidyl 6-maleimide hexanoate (2.88 g, 9.33 mmol) and triethylamine (0.858 g, 8.48 mmol) were added and stirred at room temperature for 1 hour. The reaction solution was charged with 0.1 N hydrochloric acid and extracted with chloroform and a mixed solvent of chloroform and methanol [chloroform:methanol=4:1 (v/v)]. The obtained organic layer was dried over sodium sulfate and filtered. The solvent was removed under reduced pressure and the residues obtained were purified by silica gel column chromatography [chloroform-partitioned organic layer of chloroform:methanol:water=7:3:1 (v/v/v)] to yield the titled compound as a colorless solid (3.70 g, 71%).

$^1$H-NMR (DMSO-$d_6$) δ: 1.13-1.24 (2H, m), 1.42-1.53 (4H, m), 2.11 (2H, t, J=7.4 Hz), 2.80 (1H, dd, J=13.7, 9.8 Hz), 3.06 (1H, dd, J=13.9, 4.5 Hz), 3.37 (2H, t, J=7.2 Hz), 3.56-3.78 (6H, m), 3.97 (2H, s), 4.46-4.53 (1H, m), 4.61 (2H, d, J=6.3 Hz), 7.00 (2H, s), 7.15-7.29 (5H, m), 8.03-8.20 (3H, m), 8.32 (1H, t, J=5.9 Hz), 8.60 (1H, t, J=6.7 Hz).

Process 5: N-[6-(2,5-Dioxo-2,5-dihydro-1H-pyrrol-1-yl)hexanoyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide To an N,N-dimethylformamide (40.0 mL) solution of methanesulfonic acid salt of exatecan (1.14 g, 2.00 mmol), triethylamine (0.202 g, 2.00 mmol), the compound (1.48 g, 2.40 mmol) obtained in Process 4 above, and 4-(4,6-dimethoxy-1,3,5-triazin-2-yl)-4-methylmorpholinium chloride (0.993 g, 3.00 mmol) containing 16.4% water were added at 0° C. and stirred at room temperature for 1 hour. The solvent was removed under reduced pressure and the residues obtained were purified by silica gel column chromatography [chloroform-chloroform:methanol=8:2 (v/v)] to yield the titled compound as a pale yellow solid (1.69 g, 82%). The spectral data of the compound was the same as that of the compound of Process 8 of Example 26.

Example 34 Intermediate (34)

[Formula 60]

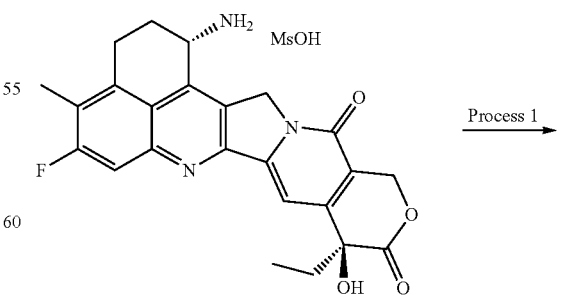

-continued

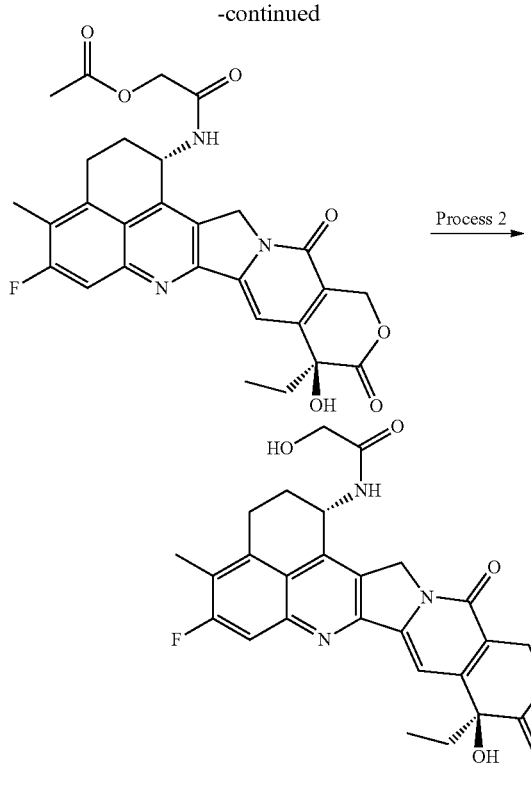

Process 2 →

Process 1: 2-{[(1S,9)-9-Ethyl-5-fluoro-9-hydroxy-4-methyl-10,13-dioxo-2,3,9,10,13,15-hexahydro-1H,12H-benzo[de]pyrano[3',4': 6,7]indolizino[1,2-b]quinolin-1-yl] amino}-2-oxoethylacetate Under ice cooling, to an N,N-dimethylformamide (20.0 mL) suspension of methanesulfonic acid salt of exatecan (0.500 g, 0.941 mmol), N,N-diisopropylethylamine (0.492 mL, 2.82 mmol) and acetoxyacetyl chloride (0.121 ml, 1.13 mmol) were added and stirred at room temperature for 1 hour. The solvent was removed under reduced pressure and the residues obtained were purified by silica gel column chromatography [chloroform -partitioned organic layer of chloroform:methanol:water=7:3:1 (v/v/v)] to yield the titled compound as a pale yellow solid (0.505 g, quantitative).

$^1$H-NMR (400 MHz, DMSO-$d_6$) δ: 0.87 (3H, t, J=7.4 Hz), 1.81-1.92 (2H, m), 2.08 (3H, s), 2.08-2.22 (2H, m), 2.41 (3H, s), 3.14-3.21 (2H, m), 4.51 (2H, dd, J=19.4, 14.7 Hz), 5.22 (2H, dd, J=40.1, 19.0 Hz), 5.43 (2H, s), 5.56-5.61 (1H, m), 6.53 (1H, s), 7.31 (1H, s), 7.81 (1H, d, J=11.0 Hz), 8.67 (1H, d, J=8.6 Hz).

MS (ESI) m/z: 536 (M+H)$^+$

Process 2: N-[(1S,9S)-9-Ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-2-hydroxyacetamide To a methanol (50.0 mL) suspension of the compound (0.504 g, 0.941 mmol) obtained in Process 1 above, a THF (20.0 ml) and an aqueous solution of 1 N sodium hydroxide (4.00 ml, 4.00 mmol) were added and stirred at room temperature for 1 hour. The reaction was terminated by the addition of 1 N hydrochloric acid (5.00 ml, 5.00 mmol), and the solvent was removed under reduced pressure. The residues obtained were purified by silica gel column chromatography [chloroform -partitioned organic layer of chloroform:methanol:water=7:3:1 (v/v/v)] to yield the titled compound as a pale yellow solid (0.412 g, 89%). This compound was confirmed in the tumor of a mouse that received the antibody-drug conjugate (45) or (46).

$^1$H-NMR (400 MHz, DMSO-$d_6$) δ: 0.87 (3H, t, J=7.3 Hz), 1.78-1.95 (2H, m), 2.09-2.28 (2H, m), 2.39 (3H, s), 3.07-3.27 (2H, m), 3.96 (2H, d, J=6.0 Hz), 5.11-5.26 (2H, m), 5.42 (2H, s), 5.46-5.54 (1H, m), 5.55-5.63 (1H, m), 6.52 (1H, s), 7.30 (1H, s), 7.78 (1H, d, J=10.9 Hz), 8.41 (1H, d, J=9.1 Hz). MS (ESI) m/z: 494 (M+H)$^+$

Example 35 (Alternative Method for Synthesizing Compound of Example 34)

[Formula 61]

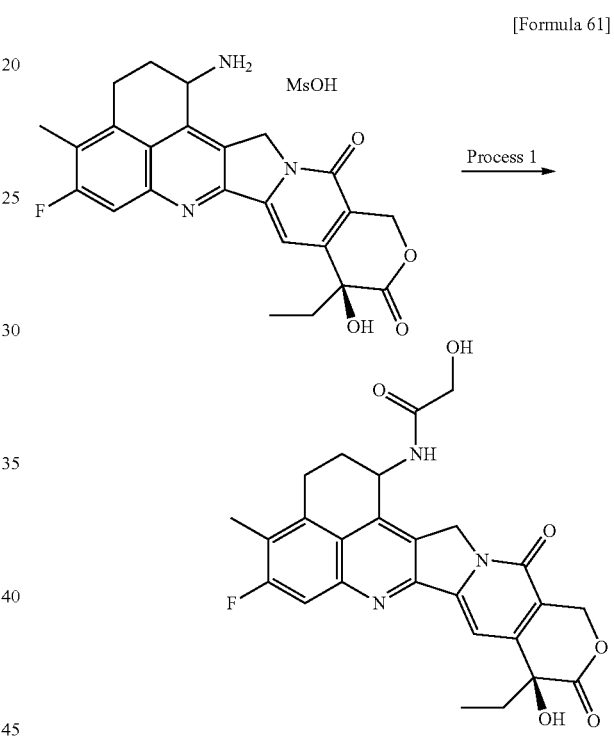

Process 1 →

Process 1: N-[(1S,9S)-9-Ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-2-hydroxyacetamide Glycolic acid (0.0201 g, 0.27 mmol) was dissolved in N,N-dimethylformamide (1.0 mL), charged with N-hydroxysuccinimide (0.0302 g, 0.27 mmol) and 1-(3-dimethylaminopropyl)-3-ethylcarbodiimide hydrochloride (0.0508 g, 0.27 mmol), and stirred for 1 hour. The reaction solution was added to an N,N-dimethylformamide suspension (1.0 mL) charged with methanesulfonic acid salt of exatecan (0.1 g, 0.176 mmol) and triethylamine (0.025 mL, 0.18 mmol) and stirred at room temperature for 24 hours. The solvent was removed under reduced pressure and the residues obtained were purified by silica gel column chromatography [chloroform-chloroform:methanol=10:1 (v/v)] to yield the titled compound as a pale yellow solid (0.080 g, 92%). The spectral data of the compound was the same as that of the compound obtained in Process 2 of Example 34.

Example 36 Antibody-Drug Conjugate (36)

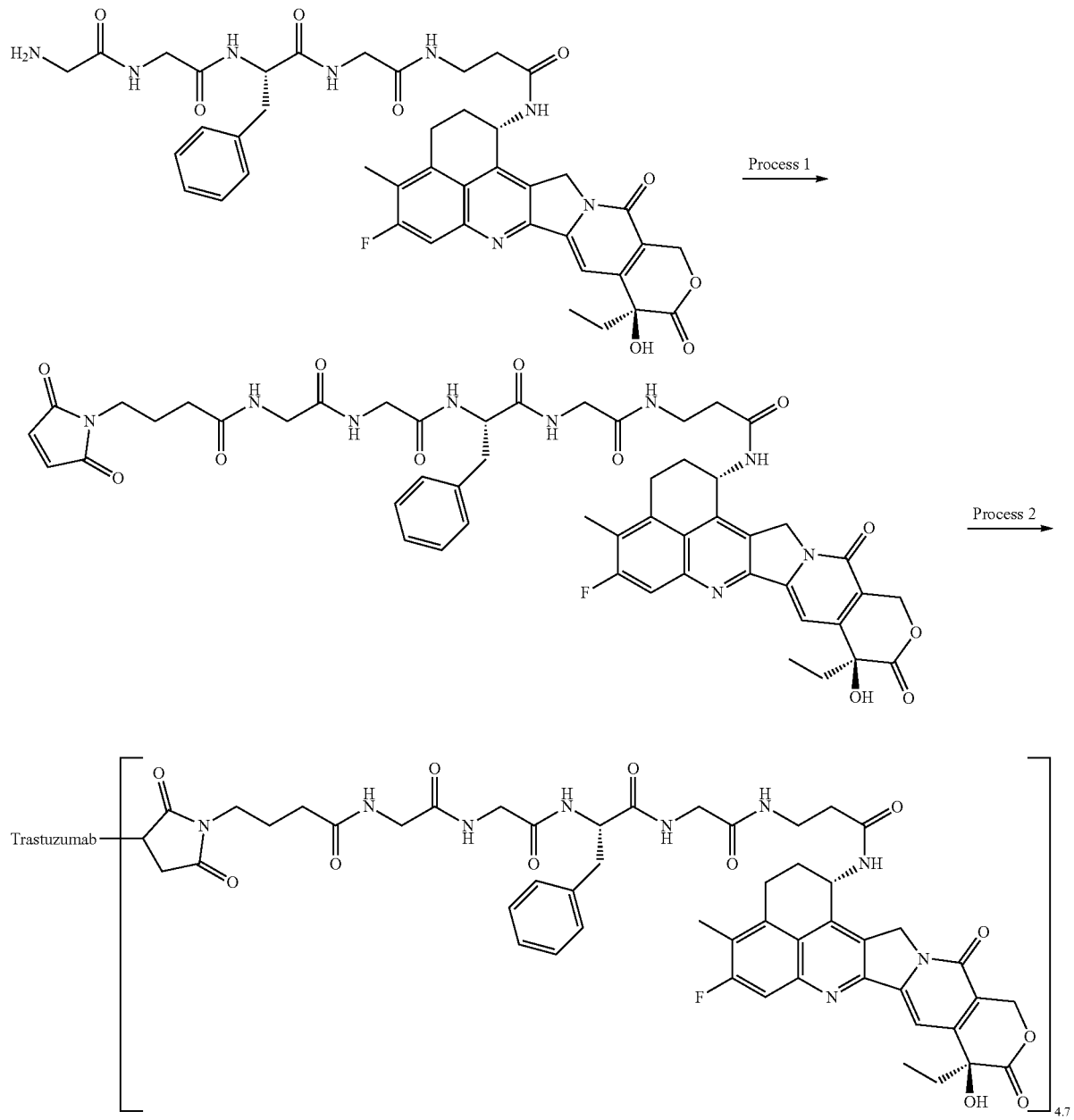

[Formula 62]

Process 1: N-[4-(2,5-Dioxo-2,5-dihydro-1H-pyrrol-1-yl)butanoyl]glycylglycyl-L-phenylalanylglycyl-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]-β-alaninamide The compound (60.0 mg, 0.0646 mmol) obtained in Process 2 of Example 15 was reacted in the same manner as Process 3 of Example 2 by using N-succinimidyl 4-maleimide butyrate instead of N-succinimidyl 6-maleimide hexanoate to yield the titled compound as a pale white solid (24.0 mg, 38%).

$^1$H-NMR (400 MHz, DMSO-$d_6$) δ: 0.86 (3H, t, J=7.2 Hz), 1.68 (2H, quin, J=7.4 Hz), 1.78-1.92 (2H, m), 2.06-2.22 (2H, m), 2.10 (2H, t, J=7.8 Hz), 2.31-2.43 (2H, m), 2.40 (3H, s), 2.78 (1H, dd, J=13.7, 9.4 Hz), 3.01 (1H, dd, J=13.7, 4.7 Hz), 3.17 (4H, d, J=5.1 Hz), 3.29-3.40 (2H, m), 3.52-3.80 (6H, m), 4.40-4.51 (1H, m), 5.19 (1H, d, J=18.4 Hz), 5.26 (1H, d, J=18.8 Hz), 5.42 (2H, s), 5.52-5.61 (1H, m), 6.53 (1H, s), 6.99 (2H, s), 7.12-7.28 (5H, m), 7.31 (1H, s), 7.74-7.84 (2H, m), 8.02 (1H, t, J=5.9 Hz), 8.08-8.16 (2H, m), 8.25 (1H, t, J=5.9 Hz), 8.52 (1H, d, J=8.2 Hz) MS (ESI) m/z: 990 (M+H)$^+$ Process 2: Antibody-Drug Conjugate (33)

By using the trastuzumab produced in Reference Example 1 and the compound obtained in Process 1 above, the titled antibody-drug conjugate was obtained in the same manner as Process 2 of Example 6.
Antibody concentration: 1.75 mg/mL, antibody yield: 10.5 mg (84%), and average number of conjugated drug molecules (n) per antibody molecule: 4.7.

Example 37 Antibody-Drug Conjugate (37)

[Formula 63]

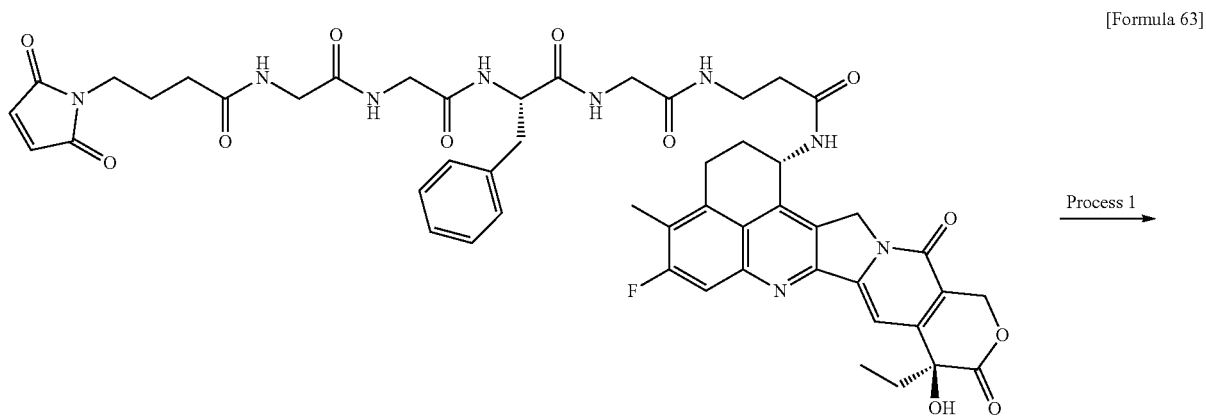

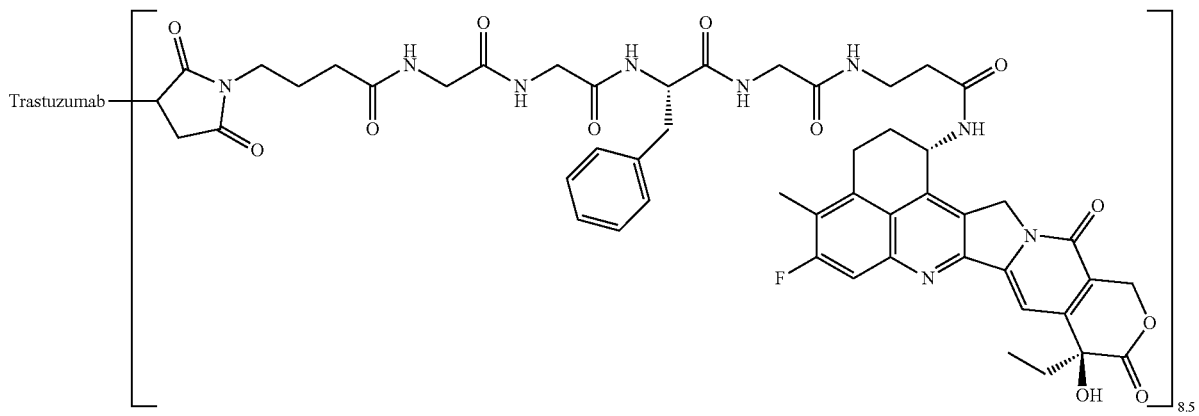

Process 1: Antibody-Drug Conjugate (37)

By using the trastuzumab produced in Reference Example 1 and the compound obtained in Process 1 of Example 36, the titled antibody-drug conjugate was obtained in the same manner as Process 1 of Example 7.

Antibody concentration: 1.89 mg/mL, antibody yield: 11.3 mg (90%), and average number of conjugated drug molecules (n) per antibody molecule: 8.5.

Example 38 Intermediate (38)

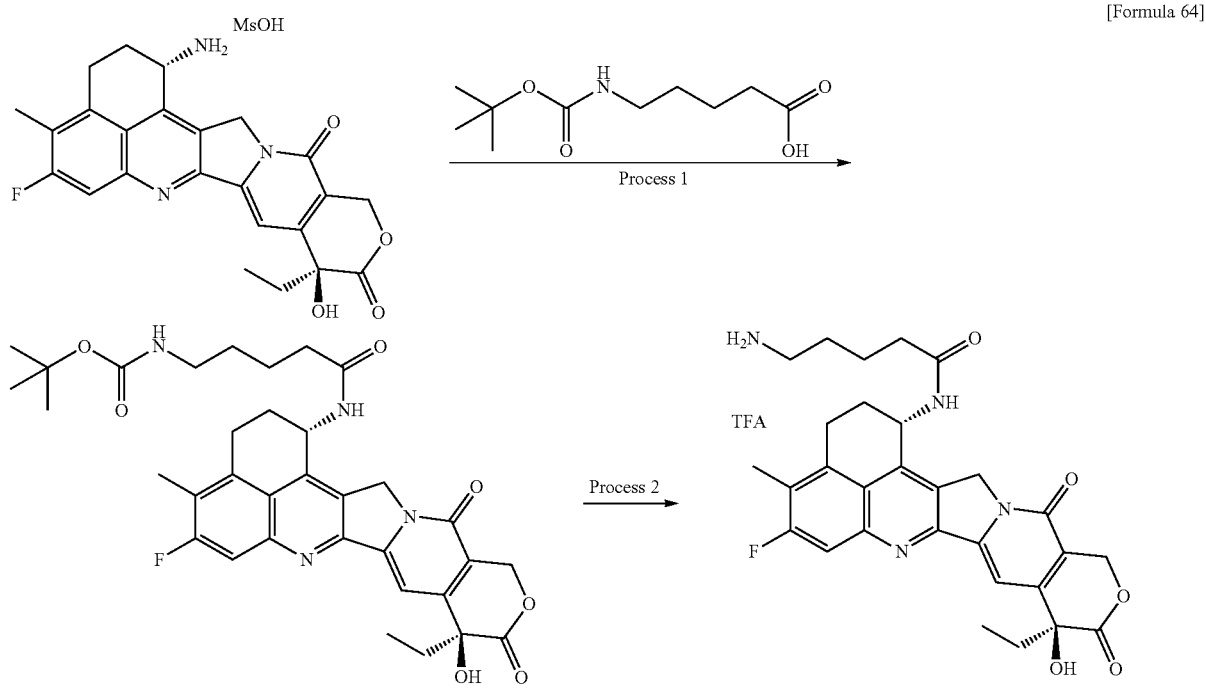

[Formula 64]

Process 1: tert-Butyl (5-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl] amino}-5-oxopentyl) carbamate Methanesulfonic acid salt of exatecan (500 mg, 0.941 mmol) was reacted in the same manner as Process 1 of Example 1 by using 5-(tert-butoxycarbonylamino)valeric acid instead of 4-(tert-butoxycarbonylamino)butanoic acid to yield the titled compound as a yellow-brown solid (571 mg, 96%). The compound was used for the next reaction without performing further purification.

MS (ESI) m/z: 635 (M+H)+

Process 2: 5-Amino-N-[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]pentanamide The compound (558 mg, 0.879 mmol) obtained in Process 1 above was reacted in the same manner as Process 2 of Example 1 to yield trifluoroacetate of the titled compound as a yellow solid (363 mg, 64%).

$^1$H-NMR (400 MHz, DMSO-$d_6$) δ: 0.88 (3H, t, J=7.4 Hz), 1.52-1.71 (4H, m), 1.87 (2H, tt, J=14.4, 6.9 Hz), 2.07-2.18 (2H, m), 2.22 (2H, t, J=7.0 Hz), 2.40 (3H, s), 2.76-2.88 (2H, m), 3.13-3.22 (2H, m), 5.18 (1H, d, J=18.8 Hz), 5.24 (1H, d, J=18.8 Hz), 5.43 (2H, s), 5.53-5.61 (1H, m), 6.55 (1H, s), 7.33 (1H, s), 7.65 (3H, br.s.), 7.81 (1H, d, J=11.3 Hz), 8.49 (1H, d, J=8.6 Hz).

MS (ESI) m/z: 535 (M+H)

Example 39 Antibody-Drug Conjugate (39)
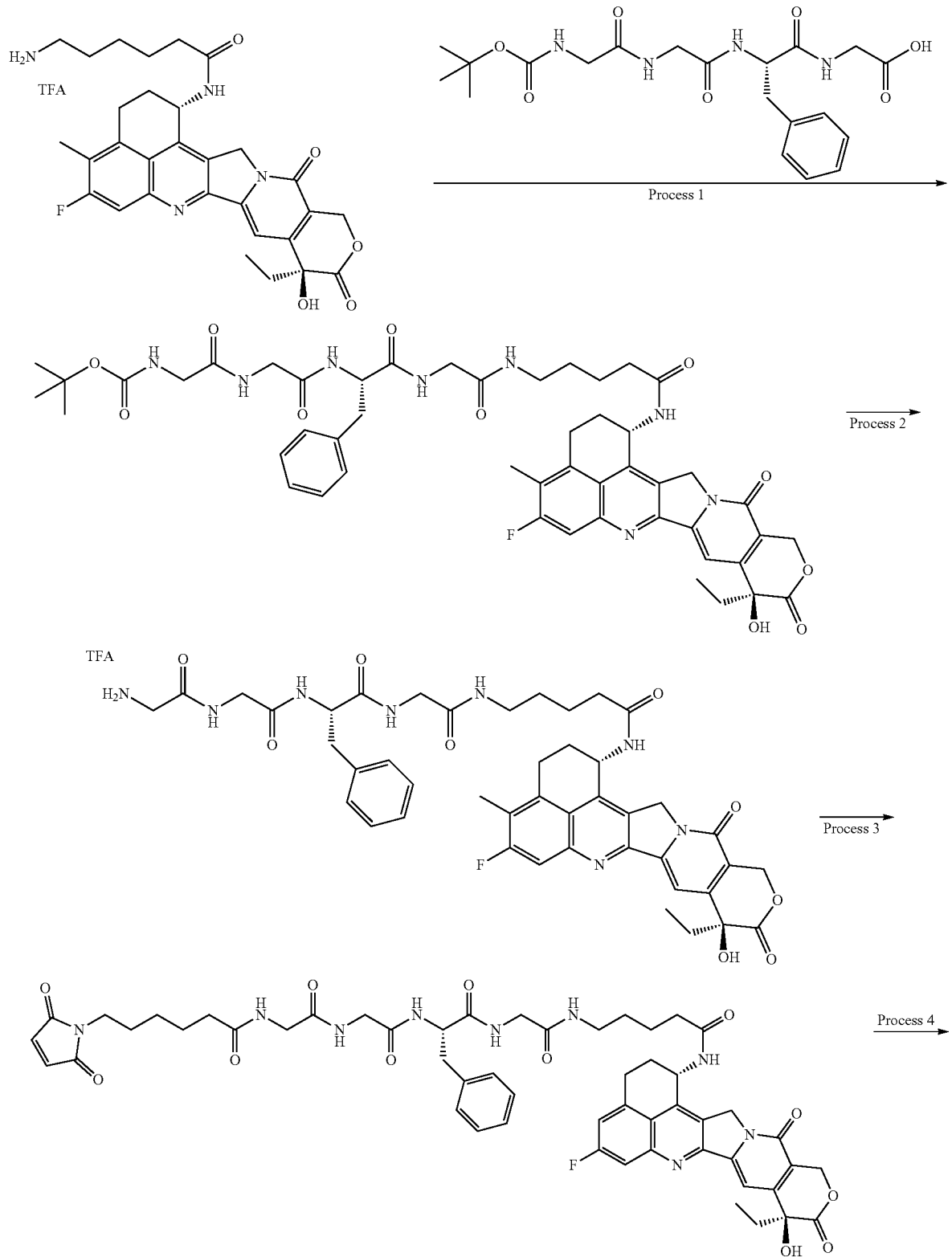

-continued

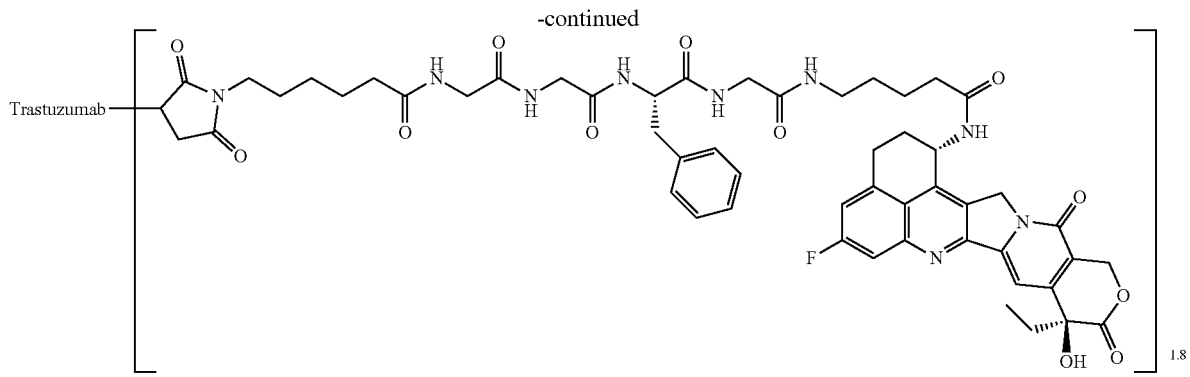

Process 1: N-(tert-Butoxycarbonyl)glycylglycyl-L-phenylalanyl-N-(5-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl] amino}-5-oxopentyl) glycinamide The compound (348 mg, 0.537 mmol) obtained in Process 2 of Example 38 was reacted in the same manner as Process 1 of Example 2 to yield the titled compound as a pale yellow solid (429 mg, 84%). The compound was used for the next reaction without performing further purification.

Process 2: Glycylglycyl-L-phenylalanyl-N-(5-{[(1S,9S)-9-ethyl-5-fluoro-9-hydroxy-10,13-dioxo-2,3,9,10,13,15-hexahydro-1H,12H-benzo[de]pyrano[3',4':6,7]indolizino[1,2-b]quinolin-1-yl]amino}-5-oxopentyl)glycinamide The compound (427 mg, 0.448 mmol) obtained in Process 1 above was reacted in the same manner as Process 2 of Example 2 to yield trifluoroacetate of the titled compound as a yellow solid (430 mg, 99%).

$^1$H-NMR (400 MHz, DMSO-$d_6$) δ: 0.87 (3H, t, J=7.2 Hz), 1.38-1.49 (2H, m), 1.54-1.66 (2H, m), 1.86 (2H, tt, J=14.5, 7.0 Hz), 2.08-2.16 (2H, m), 2.19 (2H, t, J=7.2 Hz), 2.40 (3H, s), 2.76 (1H, dd, J=13.9, 10.0 Hz), 3.00-3.12 (3H, m), 3.14-3.21 (2H, m), 3.57 (2H, d, J=4.7 Hz), 3.60-3.75 (3H, m), 3.87 (1H, dd, J=16.8, 5.9 Hz), 4.55 (1H, td, J=9.0, 4.7 Hz), 5.16 (1H, d, J=18.8 Hz), 5.23 (1H, d, J=18.4 Hz), 5.44 (2H, s), 5.53-5.60 (1H, m), 6.55 (1H, s), 7.14-7.29 (5H, m), 7.32 (1H, s), 7.74 (1H, t, J=5.5 Hz), 7.81 (1H, d, J=10.9 Hz), 7.96 (3H, br.s.), 8.30-8.37 (1H, m), 8.44-8.53 (2H, m).
MS (ESI) m/z: 853 (M+H)$^+$

Process 3: N-[6-(2,5-Dioxo-2,5-dihydro-1H-pyrrol-1-yl)hexanoyl]glycylglycyl-L-phenylalanyl-N-(5-{[(1S,9S)-9-ethyl-5-fluoro-9-hydroxy-10,13-dioxo-2,3,9,10,13,15-hexahydro-1H,12H-benzo[de]pyrano[3',4':6,7]indolizino[1,2-b]quinolin-1-yl] amino}-5-oxopentyl)glycinamide The compound (60.0 mg, 0.0621 mmol) obtained in Process 2 above was reacted in the same manner as Process 3 of Example 2 to yield the titled compound as a solid (16.0 mg, 25%).

$^1$H-NMR (400 MHz, DMSO-$d_6$) δ: 0.87 (3H, t, J=7.4 Hz), 1.13-1.21 (2H, m), 1.36-1.52 (6H, m), 1.53-1.65 (2H, m), 1.79-1.92 (2H, m), 2.05-2.15 (4H, m), 2.19 (2H, s), 2.40 (3H, s), 2.79 (1H, dd, J=13.7, 10.2 Hz), 2.98-3.10 (3H, m), 3.12-3.21 (2H, m), 3.29-3.37 (2H, m), 3.53-3.79 (6H, m), 4.41-4.50 (1H, m), 5.16 (1H, d, J=18.8 Hz), 5.23 (1H, d, J=18.8 Hz), 5.43 (2H, s), 5.52-5.60 (1H, m), 6.53 (1H, s), 6.99 (2H, s), 7.12-7.28 (5H, m), 7.31 (1H, s), 7.63 (1H, t, J=5.7 Hz), 7.80 (1H, d, J=10.6 Hz), 8.02 (1H, t, J=5.9 Hz), 8.08 (1H, t, J=5.7 Hz), 8.12 (1H, d, J=7.8 Hz), 8.24 (1H, t, J=5.7 Hz), 8.45 (1H, d, J=8.6 Hz).
MS (ESI) m/z: 1046 (M+H)$^+$

Process 4: Antibody-Drug Conjugate (39)

Reduction of the antibody: The trastuzumab produced in Reference Example 1 was prepared to have an antibody concentration of 10 mg/mL with PBS6.0/EDTA by using the Common procedure C-1 and Common procedure B (as absorption coefficient at 280 nm, 1.37 mLmg$^{-1}$ cm$^{-1}$ was used). The solution (1.0 mL) was collected into a 2 mL tube and charged with an aqueous solution of 10 mM TCEP (0.0155 mL; 2.3 equivalents per antibody molecule) and an aqueous solution of 1 M dipotassium hydrogen phosphate (0.050 mL). After confirming that the solution had a pH of 7.4±0.1, the disulfide bond at the hinge part in the antibody was reduced by incubating at 37° C. for 1 hour.

Conjugation between antibody and drug linker: After incubating the solution for 10 minutes at 22° C., a DMSO solution (0.0311 mL; 4.6 equivalents per antibody molecule) containing 10 mM of the compound obtained in Process 3 was added thereto and incubated for conjugating the drug linker to the antibody at 22° C. for 40 minutes. Next, an aqueous solution (0.00622 mL; 9.2 equivalents per antibody molecule) of 100 mM NAC was added thereto and incubated at 22° C. to terminate the reaction of the drug linker for another 20 minutes.

Purification: The above solution was subjected to purification using the Common procedure D-1 (PBS6.0 was used as buffer solution) to yield 6 mL of a solution containing the titled antibody-drug conjugate.

Physicochemical characterization: By using the Common procedure E, the following characteristic values were obtained. Antibody concentration: 1.12 mg/mL, antibody yield: 6.72 mg (67%), and average number of conjugated drug molecules (n) per antibody molecule: 1.8.

Example 40 Antibody-Drug Conjugate (40)

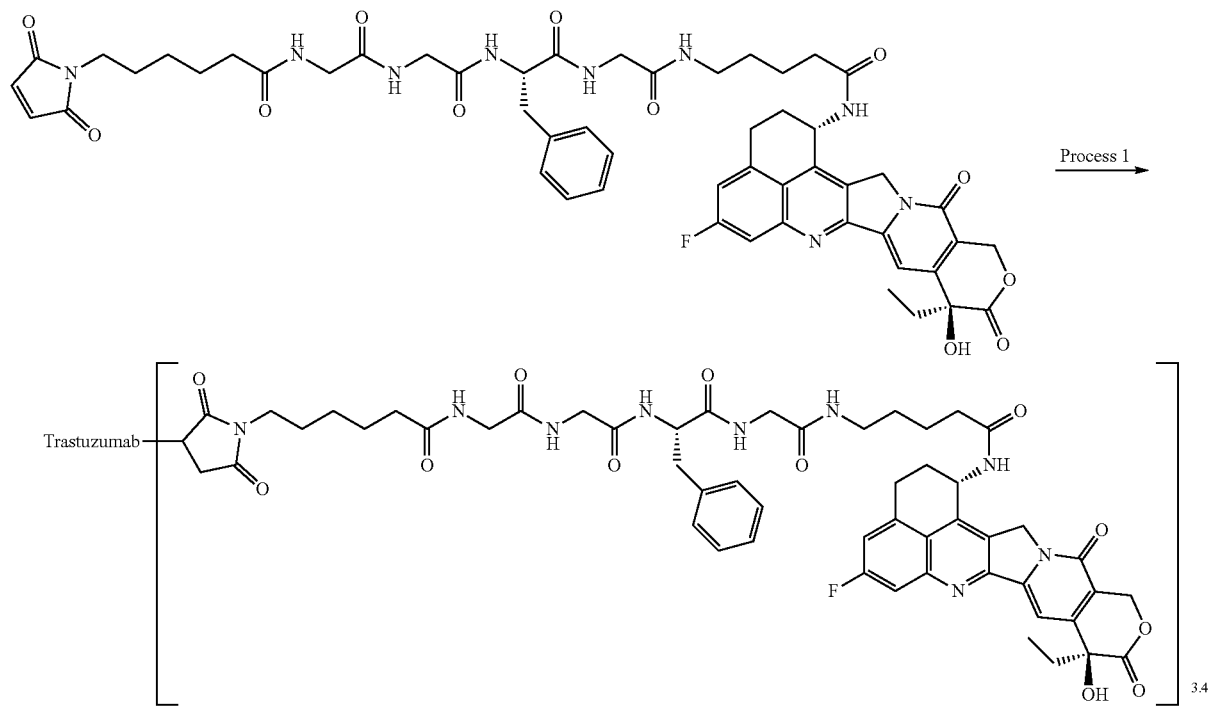

Process 1: Antibody-Drug Conjugate (40)

Reduction of the antibody: The trastuzumab produced in Reference Example 1 was prepared to have an antibody concentration of 10 mg/mL with PBS6.0/EDTA by using the Common procedure C-1 and Common procedure B (as absorption coefficient at 280 nm, 1.37 mLmg$^{-1}$ cm$^{-1}$ was used). The solution (1.0 mL) was collected into a 2 mL tube and charged with an aqueous solution of 10 mM TCEP (0.0311 mL; 4.6 equivalents per antibody molecule) and an aqueous solution of 1 M dipotassium hydrogen phosphate (0.050 mL). After confirming that the solution had a pH of 7.4±0.1, the disulfide bond at the hinge part in the antibody was reduced by incubating at 37° C. for 1 hour.

Conjugation between antibody and drug linker: After incubating the solution at 22° C. for 10 minutes, a DMSO solution (0.0622 mL; 9.2 equivalents per antibody molecule) containing 10 mM of the compound obtained in Process 3 of Example 39 was added thereto and incubated for conjugating the drug linker to the antibody at 22° C. for 40 minutes. Next, an aqueous solution (0.0124 mL; 18.4 equivalents per antibody molecule) of 100 mM NAC was added thereto and incubated at 22° C. to terminate the reaction of the drug linker for another 20 minutes.

Purification: The above solution was subjected to purification using the Common procedure D-1 (PBS6.0 was used as buffer solution) to yield 6 mL of a solution containing the titled antibody-drug conjugate.

Physicochemical characterization: By using the Common procedure E, the following characteristic values were obtained. Antibody concentration: 0.98 mg/mL, antibody yield: 5.88 mg (59%), and average number of conjugated drug molecules (n) per antibody molecule: 3.4.

Example 41 Antibody-Drug Conjugate (41)

[Formula 67]

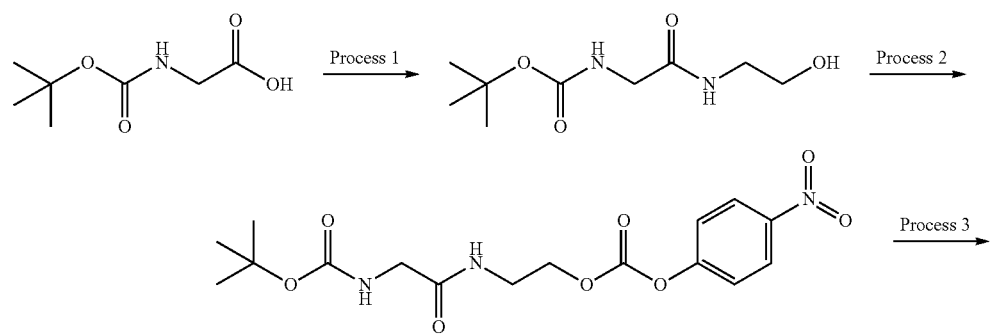

-continued
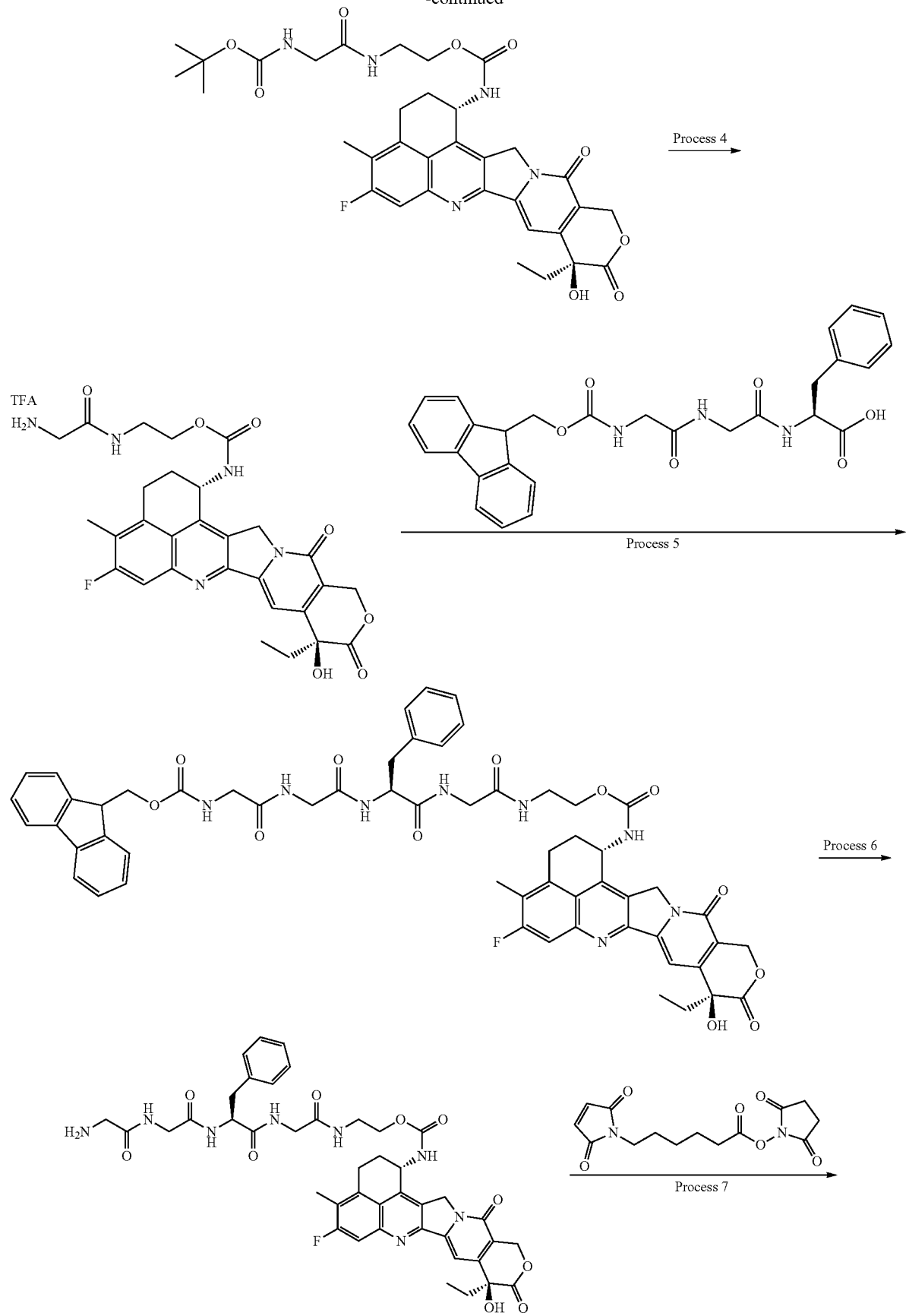

-continued

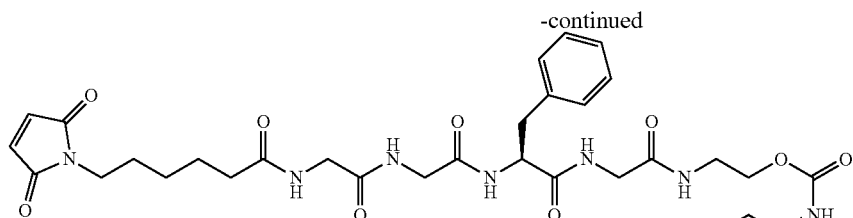
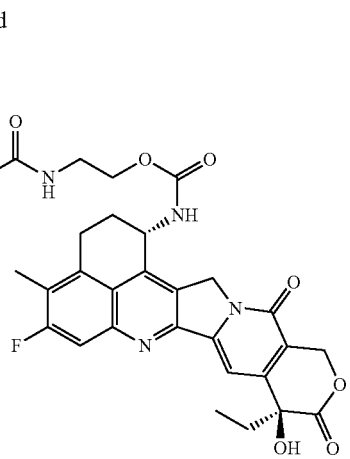

Process 8 →

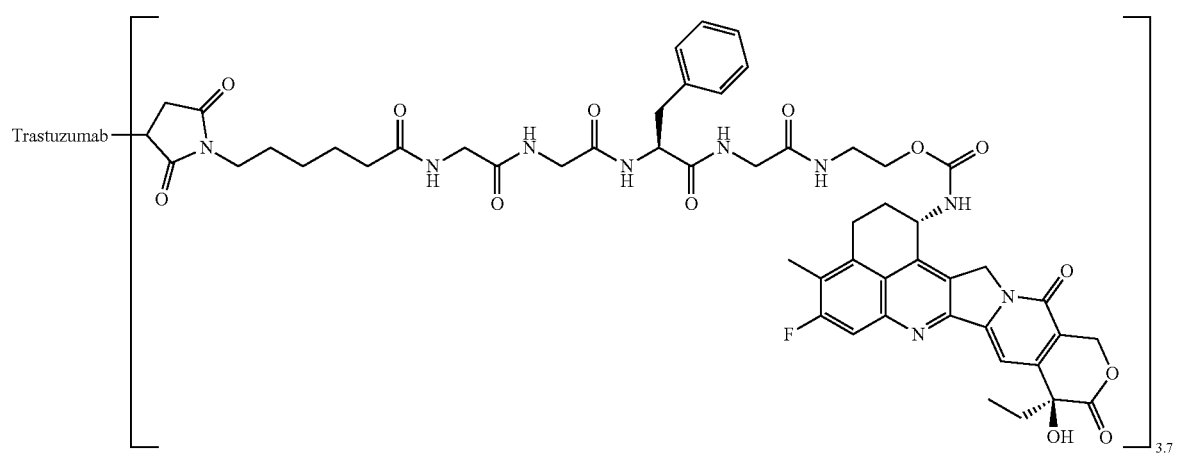

Process 1: tert-Butyl {2-[(2-hydroxyethyl)amino]-2-oxoethyl}carbamate

N-(tert-Butoxycarbonyl)glycine (4.2 g, 24 mmol) was dissolved in dimethylformamide (40 mL). After adding aminoethanol (2.9 g, 48 mmol) and 1-hydroxybenzotriazole (3.7 g, 24 mmol) and adding 1-ethyl-3-(3-dimethylaminopropyl)carbodiimide hydrochloride (6.9 g, 36 mmol), it was stirred at room temperature for 12 hours. The solvent was removed under reduced pressure, and the residue was charged with toluene for azeotropic distillation. The residue obtained were purified by silica gel column chromatography [ethyl acetate-ethyl acetate methanol=10:1 (v/v)] to yield the titled compound as a colorless oily substance (3.8 g, 72%).

$^1$H-NMR (400 MHz, CDCl$_3$) δ: 1.44 (9H, s), 1.69 (1H, brs), 3.43 (2H, td, J=5.9, 5.1 Hz), 3.71 (2H, t, J=5.1 Hz), 3.79 (2H, d, J=5.9 Hz), 5.22 (1H, brs), 6.62 (1H, brs).

Process 2: 2-{[N-(tert-Butoxycarbonyl)glycyl]amino}ethyl4-nitrophenylcarbonate To a THF (23 mL) solution of the compound (1.0 g, 4.59 mmol) obtained in Process 1 above, diisopropylethylamine (0.80 mL, 4.59 mmol) and bis(4-nitrophenyl) carbonate (1.32 g, 6.88 mmol) were added and stirred at room temperature for 12 hours. The solvent was removed under reduced pressure, and the residue obtained was purified by silica gel column chromatography [hexane-hexane:ethyl acetate=1:3 (v/v)] to yield the titled compound as a pale yellow solid (1.13 g, 64%).

$^1$H-NMR (400 MHz, CDCl$_3$) δ: 1.44 (1H, s), 3.66 (2H, td, J=5.1, 5.9 Hz), 3.81 (2H, d, J=5.9 Hz), 4.36 (2H, t, J=5.1 Hz), 5.07 (1H, s), 6.48-6.53 (1H, m), 7.38 (2H, dt, J=9.9, 2.7 Hz), 8.27 (2H, dt, J=9.9, 2.7 Hz).

Process 3: 2-({[(tert-Butoxycarbonyl)amino]acetyl}amino)ethyl[(S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]carbamate To methanesulfonic acid salt of exatecan (0.70 g, 1.2 mmol), the compound (0.57 g, 1.5 mmol) obtained in Process 2, and 1-hydroxybenzotriazole (3.7 g, 24 mmol), dimethylformamide (23 mL) was added, and diisopropylethylamine (0.43 mL, 2.5 mmol) was added and stirred at room temperature for 12 hours. The solvent was removed under reduced pressure, and the residue was charged with toluene for azeotropic distillation. The residue obtained were purified by silica gel column chromatography [chloroform-chloroform:methanol=10:1 (v/v)] to yield the titled compound (0.86 g, quantitative) as a pale yellow solid.

$^1$H-NMR (400 MHz, DMSO-$d_6$) δ: 0.87 (3H, t, J=7.4 Hz), 1.35 (9H, s), 1.78-1.94 (1H, m), 2.07-2.17 (1H, m), 2.17-2.27 (1H, m), 2.37 (3H, s), 3.05-3.16 (1H, m), 3.19-3.26 (1H, m), 3.34-3.39 (2H, m), 3.50-3.56 (2H, m), 4.00-4.07 (1H, m), 4.13-4.21 (1H, m), 5.15-5.34 (3H, m), 5.44 (2H, s), 6.54 (1H, s), 6.90-6.96 (1H, m), 7.32 (1H, s), 7.78 (1H, d, J=11.0 Hz), 7.93-8.07 (2H, m).

Process 4: 2-(Glycylamino)ethyl[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]carbamate The compound (0.86 g, 2.1 mmol) obtained in Process 3 above was dissolved in dichloromethane (15 mL). After adding trifluoroacetic acid (15 mL), it was stirred for 1 hour. The solvent was removed under reduced pressure, and the residue was charged with toluene for azeotropic distillation. The residue obtained were purified by silica gel column chromatography [chloroform-partitioned organic layer of chloroform:methanol:water=7:3:1 (v/v/v)] to yield the titled compound as a pale yellow solid (0.86 g, 99%).

$^1$H-NMR (400 MHz, DMSO-$d_6$) δ: 0.87 (3H, t, J=7.2 Hz), 1.79-1.95 (2H, m), 2.06-2.18 (1H, m), 2.18-2.29 (1H, m), 2.38 (3H, s), 3.07-3.17 (1H, m), 3.20-3.29 (1H, m), 3.36-3.50 (2H, m), 3.51-3.62 (2H, m), 3.99-4.08 (1H, m), 4.22-4.31 (1H, m), 5.16-5.35 (3H, m), 5.42 (1H, d, J=18.8 Hz), 5.46 (1H, d, J=18.8 Hz), 6.56 (1H, s), 7.34 (1H, s), 7.65 (2H, brs), 7.79 (1H, d, J=10.6 Hz), 7.99-8.06 (1H, m), 8.51 (1H, t, J=5.5 Hz).

MS (APCI) m/z: 939 (M+H)$^+$

Process 5: N-[(9H-Fluoren-9-ylmethoxy) carbonyl]glycylglycyl-L-phenylalanyl-N-[2-({[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]carbamoyl}oxy)ethyl]glycinamide N-[(9H-fluoren-9-ylmethoxy)carbonyl]glycylglycyl-L-phenylalanine (Japanese Patent Laid-Open No. 2002-60351; 0.21 g, 0.41 mmol) was dissolved in N,N-dimethylformamide (3 mL). After adding N-hydroxysuccinimide (0.052 g, 0.45 mmol) and 1-ethyl-3-(3-dimethylaminopropyl)carbodiimide hydrochloride (0.086 g, 0.45 mmol), it was stirred for 1 hour. The reaction solution was added dropwise to a N,N-dimethylformamide solution (2 mL) charged with the compound (0.24 g, 0.35 mmol) obtained in Process 4 and triethylamine (0.078 mL, 0.45 mmol), and stirred at room temperature for 1 hour. The solvent was removed under reduced pressure, and the residue obtained was purified by silica gel column chromatography [chloroform -chloroform:methanol=8:2 (v/v)] to yield the titled compound as a pale yellow solid (0.24 g, 65%).

$^1$H-NMR (400 MHz, DMSO-$d_6$) δ: 0.86 (3H, t, J=7.3 Hz), 1.79-1.90 (2H, m), 2.05-2.27 (2H, m), 2.36 (3H, s), 2.73-2.81 (1H, m), 2.98-3.12 (2H, m), 3.17-3.26 (2H, m), 3.35-3.42 (2H, m), 3.55-3.79 (6H, m), 4.00-4.10 (1H, m), 4.12-4.23 (2H, m), 4.23-4.29 (2H, m), 4.45-4.55 (1H, m), 5.13-5.33 (3H, m), 5.40 (1H, d, J=17.2 Hz), 5.44 (1H, d, J=17.2 Hz), 6.53 (1H, s), 7.11-7.26 (5H, m), 7.26-7.33 (3H, m), 7.38 (2H, t, J=7.6 Hz), 7.57 (1H, t, J=5.9 Hz), 7.68 (2H, d, J=7.4 Hz), 7.77 (1H, d, J=11.0 Hz), 7.85 (2H, d, J=9.0 Hz), 7.91-7.97 (1H, m), 7.98-8.05 (2H, m), 8.14 (1H, d, J=7.8 Hz), 8.31-8.26 (1H, m) MS (APCI) m/z: 1063 (M+H)$^+$

Process 6: Glycylglycyl-L-phenylalanyl-N-[2-({[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]carbamoyl}oxy)ethyl]glycinamide The compound (0.24 g, 0.35 mmol) obtained in Process 5 above was reacted in the same manner as Process 7 of Example 26 to yield the titled compound as a pale yellow solid (0.12 g, 65%).

$^1$H-NMR (400 MHz, DMSO-$d_6$) δ: 0.86 (3H, t, J=7.4 Hz), 1.78-1.94 (2H, m), 2.06-2.27 (2H, m), 2.37 (3H, s), 2.72-2.81 (1H, m), 2.98-3.07 (1H, m), 3.12-3.17 (2H, m), 3.57-3.81 (6H, m), 4.00-4.21 (3H, m), 4.45-4.54 (1H, m), 5.15-5.35 (3H, m), 5.41 (1H, d, J=17.2 Hz), 5.45 (1H, d, J=17.2 Hz), 6.54 (1H, s), 7.11-7.26 (6H, m), 7.32 (1H, s), 7.78 (1H, d, J=11.0 Hz), 7.93-8.00 (1H, m), 8.03 (1H, d, J=9.4 Hz), 8.06-8.13 (1H, m), 8.21-8.27 (2H, m), 8.30-8.36 (1H, m).

MS (APCI) m/z: 841 (M+H)$^+$

Process 7: N-[6-(2,5-Dioxo-2,5-dihydro-1H-pyrrol-1-yl)hexanoyl]glycylglycyl-L-phenylalanyl-N-[2-({[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]carbamoyl}oxy)ethyl]glycinamide The compound (42.0 mg, 0.0499 mmol) obtained in Process 6 was reacted in the same manner as Process 3 of Example 2 to yield the titled compound as a pale yellow solid (38.3 mg, 74%).

$^1$H-NMR (400 MHz, DMSO-$d_6$) δ: 0.87 (3H, t, J=7.4 Hz), 1.12-1.23 (2H, m), 1.40-1.51 (4H, m), 1.80-1.95 (2H, m), 2.05-2.27 (4H, m), 2.38 (3H, s), 3.43-2.40 (8H, m), 3.53-3.78 (6H, m), 4.00-4.21 (2H, m), 4.44-4.55 (1H, m), 5.17-5.36 (3H, m), 5.43 (2H, s), 6.54 (1H, s), 6.99 (2H, s), 7.19 (5H, d, J=23.9 Hz), 7.33 (1H, s), 7.78 (1H, d, J=10.6 Hz), 7.91-8.16 (5H, m), 8.24-8.31 (1H, m).

MS (ESI) m/z: 1034 (M+H)$^+$

Process 8: Antibody-Drug Conjugate (41)

By using the trastuzumab produced in Reference Example 1 and the compound obtained in Process 7 above, the titled antibody-drug conjugate was obtained in the same manner as Process 2 of Example 6.

Antibody concentration: 1.54 mg/mL, antibody yield: 9.2 mg (74%), and average number of conjugated drug molecules (n) per antibody molecule: 3.7.

Example 42 Antibody-Drug Conjugate (42)

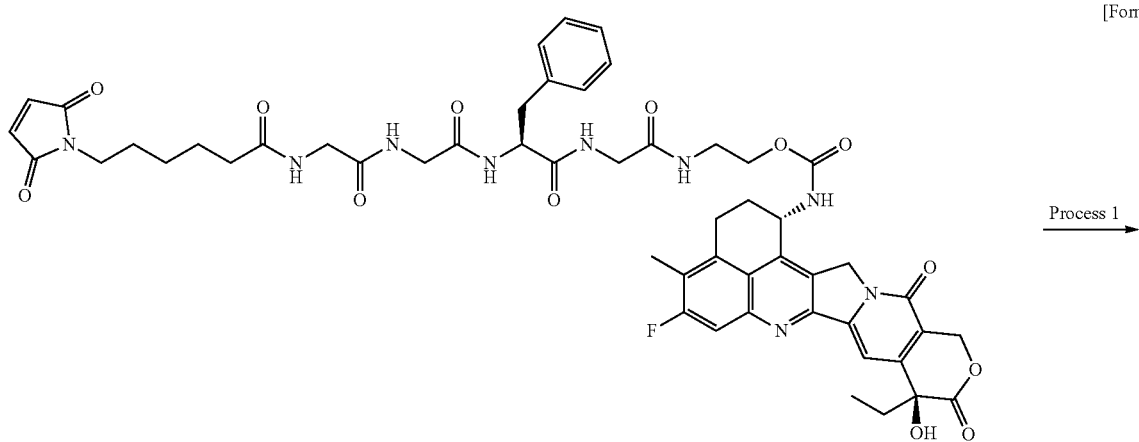

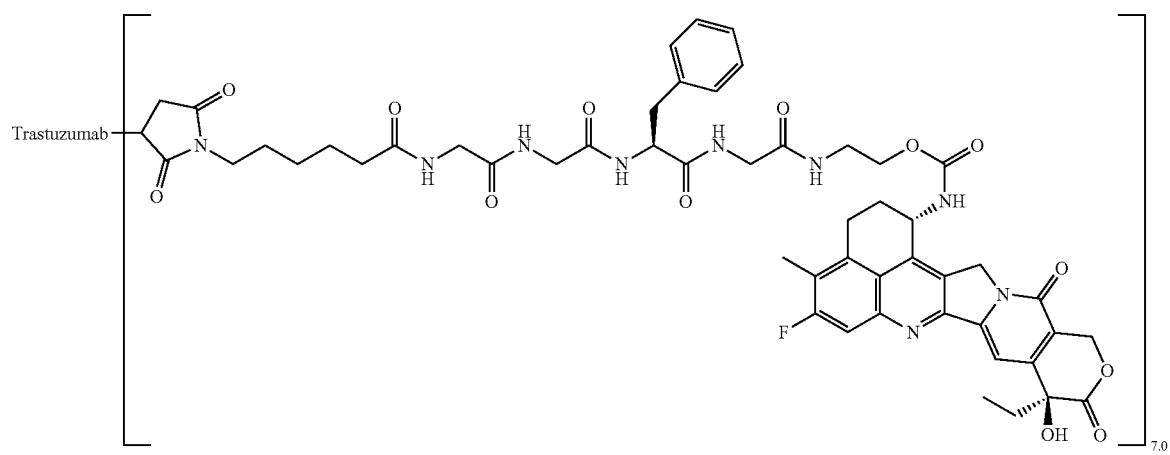

Process 1: Antibody-Drug Conjugate (42)

By using the trastuzumab produced in Reference Example 1 and the compound obtained in Process 7 of Example 41, the titled antibody-drug conjugate was obtained in the same manner as Process 1 of Example 7.

Antibody concentration: 1.47 mg/mL, antibody yield: 8.8 mg (71%), and average number of conjugated drug molecules (n) per antibody molecule: 7.0.

Example 43 Antibody-Drug Conjugate (43)
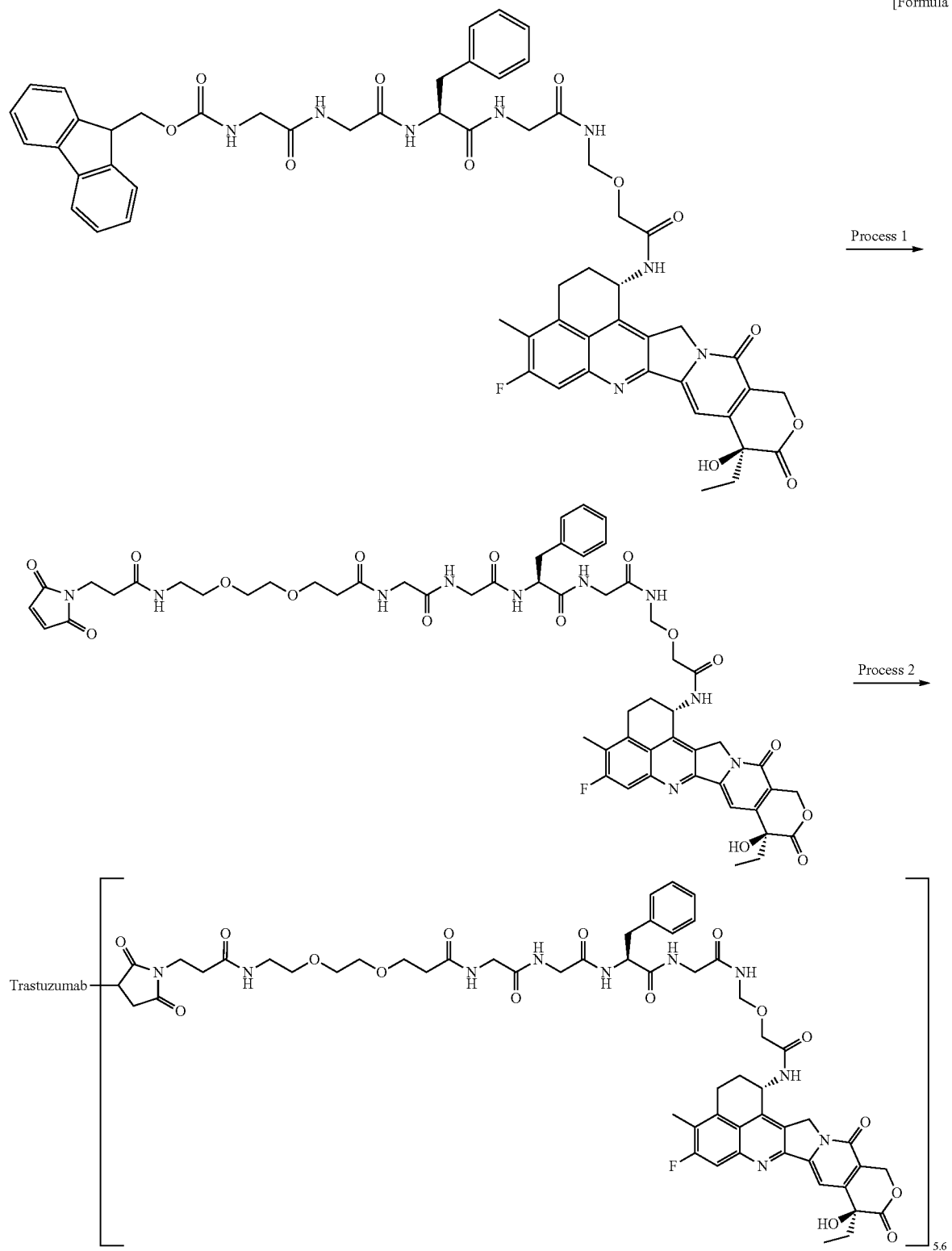

Process 1: N-{3-[2-(2-{[3-(2,5-Dioxo-2,5-dihydro-
1H-pyrrol-1-yl)propanoyl]amino}ethoxy)ethoxy]
propanoyl}glycylglycyl-L-phenylalanyl-N-[(2-{[(1,
9S)-9-ethyl-5-fluoro-9-hydroxy-4-methyl-10,13-
dioxo-2,3,9,10,13,15-hexahydro-1H,12H-benzo[de]
pyrano[3',4':6,7]indolizino[1,2-b]quinolin-1-yl]
amino}-2-oxoethoxy)methyl]glycinamide The compound (53.7 mg, 50.5 µmol) obtained in Process 6 of Example 26 was dissolved in N,N-dimethylformamide (1.50 mL) After adding 1,8-diazabicyclo(5.4.0)-7-undecene (7.5 µL, 50.5 µmol), it was stirred at room temperature for 30 minutes. The reaction solution was charged with pyridinium p-toluenesulfonate (14.0 mg, 5.56 µmol), then charged with N-succinimidyl 3-(2-(2-(3-maleinimidopropanamido)ethoxy)ethoxy)propanoate (32.3 mg, 75.8 µmol), and stirred at room temperature for 2.25 hours. The solvent was removed under reduced pressure, and the residue obtained was purified by silica gel column chromatography [[chloroform-partitioned organic layer of chloroform:methanol:water=7:3:1 (v/v/v)] to yield the titled compound as a pale yellow solid (27.1 mg, 47%).

$^{1}$H-NMR (DMSO-$d_6$) δ: 0.87 (3H, t, J=7.0 Hz), 1.79-1.91 (2H, m), 2.18 (2H, t, J=15.1 Hz), 2.29-2.33 (4H, m), 2.39 (3H, s), 2.76 (1H, dd, J=13.9, 9.2 Hz), 3.02 (1H, dd, J=13.7, 3.9 Hz), 3.13-3.15 (2H, m), 3.44-3.46 (6H, m), 3.57-3.59 (6H, m), 3.69-3.75 (6H, m), 4.01 (2H, s), 4.46-4.48 (1H, m), 4.63 (2H, d, J=6.3 Hz), 5.21 (2H, s), 5.42 (2H, s), 5.60 (1H, dd, J=13.5, 5.7 Hz), 6.54 (1H, s), 7.00 (2H, s), 7.17-7.24 (6H, m), 7.31 (1H, s), 7.79 (1H, d, J=11.0 Hz), 8.00-8.02 (2H, m), 8.13 (1H, d, J=7.8 Hz), 8.17 (1H, t, J=6.3 Hz), 8.52 (1H, d, J=9.0 Hz), 8.65 (1H, t, J=6.5 Hz).

MS (ESI) m/z=1151 (M+H)$^{+}$

Process 2: Antibody-Drug Conjugate (43)

By using the trastuzumab produced in Reference Example 1 and the compound obtained in Process 1, the titled antibody-drug conjugate was obtained in the same manner as Process 1 of Example 7.
Antibody concentration: 1.96 mg/mL, antibody yield: 17.6 mg (88%), and average number of conjugated drug molecules (n) per antibody molecule: 5.6.

Example 44 Antibody-Drug Conjugate (44)

[Formula 70]

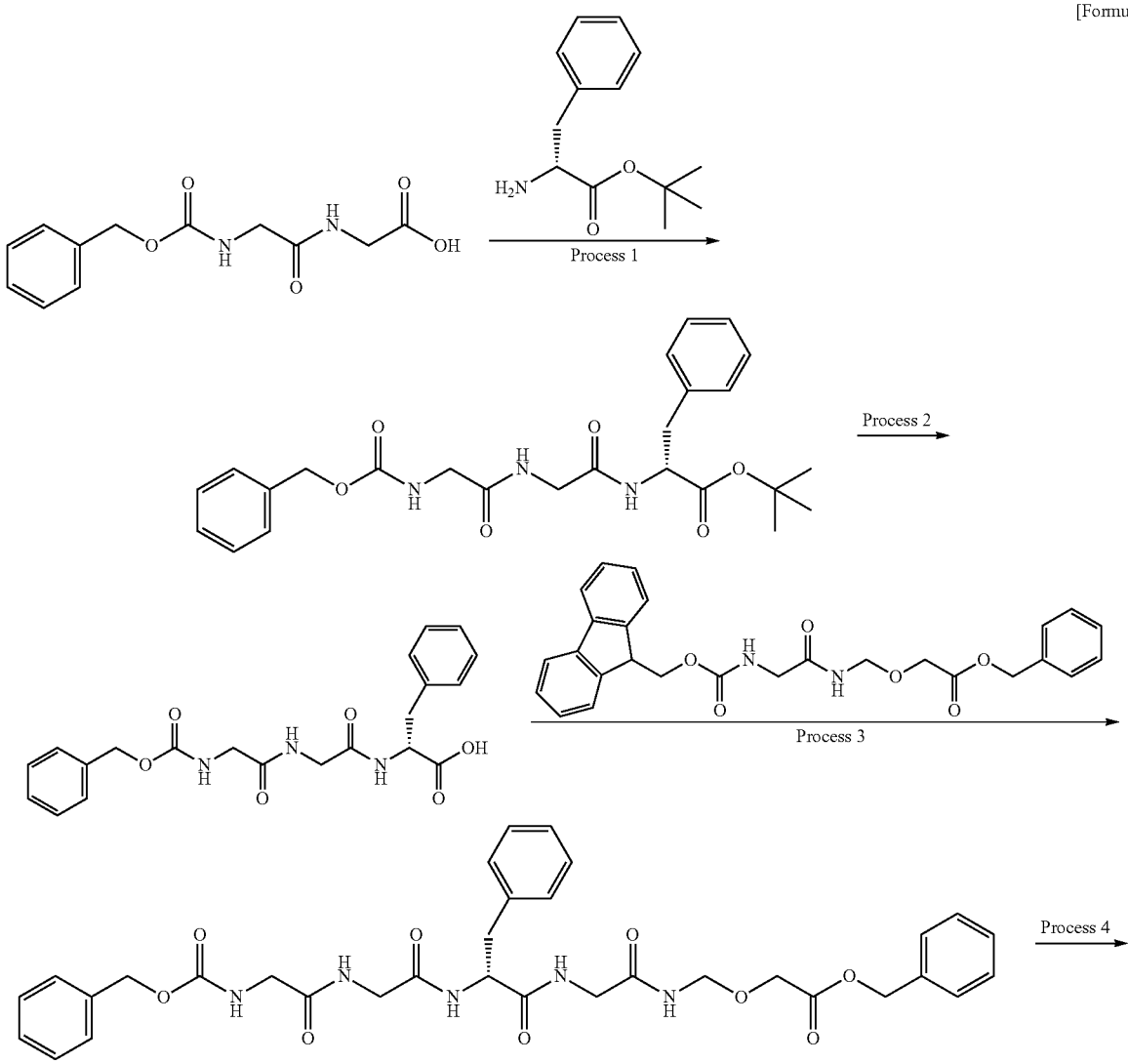

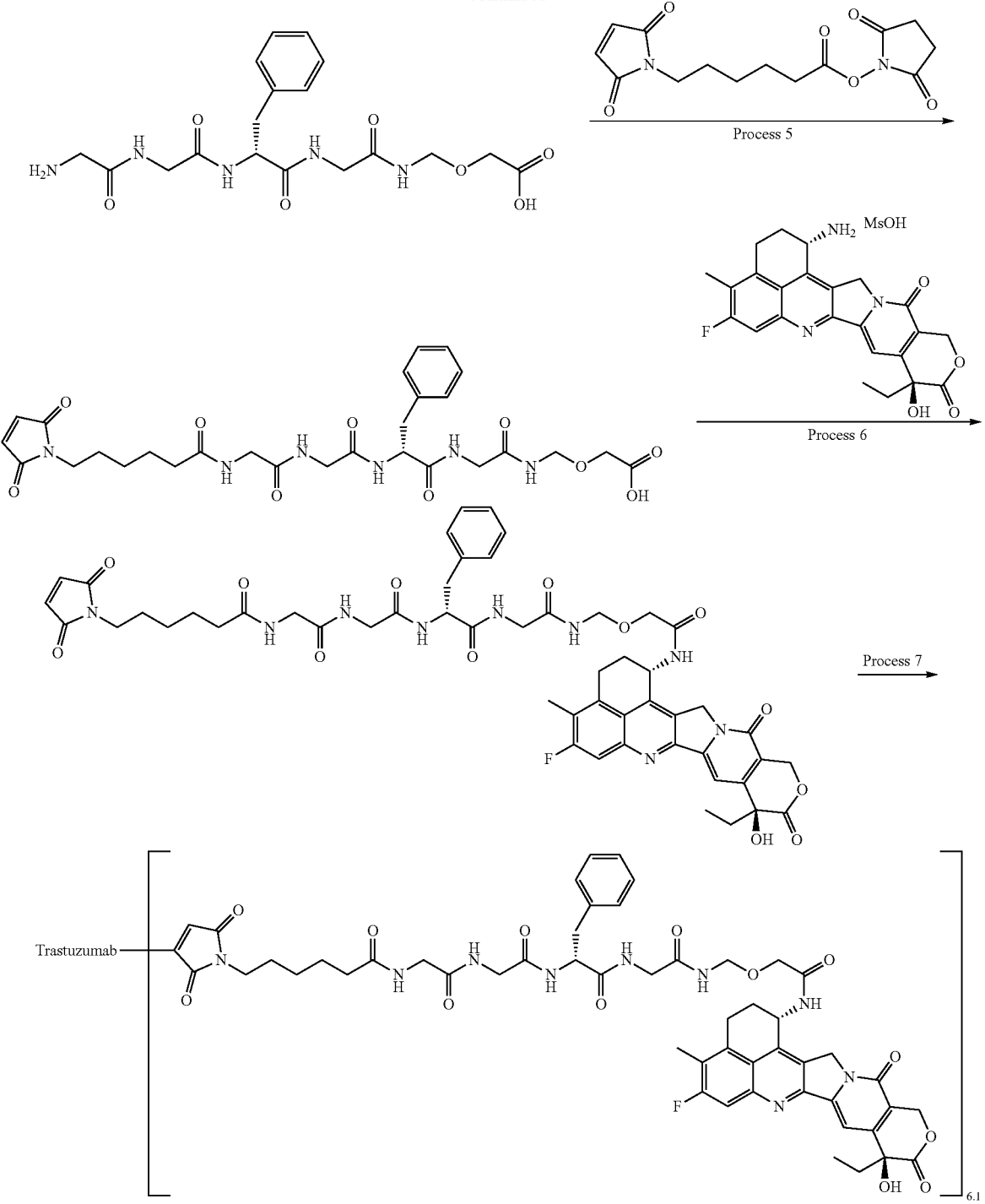

Process 1: tert-Butyl N-[(benzyloxy)carbonyl]glycylglycyl-D-phenylalaninate

N-[(Benzyloxy)carbonyl]glycylglycine (3.00 g, 11.3 mmol) was dissolved in N,N-dimethylformamide (20.0 mL). After adding N-hydroxysuccinimide (1.43 g, 12.4 mmol) and 1-ethyl-3-(3-dimethylaminopropyl)carbodiimide hydrochloride (2.37 g, 12.4 mmol), it was stirred for 1 hour. A N,N-dimethylformamide solution (10 mL) charged with D-phenylalanine tert-butyl (2.74 g, 12.38 mmol) and triethylamine (1.73 mL, 12.4 mmol) was added dropwise to the reaction solution and stirred at room temperature for 2 hours. The reaction solution was charged with dichloromethane and washed with water, 1 N hydrochloric acid, and a saturated aqueous solution of sodium bicarbonate, and then the organic layer was dried over anhydrous sodium sulfate. The solvent was removed under reduced pressure, and the residue obtained was purified by silica gel column chromatography [chloroform-chloroform:methanol=9:1 (v/v)] to yield the titled compound as a colorless solid (4.21 g, 80%).

¹H-NMR (CDCl₃) δ: 1.41 (9H, s), 3.03-3.14 (2H, m), 3.86-3.97 (4H, m), 4.70-4.77 (1H, m), 5.13 (2H, s), 5.43 (1H, brs), 6.42 (1H, d, J=10.0 Hz), 6.64-6.71 (1H, m), 7.11-7.15 (2H, m), 7.20-7.31 (4H, m), 7.31-7.38 (4H, m).
MS (APCI) m/z: 470 (M+H)⁺

Process 2: N-[(Benzyloxy)carbonyl]glycylglycyl-D-phenylalanine

The compound (4.21 g, 8.97 mmol) obtained in Process 1 was dissolved in ethyl acetate (20 mL). After adding an ethyl acetate solution (20.0 mL) of 4 N hydrogen chloride, it was left overnight at room temperature. The solvent was removed under reduced pressure, then toluene was added, and the solvent was removed under reduced pressure. The residue obtained was purified by silica gel column chromatography [chloroform-partitioned organic layer of chloroform:methanol:water=7:3:1 (v/v/v)] to yield the titled compound as a colorless solid (1.66 g, 45%).
¹H-NMR (CDCl₃) δ: 2.92-3.01 (1H, m), 3.10-3.18 (1H, m), 3.65-3.81 (3H, m), 3.88-3.98 (1H, m), 4.64-4.73 (1H, m), 5.06 (2H, s), 5.87 (1H, brs), 7.10-7.37 (13H, m).
MS (APCI) m/z: 412 (M+H)

Process 3: N-[(Benzyloxy)carbonyl]glycylglycyl-D-phenylalanyl-N-{[2-(benzyloxy)-2-oxoethoxy]methyl}glycinamide To a dioxane (25.0 mL) solution of the compound (1.25 g, 2.63 mmol) obtained in Process 1 of Example 32, piperidine (5.00 mL) and N,N-dimethylformamide (5.00 mL) were added and stirred at room temperature for 30 minutes. The solvent was removed under reduced pressure, and the residue obtained was dissolved in N,N-dimethylformamide (20.0 mL). After adding the compound (1.20 g, 2.90 mmol) of Process 2 above and 4-(4,6-dimethoxy-1,3,5-triazin-2-yl)-4-methylmorpholinium chloride (1.03 g, 3.16 mmol) containing 16.4% water, it was stirred at room temperature for 2 hours. The reaction solution was charged with chloroform and washed with water, and then the organic layer was dried over anhydrous sodium sulfate. The solvent was removed under reduced pressure, and the residue obtained was purified by silica gel column chromatography [chloroform-chloroform:methanol=9:1 (v/v)] to yield the titled compound as a colorless solid (270 mg, 16%).
¹H-NMR (DMSO-d₆) δ: 2.78 (1H, dd, J=13.6, 10.0 Hz), 3.05 (1H, dd, J=13.9, 4.2 Hz), 3.56-3.79 (6H, m), 4.15 (2H, s), 4.47-4.54 (1H, m), 4.63 (2H, d, J=6.7 Hz), 5.03 (2H, s), 5.15 (2H, s), 7.14-7.39 (15H, m), 7.50 (1H, t, J=5.7 Hz), 8.02 (1H, t, J=5.4 Hz), 8.16 (1H, d, J=7.9 Hz), 8.34 (1H, t, J=6.0 Hz), 8.60 (1H, t, J=7.0 Hz).
MS (APCI) m/z: 648 (M+H)⁺

Process 4: Glycylglycyl-D-phenylalanyl-N-[(carboxymethoxy)methyl]glycinamide

The compound (200 mg, 0.31 mmol) obtained in Process 3 above was dissolved in N,N-dimethylformamide (5.0 mL). After adding 5% palladium carbon catalyst (0.12 g), it was stirred under a hydrogen atmosphere at room temperature for 9 hours. The reaction solution was filtered through Celite, and the residue was washed with a mixed solvent of water and N,N-dimethylformamide. The filtrate and the wash were combined, and the solvent was removed under reduced pressure to yield the titled compound as a colorless solid (0.15 g, quantitative).
¹H-NMR (DMSO-d₆) δ: 2.85 (1H, dd, J=13.3, 9.7 Hz), 3.08 (1H, dd, J=13.9, 5.4 Hz), 3.43-3.52 (4H, m), 3.62-3.89 (7H, m), 4.36-4.44 (1H, m), 4.58-4.67 (2H, m), 7.12-7.29 (5H, m), 8.44 (1H, t, J=5.7 Hz), 8.67 (1H, d, J=7.3 Hz), 8.78 (1H, t, J=5.4 Hz), 8.91 (1H, brs).
MS (APCI) m/z: 424 (M+H)⁺

Process 5: N-[6-(2,5-Dioxo-2,5-dihydro-1H-pyrrol-1-yl)hexanoyl]glycylglycyl-D-phenylalanyl-N-[(carboxymethoxy)methyl]glycinamide The compound (0.15 g, 0.35 mmol) obtained in Process 4 above was dissolved in N,N-dimethylformamide (10 mL). After adding N-succinimidyl 6-maleimide hexanoate (0.11 g, 0.35 mmol), it was stirred at room temperature for 1 hour. The reaction solution was charged with chloroform and washed with water, and then the organic layer was dried over anhydrous sodium sulfate. The solvent was removed under reduced pressure, and the residue obtained was purified by silica gel column chromatography [chloroform-partitioned organic layer of chloroform:methanol:water=7:3:1 (v/v/v)] to yield the titled compound as a colorless solid (41 mg, 26%).
¹H-NMR (DMSO-d₆) δ: 1.13-1.24 (2H, m), 1.42-1.53 (4H, m), 2.12 (2H, t, J=7.3 Hz), 2.82 (1H, dd, J=13.9, 10.0 Hz), 3.09 (1H, dd, J=13.9, 4.8 Hz), 3.17 (2H, d, J=4.2 Hz), 3.47-3.89 (8H, m), 4.08-4.14 (1H, m), 4.41-4.49 (1H, m), 4.58-4.69 (2H, m), 7.00 (2H, s), 7.14-7.27 (5H, m), 8.31 (1H, t, J=6.0 Hz), 8.39 (1H, brs), 8.55 (2H, brs), 8.93 (1H, brs).
MS (APCI) m/z: 615 (M-H)

Process 6: N-[6-(2,5-Dioxo-2,5-dihydro-1H-pyrrol-1-yl)hexanoyl]glycylglycyl-D-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethoxy)methyl]glycinamide To a N,N-dimethylformamide (10 mL) solution of methanesulfonic acid salt of exatecan (22 mg, 0.388 mmol), triethylamine (5.42 μL, 0.388 mmol), the compound (29 mg, 0.466 mmol) obtained in Process 5 above, and 4-(4,6-dimethoxy-1,3,5-triazin-2-yl)-4-methylmorpholinium chloride (19 mg, 0.686 mmol) containing 16.4% water were added at 0° C. and stirred at room temperature for 1 hour. The solvent in the reaction solution was removed under reduced pressure, and then the residue obtained was purified by silica gel column chromatography [chloroform-partitioned organic layer of chloroform:methanol:water=7:3:1 (v/v/v)] to yield the titled compound as a pale yellow solid (26 mg, 65%).
¹H-NMR (DMSO-d₆) δ: 0.87 (3H, t, J=7.3 Hz), 1.12-1.22 (2H, m), 1.40-1.51 (4H, m), 1.79-1.92 (2H, m), 2.09 (2H, t, J=7.6 Hz), 2.13-2.23 (2H, m), 2.39 (3H, s), 2.78 (1H, dd, J=13.6, 9.4 Hz), 2.98-3.05 (1H, m), 3.13-3.23 (2H, m), 3.54-3.78 (8H, m), 4.02 (2H, s), 4.41-4.50 (1H, m), 4.61-4.66 (2H, m), 5.21 (2H, s), 5.42 (2H, s), 5.56-5.64 (1H, m), 6.53 (1H, s), 6.99 (2H, s), 7.14-7.27 (5H, m), 7.31 (1H, s), 7.79 (1H, d, J=10.9 Hz), 8.01 (1H, t, J=5.4 Hz), 8.07 (1H, t, J=5.7 Hz), 8.14 (1H, d, J=7.9 Hz), 8.31 (1H, t, J=5.7 Hz), 8.53 (1H, d, J=9.1 Hz), 8.63 (1H, t, J=6.3 Hz).
MS (APCI) m/z: 1034 (M+H)⁺

Process 7: Antibody-Drug Conjugate (44)

By using the trastuzumab produced in Reference Example 1 and the compound obtained in Process 6 above, the titled antibody-drug conjugate was obtained in the same manner as Process 1 of Example 7.
Antibody concentration: 1.87 mg/mL, antibody yield: 16.8 mg (84%), and average number of conjugated drug molecules (n) per antibody molecule: 6.1.

Example 45 Intermediate (45)

[Formula 71]

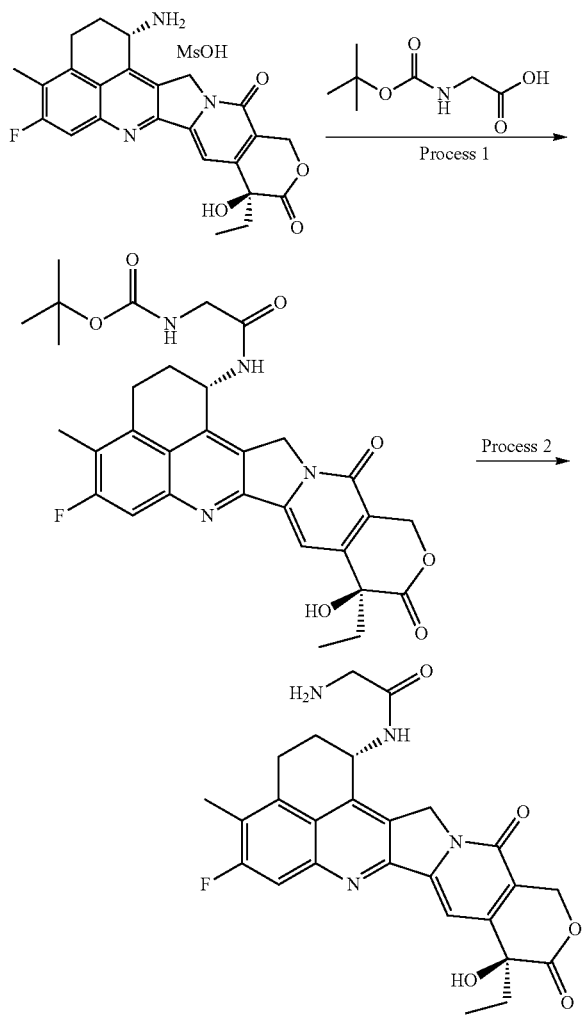

Process 1: tert-Butyl (2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]amino}-2-oxoethyl) carbamate To a dichloromethane (3.00 mL) solution of N-(tert-butoxycarbonyl)-glycine (0.395 g, 2.26 mmol), N-hydroxysuccinimide (0.260 g, 2.26 mmol) and 1-ethyl-3-(3-dimethylaminopropyl)carbodiimide hydrochloride (0.433 mg, 2.26 mmol) were added and stirred at room temperature for 1 hour. This solution was added to a solution consisting of methanesulfonic acid salt of exatecan (1.00 g, 1.88 mmol), triethylamine (0.315 mL, 2.26 mmol), and N,N-dimethylformamide (3.00 mL) and stirred at room temperature for 16.5 hours. The reaction solution was diluted with chloroform and washed with 10% citric acid solution, and then the organic layer was dried over anhydrous sodium sulfate. The solvent was removed under reduced pressure, and the residue obtained was purified by silica gel column chromatography [chloroform-chloroform:methanol=9:1 (v/v)] to yield the titled compound as a yellow solid (1.16 g, 99%).

$^1$H-NMR (400 MHz, DMSO-$d_6$) δ: 0.86 (3H, t, J=7.2 Hz), 1.30 (9H, s), 1.81-1.89 (2H, m), 2.09-2.21 (2H, m), 2.38 (3H, s), 3.15-3.17 (2H, m), 3.55-3.56 (2H, m), 5.15 (1H, d, J=18.8 Hz), 5.23 (1H, d, J=19.2 Hz), 5.41 (2H, s), 5.55-5.56 (1H, m), 6.53 (1H, s), 6.95 (1H, t, J=5.5 Hz), 7.28 (1H, s), 7.77 (1H, d, J=11.0 Hz), 8.39 (1H, d, J=8.6 Hz).

MS (APCI) m/z: 593 (M+H)$^+$

Process 2: N-[(1S,9S)-9-Ethyl-5-fluoro-9-hydroxy-4-methyl-10,13-dioxo-2,3,9,10,13,15-hexahydro-1H,12H-benzo[de]pyrano[3',4':6,7]indolizino[1,2-b]quinolin-1-yl]glycinamide The compound (0.513 g, 1.01 mmol) obtained in Process 1 above was reacted in the same manner as Process 2 of Example 1 to yield the titled compound as a yellow solid (0.463 g, 93%).

$^1$H-NMR (400 MHz, CD$_3$OD) δ: 0.96 (3H, t, J=7.0 Hz), 1.89-1.91 (2H, m), 2.14-2.16 (1H, m), 2.30 (3H, s), 2.40-2.42 (1H, m), 3.15-3.21 (2H, m), 3.79-3.86 (2H, m), 4.63-4.67 (1H, m), 5.00-5.05 (1H, m), 5.23 (1H, d, J=16.0 Hz), 5.48 (1H, d, J=16.0 Hz), 5.62-5.64 (1H, m), 7.40-7.45 (2H, m).

MS (APCI) m/z: 493 (M+H)$^+$

Example 46 Antibody-Drug Conjugate (46)

[Formula 72]

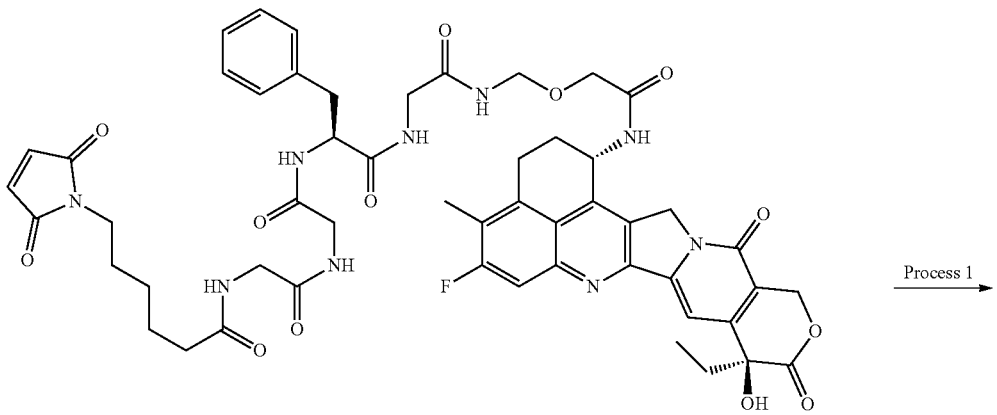

Process 1

-continued

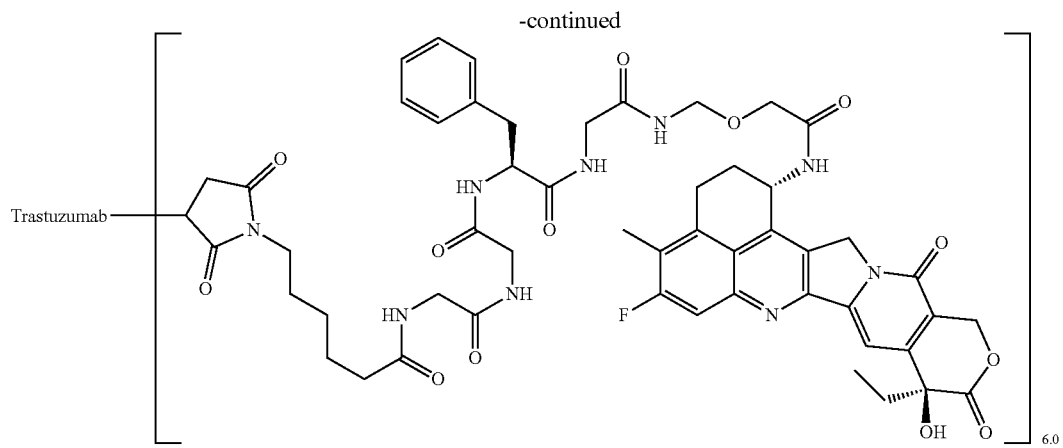

Process 1: Antibody-Drug Conjugate (46)

Reduction of the antibody: The trastuzumab produced in Reference Example 1 was prepared to have an antibody concentration of 10 mg/mL by replacing the medium with PBS6.0/EDTA by using the Common procedure C-1 and Common procedure B (as absorption coefficient at 280 nm, 1.48 mLmg$^{-1}$ cm$^{-1}$ was used). The solution (50 mL) was placed in a 125 mL polycarbonate Erlenmeyer flask, charged with an aqueous solution of 1 M dipotassium hydrogen phosphate at room temperature (0.750 mL) with stirring using a magnetic stirrer, and then charged with an aqueous solution of 10 mM TCEP (1.857 mL; 5.4 equivalents per antibody molecule). After confirming that the solution had a pH of 7.0±0.1, stirring was terminated, and the disulfide bond at the hinge part in the antibody was reduced by incubating at 37° C. for 1 hour. Conjugation between antibody and drug linker: After cooling the above solution to 15° C., a DMSO solution containing 10 mM of the compound of Process 8 of Example 26 (2.958 mL; 8.6 equivalents per antibody molecule) was gradually added dropwise thereto with stirring. At 15° C., the reaction solution was stirred for the first 30 minutes and incubated without stirring for conjugating the drug linker to the antibody for the next 1 hour. Next, an aqueous solution (0.444 mL; 12.9 equivalents per antibody molecule) of 100 mM NAC was added thereto with stirring and stirred at room temperature to terminate the reactivity of unreacted drug linkers for another 20 minutes.

Purification: By gradually adding 20% aqueous acetic acid solution (about 0.25 mL) and ABS (50 mL) to the above solution with stirring, the pH of the solution was adjusted to 5.5±0.1. This solution was subjected to microfiltration (Millipore Corp., Millex-HV filter, 0.45 µm, PVDF membrane) to remove whitish matter. This solution was subjected to ultrafiltration purification using an ultrafiltration apparatus composed of an ultrafiltration membrane (Merck Japan, Pellicon XL Cassette, Biomax 50 KDa), a tube pump (Cole-Parmer International, MasterFlex Pump model 77521-40, Pump Head model 7518-00), and a tube (Cole-Parmer International, MasterFlex Tube L/S16). Specifically, while ABS was added dropwise (a total of 800 mL) as a buffer solution for purification to the reaction solution, ultrafiltration purification was performed for removing unconjugated drug linkers and other low-molecular-weight reagents, also replacing the buffer solution with ABS, and further concentrating the solution. The purified solution obtained was subjected to microfiltration (0.22 m (Millipore Corp., Millex-GV filter, PVDF membrane) and 0.10 m (Millipore Corp., Millex-VV filter, PVDF membrane)) to yield 42.5 mL of a solution containing the titled antibody-drug conjugate. Physicochemical characterization: By using the Common procedures E and F ($\varepsilon_{D,280}$=5178 (measured value), and $\varepsilon_{D,370}$=20217 (measured value) were used), the following characteristic values were obtained.

Antibody concentration: 10.4 mg/mL, antibody yield: 442 mg (88.5%), average number of conjugated drug molecules (n) per antibody molecule measured by the Common procedure E: 6.0, and average number of conjugated drug molecules (n) per antibody molecule measured by the Common procedure F: 7.5.

Example 47 Antibody-Drug Conjugate (47)

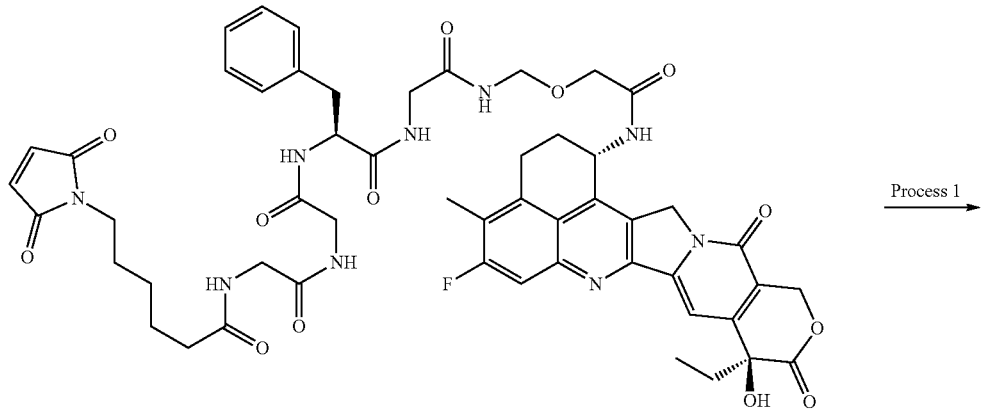

[Formula 73]

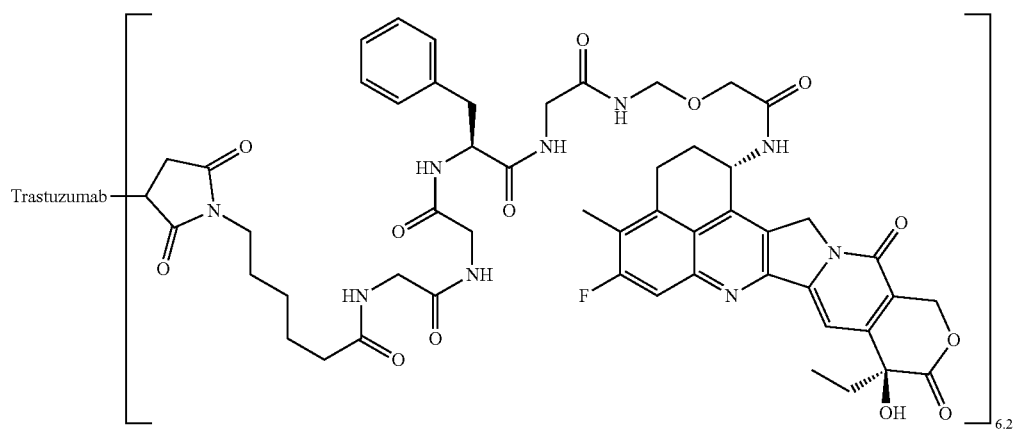

Process 1: Antibody-Drug Conjugate (47)

Reduction of the antibody: The trastuzumab produced in Reference Example 1 was prepared to have an antibody concentration of 10 mg/mL by replacing the medium with PBS6.0/EDTA by using the Common procedure C-1 and Common procedure B (as absorption coefficient at 280 nm, 1.48 mLmg$^{-1}$ cm$^{-1}$ was used). The solution (15 mL) was placed in a polypropylene tube and charged with an aqueous solution of 10 mM TCEP (0.567 mL; 5.5 equivalents per antibody molecule) and an aqueous solution of 1 M dipotassium hydrogen phosphate (0.225 mL). After confirming that the solution had a pH of 7.0±0.1, the disulfide bond at the hinge part in the antibody was reduced by incubating at 37° C. for 2 hour.

Conjugation between antibody and drug linker: After adding DMSO (0.146 mL) and a DMSO solution containing 10 mM of the compound of Process 8 of Example 26 (0.928 mL; 9.0 equivalents per antibody molecule) to the above solution at room temperature, it was incubated for conjugating the drug linker to the antibody at 15° C. for 30 minutes. Next, an aqueous solution (0.133 mL; 12.9 equivalents per antibody molecule) of 100 mM NAC was added thereto and stirred at room temperature to terminate the reactivity of unreacted drug linkers for another 20 minutes.

Purification: The above solution was subjected to purification using the Common procedure D (ABS was used as buffer solution) to yield 49 mL of a solution containing the compound of interest.

Physicochemical characterization: By using the Common procedure E ($\varepsilon_{D,280}$=5178 and $\varepsilon_{D,370}$=20217 were used), the following characteristic values were obtained.

Antibody concentration: 2.91 mg/mL, antibody yield: 143 mg (95%), and average number of conjugated drug molecules (n) per antibody molecule: 6.2.

Example 48 Antibody-Drug Conjugate (48)

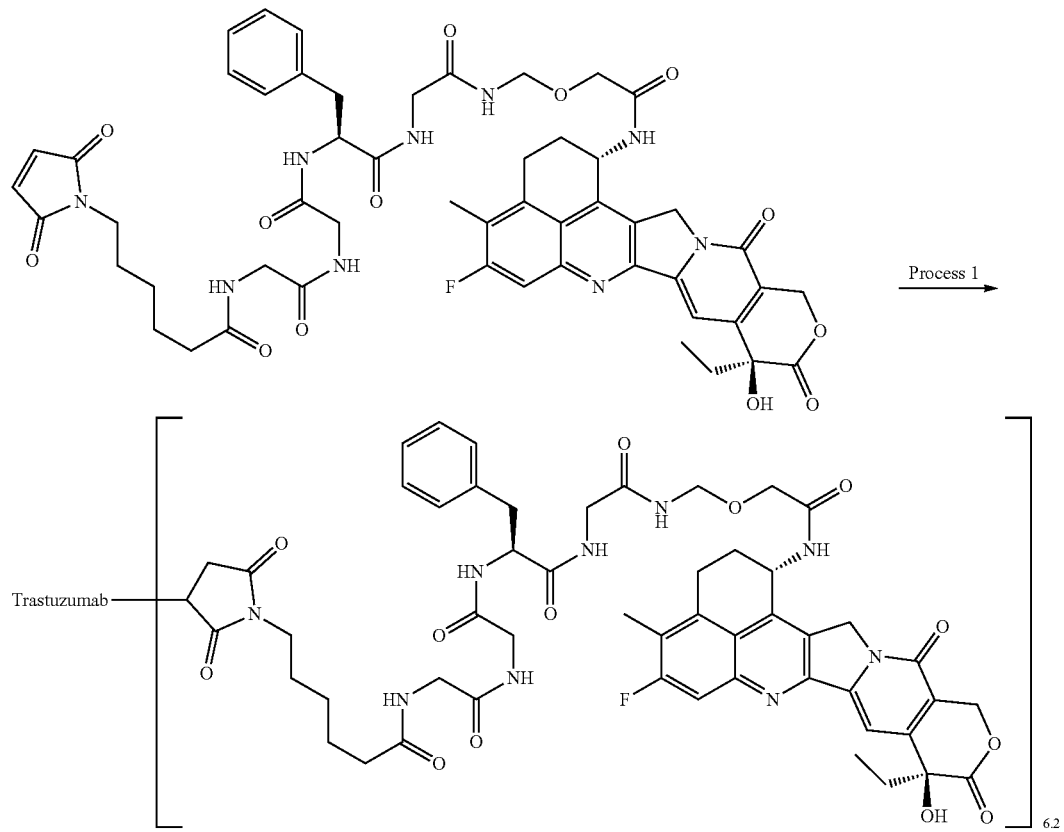

[Formula 74]

Process 1

Process 1: Antibody-Drug Conjugate (48)

Reduction of the antibody: The trastuzumab produced in Reference Example 1 was prepared to have an antibody concentration of 10 mg/mL by replacing the medium with PBS6.0/EDTA by using the Common procedure C-1 and Common procedure B (as absorption coefficient at 280 nm, 1.48 mLmg$^{-1}$ cm$^{-1}$ was used). The solution (280 mL) was placed in a 1000 mL polycarbonate Erlenmeyer flask, charged with an aqueous solution of 1 M dipotassium hydrogen phosphate at room temperature (4.200 mL) with stirring using a magnetic stirrer, and then charged with an aqueous solution of 10 mM TCEP (10.594 mL; 5.5 equivalents per antibody molecule). After confirming that the solution had a pH of 7.4±0.1, stirring was terminated, and the disulfide bond at the hinge part in the antibody was reduced by incubating at 37° C. for 2 hour. Conjugation between antibody and drug linker: After cooling the above solution to 15° C., a DMSO solution containing 10 mM of the compound of Process 8 of Example 26 (17.335 mL; 9.0 equivalents per antibody molecule) was gradually added dropwise thereto with stirring. The reaction solution was stirred at 15° C. for conjugating the drug linker to the antibody for 30 minutes. Next, an aqueous solution (2.485 mL; 12.9 equivalents per antibody molecule) of 100 mM NAC was added thereto with stirring and stirred at room temperature to terminate the reactivity of unreacted drug linkers for another 20 minutes.

Purification: By gradually adding 20% aqueous acetic acid solution (about 1.4 mL) and ABS (280 mL) to the above solution with stirring, the pH of the solution was adjusted to 5.5±0.1. This solution was subjected to microfiltration (0.45 µm, PVDF membrane) to remove whitish matter while yielding about 600 mL of a filtrate. This solution was subjected to ultrafiltration purification using an ultrafiltration apparatus composed of an ultrafiltration membrane (Merck Japan, Pellicon XL Cassette, Biomax 50 KDa), a tube pump (Cole-Parmer International, MasterFlex Pump model 77521-40, Pump Head model 7518-00), and a tube (Cole-Parmer International, MasterFlex Tube L/S16). Specifically, while ABS was added dropwise (a total of 4800 mL) as a buffer solution for purification to the reaction solution, ultrafiltration purification was performed for removing unconjugated drug linkers and other low-molecular-weight reagents, also replacing the buffer solution with ABS, and further concentrating the solution. The purified solution obtained was subjected to microfiltration (twice with 0.22 µm and 0.10 m, PVDF membrane) to yield 70 mL of a solution containing the titled antibody-drug conjugate.

Physicochemical characterization: By using the Common procedure E ($\varepsilon_{D,280}$=5178 and $\varepsilon_{D,370}$=20217 were used), the following characteristic values were obtained.

Antibody concentration: 35.96 mg/mL, antibody yield: 2517 mg (90%), and average number of conjugated drug molecules (n) per antibody molecule: 6.2.

Example 49 Antibody-Drug Conjugate (49)

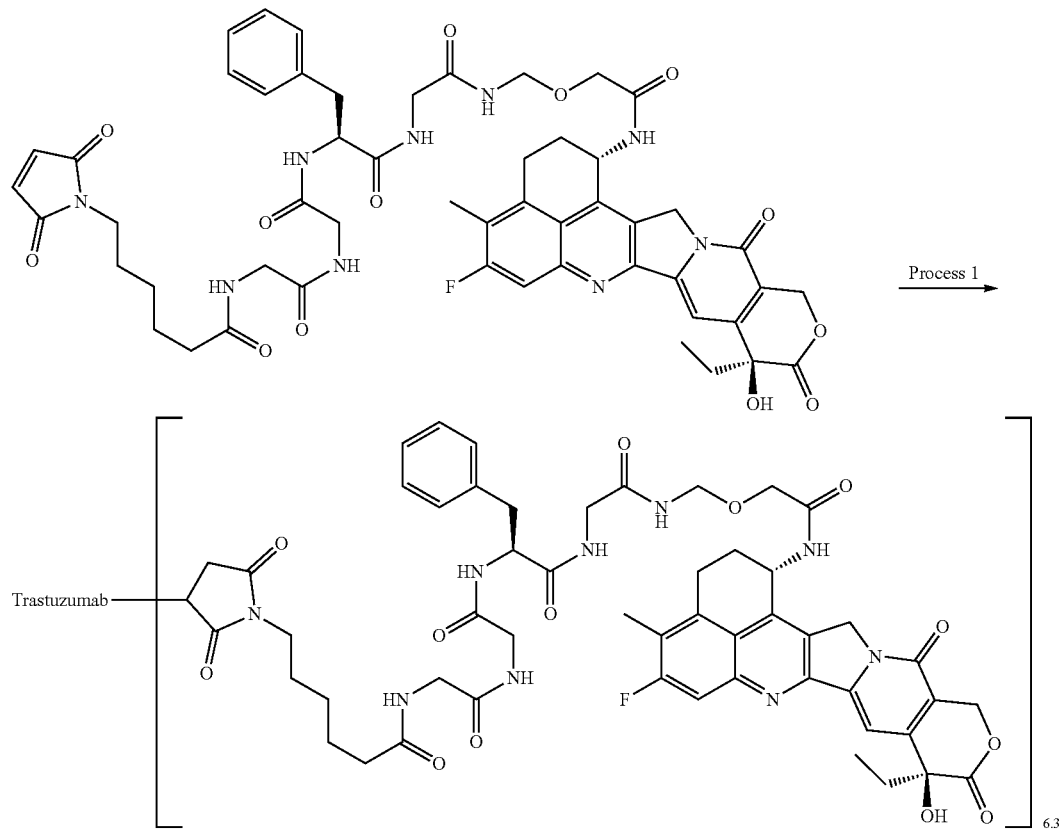

[Formula 75]

Process 1: Antibody-Drug Conjugate (49)

Reduction of the antibody: The trastuzumab produced in Reference Example 1 was prepared to have an antibody concentration of 10 mg/mL by replacing the medium with PBS6.0/EDTA by using the Common procedure C-1 and Common procedure B (as absorption coefficient at 280 nm, 1.48 mLmg$^{-1}$ cm$^{-1}$ was used). The solution (280 mL) was placed in a 1000 mL polycarbonate Erlenmeyer flask, charged with an aqueous solution of 1 M dipotassium hydrogen phosphate at room temperature (4.200 mL) with stirring using a magnetic stirrer, and then charged with an aqueous solution of 10 mM TCEP (10.594 mL; 5.5 equivalents per antibody molecule). After confirming that the solution had a pH of 7.0±0.1, stirring was terminated, and the disulfide bond at the hinge part in the antibody was reduced by incubating at 37° C. for 2 hour. Conjugation between antibody and drug linker: After cooling the above solution to 15° C., a DMSO solution containing 10 mM of the compound of Process 8 of Example 26 (17.335 mL; 9.0 equivalents per antibody molecule) was gradually added dropwise thereto with stirring. The reaction solution was stirred at 15° C. for conjugating the drug linker to the antibody for 30 minutes. Next, an aqueous solution (2.485 mL; 12.9 equivalents per antibody molecule) of 100 mM NAC was added thereto with stirring and stirred at room temperature to terminate the reactivity of unreacted drug linkers for another 20 minutes.

Purification: By gradually adding 20% aqueous acetic acid solution (about 1.4 mL) and ABS (280 mL) to the above solution with stirring, the pH of the solution was adjusted to 5.5±0.1. This solution was subjected to microfiltration (0.45 μm, PVDF membrane) to remove whitish matter while yielding about 600 mL of a filtrate. This solution was subjected to ultrafiltration purification using an ultrafiltration apparatus composed of an ultrafiltration membrane (Merck Japan, Pellicon XL Cassette, Ultracell 30 KDa), a tube pump (Cole-Parmer International, MasterFlex Pump model 77521-40, Pump Head model 7518-00), and a tube (Cole-Parmer International, MasterFlex Tube L/S16). Specifically, while ABS was added dropwise (a total of 4800 mL) as a buffer solution for purification to the reaction solution, ultrafiltration purification was performed for removing unconjugated drug linkers and other low-molecular-weight reagents, also replacing the buffer solution with ABS, and further concentrating the solution. The purified solution obtained was subjected to microfiltration (twice with 0.22 μm and 0.10 μm, PVDF membrane) to yield 130 mL of a solution containing the titled antibody-drug conjugate.

Physicochemical characterization: By using the Common procedure E ($\varepsilon_{D,280}$=5178 and $\varepsilon_{D,370}$=20217 were used), the following characteristic values were obtained.

Antibody concentration: 21.00 mg/mL, antibody yield: 2730 mg (97.5%), and average number of conjugated drug molecules (n) per antibody molecule: 6.3.

Example 50 Antibody-Drug Conjugate (50)

Process 1: Antibody-Drug Conjugate (50)

The antibody-drug conjugates (47), (48), and (49) produced in Examples 47, 48, and 49 were mixed (243 mL) and further charged with ABS (39.75 mL) to yield 283 mL of a solution containing the titled antibody-drug conjugate. Physicochemical characterization: By using the Common procedures E and F ($\varepsilon_{D,280}$=5178, and $\varepsilon_{D,370}$=20217 were used), the following characteristic values were obtained. Antibody concentration: 20.0 mg/mL, antibody yield: 5655 mg, average number of conjugated drug molecules (n) per antibody molecule measured by the Common procedure E: 6.3, and average number of conjugated drug molecules (n) per antibody molecule measured by the Common procedure F: 7.8.

Evaluation Example 1 Cell Growth Inhibitory Effect (1) of Antibody-Drug Conjugate Human breast cancer line KPL-4 of HER2 antigen-positive cells (Dr. Junichi Kurebayashi, Kawasaki Medical School, British Journal of Cancer, (1999) 79 (5/6). 707-717) or human breast cancer line MCF7 of antigen-negative cells (European Collection of Cell Cultures; ECACC) was cultured in RPMI1640 (GIBCO) containing 10% fetal bovine serum (MOREGATE) (hereinafter, referred to as medium). The KPL-4 or MCF7 was prepared to have a concentration of $2.5\times10^4$ cells/mL by using medium, added at a concentration of 100 μL/well to a 96-well microplate for cell culture, and cultured overnight.

On the next day, trastuzumab or the antibody-drug conjugate diluted into 1000 nM, 200 nM, 40 nM, 8 nM, 1.6 nM, 0.32 nM, and 0.064 nM by using medium was added at a concentration of 10 μL/well to the microplate. Medium was added at a concentration of 10 μL/well to antibody non-supplemented wells. The cells were cultured under 5% $CO_2$ at 37° C. for 5 to 7 days. After the culture, the microplate was taken out from the incubator and left standing at room temperature for 30 minutes. The culture solution was charged with an equal amount of CellTiter-Glo Luminescent Cell Viability Assay (Promega) and stirred. After the microplate was left standing at room temperature for 10 minutes, luminescence intensity of each well was measured by using a plate reader (PerkinElmer). The $IC_{50}$ value was calculated according to the following equation:

$IC_{50}$ (nM)=antilog((50−$d$)×($LOG_{10}$($b$)−$LOG_{10}$($a$))/($d$−$c$)+$LOG_{10}$($b$))

a: Concentration of sample a
b: Concentration of sample b
c: Cell viability of sample a
d: Cell viability of sample b The cell viability at each concentration was calculated according to the following equation:

Cell viability (%)=$a/b$×100 a: Average luminescence intensity of the sample wells (n=2)
b: Average luminescence intensity of the antibody non-supplemented wells (n=10)

The antibody-drug conjugates (2), (3), (5), (7), (10), (12), (13), (16), (18), (40), and (42) exhibited a cell growth inhibitory effect of $IC_{50}$<0.1 (nM) against the KPL-4 cells.

The antibody-drug conjugates (4), (6), (9), (15), (17), (21), (22), (25), (36), (37), (39), (41), and (43) exhibited a cell growth inhibitory effect of 0.1<$IC_{50}$<1 (nM) against the cells.

The antibody-drug conjugates (20), (24), and (27) exhibited a cell growth inhibitory effect of 1<$IC_{50}$<100 (nM) against the cells. Neither of the antibody-drug conjugates (19) or (26) exhibited a cell growth inhibitory effect against the cells (>100 (nM)).

On the other hand, the antibody-drug conjugates (5), (13), and (43) exhibited a cell growth inhibitory effect of 1<$IC_{50}$<100 (nM) against the MCF7 cells, whereas none of the antibody-drug conjugates (2), (3), (4), (6), (7), (9), (10), (12), (15), (16), (17), (18), (25), (26), (27), (39), (40), (41), (42), and (44) exhibited a cell growth inhibitory effect against the cells (>100 (nM)).

Trastuzumab exhibited a cell growth inhibitory effect against neither the KPL-4 cells nor the MCF7 cells (>100 (nM)).

Evaluation Example 2 Antitumor Test (1)

Mouse: 5- to 6-week-old female nude mice (Charles River Laboratories Japan, Inc.) were acclimatized for 4 to 7 days under SPF conditions before use in the experiment. The mice were fed with sterilized solid feed (FR-2, Funabashi Farms Co., Ltd) and given sterilized tap water (prepared by the addition of 5 to 15 ppm sodium hypochlorite solution).

Assay and calculation expression: In all studies, the major axis and minor axis of a tumor were measured twice a week by using an electronic digital caliper (CD-15CX, Mitutoyo Corp.), and the tumor volume ($mm^3$) was calculated. The calculation expression is as shown below.

Tumor volume ($mm^3$)=½×Major axis (mm)×[Minor axis (mm)]$^2$

All of the antibody-drug conjugates and the antibody were diluted with physiological saline (Otsuka Pharmaceutical Factory, Inc.) and used at a volume of 10 mL/kg for intravenous administration to the tail vein of each mouse.

KPL-4 cells were suspended in physiological saline, and $1.5\times10^7$ cells were subcutaneously transplanted to the right side of the body of each female nude mouse (Day 0), and the mice were randomly grouped on Day 15. The antibody-drug conjugate (27) or the anti-HER2 antibody trastuzumab (Reference Example 1) for a control group was intravenously administered at a dose of 10 mg/kg to the tail vein of each mouse at Days 15 and 22. An untreated group was established as a control group.

The results are shown in FIG. 3. The administration of trastuzumab inhibited tumor growth, whereas the administration of the antibody-drug conjugate (27) produced a more significant tumor growth inhibitory effect. In the drawing, the abscissa depicts days after tumor inoculation, and the ordinate depicts tumor volume. In addition, the mice that received trastuzumab or the antibody-drug conjugate (27) were free from notable signs such as weight loss, suggesting that the antibody-drug conjugate (27) is highly safe. In the Evaluation Examples below regarding the antitumor test, the test was conducted by the procedure used in this Evaluation Example, unless otherwise specified.

Evaluation Example 3 Antitumor Test (2)

Human gastric cancer line NCI-N87 cells purchased from ATCC (American Type Culture Collection) were suspended in physiological saline, and $1\times10^7$ cells were subcutaneously transplanted to the right side of the body of each female nude mouse (Day 0), and the mice were randomly grouped on Day 7. The antibody-drug conjugate (8) or (28), or trastuzumab emtansine (Reference Example 2) was intravenously administered at a dose of 10 mg/kg to the tail vein of each mouse on Day 7. An untreated group was established as a control group.

Figure 4:
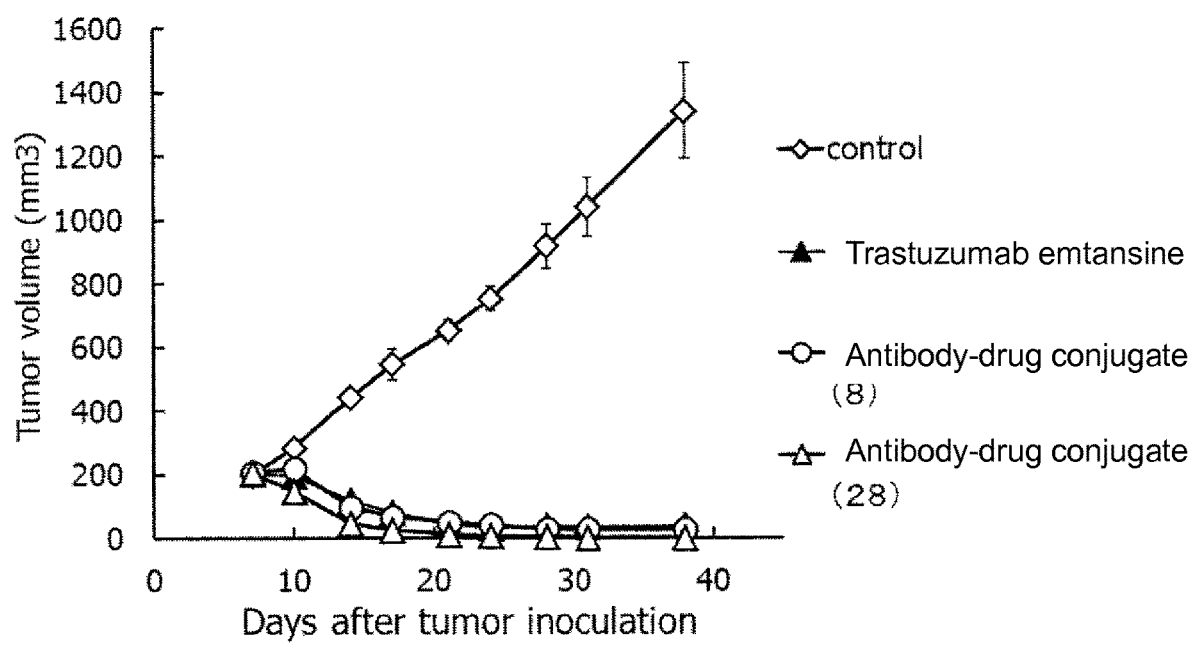
FIG. 4 is a diagram showing the antitumor effect of an antibody-drug conjugate (8), (28) or trastuzumab emtansine on a nude mouse with subcutaneously transplanted human gastric cancer line NCI-N87 cells. In the drawing, the abscissa depicts days after tumor inoculation, and the ordinate depicts tumor volume.

The results are shown in FIG. 4. The antibody-drug conjugates (8) and (28) were confirmed to have a strong antitumor effect with tumor regression equivalent to that of trastuzumab emtansine. In addition, the administration of the antibody-drug conjugate (8) or (28), or trastuzumab emtansine was found to be free from weight loss of the mice.

Evaluation Example 4 Antitumor Test (3)

Human breast cancer line JIMT-1 cells purchased from DSMZ (Deutsche Sammlung von Mikroorganismen und Zellkulturen GmbH) were suspended in physiological saline, and $3 \times 10^6$ cells were subcutaneously transplanted to the right side of the body of each female nude mouse (Day 0), and the mice were randomly grouped on Day 12. The antibody-drug conjugate (8), (29), or (30), trastuzumab, or trastuzumab emtansine was intravenously administered at a dose of 10 mg/kg to the tail vein of each mouse on Days 12 and 19. A physiological saline administration group was established as a control group.

Figure 5:
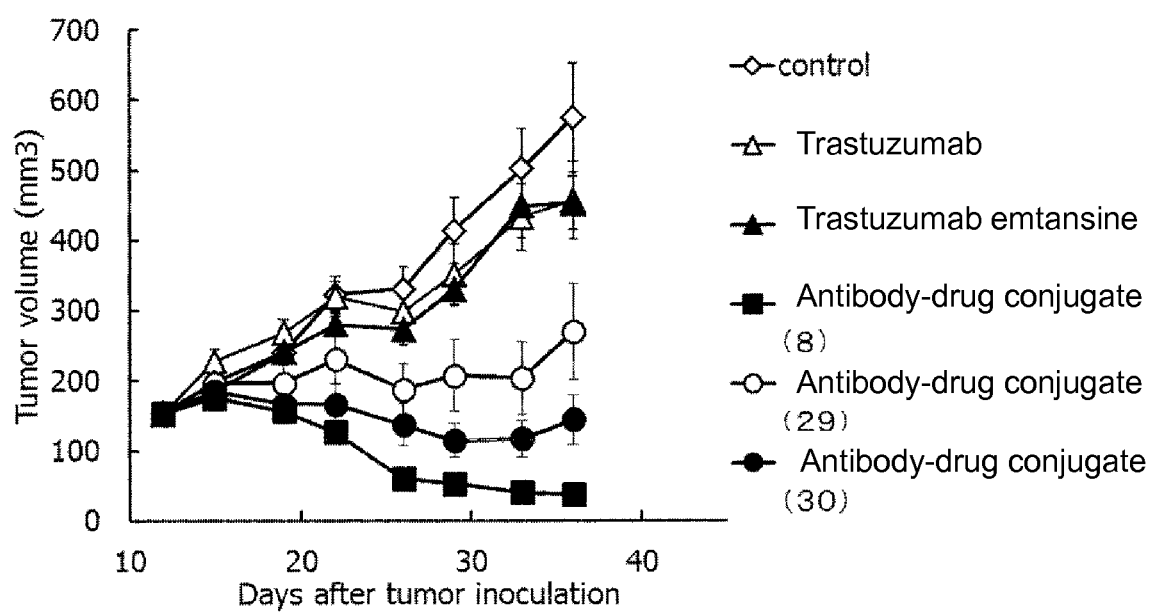
FIG. 5 is a diagram showing the antitumor effect of an antibody-drug conjugate (8), (29), (30), trastuzumab, or trastuzumab emtansine on a nude mouse with subcutaneously transplanted human breast cancer line JIMT-1 cells. In the drawing, the abscissa depicts days after tumor inoculation, and the ordinate depicts tumor volume.

The results are shown in FIG. 5. The administration of trastuzumab or trastuzumab emtansine did not inhibit the growth of the JIMT-1 tumor. On the other hand, the administration of the antibody-drug conjugate (8), (29), or (30) inhibited the growth of the tumor. In addition, the administration of the antibody-drug conjugate (8), (29), or (30), trastuzumab, or trastuzumab emtansine was found to be free from weight loss of the mice.

Evaluation Example 5 Cell Growth Inhibitory Effect (2) of Antibody-Drug Conjugate Human non-small cell lung cancer line Calu-3 (ATCC) was cultured in Eagle's Minimum Essential Medium (GIBCO) containing 10% fetal bovine serum (MOREGATE) (hereinafter, referred to as MEM medium).

Human gastric cancer line NCI-N87 (ATCC) or human gastric cancer line MKN-45 (Health Science Research Resources Bank) was cultured in RPMI1640 Medium (GIBCO) containing 10% fetal bovine serum (hereinafter, referred to as RPMI medium).

Human breast cancer line MDA-MB-453 (ATCC) or human breast cancer line MDA-MB-468 (ATCC) was cultured in Leibovitz's L-15 Medium (GIBCO) containing 10% fetal bovine serum (hereinafter, referred to as Leibovitz's medium).

Among these 5 types of cell lines, Calu-3, NCI-N87, and MDA-MB-453 are HER2-positive cells, and MKN-45 and MDA-MB-468 are HER2-negative cells.

Calu-3, NCI-N87, or MKN-45 was prepared to have a concentration of $4 \times 10^4$ cells/mL by using MEM medium or RPMI medium, added at a concentration of 25 μL/well to a 96-well microplate for cell culture charged with 65 μL/well of a medium, and cultured overnight under 5% $CO_2$ at 37° C. Also, MDA-MB-453 or MDA-MB-468 was prepared to have a concentration of $4 \times 10^4$ cells/mL by using Leibovitz's medium, added at a concentration of 25 μL/well to a 96-well microplate for cell culture charged with 65 μL/well of medium, and cultured overnight at 37° C. without setting $CO_2$ concentration.

On the next day, a test substance diluted into 1000 nM, 200 nM, 40 nM, 8 nM, 1.6 nM, 0.32 nM, and 0.064 nM by using RPMI medium or Leibovitz's medium, or RPMI medium or Leibovitz's medium was added at a concentration of 10 μL/well to the microplate. The cells were cultured under 5% $CO_2$ at 37° C. or at 37° C. without setting $CO_2$ concentration for 6 days.

For Calu-3, NCI-N87, and MDA-MB-468, the antibody-drug conjugate (46) was added as the test substance. For the other cells, the antibody-drug conjugate (50) was added as the test substance. After the culture, the microplate was taken out from the incubator and left standing at room temperature for 30 minutes. The culture solution was charged with an equal amount of CellTiter-Glo Luminescent Cell Viability Assay (Promega) and stirred with a plate mixer to completely lyse the cells. After the microplate was left standing at room temperature for 10 minutes, luminescence intensity was measured by using a plate reader.

Cell viability was calculated according to the following equation:

Cell viability (%)=$a/b \times 100$ a: Average luminescence intensity of the test substance-supplemented wells
b: Average luminescence intensity of the medium-supplemented wells The $IC_{50}$ value was calculated according to the following equation:

$IC_{50}$ (nM)=antilog((50−$d$)×($LOG_{10}(b)$−$LOG_{10}(a)$)/($d$−$c$)+$LOG_{10}(b)$))

a: Concentration a of the test substance
b: Concentration b of the test substance
c: Cell viability supplemented with the test substance having the concentration a
d: Cell viability supplemented with the test substance having the concentration b The concentrations a and b establish the relation a>b crossing 50% of cell viability.

The antibody-drug conjugate (46) exhibited a cell growth inhibitory effect of $IC_{50}<1$ (nM) against the HER2-positive cells Calu-3 and NCI-N87. On the other hand, the antibody-drug conjugate (46) exhibited no cell growth inhibitory effect against the HER2-negative cells MDA-MB-468 (>100 (nM)).

The antibody-drug conjugate (50) exhibited a cell growth inhibitory effect of $IC_{50}<1$ (nM) against the HER2-positive cells MDA-MB-453. On the other hand, the antibody-drug conjugate (50) exhibited no cell growth inhibitory effect against the HER2-negative cells MKN-45 (>100 (nM)).

Evaluation Example 6 Antitumor Test (4)

Human pancreatic cancer line Capan-1 cells (ATCC) weakly expressing HER2 were suspended in physiological saline, and $4 \times 10^7$ cells were subcutaneously transplanted to the right side of the body of each female nude mouse to generate Capan-1 solid tumor. Thereafter, this solid tumor was maintained at several passages by transplantation to female nude mice and used in this test. A tumor section of the solid tumor was subcutaneously transplanted to the right side of the body of each female nude mouse (Day 0), and the mice were randomly grouped on Day 20.

The antibody-drug conjugate (31), trastuzumab, or trastuzumab emtansine was intravenously administered at a dose of 10 mg/kg to the tail vein of each mouse on Day 20. A physiological saline administration group was established as a control group.

Figure 6:
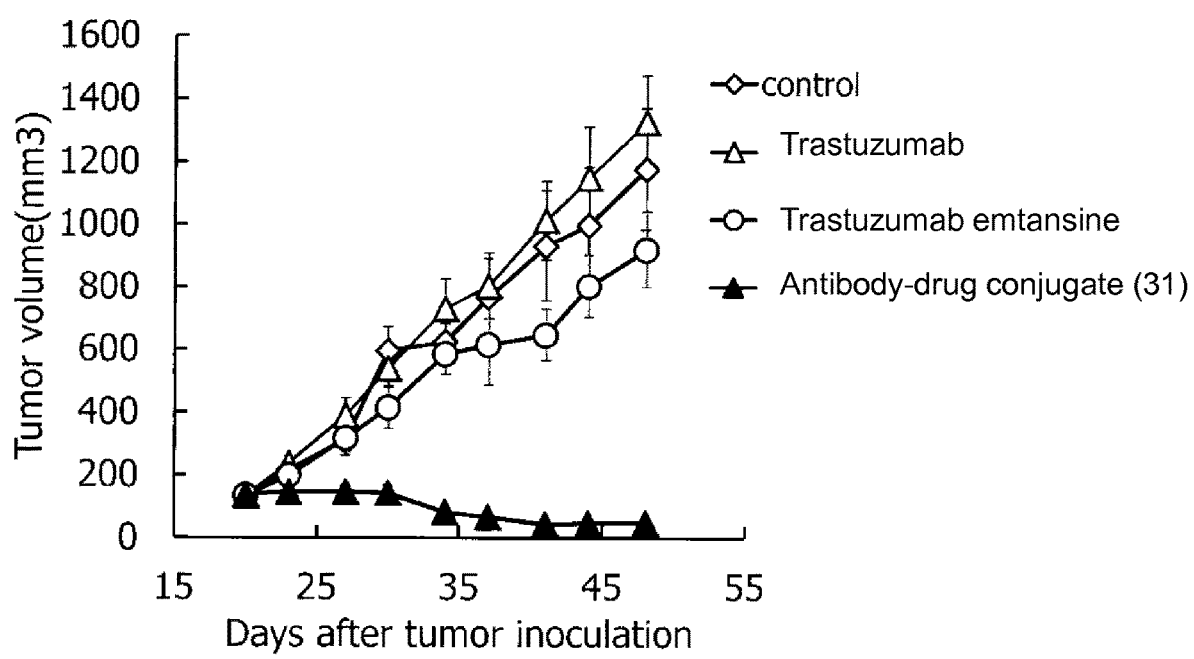
FIG. 6 is a diagram showing the antitumor effect of an antibody-drug conjugate (31), trastuzumab, or trastuzumab emtansine on a nude mouse with subcutaneously transplanted human pancreatic cancer line Capan-1 cells. In the drawing, the abscissa depicts days after tumor inoculation, and the ordinate depicts tumor volume.

The results are shown in FIG. 6. The administration of trastuzumab or trastuzumab emtansine did not inhibit the growth of the Capan-1 tumor. By contrast, the administration of the antibody-drug conjugate (31) inhibited the growth of the tumor, demonstrating that the antibody-drug conjugate (31) is effective for even tumor with low HER2 expression. The antibody-drug conjugate (31) did not inhibit the growth of HER2 non-expressing gastric cancer line GCIY tumor.

As for the expression of HER2 in tumor, on the basis of measurement results of immunohistochemical staining described in the 3rd edition of the guidelines for HER2 testing (developed by the Japanese Pathology Board for Optimal Use of Trastuzumab, The Japanese Society of Pathology), classification was performed such that score of 3+: high expression, 2+: moderate expression, and 1+: low expression. Even if the score was 0 in this measurement method, tumor found HER2-positive by other measurement methods such as a measurement method using a flow cytometer was classified as low expressing tumor.

Evaluation Example 7 Antitumor Test (5)

Human gastric cancer line NCI-N87 cells purchased from ATCC were suspended in physiological saline, and $1\times10^7$ cells were subcutaneously transplanted to the right side of the body of each female nude mouse (Day 0), and the mice were randomly grouped on Day 6. The antibody-drug conjugate (50) was intravenously administered at each dose of 0.3, 1, 3, or 10 mg/kg to the tail vein of each mouse on Day 6. An acetate buffer solution administration group was established as a control group.

Figure 7:
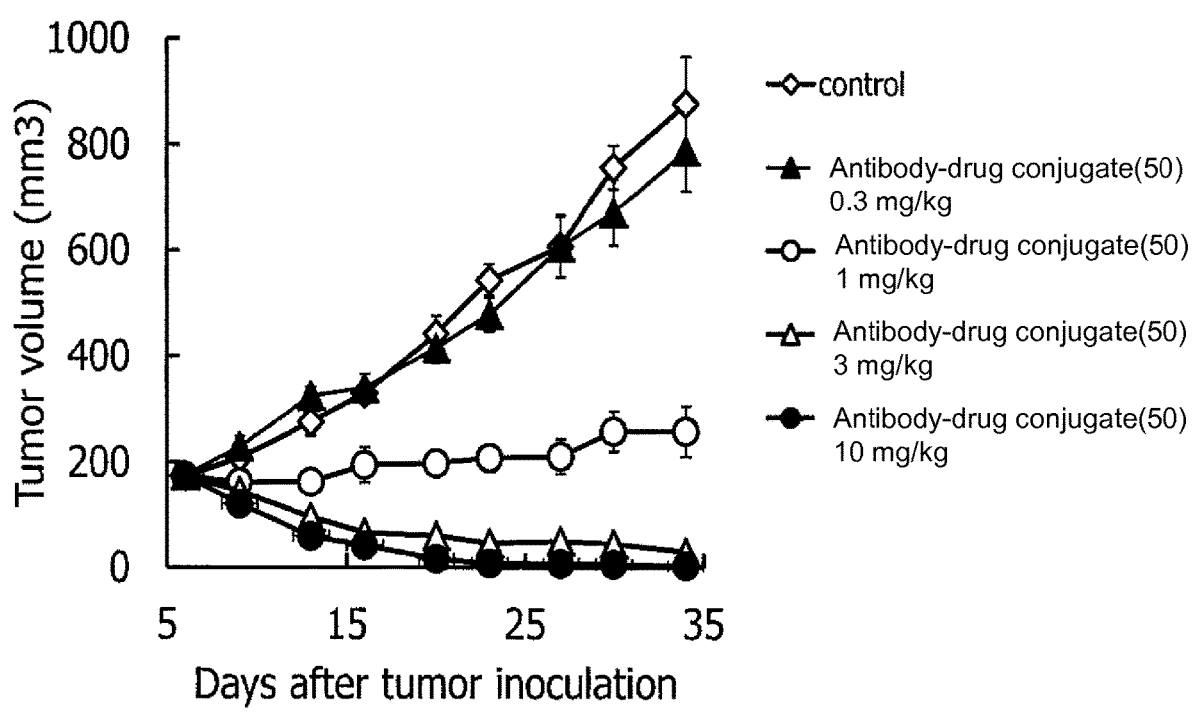
FIG. 7 is a diagram showing the antitumor effect of an antibody-drug conjugate (50) on a nude mouse with subcutaneously transplanted human gastric cancer line NCI-N87 cells. In the drawing, the abscissa depicts days after tumor inoculation, and the ordinate depicts tumor volume.

The results are shown in FIG. 7. The antibody-drug conjugate (50) exhibited a dose-dependent antitumor effect. In addition, the administration of the antibody-drug conjugate (50) was found to be free from weight loss of the mice.

Evaluation Example 8 Antitumor Test (6)

This test was carried out by the following method.
Mouse: 6- to 12-week-old female nude mice (Charles River Laboratories Japan, Inc.) were subjected to the experiment.
Assay and calculation expression: The major axis and minor axis of tumor were measured twice a week by using an electronic digital caliper, and the tumor volume (mm$^3$) was calculated. The calculation expression is as shown below.

Tumor volume (mm$^3$)=0.52×Major axis (mm)×[Minor axis (mm)]$^2$

The antibody-drug conjugate, trastuzumab, and trastuzumab emtansine were diluted with an acetate buffer solution and used at a volume of 10 mL/kg for intravenous administration to the tail vein of each mouse.

Tumor (ST225; South Texas Accelerated Research Therapeutics (START)) excised from a breast cancer patient and maintained at several passages by transplantation to female nude mice was used in this test. This tumor moderately expressed HER2 (which received a score of 2+ in immunohistochemical staining).

A tumor section of the solid tumor was subcutaneously transplanted to the side of the body of each female nude mouse, and the mice were randomly grouped when the tumor volume reached 100 to 300 mm$^3$. The date of grouping was defined as Day 0. The antibody-drug conjugate (50), trastuzumab, or trastuzumab emtansine was intravenously administered at a dose of 10 mg/kg to the tail vein of each mouse on Day 0. An acetate buffer solution administration group was established as a control group.

Figure 8:
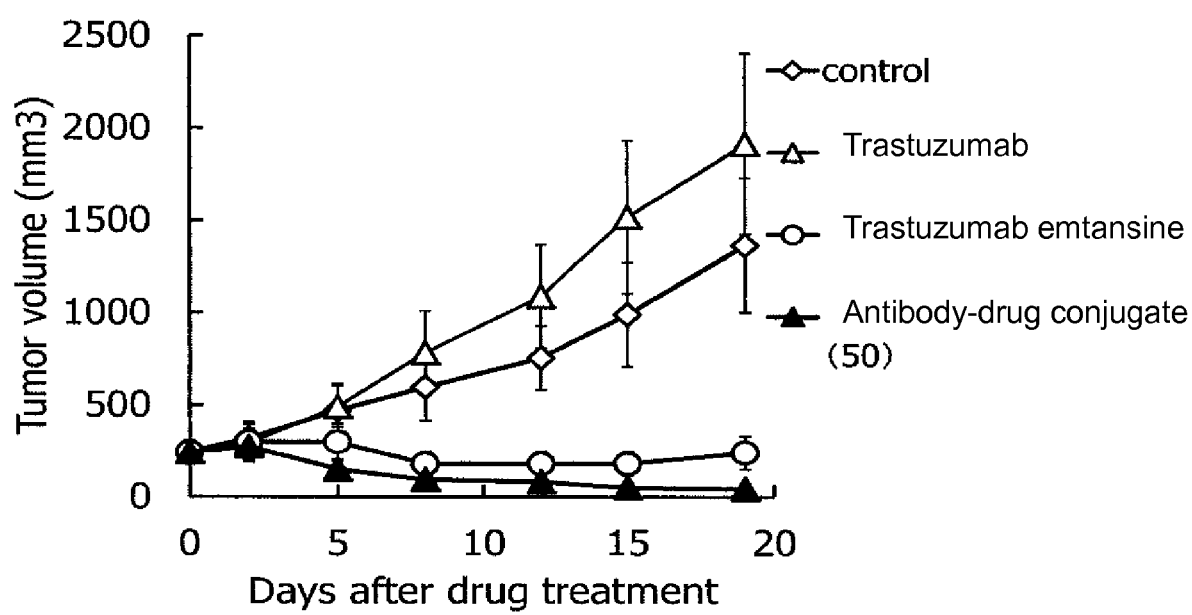
FIG. 8 is a diagram showing the antitumor effect of an antibody-drug conjugate (50), trastuzumab, or trastuzumab emtansine on a nude mouse with subcutaneously transplanted human breast cancer ST225 cells. In the drawing, the abscissa depicts days after tumor inoculation, and the ordinate depicts tumor volume.

The results are shown in FIG. 8. The administration of trastuzumab did not inhibit the growth of the breast cancer ST225 tumor moderately expressing HER2. By contrast, the administration of trastuzumab emtansine or the antibody-drug conjugate (50) remarkably inhibited the growth of the tumor.

Evaluation Example 9 Antitumor Test (7)

Tumor (ST910; START) excised from a breast cancer patient and maintained at several passages by transplantation to female nude mice was used in this test. This tumor low expressed HER2 (which received a score of 1+ in immunohistochemical staining).

A tumor section of the solid tumor was subcutaneously transplanted to the side of the body of each female nude mouse, and the mice were randomly grouped when the tumor volume reached 100 to 300 mm$^3$. The date of grouping was defined as Day 0. The antibody-drug conjugate (50), trastuzumab, or trastuzumab emtansine was intravenously administered at a dose of 10 mg/kg to the tail vein of each mouse on Day 0. An acetate buffer solution administration group was established as a control group.

Figure 9:
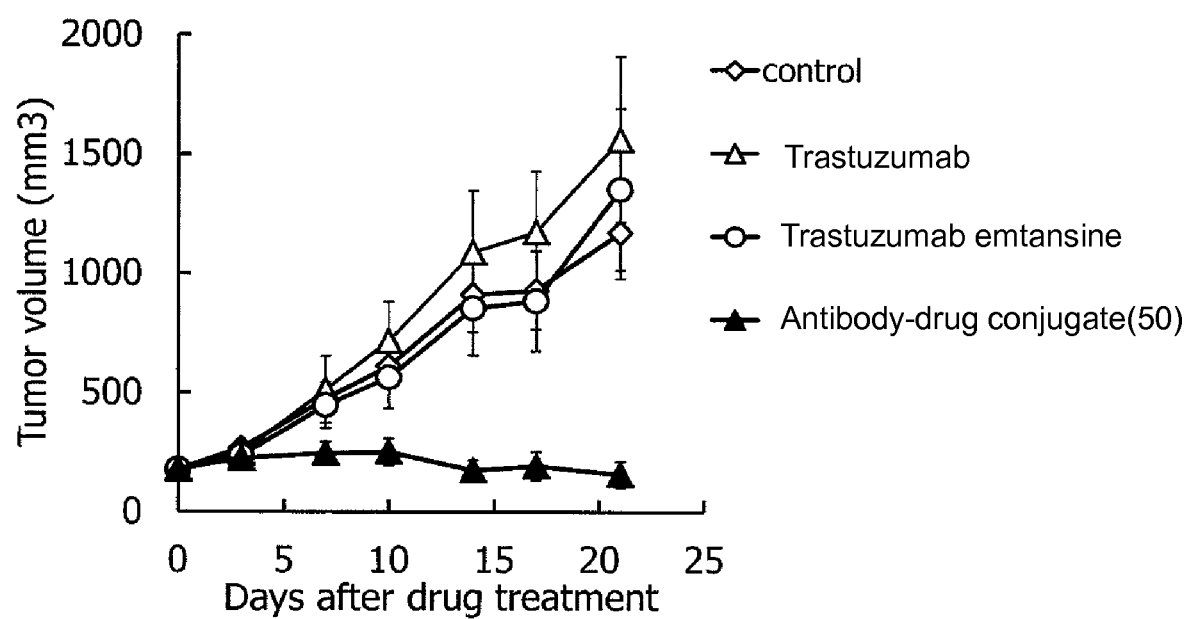
FIG. 9 is a diagram showing the antitumor effect of an antibody-drug conjugate (50), trastuzumab, or trastuzumab emtansine on a nude mouse with subcutaneously transplanted human breast cancer ST910 cells. In the drawing, the abscissa depicts days after tumor inoculation, and the ordinate depicts tumor volume.

The results are shown in FIG. 9. The administration of trastuzumab or trastuzumab emtansine did not inhibit the growth of the breast cancer ST910 tumor low expressing HER2. By contrast, the administration of the antibody-drug conjugate (50) remarkably inhibited the growth of the tumor, demonstrating that the antibody-drug conjugate (50) is effective for breast cancer tumor low expressing HER2. This Evaluation Example 9 was carried out by the same procedure as Evaluation Example 8.

Evaluation Example 10 Antitumor Test (8)

This test was carried out by the following procedure. Evaluation Examples 11 to 13 were also carried out by this procedure.
Mouse: 5- to 8-week-old female nude mice (Harlan Laboratories Ltd.) were subjected to the experiment.
Assay and calculation expression: The major axis and minor axis of tumor were measured twice a week by using an electronic digital caliper, and the tumor volume (mm$^3$) was calculated. The calculation expression is as shown below.

Tumor volume (mm$^3$)=0.52×Major axis (mm)×[Minor axis (mm)]$^2$

The antibody-drug conjugate, trastuzumab, and trastuzumab emtansine were diluted with an acetate buffer solution and used at a volume of 10 mL/kg for intravenous administration to the tail vein of each mouse.

Tumor (CTG-0401; Champions Oncology Inc.) excised from a colorectal cancer patient and maintained at several passages by transplantation to female nude mice was used in this test. This tumor low or moderately expressed HER2 (which received a score of 1+ or 2+ in immunohistochemical staining).

A tumor section of the solid tumor was subcutaneously transplanted to the left side of the body of each female nude mouse, and the mice were randomly grouped when the tumor volume reached 100 to 300 mm$^3$. The date of grouping was defined as Day 0. The antibody-drug conjugate (50), trastuzumab, or trastuzumab emtansine was intravenously administered at a dose of 10 mg/kg to the tail vein of each mouse on Day 0. An acetate buffer solution administration group was established as a control group.

Figure 10:
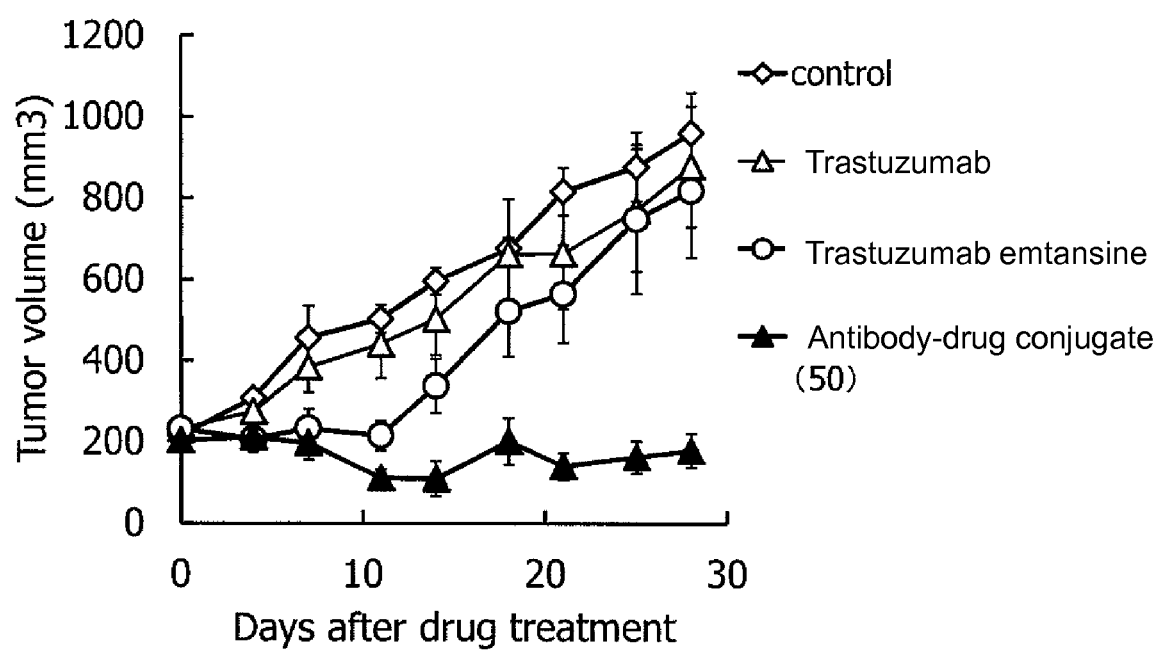
FIG. 10 is a diagram showing the antitumor effect of an antibody-drug conjugate (50), trastuzumab, or trastuzumab emtansine on a nude mouse with subcutaneously transplanted human colorectal cancer line CTG-0401 cells. In the drawing, the abscissa depicts days after tumor inoculation, and the ordinate depicts tumor volume.

The results are shown in FIG. 10. The administration of trastuzumab or trastuzumab emtansine did not inhibit the growth of the colorectal cancer CTG-0401 tumor low or moderately expressing HER2. By contrast, the administration of the antibody-drug conjugate (50) remarkably inhibited the growth of the tumor.

Evaluation Example 11 Antitumor Test (9)

Tumor (CTG-0860; Champions Oncology Inc.) excised from a non-small cell lung cancer patient and maintained at several passages by transplantation to female nude mice was used in this test. This tumor moderately expressed HER2 (which received a score of 2+ in immunohistochemical staining).

A tumor section of the solid tumor was subcutaneously transplanted to the left side of the body of each female nude mouse, and the mice were randomly grouped when the tumor volume reached 100 to 300 mm$^3$. The date of grouping was defined as Day 0. The antibody-drug conjugate (50), trastuzumab, or trastuzumab emtansine was intravenously administered at a dose of 10 mg/kg to the tail vein of each mouse on Day 0. An acetate buffer solution administration group was established as a control group.

Figure 11:
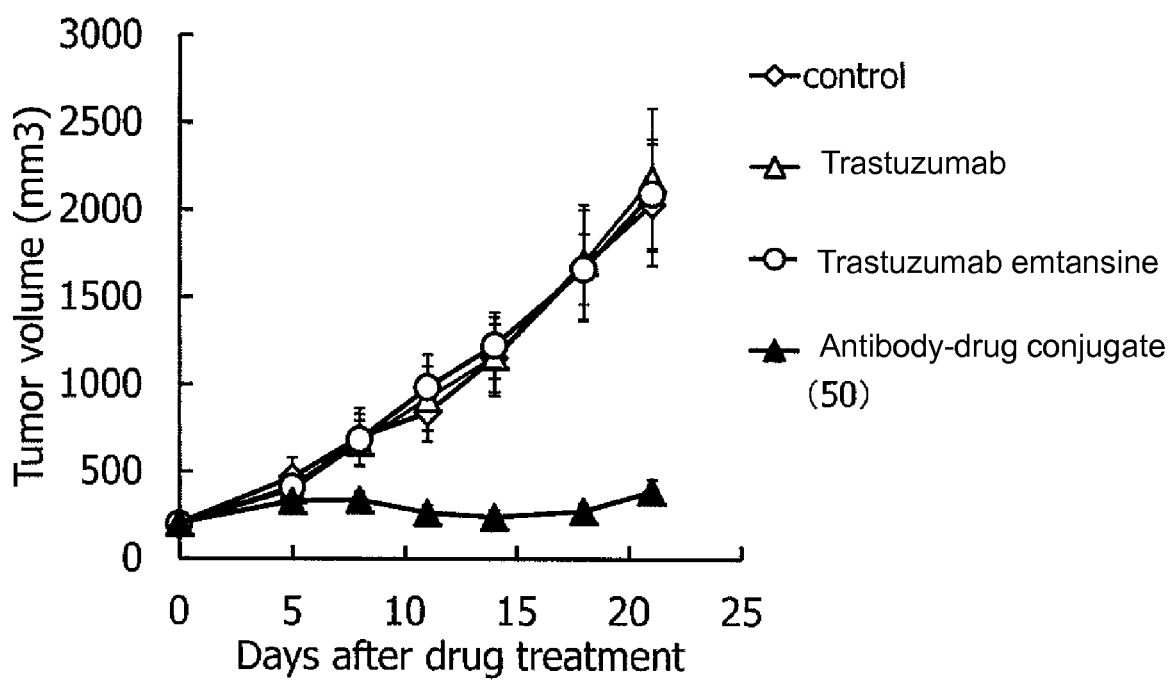
FIG. 11 is a diagram showing the antitumor effect of an antibody-drug conjugate (50), trastuzumab, or trastuzumab emtansine on a nude mouse with subcutaneously transplanted human non-small cell lung cancer CTG-0860 cells. In the drawing, the abscissa depicts days after tumor inoculation, and the ordinate depicts tumor volume.

The results are shown in FIG. 11. The administration of trastuzumab or trastuzumab emtansine did not inhibit the growth of the non-small cell lung cancer CTG-0860 tumor moderately expressing HER2. By contrast, the administration of the antibody-drug conjugate (50) remarkably inhibited the growth of the tumor.

Evaluation Example 12 Antitumor Test (10)

Tumor (CTG-0927; Champions Oncology Inc.) excised from a bile duct cancer patient and maintained at several passages by transplantation to female nude mice was used in this test. This tumor highly expressed HER2 (which received a score of 3+ in immunohistochemical staining).

A tumor section of the solid tumor was subcutaneously transplanted to the left side of the body of each female nude mouse, and the mice were randomly grouped when the tumor volume reached 100 to 300 mm$^3$. The date of grouping was defined as Day 0. The antibody-drug conjugate (50), trastuzumab, or trastuzumab emtansine was intravenously administered at a dose of 10 mg/kg to the tail vein of each mouse on Day 0. An acetate buffer solution administration group was established as a control group.

Figure 12:
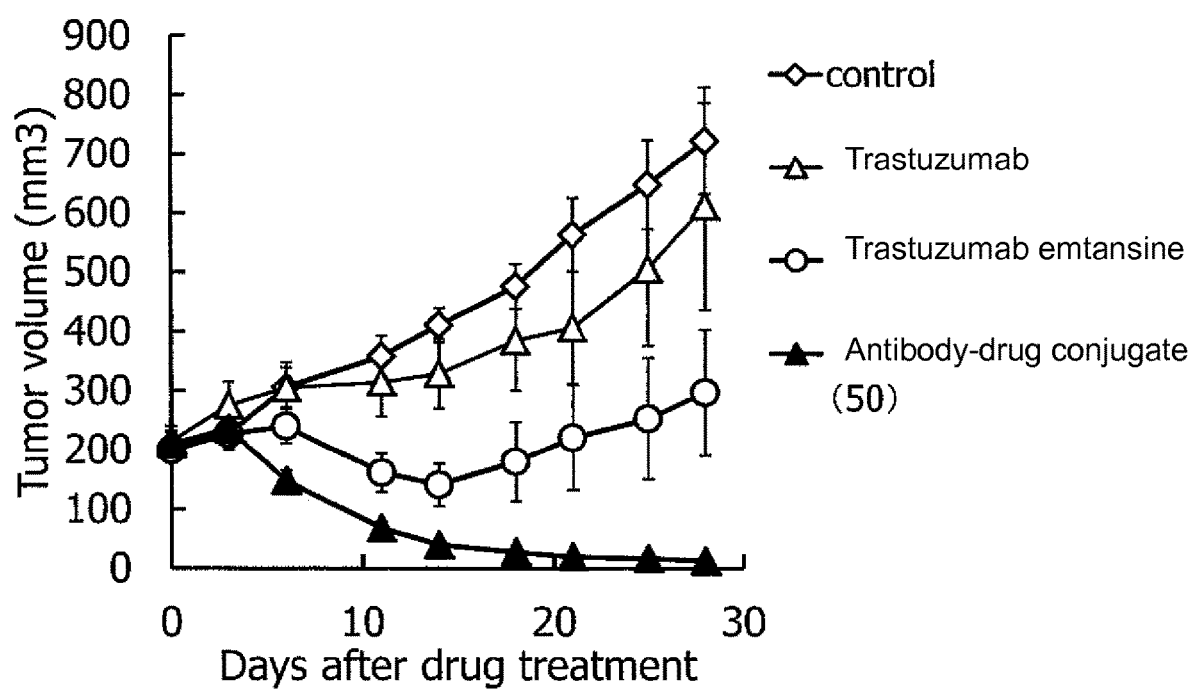
FIG. 12 is a diagram showing the antitumor effect of an antibody-drug conjugate (50), trastuzumab, or trastuzumab emtansine on a nude mouse with subcutaneously transplanted human bile duct cancer line CTG-0927 cells. In the drawing, the abscissa depicts days after tumor inoculation, and the ordinate depicts tumor volume.

The results are shown in FIG. 12. The administration of trastuzumab did not inhibit the growth of the bile duct cancer CTG-0927 tumor highly expressing HER2. By contrast, the administration of trastuzumab emtansine inhibited the growth of the tumor. Furthermore, the administration of the antibody-drug conjugate (50) induced the regression of the tumor.

Evaluation Example 13 Antitumor Test (11)

Tumor (CTG-0137; Champions Oncology Inc.) excised from an esophageal cancer patient and maintained at several passages by transplantation to female nude mice was used in this test. This tumor highly expressed HER2 (which received a score of 3+ in immunohistochemical staining).

A tumor section of the solid tumor was subcutaneously transplanted to the left side of the body of each female nude mouse, and the mice were randomly grouped when the tumor volume reached 100 to 300 mm$^3$. The date of grouping was defined as Day 0. The antibody-drug conjugate (50), trastuzumab, or trastuzumab emtansine was intravenously administered at a dose of 10 mg/kg to the tail vein of each mouse on Day 0. An acetate buffer solution administration group was established as a control group.

Figure 13:
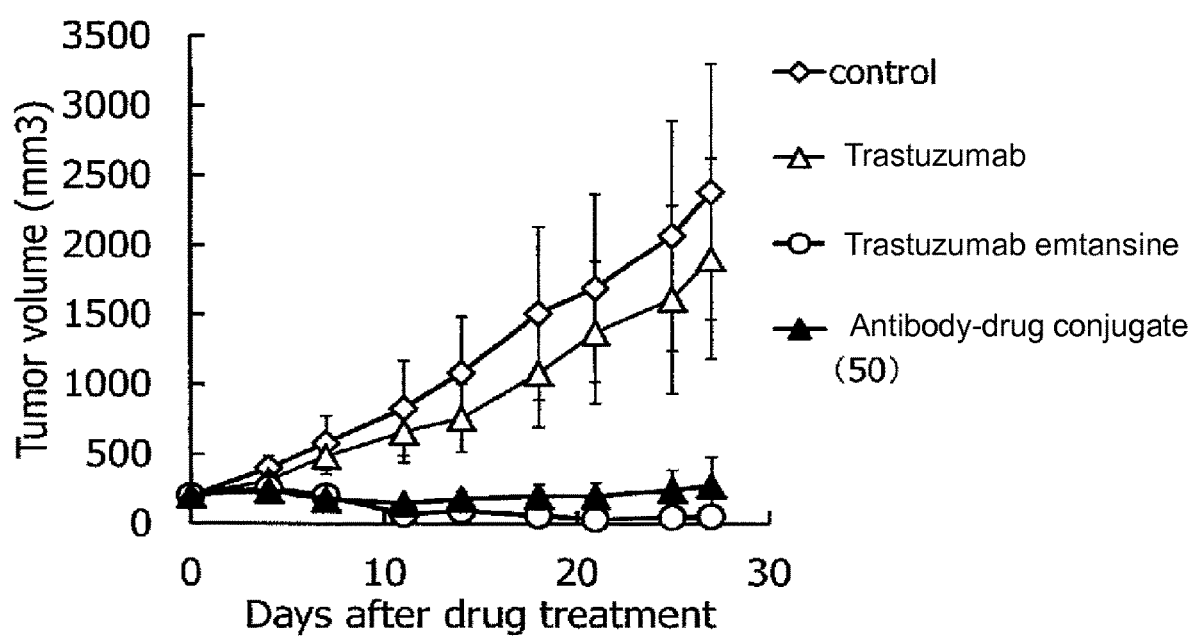
FIG. 13 is a diagram showing the antitumor effect of an antibody-drug conjugate (50), trastuzumab, or trastuzumab emtansine on a nude mouse with subcutaneously transplanted human esophageal cancer line CTG-0137 cells. In the drawing, the abscissa depicts days after tumor inoculation, and the ordinate depicts tumor volume.

The results are shown in FIG. 13. The administration of trastuzumab did not inhibit the growth of the esophageal cancer CTG-0137 tumor highly expressing HER2. By contrast, the administration of trastuzumab emtansine or the antibody-drug conjugate (50) remarkably inhibited the growth of the tumor.

Evaluation Example 14 Antitumor Test (12)

Human ovarian cancer line SK-OV-3 cells highly expressing HER2 purchased from ATCC were suspended in physiological saline, and $4 \times 10^7$ cells were subcutaneously transplanted to the right side of the body of each female nude mouse to prepare SK-OV-3 solid tumor. Thereafter, this solid tumor was maintained at several passages by transplantation to female nude mice and used in this test.

A tumor section of the solid tumor was subcutaneously transplanted to the right side of the body of each female nude mouse, and the mice were randomly grouped when the tumor volume reached 100 to 300 mm$^3$. The date of grouping was defined as Day 0. The antibody-drug conjugate (50), trastuzumab, or trastuzumab emtansine was intravenously administered at a dose of 10 mg/kg to the tail vein of each mouse on Day 0. A physiological saline administration group was established as a control group.

Figure 14:
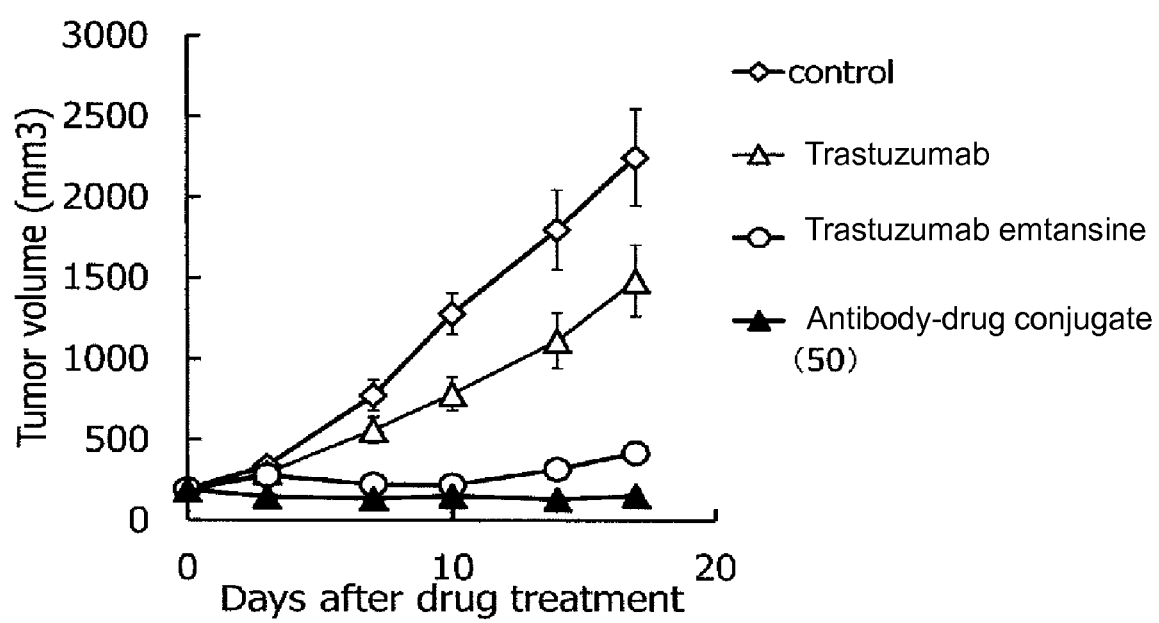
FIG. 14 is a diagram showing the antitumor effect of an antibody-drug conjugate (50), trastuzumab, or trastuzumab emtansine on a nude mouse with subcutaneously transplanted human ovarian cancer line SK-OV-3 cells. In the drawing, the abscissa depicts days after tumor inoculation, and the ordinate depicts tumor volume.

The results are shown in FIG. 14. The administration of trastuzumab did not inhibit the growth of the SK-OV-3 tumor. By contrast, the administration of trastuzumab emtansine or the antibody-drug conjugate (50) remarkably inhibited the growth of the tumor.

Free Text of Sequence Listing

SEQ ID NO: 1—Amino acid sequence of a heavy chain of the humanized anti-HER2 monoclonal antibody SEQ ID NO: 2—Amino acid sequence of a light chain of the humanized anti-HER2 monoclonal antibody

The invention claimed is:

1. A method of treating HER2-low expressing cancer in an individual comprising administering to an individual with HER2-low expressing cancer a drug containing an antibody-drug conjugate or a salt thereof, wherein the antibody-drug conjugate comprises a linker and an antitumor compound represented by the following formula and anti-HER2 antibody connected to the linker:

-(Succinimid-3-yl-N)—$CH_2CH_2CH_2CH_2CH_2$—C(=O)-GGFG (SEQ ID NO: 3)-NH—$CH_2$—O—$CH_2$—C(=O)—(NH-DX)

wherein

-(Succinimid-3-yl-N)- has a structure represented by the following formula:

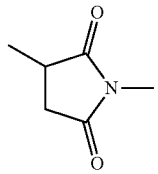

which is connected to the antibody at position 3 thereof and is connected to a methylene group in the linker structure containing this structure on the nitrogen atom at position 1, and (NH-DX) represents a group represented by the following formula:

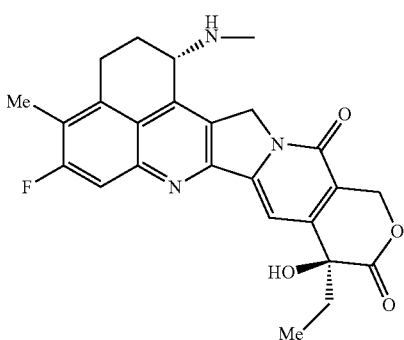 [SMILES: CC[C@@]1(O)C(=O)OCc2c1cc1n(c2=O)Cc2c-1nc1cc(F)c(C)c3c1c2[C@@H](NC)CC3]

wherein the nitrogen atom of the amino group at position 1 is the connecting position, and wherein the HER2-low expressing cancer is lung cancer, urothelial cancer, colorectal cancer, prostate cancer, ovarian cancer, pancreatic cancer, breast cancer, bladder cancer, gastric cancer, gastrointestinal stromal tumor, uterine cervix cancer, esophageal cancer, squamous cell carcinoma, peritoneal cancer, liver cancer, hepatocellular cancer, colon cancer, rectal cancer, colorectal cancer, endometrial cancer, uterine cancer, salivary gland cancer, kidney cancer, vulval cancer, thyroid cancer, penis cancer, leukemia, malignant lymphoma, plasmacytoma, myeloma, or sarcoma.

2. The method of treating HER2-low expressing cancer according to claim 1, wherein the anti-HER2 antibody comprises a heavy chain and a light chain selected from the group:
   a heavy chain consisting of an amino acid sequence consisting of amino acid residues 1 to 449 of SEQ ID NO: 1 and a light chain consisting of an amino acid sequence consisting of amino acid residues 1 to 214 of SEQ ID NO: 2, and
   a heavy chain consisting of the amino acid sequence of SEQ ID NO: 1 and a light chain consisting of the amino acid sequence of SEQ ID NO: 2.

3. The method of treating HER2-low expressing cancer according to claim 1, wherein the anti-HER2 antibody comprises a heavy chain consisting of the amino acid sequence consisting of amino acid residues 1 to 449 of SEQ ID NO: 1 and a light chain consisting of the amino acid sequence consisting of amino acid residues 1 to 214 of SEQ ID NO: 2.

4. The method of treating HER2-low expressing cancer according to claim 1, wherein the anti-HER2 antibody comprises a heavy chain consisting of the amino acid sequence of SEQ ID NO: 1 and a light chain consisting of the amino acid sequence of SEQ ID NO: 2.

5. The method of treating HER2-low expressing cancer according to claim 1, wherein the antibody-drug conjugate has an average number of units of the drug-linker structure conjugated per antibody in a range of from 2 to 8.

6. The method of treating HER2-low expressing cancer according to claim 1, wherein the antibody-drug conjugate has an average number of units of the drug-linker structure conjugated per antibody in a range of from 3 to 8.

7. A method of treating HER2-low expressing cancer in an individual comprising administering to an individual with HER2-low expressing cancer a pharmaceutical composition containing an antibody-drug conjugate or a salt thereof as an active component and a pharmaceutically acceptable formulation component, wherein the antibody-drug conjugate comprises a linker and an antitumor compound represented by the following formula and anti-HER2 antibody connected to the linker:

-(Succinimid-3-yl-N)—CH$_2$CH$_2$CH$_2$CH$_2$CH$_2$—C(=O)-GGFG (SEQ ID NO: 3)-NH—CH$_2$—O—CH$_2$—C(=O)—(NH-DX)

wherein

-(Succinimid-3-yl-N)- has a structure represented by the following formula:

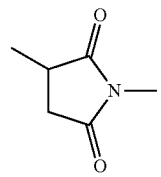

which is connected to the antibody at position 3 thereof and is connected to a methylene group in the linker structure containing this structure on the nitrogen atom at position 1, and (NH-DX) represents a group represented by the following formula:

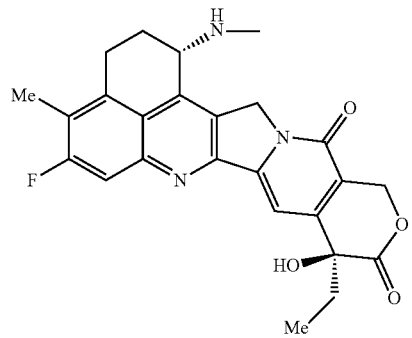 [SMILES: CC[C@@]1(O)C(=O)OCc2c1cc1n(c2=O)Cc2c-1nc1cc(F)c(C)c3c1c2[C@@H](NC)CC3]

wherein the nitrogen atom of the amino group at position 1 is the connecting position, and wherein the HER2-low expressing cancer is lung cancer, urothelial cancer, colorectal cancer, prostate cancer, ovarian cancer, pancreatic cancer, breast cancer, bladder cancer, gastric cancer, gastrointestinal stromal tumor, uterine cervix cancer, esophageal cancer, squamous cell carcinoma, peritoneal cancer, liver cancer, hepatocellular cancer, colon cancer, rectal cancer, colorectal cancer, endometrial cancer, uterine cancer, salivary gland cancer, kidney cancer, vulval cancer, thyroid cancer, penis cancer, leukemia, malignant lymphoma, plasmacytoma, myeloma, or sarcoma.

8. The method of treating HER2-low expressing cancer according to claim 7, wherein the anti-HER2 antibody comprises a heavy chain and a light chain selected from the group:
   a heavy chain consisting of an amino acid sequence consisting of amino acid residues 1 to 449 of SEQ ID NO: 1 and a light chain consisting of an amino acid sequence consisting of amino acid residues 1 to 214 of SEQ ID NO: 2, and
   a heavy chain consisting of the amino acid sequence of SEQ ID NO: 1 and a light chain consisting of the amino acid sequence of SEQ ID NO: 2.

9. The method of treating HER2-low expressing cancer according to claim 7, wherein the anti-HER2 antibody comprises a heavy chain consisting of the amino acid sequence consisting of amino acid residues 1 to 449 of SEQ ID NO: 1 and a light chain consisting of the amino acid sequence consisting of amino acid residues 1 to 214 of SEQ ID NO: 2.

10. The method of treating HER2-low expressing cancer according to claim 7, wherein the anti-HER2 antibody comprises a heavy chain consisting of the amino acid sequence of SEQ ID NO: 1 and a light chain consisting of the amino acid sequence of SEQ ID NO: 2.

11. The method of treating HER2-low expressing cancer according to claim 7, wherein the antibody-drug conjugate has an average number of units of the drug-linker structure conjugated per antibody in a range of from 2 to 8.

12. The method of treating HER2-low expressing cancer according to claim 7, wherein the antibody-drug conjugate has an average number of units of the drug-linker structure conjugated per antibody in a range of from 3 to 8.

* * * * *